(12) United States Patent
Koo et al.

(10) Patent No.: US 6,201,006 B1
(45) Date of Patent: Mar. 13, 2001

(54) AROMATIC AMIDINE DERIVATIVES USEFUL AS SELECTIVE THROMBIN INHIBITORS

(75) Inventors: Bon Am Koo, Seoul; Jae Ki Min, Kyunggi-Do; Woo Sang Hong, Kyunggi-do; Eun Jung Ryu, Kyunggi-do; Woong Hyun Nam, Kyunggi-do; Jong Min Kim, Kyunggi-do, all of (KR)

(73) Assignee: C & C Research Laboratories, Kyunggi-Do (KR)

( * ) Notice: Subject to any disclaimer, the term of this patent is extended or adjusted under 35 U.S.C. 154(b) by 0 days.

(21) Appl. No.: 09/180,675

(22) PCT Filed: May 31, 1997

(86) PCT No.: PCT/KR97/00100

§ 371 Date: Nov. 13, 1998

§ 102(e) Date: Nov. 13, 1998

(87) PCT Pub. No.: WO97/45424

PCT Pub. Date: Dec. 4, 1997

(30) Foreign Application Priority Data

May 31, 1996 (KR) .................................................. 96-19282

(51) Int. Cl.[7] ..................... C07D 403/06; A61K 31/4045
(52) U.S. Cl. .......................... 514/414; 546/145; 546/201; 548/455; 548/468; 548/518; 548/525; 548/538
(58) Field of Search ............................ 514/414; 548/468, 548/455, 518, 525, 538; 546/201, 145

(56) References Cited

U.S. PATENT DOCUMENTS 4,258,192    3/1981    Okamoto .

OTHER PUBLICATIONS

Chemical Abstracts, vol. 125, No. 11, 1996, p. 28, abstract 131628h.
Chemical Abstracts, vol. 99, No. 5, 1983, p. 501, abstract 38220d.
Chemical Abstracts, vol. 98, No. 9, 1983, p. 19, abstract 65141q.

"Derivatives of 5–amidine Indole as Inhibitors of Thrombin Catalytic Activity", E.J. Iwanowicz, et al., Chemical Abstracts, vol. 125, No. 11; Sep. 9, 1996, p. 28. col. 1, abstract No.131268h.

"Phenyl Esters", Chemical Abstracts, vol. 99, No. 5, Aug. 1, 1983, p. 501, col. 1, abstract No. 38220d.

"Aromatic Amidines. Comparison of Their Ability to Block Respiratory Syncytial Virus Induced Cell Fusion and to Inhibit Plasmin, Urokinase, Thrombin, and Trypsin", R.R. Tidwell, et al., Chemical Abstracts, vol. 98, No. 9.Feb. 28, 1983, p. 19, col. 2, abstract No. 65141q.

"Active Site–Directed Thromin Inhibitors:alpha–hydroxya-cyl–prolyl–arginals. New Orally Active Stable Analogs of delta–Phe–Pro–Arg–H", S. Bajusz, et al., Chemical Abstracts, No. 123. No. 23, Dec. 4, 1995, p. 50, col. 1, absstract No. 306203d.

"Challenges in the Development of Orally Bioavailable Thrombin Active Site Inhibitors ", S.D. Kimball, Chemical Abstracts, vol. 124, No. 23, Dec. 4, 1995, p. 50, col. 1, abstract No. 306203d.

*Primary Examiner*—Robert Gerstl
(74) *Attorney, Agent, or Firm*—McDermott, Will & Emery

(57) ABSTRACT

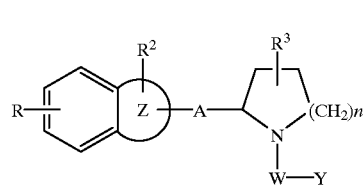

(I)

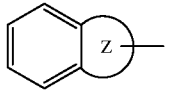

(a)

The present invention relates to a novel thrombin inhibitor which is effective even when orally administered. More specifically, the present invention relates to an aromatic amidine derivative represented by formula (I) and the salts thereof, which show potent selective inhibitory activity for thrombin in which (a), R, $R^1$, $R^2$, $R^3$, A, W, Y and n are defined as described in the specification.

14 Claims, No Drawings

AROMATIC AMIDINE DERIVATIVES USEFUL AS SELECTIVE THROMBIN INHIBITORS

TECHNICAL FIELD

The present invention relates a novel thrombin inhibitor which is effective even when orally administered. More specifically, the present invention relates to an aromatic amidine derivative represented by formula (I) and the salts thereof, which show potent selective inhibitory activity for thrombin:

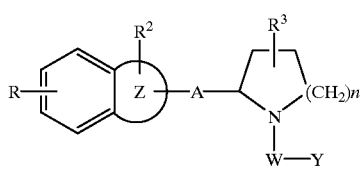

(I)

in which

R represents a group of formula

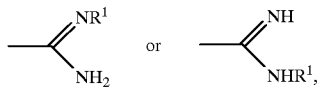

wherein $R^1$ represents hydrogen, hydroxy, alkyl, alkoxy, alkylcarbonyl, alkylcarbonyloxy, aralkoxycarbonyl, or a radical of formula (a).

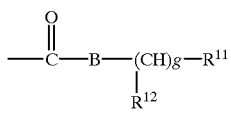

(a)

wherein

B represents oxygen or sulfur;

$R^{11}$ and $R^{12}$ independently of one another represent hydrogen, haloalkyl, alkylcarbonyloxy, dialkylamino, or substituted or unsubstituted 3- to 7-membered saturated or unsaturated heterocyclic or carbocyclic ring; and g denotes an integer of 0 to 3;

$R^2$ represents hydrogen, hydroxy, halogen, carboxy, aminocarbonyl, alkyl, alkoxy, hydroxyalkyl, aminoalkyl, alkylcarbonyl, alkylsulfonyl, carboxyalkyl, aminocarbonylalkyl, alkoxycarbonylalkyl, or substituted or unsubstituted arylsulfonyl;

$R^3$ represents hydrogen, halogen, alkyl, hydroxyalkyl, carboxyalkyl, alkoxycarbonylalkyl, alkoxycarbonyl, carboxy, amino, aminoalkyl, aminocarbonyl, aminocarbonylalkyl, or a radical of formula (b),

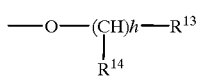

(b)

wherein $R^{13}$ and $R^{14}$ independently of one another represent hydrogen, alkyl, or substituted or unsubstituted 3- to 7-membered saturated or unsaturated heterocyclic or carbocyclic ring; and h denotes an integer of 0 to 3;

the group of formula

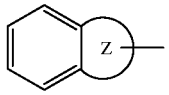

represents a radical selected from the group consisting of indolyl, benzofuranyl, benzothienyl, benzoimidazolyl, benzoxazolyl, benzothiazolyl, naphthyl, tetrahydronaphthyl, indanyl, dihydrobenzofuranyl and dihydrobenzothienyl;

A represents a saturated or unsaturated alkylene group having 2 to 4 carbon atoms, which may have 1 or 2 substituents selected from the group consisting of carboxy, alkyl, hydroxyalkyl, carboxyalkyl, alkylcarbonyl, alkoxycarbonyl and alkoxycarbonylalkyl;

W represents a group of formula (c), (d) or (e),

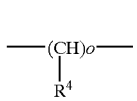

(c)

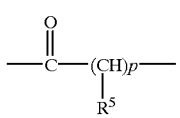

(d)

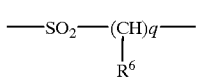

(e)

wherein o, p and q independently of one another denote an integer of 0 to 3, $R^4$, $R^5$ and $R^6$ independently of one another represent hydrogen, hydroxy, carboxy, alkoxycarbonyl, substituted or unsubstituted arylsulfonyl, or substituted or unsubstituted 3- to 7-membered saturated or unsaturated heterocyclic or carbocyclic ring, or represents a group of formula (f), (g) or (h),

(f)

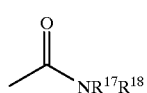

(g)

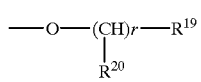

(h)

wherein $R^{15}$, $R^{16}$, $R^{17}$ and $R^{18}$ independently of one another represent hydrogen, alkyl, alkylsulfonyl, carboxyalkyl, alkylcarbonyl, aminocarbonylalkyl, alkoxycarbonylalkyl, substituted or unsubstituted arylsulfonyl, substituted or unsubstituted aralkyl, or substituted or unsubstituted 3- to 7-membered saturated or unsaturated heterocyclic or carbocyclic ring;

$R^{19}$ and $R^{20}$ independently of one another represent hydrogen, carboxy, aminocarbonyl or alkoxycarbonyl, or represents 3- to 7-membered saturated or unsaturated heterocyclic or carbocyclic ring which may be fused with one or more 3- to 7-membered saturated or unsaturated heterocyclic or carbocyclic rings; and r denotes an integer of 0 to 3;

Y represents hydrogen or a 3- to 7-membered saturated or unsaturated heterocyclic or carbocyclic ring which may be fused with one or more 3- to 7-membered saturated or unsaturated heterocyclic or carbocyclic rings and which may be substituted on any atom of the ring with a substituent selected from the group consisting of oxygen, halogen, nitro, alkyl, haloalkyl, hydroxyalkyl, alkylsulfonyl, substituted or unsubstituted arylsulfonyl, substituted or unsubstituted 3- to 7-membered saturated or unsaturated heterocyclic or carbocyclic ring, and a group of formula (i), (j) and (k),

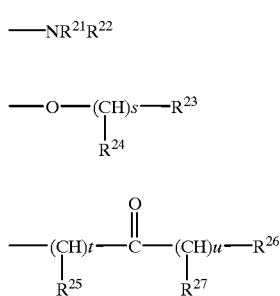

wherein $R^{21}$ and $R^{22}$ independently of one another represent hydrogen, alkyl, alkylsulfonyl, carboxyalkyl, alkylcarbonyl, alkoxycarbonylalkyl, or substituted or unsubstituted arylsulfonyl;

$R^{23}$ and $R^{24}$ independently of one another represent hydrogen, carboxy, aminocarbonyl, alkoxycarbonyl, or 3- to 7-membered saturated or unsaturated heterocyclic or carbocyclic ring which may be fused with one or more 3- to 7-membered saturated or unsaturated heterocyclic or carbocyclic rings;

$R^{25}$, $R^{26}$ and $R^{27}$ independently of one another represent hydrogen, hydroxy, thio, amino, carboxy, aminocarbonyl, alkoxy, alkoxycarbonyl, alkylamino, alkylsulfonylamino, alkenyl, alkoxycarbonylamino, cycloalkylamino, alkoxycarbonylalkylamino, substituted or unsubstituted arylsulfonylamino, or substituted or unsubstituted 3- to 7-membered saturated or unsaturated heterocyclic or carbocyclic ring;

s denotes an integer of 0 to 3;

t denotes an integer of 0 to 6; and u denotes an integer of 0 to 8;

n denotes an integer of 0 to 2, provided that when each of g, h, o, p, q, r, s, t and u denotes number of 3 or more, the corresponding alkylene chain may be straight or branched.

The present invention also relates to a process for preparation of the compound of formula (I), and a thrombin inhibitor composition containing the compound of formula (I) as an active component.

BACKGROUND ART

Thrombosis is a pathological process in which platelets aggregation or a fibrin clot occludes a blood vessel. Anticoagulants interfere with fibrin formation and are used for prophylaxis of thrombosis.

The blood coagulation system involves a number of zymogens (inactive enzymes) that are activated through a cascade of enzymatic reactions. The final step in coagulation is the formation of the fibrin clot from fibrinogen by a trypsin-like serine protease thrombin, which in turn is generated from prothrombin by the action of factor Xa. Accordingly, the blood coagulation enzyme thrombin plays a central role in hemostasis and thrombosis. Thrombin inhibitors are therefore expected to be effective anticoagulants by inhibition of platelets, fibrin formation and fibrin stabilization. It also activates factor V and factor VIII in a positive feed back reaction.

In recent years, numerous thrombin inhibitors have been developed as potential antithrombotic and anticoagulant agents, for example, tripeptide derivatives such as PPACK [D-Phe-Pro-Arg-$CH_2Cl$, Thromb. Res., 14, 969 (1979)], D-Phe-Pro-Arg, Boc-D-Phe-Pro-Arg, and D-MePhe-Pro-Arg [J. Med. Chem., 33, 1729 (1990)], DuP-714 [Ac-(D)-Phe-Pro-boroArg-OH, J. Biol. Chem., 265, 18289 (1990)], Efegatran [D-MePhe-Pro-Arg.$H_2SO_4$, Thromb. Haemost., 67, 325 (1992)], Inogatran [HOOC—$CH_2$—(R)Cha-Pic-Nag, where Cha: cyclohexylamine, Pic: pipecolic acid and Nag: noragmatine, WO 93/11152, Blood Coag. Fibrinol., 7, 69 (1996)] and CVS-1123 [($CH_3CH_2CH_2$)$_2$—CHCO—Asp($OCH_3$)-Pro-Arg, WO 93/15756] and piperidine amide derivatives such as Argatroban [U.S. Pat. No. 4,258,192, Thromb. Haemost., 18, 13 (1992)] and NAPAP [J. Biol. Chem., 266, 20085 (1991)]. But, they are not necessarily sufficient for practical use in view of oral bioavailability, inhibition selectivity for thrombin over other serine proteases, stability, duration of action and toxicity at the therapeutic dosages.

In view of the above, the present inventors have conducted intensive studies to develop potent thrombin inhibitors which are orally bioavailable, selective in inhibition of thrombin over other serine proteases and sufficient for practical use. As a result of such efforts, we have found that the compound of formula (I) exhibits excellent thrombin inhibitory activity even when orally administered and has a high selectivity for thrombin in comparison to trypsin, and have thereby completed the present invention.

DISCLOSURE OF THE INVENTION

The present invention relates to an aromatic amidine derivative of formula (I), as defined above, and pharmaceutically acceptable salts thereof.

In addition, the present invention relates to a process for preparation of the compound of formula (I).

The present invention further relates to a thrombin inhibitor composition containing the compound of formula (I) or its pharmaceutically acceptable salts as an active component.

BEST MODE FOR CARRYING OUT THE INVENTION

The compound according to the present invention is represented by formula (I) as defined above.

Preferred compound of formula (I) according to the present invention includes those, in which R represent a group of formula

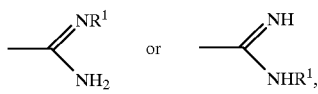 or 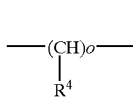, wherein

R¹ represents hydrogen, hydroxy, $C_1$–$C_4$ alkyl, $C_1$–$C_4$ alkoxy, $C_2$–$C_4$ alkylcarbonyl $C_2$–$C_4$ alkylcarbonyloxy, or a radical of formula (a),

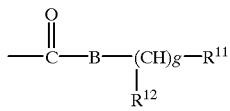

(a)

wherein

B represents oxygen or sulfur,

R¹¹ and R¹² independently of one another represents hydrogen, $C_1$–$C_4$ haloalkyl, $C_2$–$C_4$ alkylcarbonyloxy, $C_2$–$C_6$ dialkylamino, or substituted or unsubstituted 6-membered carbocyclic ring, and g denotes an integer of 0 to 3;

R² represents hydrogen, halogen, carboxy, $C_1$–$C_4$ alkyl, $C_1$–$C_4$ alkoxy, $C_1$–$C_4$ hydroxyalkyl, $C_1$–$C_4$ aminoalkyl, $C_2$–$C_4$ alkylcarbonyl, $C_1$–$C_4$ alkylsulfonyl, $C_2$–$C_4$ carboxyalkyl, $C_2$–$C_4$ aminocarbonylalkyl or $C_3$–$C_7$ alkoxycarbonylalkyl;

R₃ represents hydrogen, halogen, $C_1$–$C_4$ alkyl, $C_1$–$C_4$ hydroxyalkyl, $C_2$–$C_4$ carboxyalkyl, $C_3$–$C_7$ alkoxycarbonylalkyl, or a radica of formula (b),

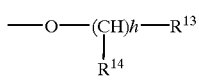

(b)

wherein

R¹³ and R¹⁴ independently of one another represent hydrogen or phenyl, and h denotes an integer of 0 to 1;

the group of formula

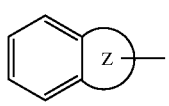

represents a radical selected from the group consisting of indolyl, benzofuranyl, benzothienyl, benzoimidazolyl and naphthyl;

A represents saturated or unsaturated alkylene group having 2 to 4 carbon atoms, which may have 1 to 2 substituents selected from the group consisting of carboxy, $C_1$–$C_4$ hydroxyalkyl and $C_2$–$C_4$ alkoxycarbonyl;

W represents a group of formula (c), (d) or (e),

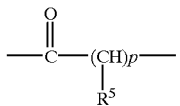

(c)

(d)

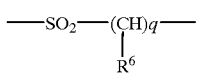

(e)

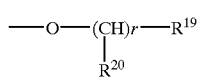

wherein o, p and q independently of one another denote an integer of 0 to 3,

R⁴, R⁵ and R⁶ independently of one another represent hydrogen, hydroxy, carboxy, $C_2$–$C_4$ alkoxycarbonyl, phenylsulfonyl, or substituted or unsubstituted 3- to 5-membered saturated or unsaturated heterocyclic or carbocyclic ring, or represents a group of formula (f), (g) or (h),

(f)

(g)

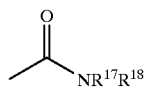

(h)

—O—(CH)r—R¹⁹
       |
       R²⁰ wherein

R¹⁵, R¹⁶, R¹⁷ and R¹⁸ independently of one another represent hydrogen, $C_1$–$C_4$ alkyl, $C_1$–$C_4$ alkylsulfonyl, $C_2$–$C_4$ carboxyalkyl, $C_2$–$C_4$ alkylcarbonyl, $C_2$–$C_4$ aminocarbonylalkyl, $C_3$–$C_7$ alkoxycarbonylalkyl, or substituted or unsubstituted 3- to 5-membered saturated or unsaturated heterocyclic or carbocyclic ring, R¹⁹ and R²⁰ independently of one another represent hydrogen, carboxy, aminocarbonyl or $C_2$–$C_4$ alkoxycarbonyl, or represents 5- to 6-membered saturated or unsaturated heterocyclic or carbocyclic ring which may be fused with other one or more 5- to 6-membered saturated or unsaturated heterocyclic or carbocyclic ring, and r denotes an integer of 0 to 3;

Y represents hydrogen, or represents 5- to 6-membered saturated or unsaturated heterocyclic or carbocyclic ring which may be fused with other one or more 5- to 6-membered saturated or unsaturated heterocyclic or carbocyclic ring and which can be substituted on any atom of the ring with substituent selected from the group consisting of oxygen, halogen, nitro, $C_1$–$C_4$ alkyl, $C_1$–$C_4$ haloalkyl, $C_1$–$C_4$ hydroxyalkyl, $C_1$–$C_4$ alkylsulfonyl, phenylsulfonyl, substituted or unsubstituted 3- to 5-membered saturated or unsaturated heterocyclic or carbocyclic ring, and a group of formula (i), (j) and (k), —NR²¹R²² (i)

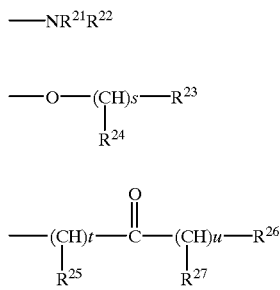
(j)

(k)

wherein
R²¹ and R²² independently of one another represent hydrogen, $C_1$–$C_4$ alkyl, $C_1$–$C_4$ alkylsulfonyl, $C_2$–$C_5$ carboxyalkyl, $C_2$–$C_5$ alkylcarbonyl, $C_3$–$C_7$ alkoxycarbonylalkyl or phenylsulfonyl,
R²³ and R²⁴ independently of one another represent hydrogen, carboxy, aminocarbonyl, $C_2$–$C_4$ alkoxycarbonyl, or 3- to 5-membered saturated or unsaturated heterocyclic or carbocyclic ring which may be fused with other one or more 3- to 5-membered saturated or unsaturated heterocyclic or carbocyclic ring,
R²⁵, R²⁶ and R²⁷ independently of one another represents hydrogen hydroxy, thio, amino, carboxy, aminocarbonyl, $C_1$–$C_4$ alkoxy, $C_2$–$C_4$ alkoxycarbonyl, $C_1$–$C_4$ alkylamino, $C_1$–$C_4$ alkylsulfonylamino, $C_2$–$C_5$ alkenyl, $C_2$–$C_4$ alkoxycarbonylamino, $C_3$–$C_6$ alkoxycarbonylalkylamino, $C_3$–$C_6$ cycloalkylamino, phenylsulfonylamino, or substituted or unsubstituted 3- to 5-membered saturated or unsaturated heterocyclic or carbocyclic ring,
s denotes an integer of 0 to 3,
t denotes an integer of 0 to 6, and
u denotes an integer of 0 to 8, and
n denotes an integer of 0 to 2,
provided that when each of g, h, o, p, q, r, s, t and u denotes number of 3 or more, the corresponding alkylene chain may be straight or branched.

Typical examples of the compound of formula (I) which can be provided by the present invention are listed in the following Table 1.

TABLE 1
| compound No. | 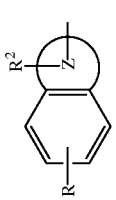 | A | R³ | n | W-Y |
|---|---|---|---|---|---|
| 1 | 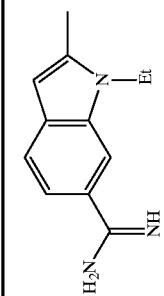 | CH₂CH₂ | H | 1 | 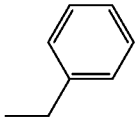 |
| 2 | 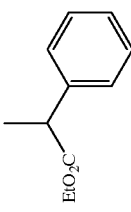 | CH₂CH₂ | H | 1 | 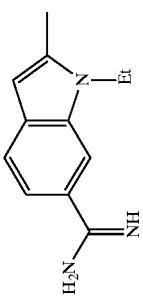 |
| 3 | 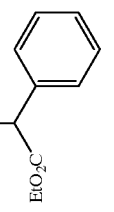 | CH₂CH₂ | H | 1 | 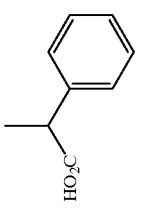 |
| 4 | 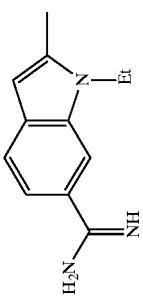 | CH₂CH₂ | H | 1 | 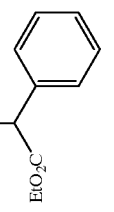 |
| 5 | 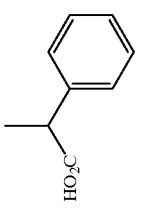 | CH₂CH₂ | H | 1 | 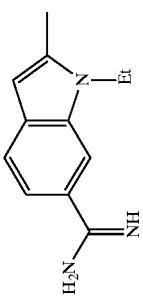 |

TABLE 1-continued

| compound No. | R²–N⟨⟩–R | A | R³ | n | W-Y |
|---|---|---|---|---|---|
| 6 | 2-methyl-1-ethyl-indol-6-yl-C(=NH)NH₂ | CH₂CH₂ | H | 1 | benzo[1,3]dioxol-5-yl-ethyl |
| 7 | 2-methyl-1-ethyl-indol-6-yl-C(=NH)NH₂ | CH₂CH₂ | H | 1 | 3-ethyl-2-(methoxycarbonyl)benzothiophene |
| 8 | 2-methyl-1-ethyl-indol-6-yl-C(=NH)NH₂ | CH₂CH₂ | H | 1 | 3-ethyl-2-(carbamoyl)benzothiophene |
| 9 | 2-methyl-1-ethyl-indol-6-yl-C(=NH)NH₂ | CH₂CH₂ | H | 1 | 3-ethyl-2-(carbamoyl)benzothiophene |
| 10 | 2-methyl-1-ethyl-indol-6-yl-C(=NH)NH₂ | | | | 3-ethyl-2-(N-methylcarbamoyl)benzothiophene |

TABLE 1-continued
| compound No. | 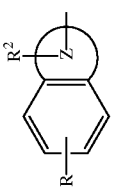 | A | R³ | n | W-Y |
|---|---|---|---|---|---|
| 11 | 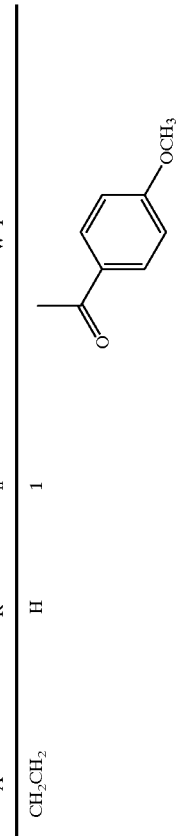 | CH₂CH₂ | H | 1 | 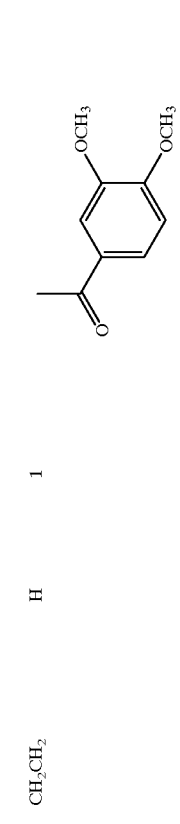 |
| 12 | | CH₂CH₂ | H | 1 | |
| 13 | | CH₂CH₂ | H | 1 | |
| 14 | | CH₂CH₂ | H | 1 | |
| 15 | | CH₂CH₂ | H | 1 | |

TABLE 1-continued
| compound No. | 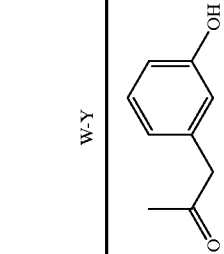 | A | R³ | n | W-Y |
|---|---|---|---|---|---|
| 16 | 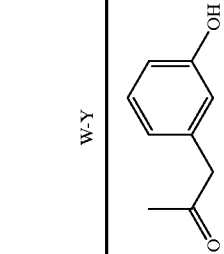 | CH₂CH₂ | H | 1 | 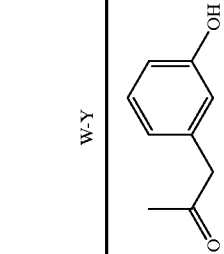 |
| 17 | 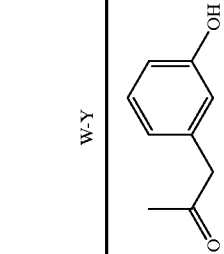 | CH₂CH₂ | H | 1 | 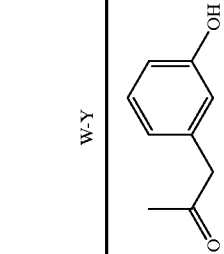 |
| 18 | 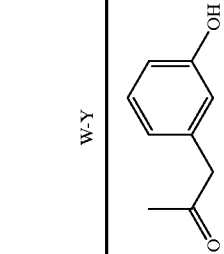 | CH₂CH₂ | H | 1 | 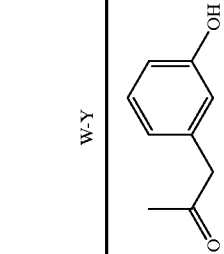 |
| 19 | 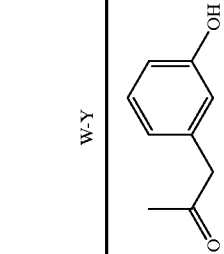 | CH₂CH₂ | H | 1 | 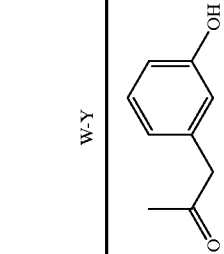 |
| 20 | 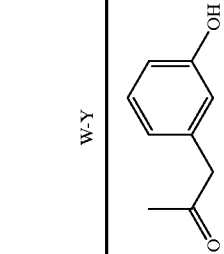 | CH₂CH₂ | H | 1 | 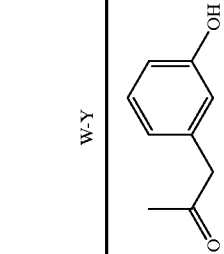 |

TABLE 1-continued

| compound No. | (R²,R structure) | A | R³ | n | W-Y |
|---|---|---|---|---|---|
| 21 | 2-methyl-1-ethyl-6-amidino-indole | CH₂CH₂ | H | 1 | 2-nitrophenyl-CH₂C(O)- |
| 22 | 2-methyl-1-ethyl-6-amidino-indole | CH₂CH₂ | H | 1 | 2-(NHSO₂CH₃)phenyl-CH₂C(O)- |
| 23 | 2-methyl-1-ethyl-6-amidino-indole | CH₂CH₂ | H | 1 | 2-(CO₂Et)phenyl-CH₂C(O)- |
| 24 | 2-methyl-1-ethyl-6-amidino-indole | CH₂CH₂ | H | 1 | 2-(CO₂H)phenyl-CH₂C(O)- |
| 25 | 2-methyl-1-ethyl-6-amidino-indole | CH₂CH₂ | H | 1 | 4-hydroxy-2-(CO₂H)phenyl-CH₂C(O)- |

TABLE 1-continued
| compound No. | (R-, R²-N ring) | A | R³ | n | W-Y |
|---|---|---|---|---|---|
| 26 | 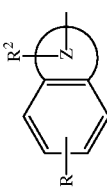 | CH₂CH₂ | H | 1 | 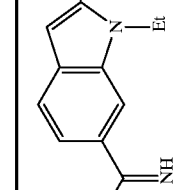 |
| 27 | 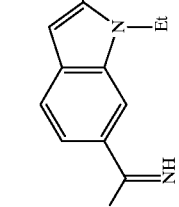 | CH₂CH₂ | H | 1 | 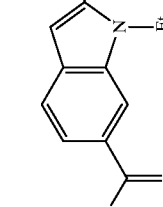 |
| 28 | 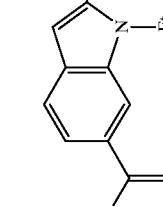 | CH₂CH₂ | H | 1 | 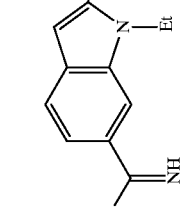 |
| 29 | | CH₂CH₂ | H | 2 | |
| 30 | | CH₂CH₂ | H | 1 |  |

TABLE 1-continued
| compound No. | 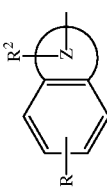 | A | R³ | n | W-Y |
|---|---|---|---|---|---|
| 31 | 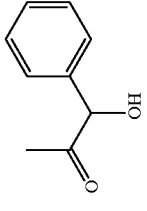 | CH₂CH₂ | H | 1 |  |
| 32 | 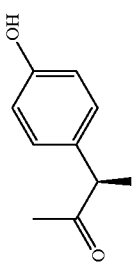 | CH₂CH₂ | H | 1 | 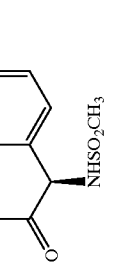 |
| 33 | 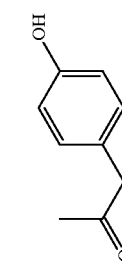 | CH₂CH₂ | H | 1 | 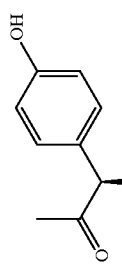 |
| 34 | 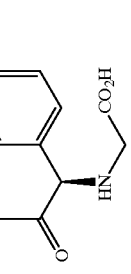 | CH₂CH₂ | H | 1 | 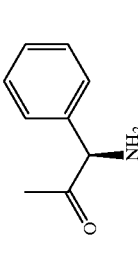 |
| 35 | 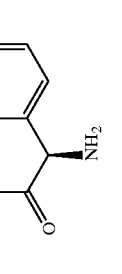 | CH₂CH₂ | H | 1 | |

TABLE 1-continued
| compound No. | 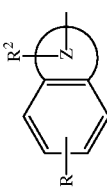 | A | $R^3$ | n | W-Y |
|---|---|---|---|---|---|
| 36 | 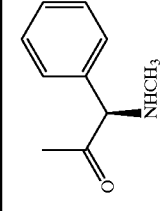 | $CH_2CH_2$ | H | 1 | |
| 37 | | $CH_2CH_2$ | H | 1 | |
| 38 | | $CH_2CH_2$ | H | 1 | |
| 39 | | $CH_2CH_2$ | H | 1 | |
| 40 | | $CH_2CH_2$ | H | 1 | |

TABLE 1-continued
| compound No. | 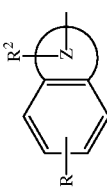 | A | R³ | n | W-Y |
|---|---|---|---|---|---|
| 41 | 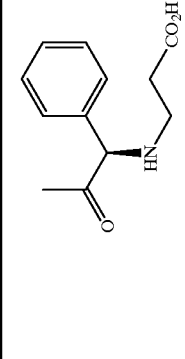 | CH₂CH₂ | H | 1 | 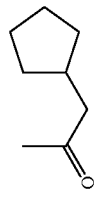 |
| 42 | 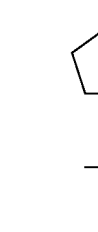 | CH₂CH₂ | H | 1 | 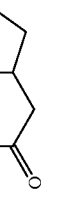 |
| 43 |  | CH₂CH₂ | H | 1 | 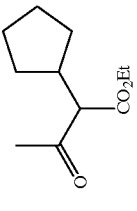 |
| 44 |  | CH₂CH₂ | H | 1 | 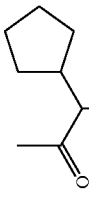 |
| 45 | 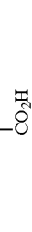 | CH₂CH₂ | H | 1 |  |

TABLE 1-continued

| compound No. | 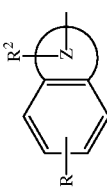 | A | R³ | n | W-Y |
|---|---|---|---|---|---|
| 46 | 2-methyl-1-ethyl-indole-6-carboxamidine | CH₂CH₂ | H | 1 | cyclohexyl-CH₂-C(=O)-CH₃ |
| 47 | 2-methyl-1-ethyl-indole-6-carboxamidine | CH₂CH₂ | H | 1 | cyclohexyl-CH(NH₂)-C(=O)-CH₃ |
| 48 | 2-methyl-1-ethyl-indole-6-carboxamidine | CH₂CH₂ | H | 1 | cyclohexyl-CH(NHCH₂CO₂H)-C(=O)-CH₃ |
| 49 | 2-methyl-1-ethyl-indole-6-carboxamidine | CH₂CH₂ | H | 1 | cyclohexyl-CH(NHSO₂CH₃)-C(=O)-CH₃ |
| 50 | 2-methyl-1-ethyl-indole-6-carboxamidine | CH₂CH₂ | H | 1 | phenyl-CH₂-CH₂-C(=O)-CH₃ |

TABLE 1-continued

| compound No. | (R²-N ring with R) | A | R³ | n | W-Y |
|---|---|---|---|---|---|
| 51 | 2-methyl-1-ethyl-6-amidino-indole | CH₂CH₂ | H | 1 | -CH(NH₂)-C(=O)-CH₂-Ph |
| 52 | 2-methyl-1-ethyl-6-amidino-indole | CH₂CH₂ | H | 1 | -CH(NHCH₃)-C(=O)-CH₂-Ph |
| 53 | 2-methyl-1-ethyl-6-amidino-indole | CH₂CH₂ | H | 1 | -CH(NHCOCH₃)-C(=O)-CH₂-Ph |
| 54 | 2-methyl-1-ethyl-6-amidino-indole | CH₂CH₂ | H | 1 | -CH(NHSO₂CH₃)-C(=O)-CH₂-Ph |
| 55 | 2-methyl-1-ethyl-6-amidino-indole | CH₂CH₂ |  | 1 | -CH(NHCH₂CO₂H)-C(=O)-CH₂-Ph |

TABLE 1-continued
| compound No. | 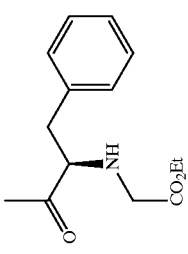 | A | R³ | n | W-Y |
|---|---|---|---|---|---|
| 56 | 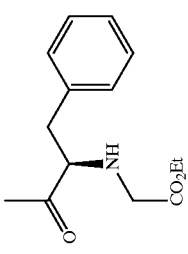 | CH₂CH₂ | H | 1 |  |
| 57 |  | CH₂CH₂ | H | 1 | 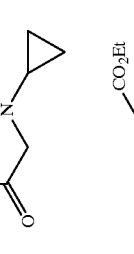 |
| 58 | 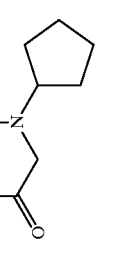 | CH₂CH₂ | H | 1 | (SO₂CH₃, N-cyclopropyl, propan-2-one) |
| 59 | (same indole-amidine) | CH₂CH₂ | H | 1 | (CO₂Et, N-cyclopropyl, propan-2-one) |
| 60 | (same indole-amidine) | CH₂CH₂ | H | 1 | (CO₂Et, N-cyclopentyl, propan-2-one) |

TABLE 1-continued

| compound No. | (R²-N / R- ring) | A | R³ | n | W-Y |
|---|---|---|---|---|---|
| 61 | 2-methyl-1-ethyl-indole-6-carboxamidine | CH₂CH₂ | H | 1 | N-benzyl, N-(CH₂CO₂Et), CH₂C(=O)CH₃ |
| 62 | 2-methyl-1-ethyl-indole-6-carboxamidine | CH₂CH₂ | H | 1 | N-cyclopropyl, N-(CH₂CO₂Et), CH₂C(=O)CH₃ |
| 63 | 2-methyl-1-ethyl-indole-6-carboxamidine | CH₂CH₂ | H | 1 | N-cyclopropyl, N-(CH₂CO₂H), CH₂C(=O)CH₃ |
| 64 | 2-methyl-1-ethyl-indole-6-carboxamidine | CH₂CH₂ | H | 1 | N-cyclopropyl, N-(CH₂CO₂Et), CH(CH₃)C(=O)CH₃ |
| 65 | 2-methyl-1-ethyl-indole-6-carboxamidine | CH₂CH₂ | H | 1 | N-cyclopropyl, N-(CH₂CO₂H), CH(CH₃)C(=O)CH₃ |

TABLE 1-continued

| compound No. | R²-N ring with R | A | R³ | n | W-Y |
|---|---|---|---|---|---|
| 66 | 2-methyl-1-ethyl-indole-6-carboxamidine | CH₂CH₂ | H | 1 | (S)-CH₃-CH(NH-)-C(=O)-CH₃ with CH₂CO₂Et |
| 67 | 2-methyl-1-ethyl-indole-6-carboxamidine | CH₂CH₂ | H | 1 | (S)-CH₃-CH(NH-)-C(=O)-CH₃ with CH₂CO₂H |
| 68 | 2-methyl-1-ethyl-indole-6-carboxamidine | CH₂CH₂ | H | 1 | (S)-CH(CH₃)-CH(NH-)-C(=O)-CH₃ with CH₂CO₂H |
| 69 | 2-methyl-1-ethyl-indole-6-carboxamidine | CH₂CH₂ | H | 1 | (S)-HOCH₂-CH(NH-)-C(=O)-CH₃ with CH₂CO₂Et |
| 70 | 2-methyl-1-ethyl-indole-6-carboxamidine | CH₂CH₂ | H | 1 | HOCH₂-CH(N(cyclopropyl)-)-C(=O)-CH₃ with CH₂CO₂H |

TABLE 1-continued

| compound No. | (R-Ar-N-R²) | A | R³ | n | W-Y |
|---|---|---|---|---|---|
| 71 | 2-methyl-1-ethyl-6-amidino-indole | CH₂CH₂ | H | 1 | CH₂OH, CH(N(SO₂CH₃)(cyclopropyl)), C(O)CH₃ |
| 72 | 2-methyl-1-ethyl-6-amidino-indole | CH₂CH₂ | H | 1 | CH₂CO₂Et, CH(NH-cyclopropyl), C(O)CH₃ |
| 73 | 2-methyl-1-ethyl-6-amidino-indole | CH₂CH₂ | H | 1 | CH₂CO₂H, CH(NH-cyclopropyl), C(O)CH₃ |
| 74 | 2-methyl-1-ethyl-6-amidino-indole | CH₂CH₂ | H | 1 | CH₂CO₂H, CH(N(SO₂CH₃)(cyclopropyl)), C(O)CH₃ |

TABLE 1-continued
| compound No. | 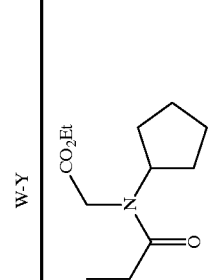 | A | R³ | n | W-Y |
|---|---|---|---|---|---|
| 75 | | $CH_2CH_2$ | H | 1 | |
| 76 | | $CH_2CH_2$ | H | 1 | |
| 77 | | $CH_2CH_2$ | H | 1 | |
| 78 | | $CH_2CH_2$ | H | 2 | |
| 79 | | $CH_2CH_2$ | H | 1 | |

TABLE 1-continued

| compound No. | ![structure] | A | R³ | n | W-Y |
|---|---|---|---|---|---|
| 80 | 2-methyl-1-ethyl-indole-6-carboxamidine | CH₂CH₂ | H | 2 | naphthalen-1-ylsulfonyl (methyl) |
| 81 | 2-methyl-1-ethyl-indole-6-carboxamidine | CH₂CH₂ | H | 1 | C(O)CH₃ |
| 82 | 2-methyl-1-ethyl-indole-6-carboxamidine | CH₂CH₂ | H | 1 | CH₂C(O)CH₂S(O)₂Ph |
| 83 | 2-methyl-1-ethyl-indole-6-carboxamidine | CH₂CH₂ | H | 1 | C(O)-(2-pyrrolidinyl), NH free |
| 84 | 2-methyl-1-ethyl-indole-6-carboxamidine | CH₂CH₂ | H | 1 | C(O)-(2-pyrrolidinyl)-N-CH₂CO₂Et |

TABLE 1-continued

| compound No. | [indole structure] | A | R³ | n | W-Y |
|---|---|---|---|---|---|
| 85 | 2-methyl-1-ethyl-6-amidino-indole | CH₂CH₂ | H | 0 | 2-acetyl-pyrrolidine-N-CH₂CO₂Et |
| 86 | 2-methyl-1-ethyl-6-amidino-indole | CH₂CH₂ | H | 1 | 2-acetyl-pyrrolidine-N-CH₂CO₂Et |
| 87 | 2-methyl-1-ethyl-6-amidino-indole | CH₂CH₂ | H | 2 | 2-acetyl-pyrrolidine-N-CH₂CO₂Et |
| 88 | 2-methyl-1-ethyl-6-amidino-indole | CH₂CH₂ | H | 1 | 2-acetyl-pyrrolidine-N-CH₂CO₂H |

TABLE 1-continued

| compound No. | R²-N / R-⟨⟩ | A | R³ | n | W-Y |
|---|---|---|---|---|---|
| 89 | 2-methyl-1-ethyl-indole-6-C(NH)NH₂ | CH₂CH₂ | H | 2 | 2-acetyl-pyrrolidine-N-CH₂-CO₂H |
| 90 | 2-methyl-1-ethyl-indole-6-C(NH)NH₂ | CH₂CH₂CH₂ | H | 1 | 2-acetyl-pyrrolidine-N-CH₂-CO₂H |
| 91 | 2-methyl-1-ethyl-indole-6-C(NH)NH₂ | —CH(CH₂CO₂Et)— | H | 1 | 2-acetyl-pyrrolidine-N-CH₂-CO₂Et |
| 92 | 2-methyl-1-ethyl-indole-6-C(NH)NH₂ | —CH(CH₂CO₂H)— | H | 1 | 2-acetyl-pyrrolidine-N-CH₂-CO₂H |

TABLE 1-continued

| compound No. | $\underset{R}{\overset{R^2}{\bigcirc}}\!\!\!\!\!\!\!\!\!\!\!\!\!\!\!\!\!\!\!\!\!\!\!\!\!\!\!\!\!\!$ | A | R³ | n | W-Y |
|---|---|---|---|---|---|
| 93 | 2-methyl-1-ethyl-6-amidino-indole | —CH₂CH₂—CO₂Et | H | 1 | 2-acetyl-pyrrolidine-N-CH₂CO₂Et |
| 94 | 2-methyl-1-ethyl-6-amidino-indole | —CH₂CH₂—CO₂H | H | 1 | 2-acetyl-pyrrolidine-N-CH₂CO₂H |
| 95 | 2-methyl-1-ethyl-6-amidino-indole | —CH₂—CO₂H | H | 1 | 2-acetyl-pyrrolidine-N-CH₂CO₂H |
| 96 | 2-methyl-1-ethyl-6-amidino-indole | —CH₂—CO₂H | H | 1 | 2-acetyl-pyrrolidine-N-CH₂CO₂H |

TABLE 1-continued

| compound No. | (R²,R structure) | A | R³ | n | W-Y |
|---|---|---|---|---|---|
| 97 | 6-amidino-2-methyl-1-ethyl-indole | CH₂CH₂ | 4(S)—CH₃ | 1 | (S)-2-acetyl-pyrrolidine-N-CH₂CO₂Et |
| 98 | 6-amidino-2-methyl-1-ethyl-indole | CH₂CH₂ | 4(S)—CH₃ | 1 | (S)-2-acetyl-pyrrolidine-N-CH₂CO₂H |
| 99 | 6-amidino-2-methyl-1-ethyl-indole | CH₂CH₂ | 4(S)—CH₃ | 1 | (S)-2-acetyl-pyrrolidine-N-CH₂CO₂Et |
| 100 | 6-amidino-2-methyl-1-ethyl-indole | CH₂CH₂ | 4(S)—OPh | 1 | (S)-2-acetyl-pyrrolidine-N-CH₂CO₂H |

TABLE 1-continued
| compound No. | 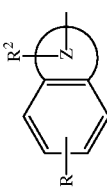 | A | R³ | n | W-Y |
|---|---|---|---|---|---|
| 101 | 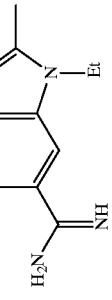 | CH₂CH₂ | 4(S) —OCH₂Ph | 1 | 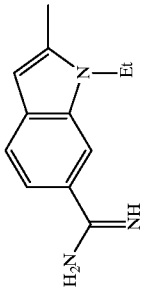 |
| 102 | | CH₂CH₂ | 4 —OH | 1 | |
| 103 | | CH₂CH₂ | 4 —F | 1 | |
| 104 | | CH₂CH₂ | 4 —CH₂CO₂Et | 1 | |

TABLE 1-continued

| compound No. | R²—N⟨⟩—R | A | R³ | n | W-Y |
|---|---|---|---|---|---|
| 105 | 2-methyl-1-ethyl-6-amidinoindole | CH₂CH₂ | 4—CH₂CO₂H | 1 | 2-acetyl-pyrrolidine-N-CH₂CO₂H |
| 106 | 2-methyl-1-ethyl-6-amidinoindole | CH₂CH₂ | 4—CH₂CH₂OH | 1 | 2-acetyl-pyrrolidine-N-CH₂CO₂H |
| 107 | 2-methyl-1-ethyl-6-amidinoindole | CH₂CH₂ | 4—CH₂CH₂CO₂H | 1 | 2-acetyl-pyrrolidine-N-CH₂CO₂H |
| 108 | 2-methyl-1-ethyl-6-amidinoindole | CH₂CH₂ | 4—CH₂CH₂CH₂OH | 1 | 2-acetyl-pyrrolidine-N-CH₂CO₂H |

TABLE 1-continued

| compound No. | (R²,R ring) | A | R³ | n | W-Y |
|---|---|---|---|---|---|
| 109 | 2-methyl-1-Et-indole-6-C(=NH)NH₂ | CH₂CH₂ | H | 1 | 2-acetyl-pyrrolidine-N-CH(CH₃)-CO₂Et |
| 110 | 2-methyl-1-Et-indole-6-C(=NH)NH₂ | CH₂CH₂ | H | 1 | 2-acetyl-pyrrolidine-N-CH(C₂H₅)-CO₂Et |
| 111 | 2-methyl-1-Et-indole-6-C(=NH)NH₂ | CH₂CH₂ | H | 1 | 2-acetyl-pyrrolidine-N-CH(n-Bu)-CO₂Et |
| 112 | 2-methyl-1-Et-indole-6-C(=NH)NH₂ | CH₂CH₂ | H | 1 | 2-acetyl-pyrrolidine-N-CH(Ph)-CO₂Et |

TABLE 1-continued

| compound No. | [R-N(R²) indole core] | A | R³ | n | W-Y |
|---|---|---|---|---|---|
| 113 | 2-methyl-1-ethyl-6-amidino-indole | CH₂CH₂ | H | 1 | 2-acetylpyrrolidin-1-yl-[(3-bromo-4-methoxyphenyl)(ethoxycarbonyl)methyl] |
| 114 | 2-methyl-1-ethyl-6-amidino-indole | CH₂CH₂ | H | 1 | 2-acetylpyrrolidin-1-yl-CH₂-CONH₂ |
| 115 | 2-methyl-1-ethyl-6-amidino-indole | CH₂CH₂ | H | 1 | 2-acetylpyrrolidin-1-yl-CH₂-C(O)NH-cyclopropyl |

TABLE 1-continued

| compound No. | (R²-N ring with R) | A | R³ | n | W-Y |
|---|---|---|---|---|---|
| 116 | 2-methyl-1-ethyl-indole-6-carboxamidine | CH₂CH₂ | H | 1 | 2-acetylpyrrolidin-1-yl-CH₂-C(O)-NH-CH(CH₃)-CO₂Et |
| 117 | 2-methyl-1-ethyl-indole-6-carboxamidine | CH₂CH₂ | H | 1 | 2-acetylpyrrolidin-1-yl-CH(CONH₂)-CH₂-CH₂-OH |
| 118 | 2-methyl-1-ethyl-indole-6-carboxamidine | CH₂CH₂ | H | 1 | 2-acetylpyrrolidin-1-yl-CH(CO₂H)-CH₂-CH₂-OH |
| 119 | 2-methyl-1-ethyl-indole-6-carboxamidine | CH₂CH₂ | H | 1 | 2-acetylpyrrolidin-1-yl-CH(CO₂Et)-CH₂-CH₂-OCH₃ |

TABLE 1-continued
| compound No. | 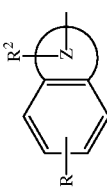 | A | R³ | n | W-Y |
|---|---|---|---|---|---|
| 120 | 2-methyl-1-ethyl-6-amidino-indole | CH₂CH₂ | H | 1 | pyrrolidinyl-acetyl, CH(CH₂OH)CO₂H |
| 121 | 2-methyl-1-ethyl-6-amidino-indole | CH₂CH₂ | H | 1 | pyrrolidinyl-acetyl, CH(CH₂NH₂)CO₂H |
| 122 | 2-methyl-1-ethyl-6-amidino-indole | CH₂CH₂ | H | 1 | pyrrolidinyl-acetyl, CH(CH₂NHSO₂CH₃)CO₂H |
| 123 | 2-methyl-1-ethyl-6-amidino-indole | CH₂CH₂ | H | 1 | pyrrolidinyl-acetyl, CH(CH₂CO₂H)CO₂H |

TABLE 1-continued

| compound No. | (R²/R structure) | A | R³ | n | W-Y |
|---|---|---|---|---|---|
| 124 | 2-methyl-1-ethyl-indole-6-carboxamidine | CH₂CH₂ | H | 1 | 2-acetyl-pyrrolidinyl-N-CH(CO₂H)CH₂CONH₂ |
| 125 | 2-methyl-1-ethyl-indole-6-carboxamidine | CH₂CH₂ | H | 1 | 2-acetyl-pyrrolidinyl-N-(tetrahydrofuran-2-one-3-yl) |
| 126 | 2-methyl-1-ethyl-indole-6-carboxamidine | CH₂CH₂ | H | 1 | 2-acetyl-pyrrolidinyl-N-(CH₂)₃CH(CO₂Et) |
| 127 | 2-methyl-1-ethyl-indole-6-carboxamidine | CH₂CH₂ | H | 1 | 2-acetyl-pyrrolidinyl-N-(CH₂)₃CH(CO₂H) |

TABLE 1-continued
| compound No. | 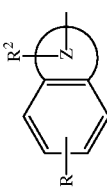 | A | R³ | n | W-Y |
|---|---|---|---|---|---|
| 128 | 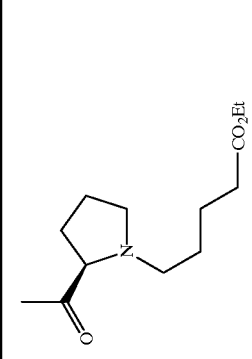 | CH₂CH₂ | H | 1 | (pyrrolidinyl-acetyl group with N-(CH₂)₄-CO₂Et) |
| 129 | 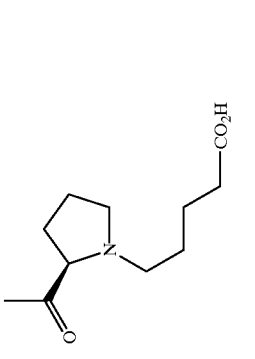 | CH₂CH₂ | H | 1 | (pyrrolidinyl-acetyl group with N-(CH₂)₄-CO₂H) |
| 130 | 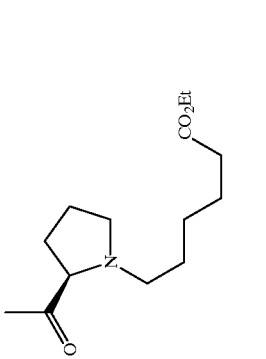 | CH₂CH₂ | H | 1 | (pyrrolidinyl-acetyl group with N-(CH₂)₅-CO₂Et) |

TABLE 1-continued

| compound No. | R²-N / R- ring | A | R³ | n | W-Y |
|---|---|---|---|---|---|
| 131 | 2-methyl-1-ethyl-indole-6-carboxamidine | CH₂CH₂ | H | 1 | 2-acetyl-pyrrolidine N-(CH₂)₅-CO₂H |
| 132 | 2-methyl-1-ethyl-indole-6-carboxamidine | CH₂CH₂ | H | 1 | 2-acetyl-pyrrolidine N-CH(CH₂CH₂OH)(CH₂CH₂CO₂H) |
| 133 | 2-methyl-1-ethyl-indole-6-carboxamidine | CH₂CH₂ | H | 1 | 2-acetyl-pyrrolidine N-CH₂CH₂CH(CH₂OH)(CO₂H) |

TABLE 1-continued
| compound No. | 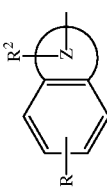 | A | R³ | n | W-Y |
|---|---|---|---|---|---|
| 134 | 2-methyl-1-ethyl-6-amidino-indole | CH₂CH₂ | H | 1 | pyrrolidine with 2-acetyl and N-CH₂CH(CH₂CO₂H)CH₂CH₂OH |
| 135 | 2-methyl-1-ethyl-6-amidino-indole | CH₂CH₂ | H | 1 | 4-methoxy-2-acetyl-pyrrolidine-N-CH₂CO₂Et |
| 136 | 2-methyl-1-ethyl-6-amidino-indole | CH₂CH₂ | H | 2 | 4-methoxy-2-acetyl-pyrrolidine-N-CH₂CO₂Et |
| 137 | 2-methyl-1-ethyl-6-amidino-indole | CH₂CH₂ | H | 2 | 4-phenoxy-2-acetyl-pyrrolidine-N-CH₂CO₂H |

TABLE 1-continued
| compound No. | 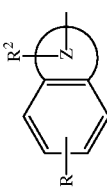 | A | R³ | n | W-Y |
|---|---|---|---|---|---|
| 138 | | CH₂CH₂ | H | 2 | |
| 139 | | CH₂CH₂ | H | 2 | |
| 140 | | CH₂CH₂ | H | 1 | |
| 141 | | CH₂CH₂ | H | 1 | |

TABLE 1-continued

| compound No. | [R²-N ring with R] | A | R³ | n | W-Y |
|---|---|---|---|---|---|
| 142 | 2-methyl-1-ethyl-indole-6-carboxamidine | CH₂CH₂ | H | 1 | 2-acetylpyrrolidine-N-CO-CH₂-NHCH₃ |
| 143 | 2-methyl-1-ethyl-indole-6-carboxamidine | CH₂CH₂ | H | 1 | 2-acetylpyrrolidine-N-CO-CH(NH₂)-CH₃ |
| 144 | 2-methyl-1-ethyl-indole-6-carboxamidine | CH₂CH₂ | H | 1 | 2-acetylpyrrolidine-N-CO-CH(NH₂)-CH₂-CH₃ |

TABLE 1-continued
| compound No. | 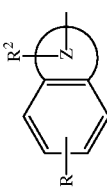 | A | R³ | n | W-Y |
|---|---|---|---|---|---|
| 145 | 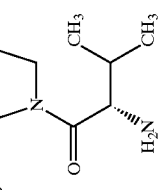 | CH₂CH₂ | H | 1 | |
| 146 | 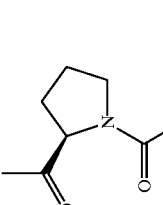 | CH₂CH₂ | H | 1 | |
| 147 | 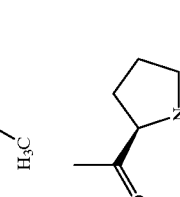 | CH₂CH₂ | H | 1 | |

TABLE 1-continued

| compound No. | [ring structure] | A | R³ | n | W-Y |
|---|---|---|---|---|---|
| 148 | 2-methyl-1-ethyl-6-amidino-indole | CH₂CH₂ | H | 1 | pyrrolidinyl-CO-CH(NH₂)-CH₂-CONH₂ |
| 149 | 2-methyl-1-ethyl-6-amidino-indole | CH₂CH₂ | H | 1 | pyrrolidinyl-CO-CH(NH₂)-CH₂-CO₂H |
| 150 | 2-methyl-1-ethyl-6-amidino-indole | CH₂CH₂ | H | 1 | pyrrolidinyl-CO-CH(NHSO₂CH₃)-CH₂-CO₂H |

TABLE 1-continued
| compound No. | 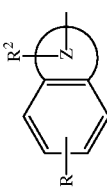 | A | R³ | n | W-Y |
|---|---|---|---|---|---|
| 151 | 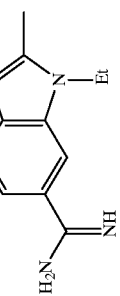 | CH₂CH₂ | H | 1 |  |
| 152 | 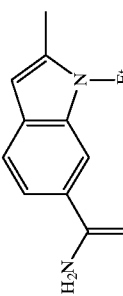 | CH₂CH₂ | H | 1 | 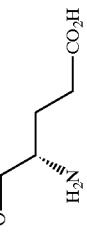 |
| 153 | 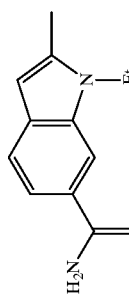 | CH₂CH₂ | H | 1 | 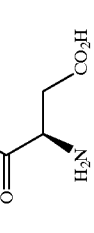 |

TABLE 1-continued
| compound No. | 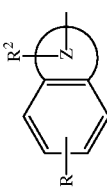 | A | R³ | n | W-Y |
|---|---|---|---|---|---|
| 154 | 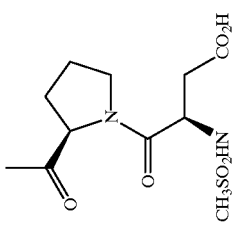 | CH₂CH₂ | H | 1 | 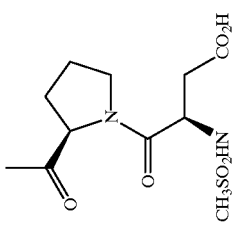 |
| 155 | 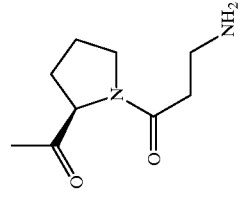 | CH₂CH₂ | H | 1 | 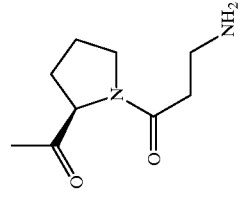 |
| 156 | 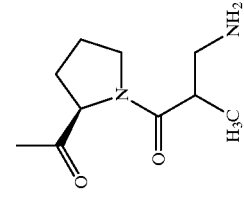 | CH₂CH₂ | H | 1 | 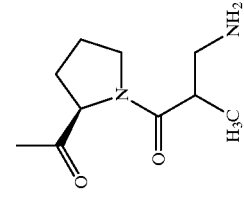 |

TABLE 1-continued

| compound No. | [R²-N ring with R] | A | R³ | n | W-Y |
|---|---|---|---|---|---|
| 157 | 2-methyl-1-ethyl-6-amidino-indole | CH₂CH₂ | H | 1 | 2-acetyl-pyrrolidine-N-C(O)-CH₂-CH(CH₃)(NH₂) |
| 158 | 2-methyl-1-ethyl-6-amidino-indole | CH₂CH₂ | H | 1 | 2-acetyl-pyrrolidine-N-C(O)-CH₂-CH₂-NHSO₂CH₃ |
| 159 | 2-methyl-1-ethyl-6-amidino-indole | CH₂CH₂ | H | 1 | 2-acetyl-pyrrolidine-N-C(O)-CH₂-CH(NH₂)-CO₂Et |

TABLE 1-continued

| compound No. | (R²-N ring with R) | A | R³ | n | W-Y |
|---|---|---|---|---|---|
| 160 | 2-methyl-1-ethyl-indole-6-yl (H₂N-C(=NH)-) | CH₂CH₂ | H | 1 | 2-acetyl-pyrrolidine-N-C(=O)-CH₂-CH(NH₂)-CONH₂ |
| 161 | 2-methyl-1-ethyl-indole-6-yl (H₂N-C(=NH)-) | CH₂CH₂ | H | 1 | 2-acetyl-pyrrolidine-N-C(=O)-CH₂-CH(NH₂)-CO₂H |
| 162 | 2-methyl-1-ethyl-indole-6-yl (H₂N-C(=NH)-) | CH₂CH₂ | H | 1 | 2-acetyl-pyrrolidine-N-C(=O)-CH₂-CH(NHSO₂CH₃)-CONH₂ |

TABLE 1-continued

| compound No. | R—⟨⟩—N(R²) | A | R³ | n | W-Y |
|---|---|---|---|---|---|
| 163 | 2-methyl-1-ethyl-indole-6-yl-C(=NH)NH₂ | CH₂CH₂ | H | 1 | 2-acetyl-pyrrolidine-N-C(=O)-CH₂-CH(NHSO₂CH₃)-CO₂H |
| 164 | 2-methyl-1-ethyl-indole-6-yl-C(=NH)NH₂ | CH₂CH₂ | H | 1 | 2-acetyl-pyrrolidine-N-C(=O)-CH₂-CH₂-CH(NH₂)-CO₂H |
| 165 | 2-methyl-1-ethyl-indole-6-yl-C(=NH)NH₂ | CH₂CH₂ | H | 1 | 2-acetyl-pyrrolidine-N-C(=O)-CH(NH₂)-CO₂H |

TABLE 1-continued

| compound No. | (R²-N ring with R) | A | R³ | n | W-Y |
|---|---|---|---|---|---|
| 166 | 2-methyl-1-Et-indole-6-C(NH)NH₂ | CH₂CH₂ | H | 1 | pyrrolidine-N-C(O)-(CH₂)₃-NH₂ |
| 167 | 2-methyl-1-Et-indole-6-C(NH)NH₂ | CH₂CH₂ | H | 1 | pyrrolidine-N-C(O)-piperidin-2-yl |
| 168 | 2-methyl-1-Et-indole-6-C(NH)NH₂ | CH₂CH₂ | H | 1 | pyrrolidine-N-C(O)-piperidin-3-yl |

TABLE 1-continued
| compound No. | 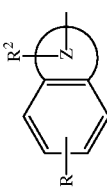 | A | R³ | n | W-Y |
|---|---|---|---|---|---|
| 169 | | CH₂CH₂ | H | 1 | |
| 170 | | CH₂CH₂ | H | 1 | |
| 171 | | CH₂CH₂ | H | 1 | |
| 172 | | CH₂CH₂ | 4—CH₂CO₂H | 1 | |

TABLE 1-continued

| compound No. | R²-N / R- (ring) | A | R³ | n | W-Y |
|---|---|---|---|---|---|
| 173 | 2-methyl-1-ethyl-indole-6-carboxamidine | CH₂CH₂ | H | 1 | 2-acetyl-pyrrolidine-N-CO-CH(CH₂CH₂CH₃)₂ |
| 174 | 2-methyl-1-ethyl-indole-6-carboxamidine | CH₂CH₂ | H | 1 | 2-acetyl-pyrrolidine-N-CO-CH₂-CO₂Et |
| 175 | 2-methyl-1-ethyl-indole-6-carboxamidine | CH₂CH₂ | H | 1 | 2-acetyl-pyrrolidine-N-CO-CH₂-CONH₂ |

TABLE 1-continued
| compound No. | 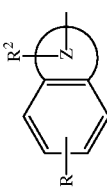 | A | R³ | n | W-Y |
|---|---|---|---|---|---|
| 176 | 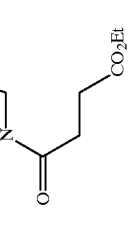 | CH₂CH₂ | H | 1 | |
| 177 | 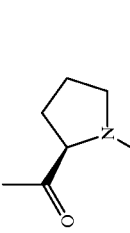 | CH₂CH₂ | H | 1 | |
| 178 | 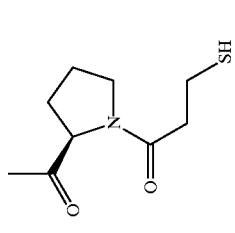 | CH₂CH₂ | H | 1 | |

TABLE 1-continued
| compound No. | 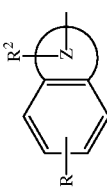 | A | R³ | n | W-Y |
|---|---|---|---|---|---|
| 179 | 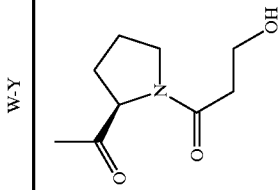 | CH₂CH₂ | H | 1 | 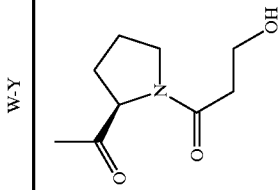 |
| 180 | 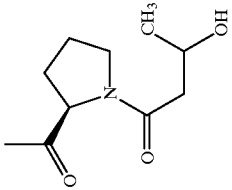 | CH₂CH₂ | H | 1 | 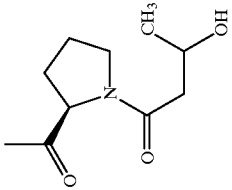 |
| 181 | 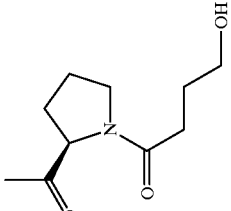 | CH₂CH₂ | H | 1 | 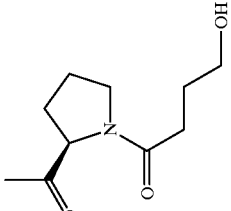 |

TABLE 1-continued
| compound No. | 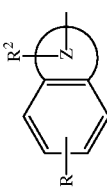 | A | R³ | n | W-Y |
|---|---|---|---|---|---|
| 182 |  | CH₂CH₂ | H | 1 | 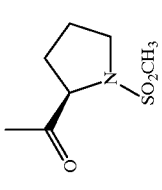 |
| 183 |  | CH₂CH₂ | H | 1 | 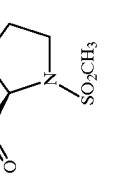 |
| 184 |  | CH₂CH₂ | H | 1 | 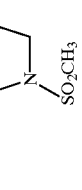 |
| 185 | | CH₂CH₂ | 4—CH₂CO₂H | 1 | |

TABLE 1-continued
| compound No. | 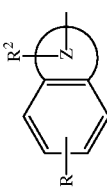 | A | R³ | n | W-Y |
|---|---|---|---|---|---|
| 186 | 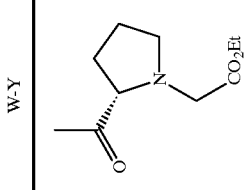 | CH₂CH₂ | H | 1 | |
| 187 | | CH₂CH₂ | H | 1 | |
| 188 | | CH₂CH₂ | H | 1 | |
| 189 | | CH₂CH₂ | H | 1 | |

TABLE 1-continued

| compound No. | ![structure] | A | R³ | n | W-Y |
|---|---|---|---|---|---|
| 190 | 2-methyl-1-ethyl-6-amidino-indole | CH₂CH₂ | H | 1 | 2-acetyl-piperidine-N-CH₂CO₂Et |
| 191 | 2-methyl-1-ethyl-6-amidino-indole | CH₂CH₂ | H | 2 | 2-acetyl-piperidine-N-CH₂CO₂Et |
| 192 | 2-methyl-1-ethyl-6-amidino-indole | CH₂CH₂ | H | 1 | 2-acetyl-piperidine-N-CH₂CO₂Me |
| 193 | 2-methyl-1-ethyl-6-amidino-indole | CH₂CH₂ | H | 1 | 2-acetyl-piperidine-N-CH₂CO₂H |

TABLE 1-continued

| compound No. | [R²-N ring with R] | A | R³ | n | W-Y |
|---|---|---|---|---|---|
| 194 | 2-methyl-1-Et-indole-6-carboxamidine | CH₂CH₂ | H | 1 | 3-acetyl-piperidine (NH) |
| 195 | 2-methyl-1-Et-indole-6-carboxamidine | CH₂CH₂ | H | 1 | 4-acetyl-piperidine (NH) |
| 196 | 2-methyl-1-Et-indole-6-carboxamidine | CH₂CH₂ | H | 1 | pyrrolidine-2-CO₂Et, N-CH₂C(O)- |
| 197 | 2-methyl-1-Et-indole-6-carboxamidine | CH₂CH₂ | H | 1 | pyrrolidine-2-CO₂H, N-CH₂C(O)- |
| 198 | 2-methyl-1-Et-indole-6-carboxamidine | CH₂CH₂ | H | 1 | piperidine-2-CO₂Et, N-CH₂C(O)- |

TABLE 1-continued
| compound No. | 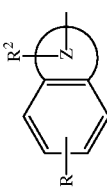 | A | R³ | n | W-Y |
|---|---|---|---|---|---|
| 199 | 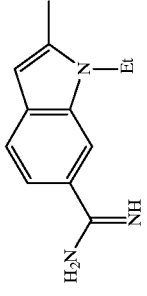 | CH₂CH₂ | H | 1 | 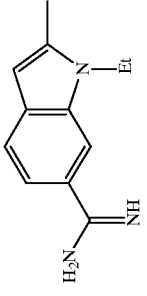 |
| 200 | 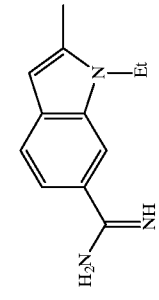 | CH₂CH₂ | H | 1 | 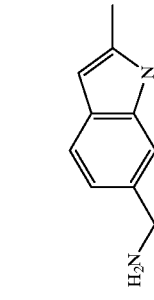 |
| 201 | 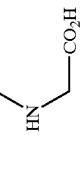 | CH₂CH₂ | H | 1 | 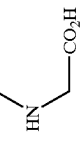 |
| 202 | | CH₂CH₂ | H | 1 | |

TABLE 1-continued
| compound No. | 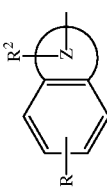 | A | R³ | n | W-Y |
|---|---|---|---|---|---|
| 203 | 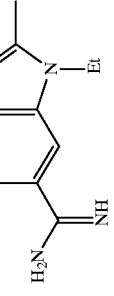 | CH₂CH₂ | H | 1 | 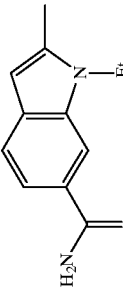 |
| 204 | 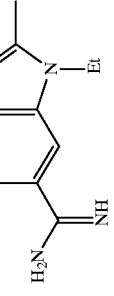 | CH₂CH₂ | H | 1 | 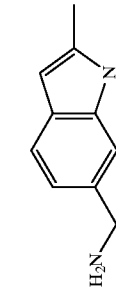 |
| 205 | 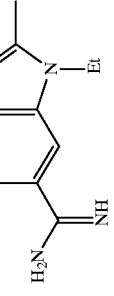 | CH₂CH₂ | H | 1 | 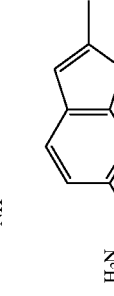 |
| 206 | 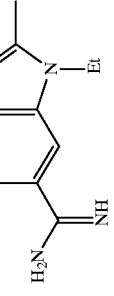 | CH₂CH₂ | H | 1 |  |

TABLE 1-continued
| compound No. | 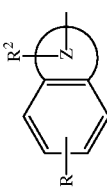 | A | R³ | n | W-Y |
|---|---|---|---|---|---|
| 207 | 2-methyl-1-ethyl-indole-6-carboxamidine | CH₂CH₂ | H | 1 | 2-acetyl-cyclohexyl-NH-CH₂-CO₂H |
| 208 | 2-methyl-1-ethyl-indole-6-carboxamidine | CH₂CH₂ | H | 2 | 1-acetyl-isoindoline |
| 209 | 2-methyl-1-ethyl-indole-6-carboxamidine | CH₂CH₂ | H | 2 | 1-acetyl-isoindoline-N-CH₂CO₂H |
| 210 | 2-methyl-1-ethyl-indole-6-carboxamidine | CH₂CH₂ | H | 2 | 2-acetyl-indoline |

TABLE 1-continued

| compound No. | R²-N / R- (ring) | A | R³ | n | W-Y |
|---|---|---|---|---|---|
| 211 | 2-methyl-1-ethyl-indole-6-carboxamidine | CH₂CH₂ | H | 2 | 2-acetyl-indoline-N-CH₂-CO₂H |
| 212 | 2-methyl-1-ethyl-indole-6-carboxamidine | CH₂CH₂ | H | 2 | 1-acetyl-octahydroindole-N-CH₂-CO₂H |
| 213 | 2-methyl-1-ethyl-indole-6-carboxamidine | CH₂CH₂ | H | 2 | 2-acetyl-octahydroindole-N-CH₂-CO₂H |
| 214 | 2-methyl-1-ethyl-indole-6-carboxamidine | CH₂CH₂ | H | 1 | 3-acetyl-1,2,3,4-tetrahydroisoquinoline |

TABLE 1-continued
| compound No. | | A | R³ | n | W-Y |
|---|---|---|---|---|---|
| 215 | 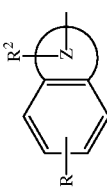 | CH₂CH₂ | H | 2 | |
| 216 | | CH₂CH₂ | H | 2 | |
| 217 | | CH₂CH₂ | H | 2 | |
| 218 | | CH₂CH₂ | H | 2 | |

TABLE 1-continued
| compound No. | 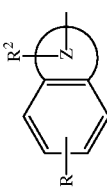 | A | R³ | n | W-Y |
|---|---|---|---|---|---|
| 219 | | CH₂CH₂ | H | 2 | |
| 220 | | CH₂CH₂ | H | 1 | |
| 221 | | CH₂CH₂ | H | 1 | |
| 222 | | CH₂CH₂ | H | 1 | |

TABLE 1-continued

| compound No. | [indole structure with R, R²] | A | R³ | n | W-Y |
|---|---|---|---|---|---|
| 223 | 2-methyl-indole, N-CH₂CO₂Et, 6-C(=NH)NH₂ | CH₂CH₂ | H | 1 | pyrrolidine-C(=O)-, N-SO₂CH₃ |
| 224 | 2-methyl-indole, N-CH₂CONH₂, 6-C(=NH)NH₂ | CH₂CR2 | H | 1 | pyrrolidine-C(=O)-, N-C(=O)CH₃ |
| 225 | 2-methyl-indole, N-CH₂CO₂H, 6-C(=NH)NH₂ | CH₂CH₂ | H | 1 | pyrrolidine-C(=O)-, N-C(=O)CH₃ |
| 226 | 2-methyl-indole, N-CH₂CO₂H, 6-C(=NH)NH₂ | CH₂CH₂ | H | 1 | pyrrolidine-C(=O)-, N-SO₂CH₃ |

TABLE 1-continued
| compound No. | 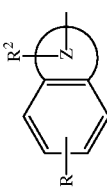 | A | R³ | n | W-Y |
|---|---|---|---|---|---|
| 227 | 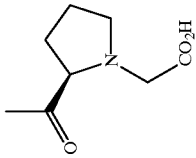 | CH₂CH₂ | H | 1 | 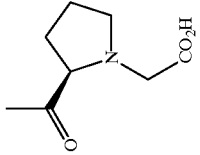 |
| 228 | 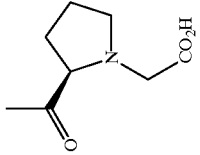 | CH₂CH₂ | H | 1 | 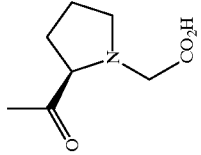 |
| 229 | 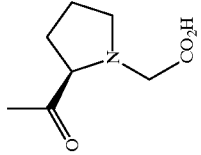 | CH₂CH₂ | H | 1 | 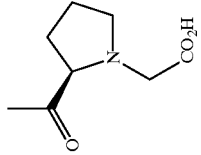 |
| 230 | 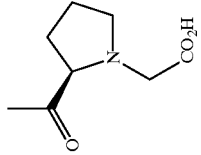 | CH₂CH₂ | H | 1 | |

TABLE 1-continued
| compound No. | 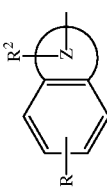 | A | R³ | n | W-Y |
|---|---|---|---|---|---|
| 231 | 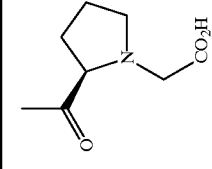 | CH₂CH₂ | H | 1 | 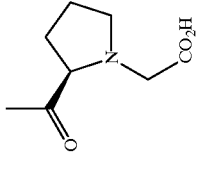 |
| 232 | | CH₂CH₂ | H | 1 | |
| 233 | | CH₂CH₂ | H | 1 | |
| 234 | | CH₂CH₂ | H | 1 | |

TABLE 1-continued

| compound No. | (R²-N ring with R) | A | R³ | n | W-Y |
|---|---|---|---|---|---|
| 235 | indole with 2-CH₃, 3-CO₂H, N-C₂H₅, 6-C(=NH)NH₂ | CH₂CH₂ | H | 1 | 2-acetyl-pyrrolidine-N-C(O)CH₃ |
| 236 | indole with 2-CH₃, 3-CH₂CO₂Et, N-C₂H₅, 6-C(=NH)NH₂ | CH₂CH₂ | H | 1 | 2-acetyl-pyrrolidine-N-C(O)CH₃ |
| 237 | indole with 2-CH₃, 3-CH₂CONH₂, N-C₂H₅, 6-C(=NH)NH₂ | CH₂CH₂ | H | 1 | 2-acetyl-pyrrolidine-N-CH₂CO₂H |
| 238 | indole with 2-CH₃, 3-CH₂CONH₂, N-C₂H₅, 6-C(=NH)NH₂ | CH₂CH₂ | H | 1 | 2-acetyl-pyrrolidine-N-C(O)CH₃ |

TABLE 1-continued

| compound No. | (R²-Z ring with R) | A | R³ | n | W-Y |
|---|---|---|---|---|---|
| 239 | 2-methyl-3-(CH₂CONH₂)-1-C₂H₅-indole-6-C(=NH)NH₂ | CH₂CH₂ | H | 1 | 2-acetyl-pyrrolidine-N-SO₂CH₃ |
| 240 | 2-methyl-3-(CH₂CONH₂)-1-C₂H₅-indole-6-C(=NH)NH₂ | CH₂CH₂ | H | 1 | 2-acetyl-pyrrolidine-N-CH₂CO₂H |
| 241 | 2-methyl-3-(CH₂CONH₂)-1-C₂H₅-indole-6-C(=NH)NH₂ | CH₂CH₂ | H | 1 | 2-acetyl-pyrrolidine-N-CH₂CO₂H |
| 242 | 2-methyl-1-CH₃-indole-5-C(=NH)NH₂ | CH₂CH₂ | H | 1 | 2-acetyl-pyrrolidine-N-CH₂CO₂Et |

TABLE 1-continued
| compound No. | 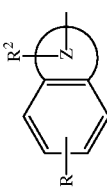 | A | R³ | n | W-Y |
|---|---|---|---|---|---|
| 243 | 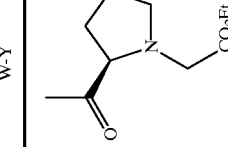 | CH₂CH₂ | H | 1 | 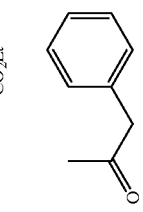 |
| 244 |  | CH₂CH₂ | H | 1 | 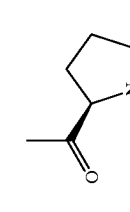 |
| 245 | 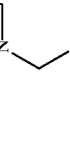 | CH₂CH₂ | H | 1 | 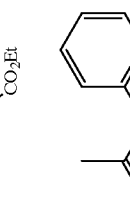 |
| 246 | 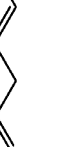 | CH₂CH₂ | H | 1 |  |

TABLE 1-continued
| compound No. | 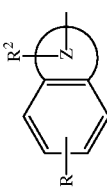 | A | R³ | n | W-Y |
|---|---|---|---|---|---|
| 247 | 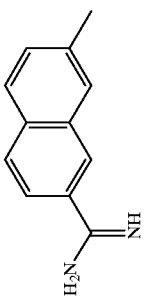 | CH₂CH₂ | H | 1 | 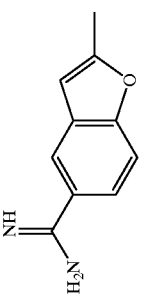 |
| 248 | 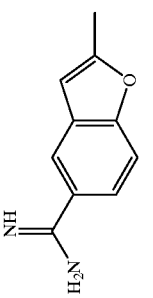 | CH₂CH₂ | H | 1 | 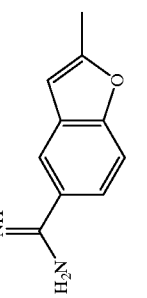 |
| 249 | 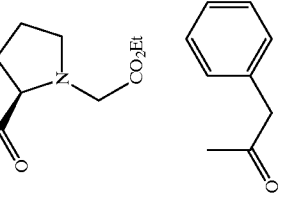 | HC—CH | H | 1 | 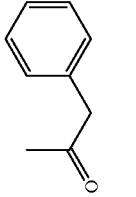 |
| 250 | 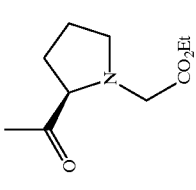 | CH₂CH₂ | H | 1 | |

TABLE 1-continued
| compound No. | 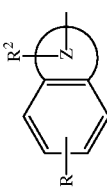 | A | R³ | n | W-Y |
|---|---|---|---|---|---|
| 251 | 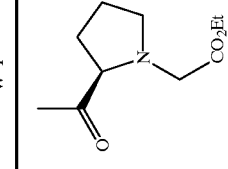 | CH₂CH₂ | H | 1 | |
| 252 | | CH₂CH₂ | H | 1 | |
| 253 | | CH₂CH₂ | H | 1 | |
| 254 | 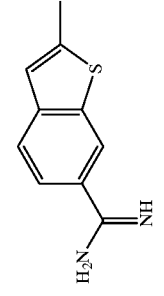 | CH₂CH₂ | H | 1 | |

TABLE 1-continued
| compound No. | 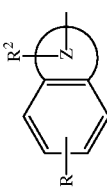 | A | R³ | n | W-Y |
|---|---|---|---|---|---|
| 255 | 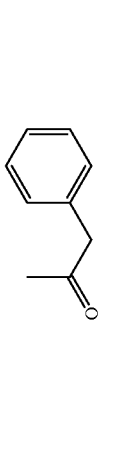 | CH₂CH₂ | H | 1 | 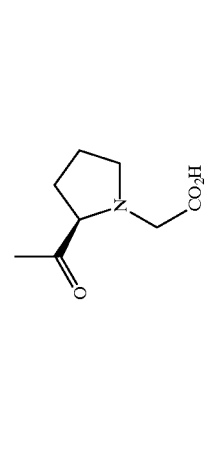 |
| 256 | 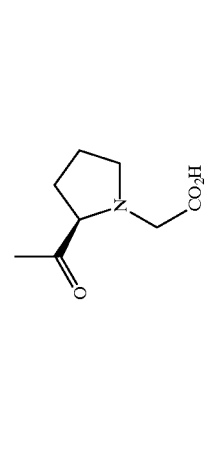 | CH₂CH₂ | H | 1 | 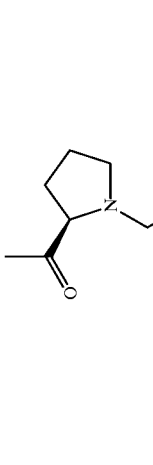 |
| 257 | 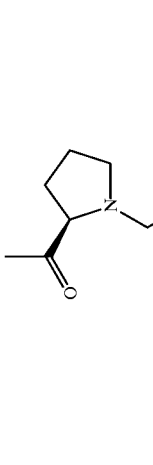 | CH₂CH₂ | H | 1 | 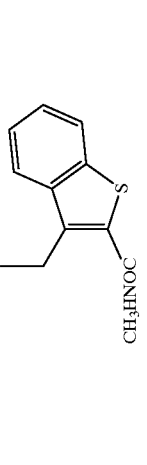 |
| 258 | 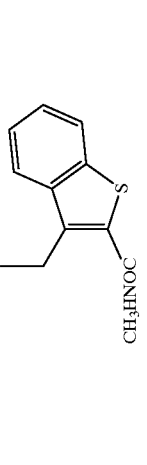 | CH₂CH₂ | H | 1 | 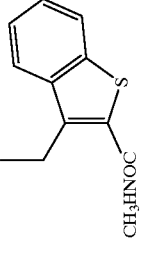 |

TABLE 1-continued
| compound No. | 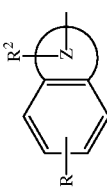 | A | R³ | n | W-Y |
|---|---|---|---|---|---|
| 259 | 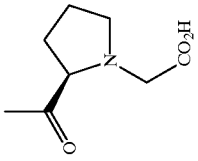 | CH₂CH₂ | H | 1 | 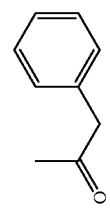 |
| 260 | | CH₂CH₂ | H | 1 | |
| 261 | | CH₂CH₂ | H | 1 | |
| 262 | | CH₂CH₂ | H | 1 | |

TABLE 1-continued

| compound No. | (R²-N ring with R) | A | R³ | n | W-Y |
|---|---|---|---|---|---|
| 263 | 2-methyl-1-ethyl-indole-6-yl with C(=N-OCH₃)NH₂ | $CH_2CH_2$ | H | 1 | 2-acetyl-pyrrolidin-1-yl-CH₂-CO₂Et |
| 264 | 2-methyl-1-ethyl-indole-6-yl with C(=N-OOCCH₃)NH₂ | $CH_2CH_2$ | H | 1 | 2-acetyl-pyrrolidin-1-yl-CH₂-CO₂Et |
| 265 | 2-methyl-1-ethyl-indole-6-yl with C(=N-C(=O)CH₃)NH₂ | $CH_2CH_2$ | H | 1 | 2-acetyl-pyrrolidin-1-yl-CH₂-CO₂Et |
| 266 | 2-methyl-1-ethyl-indole-6-yl with C(=N-C(=O)OC₂H₅)NH₂ | $CH_2CH_2$ | H | 1 | phenyl-CH₂-C(=O)-CH₃ |

TABLE 1-continued

| compound No. | (R²/R structure) | A | R³ | n | W-Y |
|---|---|---|---|---|---|
| 267 | 2-methyl-1-ethylindole-6-yl with C(=N-)(NH₂) linked to OC(=O)OC₂H₅ | CH₂CH₂ | H | 1 | 2-acetylpyrrolidine-N-CH₂CO₂Et |
| 268 | 2-methyl-1-ethylindole-6-yl with C(=N-)(NH₂) linked to OC(=O)OC₂H₅ | CH₂CH₂ | H | 1 | 2-acetylpyrrolidine-N-CH₂CO₂H |
| 269 | 2-methyl-1-ethylindole-6-yl with C(=N-)(NH₂) linked to SC(=O)C₂H₅ | CH₂CH₂ | H | 1 | 2-acetylpyrrolidine-N-CH₂CO₂Et |
| 270 | 2-methyl-1-ethylindole-6-yl with C(=N-)(NH₂) linked to OC(=O)OCH₂CH(CH₃)₂ | CH₂CH₂ | H | 1 | 2-acetylpyrrolidine-N-CH₂CO₂Et |

TABLE 1-continued

| compound No. | (R²–N ring with R) | A | R³ | n | W–Y |
|---|---|---|---|---|---|
| 271 | 2-methyl-1-ethylindol-6-yl C(NH₂)=N–C(O)O–CH₂CH(CH₃)₂ | CH₂CH₂ | H | 1 | 2-acetylpyrrolidin-1-yl-CH₂-CO₂H |
| 272 | 2-methyl-1-ethylindol-6-yl C(NH₂)=N–C(O)O–CH₂CCl₃ | CH₂CH₂ | H | 1 | 2-acetylpyrrolidin-1-yl-CH₂-CO₂Et |
| 273 | 2-methyl-1-ethylindol-6-yl C(NH₂)=N–C(O)O–phenyl | CH₂CH₂ | H | 1 | 2-acetylpyrrolidin-1-yl-CH₂-CO₂Et |
| 274 | 2-methyl-1-ethylindol-6-yl C(NH₂)=N–C(O)O–(4-fluorophenyl) | CH₂CH₂ | H | 1 | 2-acetylpyrrolidin-1-yl-CH₂-CO₂H |

TABLE 1-continued

| compound No. | [structure] | A | R³ | n | W-Y |
|---|---|---|---|---|---|
| 275 | 2-methyl-1-ethyl-indole with C(=NH)NH₂ linked to OC(O)N=, O-phenyl-OCH₃ | CH₂CH₂ | H | 1 | 2-acetyl-pyrrolidine-N-CH₂CO₂H |
| 276 | 2-methyl-1-ethyl-indole with C(=NH)NH₂ linked to OC(O)N=, OCH(CH₃)OC(O)CH₃ | CH₂CH₂ | H | 1 | 2-acetyl-pyrrolidine-N-CH₂CO₂H |
| 277 | 2-methyl-1-ethyl-indole with C(=NH)NH₂ linked to OC(O)N=, OCH₂CH₂N(CH₃)₂ | CH₂CH₂ | H | 1 | 2-acetyl-pyrrolidine-N-CH₂CO₂H |

Specific examples of the paticularly preferred compound of formula (I) according to the present invention are as follows:

3-[[(S)-2-[2-(6-amidino-1-ethylindol-2-yl)ethyl]pyrrolidin-2-yl]methyl]benzo[b]thiophene-2-carboxamide, 3-[[(S)-2-[2-(6-amidino-1-methylindol-2-yl)ethyl]pyrrolidin-2-yl]methyl]benzo[b]thiophene-2-carboxamide, 1-ethyl-2-[2-[(S)-1-[2-(3-chlorophenyl)acetyl]pyrrolidin-2-yl]ethyl]indole-6-carboxamidine, 2-[2-[(S)-2-[2-(6-amidino-1-ethylindol-2-yl)ethyl]pyrrolidinyl]-2-oxoethyl]benzoic acid, 1-ethyl-2-[2-[(S)-1-(2-cyclopentyl-2-phenylacetyl)pyrrolidin-2-yl]ethyl]indole-6-carboxamidine, 1-ethyl-2-[2-[(S)-1-((R)-2-methylsulfonylamino-2-phenylacetyl)pyrrolidin-2-yl]ethyl]indole-6-carboxamidine, ethyl 2-[[(R)-2-[2-[(S)-2-[2-(6-amidino-1-ethylindol-2-yl)ethyl]pyrrolidinyl]-2-oxo-1-phenyl]ethyl]amino]acetate, 1-ethyl-2-[2-[(S)-1-[(R)-2-(carbamoylmethylamino)-2-phenylacetyl]pyrrolidin-2-yl]ethyl]indole-6-carboxamidine, 2-[[(R)-2-[2-[(S)-2-[2-(6-amidino-1-ethylindol-2-yl)ethyl]pyrrolidinyl]-2-oxo-1-phenylethyl]amino]acetic acid, 1-ethyl-2-[2-[(S)-1-cyclopentylacetyl)pyrrolidin-2-yl]ethyl]indole-6-carboxamidine, ethyl 3-[(S)-2-[2-(6-amidino-1-ethylindol-2-yl)ethyl]pyrrolidinyl]-2-cyclopentyl-3-oxopropanoate, 1-ethyl-2-[2-[(S)-1-(2-cyclohexylacetyl)pyrrolidin-2-yl]ethyl]indole-6-carboxamidine, 1-ethyl-2-[2-[(S)-1-(2-cyclopropylaminoacetyl)pyrrolidin-2-yl]ethyl]indole-6-carboxamidine, 1-ethyl-2-[2-[(S)-1-[2-[cyclopropyl(methylsulfonyl)amino]acetyl]pyrrolidin-2-yl]ethyl]indole-6-carboxamidine, ethyl 2-[[2-[(S)-2-[2-(6-amidino-1-ethylindol-2-yl)ethyl]pyrrolidinyl]-2-oxoethyl]cyclopropylamino]acetate, ethyl 2-[[2-[(S)-2-[2-(6-amidino-1-ethylindol-2-yl)ethyl]pyrrolidinyl]-1-methyl-2-oxoethyl]cyclopropylamino]acetate, 2-[[-[(S)-2-[2-(6-amidino-1-ethylindol-2-yl)ethyl]pyrrolidinyl]-1-methyl-2-oxoethyl]cyclopropylamino]acetic acid, ethyl 4-[(S)-2-[2-(6-amidino-1-ethylindol-2-yl)ethyl]pyrrolidinyl]-2-cyclopropylamino-4-oxobutanoate, 4-[(S)-2-[2-(6-amidino-1-ethylindol-2-yl)ethyl]pyrrolidinyl]-3-cyclopropylamino-4-oxobutanoic acid, 1-ethyl-2-[2-[(S)-1-((R)-pyrrolidin-2-ylcarbonyl)pyrrolidin-2-yl]ethyl]indole-6-carboxamidine, ethyl 2-[(R)-2-[[(S)-2-[2-(6-amidino-1-methylindol-2-yl)ethyl]pyrrolidinyl]carbonyl]pyrrolidinyl]acetate, ethyl 2-[(R)-2-[[(S)-2-[2-(6-amidino-1-ethylindol-2-yl)ethyl]pyrrolidinyl]carbonyl]pyrrolidinyl]acetic acid, 2-[(R)-2-[[(S)-2-[2-(6-amidino-1-ethylindol-2-yl)ethyl]pyrrolidinyl]carbonyl]pyrrolidinyl]acetic acid, 2-[(R)-2-[[(S)-2-[2-(6-amidino-1-ethylindol-2-yl)ethyl]-(S)-4-methylpyrrolidinyl]carbonyl]pyrrolidinyl]acetic acid, ethyl-2-[(R)-2-[[(S)-2-[2-(6-amidino-1-ethylindol-2-yl)ethyl]pyrrolidinyl]carbonyl]pyrrolidinyl]propionate, ethyl-2-[(R)-2-[[(S)-2-[2-(6-amidino-1-ethylindol-2-yl)ethyl]pyrrolidinyl]carbonyl]pyrrolidinyl]butanoate, ethyl-2-[(R)-2-[[(S)-2-[2-(6-amidino-1-ethylindol-2-yl)ethyl]pyrrolidinyl]carbonyl]pyrrolidinyl]-2-phenylacetate, 1-ethyl-2-[2-[(S)-1-[[(R)-1-(carbamoylmethyl)pyrrolidin-2-yl]carbonyl]pyrrolidin-2-yl]ethyl]indole-6-carboxamidine, 1-ethyl-2-[2-[(S)-1-[[(R)-1-[(N-cyclopropylcarbomoyl)methyl]pyrrolidin-2-yl]carbonyl]pyrrolidin-2-yl]ethyl]indole-6-carboxamidine, ethyl (S)-2-[2-[(R)-2-[[(S)-2-[2-(6-amidino-1-ethylindol-2-yl)ethyl]pyrrolidinyl]carbonyl]pyrrolidinyl]acetylamino]propanoate, 1-ethyl-2-[2-[(S)-1-[[(R)-1-carbamoyl-3-hydroxypropyl)pyrrolidin-2-yl]carbonyl]pyrrolidin-2-yl]ethyl]indole-6-carboxamidine, 2-[(R)-2-[[(S)-2-[2-(6-amidino-1-ethylindol-2-yl)ethyl]pyrrolidinyl]carbonyl]pyrrolidinyl]-4-hydroxybutanoic acid, 1-[(R)-2-[[(S)-2-[2-(6-amidino-1-ethylindol-2-yl)ethyl]pyrrolidinyl]carbonyl]pyrrolidinyl]ethane-1,2-dicarboxylic acid, 1-ethyl-2-[2-[(S)-1-[[1-(2-oxo-3-oxolanyl)pyrrolidin-2-yl]carbonyl]pyrrolidin-2-yl]ethyl]indole-6-carboxamidine, ethyl 4-[(R)-2-[[(S)-2-[2-(6-amidino-1-ethylindol-2-yl)ethyl]pyrrolidinyl]carbonyl]pyrrolidinyl]butanoate, 4-[(R)-2-[[(S)-2-[2-(6-amidino-1-ethylindol-2-yl)ethyl]pyrrolidinyl]carbonyl]pyrrolidinyl]butanoic acid, ethyl 5-[(R)-2-[[(S)-2-[2-(6-amidino-1-ethylindol-2-yl)ethyl]pyrrolidinyl]carbonyl]pyrrolidinyl]pentanoate, 5-[(R)-2-[[(S)-2-[2-(6-amidino-1-ethylindol-2-yl)ethyl]pyrrolidinyl]carbonyl]pyrrolidinyl]pentanoic acid, ethyl 6-[(R)-2-[[(S)-2-[2-(6-amidino-1-ethylindol-2-yl)ethyl]pyrrolidinyl]carbonyl]pyrrolidinyl]hexanoate, 6-[(R)-2-[[(S)-2-[2-(6-amidino-1-ethylindol-2-yl)ethyl]pyrrolidinyl]carbonyl]pyrrolidinyl]hexanoic acid, 1-ethyl-2-[2-[(S)-1-[[(R)-1-[2-(methylamino)acetyl]pyrrolidin-2-yl]carbonyl]pyrrolidin-2-yl]ethyl]indole-6-carboxamidine, 1-ethyl-2-[2-[(S)-1-[[(R)-1-((S)-2-aminopropanoyl)pyrrolidin-2-yl]carbonyl]pyrrolidin-2-yl]ethyl]indole-6-carboxamidine, 1-ethyl-2-[2-[(S)-1-[[(R)-1-(2-aminobutanoyl)pyrrolidin-2-yl]carbonyl]pyrrolidin-2-yl]ethyl]indole-6-carboxamidine, 1-ethyl-2-[2-[(S)-1-[[(R)-1-((S)-2-amino-3-methylbutanoyl)pyrrolidin-2-yl]carbonyl]pyrrolidin-2-yl]ethyl]indole-6-carboxamidine, 1-ethyl-2-[2-[(S)-1-[[(R)-1-[(S)-2-(methanesulfonylamino)propanoyl]pyrrolidin-2-yl]carbonyl]pyrrolidin-2-yl]ethyl]indole-6-carboxamidine, ethyl 4-[(R)-2-[[(S)-2-[2-(6-amidino-1-ethylindol-2-yl)ethyl]pyrrolidinyl]carbonyl]pyrrolidinyl]-(S)-3-amino-4-oxobutanoate, 1-ethyl-2-[2-[(S)-1-[[(R)-1-((S)-2-amino-3-carbamoylpropanoyl)pyrrolidin-2-yl]carbonyl]pyrrolidin-2-yl]ethyl]indole-6-carboxamidine, 4-[(R)-2-[[(S)-2-[2-(6-amidino-1-ethylindol-2-yl)ethyl]pyrrolidinyl]carbonyl]pyrrolidinyl]-(S)-3-amino-4-oxobutanoic acid, 1-ethyl-2-[2-[((S)-1-[[(R)-1-(3-aminopropanoyl)pyrrolidin-2-yl]carbonyl]pyrrolidin-2-yl]ethyl]indole-6-carboxamidine, 1-ethyl-2-[2-[(S)-1-[[(R)-1-(3-amino-2-methylpropanoyl)pyrrolidin-2-yl]carbonyl]pyrrolidin-2-yl]ethyl]indole-6-carboxamidine, 1-ethyl-2-[2-[(S)-1-[[(R)-1-(3-aminobutanoyl)pyrrolidin-2-yl]carbonyl]pyrrolidin-2-yl]ethyl]indole-6-carboxamidine, 1-ethyl-2-[2-[(S)-1-[[(R)-1-[3-[(methanesulfonyl)amino]propanoyl]pyrrolidin-2-yl]carbonyl]pyrrolidin-2-yl]ethyl]indole-6-carboxamidine, ethyl 4-[(R)-2-[[(S)-2-[2-(6-amidino-1-ethylindol-2-yl)ethyl]pyrrolidinyl]carbonyl]pyrrolidinyl]-(S)-2-amino-4-oxobutanoate, 1-ethyl-2-[2-[(S)-1-[[(R)-1-((S)-3-amino-3-carbamoylpropanoyl)pyrrolidin-2-yl]carbonyl]pyrrolidin-2-yl]ethyl]indole-6-carboxamidine,
4-[(R)-2-[[(S)-2-[2-(6-amidino-1-ethylindol-2-yl)ethyl]pyrrolidinyl]carbonyl]pyrrolidinyl]-(S)-2-amino-4-oxobutanoic acid,
1-ethyl-2-[2-[(S)-1-[[1-[(R)-1-[3-carbamoyl-(S)-3-[(methanesulfonyl)amino]propanoyl]pyrrolidin-2-yl]carbonyl]pyrrolidin-2-yl]ethyl]indole-6-carboxamidine,
4-[(R)-2-[[(S)-2-[2-(6-amidino-1-ethylindol-2-yl)ethyl]pyrrolidinyl]carbonyl]pyrrolidinyl]-(S)-2-[(methanesulfonyl)amino]-4-oxobutanoic acid,
1-ethyl-2-[2-[(S)-1-[[(R)-1-(4-aminobutanoyl)pyrrolidin-2-yl]carbonyl]pyrrolidin-2-yl]ethyl]indole-6-carboxamidine,
1-ethyl-2-[2-[(S)-1-[[(R)-1-[(2-piperidinyl)carbonyl]pyrrolidin-2-yl]carbonyl]pyrrolidin-2-yl]ethyl]indole-6-carboxamidine,
1-ethyl-2-[2-[(S)-1-[[(R)-1-(3-piperidinylcarbonyl)pyrrolidin-2-yl]carbonyl]pyrrolidin-2-yl]ethyl]indole-6-carboxamidine,
1-ethyl-2-[2-[(S)-1-[[(R)-1-[(4-piperidinyl)carbonyl]pyrrolidin-2-yl]carbonyl]pyrrolidin-2-yl]ethyl]indole-6-carboxamidine,
1-methyl-2-[2-[(S)-1-[((R)-1-acetylpyrrolidin-2-yl)carbonyl]pyrrolidin-2-yl]ethyl]indole-6-carboxamidine,
1-ethyl-2-[2-[(S)-1-[((R)-1-acetylpyrrolidin-2-yl)carbonyl]pyrrolidin-2-yl]ethyl]indole-6-carboxamidine,
1-ethyl-2-[2-[(S)-1-[[(R)-1-(2-propylpentanoyl)pyrrolidin-2-yl]carbonyl]pyrrolidin-2-yl]ethyl]indole-6-carboxamidine,
ethyl 3-[(R)-2-[[(S)-2-[2-(6-amidino-1-ethylindol-2-yl)ethyl]pyrrolidinyl]carbonyl]pyrrolidinyl]-3-oxopropanoate,
1-ethyl-2-[2-[(S)-1-[[(R)-1-(2-carbamoylacetyl)pyrrolidin-2-yl]carbonyl]pyrrolidin-2-yl]ethyl]indole-6-carboxamidine,
ethyl 4-[(R)-2-[[(S)-2-[2-(6-amidino-1-ethylindol-2-yl)ethyl]pyrrolidinyl]carbonyl]pyrrolidinyl]-4-oxobutanoate,
4-[(R)-2-[[(S)-2-[2-(6-amidino-1-ethylindol-2-yl)ethyl]pyrrolidinyl]carbonyl]pyrrolidinyl]-4-oxobutanoic acid,
1-ethyl-2-[2-[(S)-1-[[(R)-1-(3-hydroxybutanoyl)pyrrolidin-2-yl]carbonyl]pyrrolidin-2-yl]ethyl]indole-6-carboxamidine,
1-ethyl-2-[2-[(S)-1-[((R)-1-prop-2-enoylpyrrolidin-2-yl)carbonyl]pyrrolidin-2-yl]ethyl]indole-6-carboxamidine,
1-ethyl-2-[2-[(S)-1-[[(R)-1-(methanesulfonyl)pyrrolidin-2-yl]carbonyl]pyrrolidin-2-yl]ethyl]indole-6-carboxamidine,
1-ethyl-2-[2-[(S)-1-[[(R)-1-(carbamoylmethyl)-5-oxopyrrolidin-2-yl]carbonyl]pyrrolidin-2-yl]ethyl]indole-6-carboxamidine,
methyl-2-[2-[[(S)-2-[2-(6-amidino-1-ethylindol-2-yl)ethyl]pyrrolidinyl]carbonyl]piperidinyl]acetate,
1-ethyl-2-[2-[(S)-1-[(3-piperidinyl)carbonyl]pyrrolidin-2-yl]ethyl]indole-6-carboxamidine,
ethyl 1-[2-[(S)-2-[2-(6-amidino-1-ethylindol-2-yl)ethyl]pyrrolidinyl]-2-oxoethyl]pyrrolidine-2-carboxlate,
ethyl 2-[2-[2-[(S)-1-[((R)-1-acetylpyrrolidin-2-yl)carbonyl]pyrrolidin-2-yl]ethyl]-6-amidinoindolyl]acetate,
2-[2-[(S)-1-[((R)-1-acetylpyrrolidin-2-yl)carbonyl]pyrrolidin-2-yl]ethyl]-1-(carbamoylmethyl)indole-6-carboxamidine, and
6-[2-[(S)-1-(2-phenylacetyl)pyrrolidin-2-yl]ethyl]naphthalene-2-carboxamidine.

The compound of formula (I) according to the present invention can form its pharmaceutically acceptable salt.

Such pharmaceutically acceptable salts include acid addition salts produced by acid containing pharmaceutically acceptable anion which can form a non-toxic salt, for example, an inorganic acid such as hydrochloric acid, sulfuric acid, nitric acid, phosphoric acid, hydrobromic acid, hydroiodic acid, an organic carbonic acid such as tartaric acid, formic acid, citric acid, acetic acid, trichloroacetic acid or trifluoroacetic acid, gluconic acid, benzoic acid, lactic acid, fumaric acid, maleic acid, etc., or sulfonic acid such as methansulfonic acid, benzenesulfonic acid, p-toluenesulfonic acid, naphthalene-sulfonic acid, etc.

The purpose of the present invention is also to provide a process for preparation of the compound of formula (I).

According to the method of the present invention, the compound of formula (I) and its salt can be prepared by a process wherein:

(a) an amino-protecting group of a compound of formula (V):

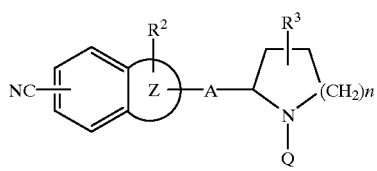

(V)

wherein

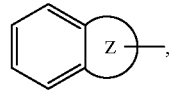

$R^2$, $R^3$, A and n are defined as in formula (I) and Q represents an amino-protecting group, is removed to obtain a compound of formula (IV):

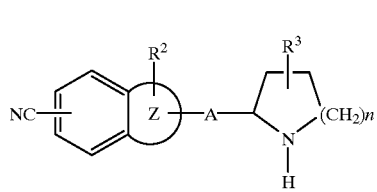

(IV)

wherein

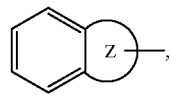

$R^2$, $R^3$, A and n are defined as in formula (I);

(b) the nitrile compound of formula (IV) thereby obtained is reacted with a compound of formula (VI):

Y—W—D             (VI)

wherein Y and W are defined as in formula (I) and D represents hydroxy or halogen, to obtain a compound of formula (III):

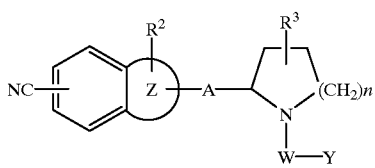
(III)

wherein

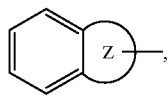

$R^2$, $R^3$, A, Y, W and n are defined as in formula (I);
(c) the compound of formula (III) is reacted with an alcohol compound of formula (VII):

$R^1OH$ (VII)

wherein $R^1$ is defined as in formula (I), in the presence of a hydrogen halide to obtain a compound of formula (II):

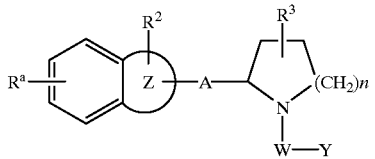
(II)

wherein

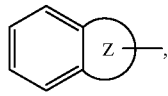

$R^2$, $R^3$, A, Y, W and n are defined as in formula (I) and $R^a$ is a group of formula

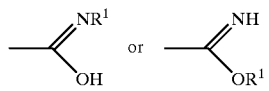

wherein $R^1$ is defined as in formula (I); and
(d) the compound of formula (II) is reacted with ammonia.

According to the method of the present invention, in step (a) the amino-protecting group Q is removed from the compound of formula (V) to produce the compound of formula (IV).

In the compound of formula (V), a suitable amino-protecting group includes conventional groups for protecting amino radical, particularly, acyl such as carbamoyl, aliphatic acyl, aromatic acyl, heterocyclic acyl and aliphatic acyl substituted with aromatic group or heterocyclic group which are derived from carboxylic, carbonic, sulfonic and carbamic acids. For example, lower alkanoyl, lower alkylsulfonyl, carbamoyl, N-alkyl-carbamoyl, lower alkoxycarbonyl, lower alkenyloxycarbonyl, alkenoyl, aroyl, arenesulfonyl, aralkanoyl, aralkoxycarbonyl, aryloxyalkanoyl, etc. may be mentioned. Particularly preferred amino-protecting group is t-butoxycarbonyl or benzyloxycarbonyl.

The reaction for removing amino-protecting group of step (a) can be carried out by a conventional method, for example, hydrolysis in the presence of an acid (e.g. an organic acid such as formic acid, acetic acid, propionic acid, trifluoroacetic acid, benzenesulfonic acid or an inorganic acid such as hydrochloric acid, sulfuric acid, phosphoric acid, etc.) or a base (e.g. a hydroxide, hydride, carbonate or bicarbonate of alkali metal or alkaline earth metal such as sodium hydroxide, potassium hydroxide, sodium hydride, sodium carbonate, potassium carbonate, sodium bicarbonate, etc.), reduction by using a combination of a metal (e.g. zinc) or a chrome compound (e.g. chromous chloride) and an organic or inorganic acid ( e.g. acetic acid, propionic acid, sulfuric acid, phosphoric acid, etc.) or by using hydrogen in the presence of a catalyst (e.g. a metallic catalyst such as palladium, platinum, nickel, etc.), and the like.

In any case, the reaction can generally be carried out in the presence of a solvent which does not adversely influence the reaction. Examples of the solvent which can preferably be used include water, dichloromethane, alcohols such as methanol, ethanol, etc., tetrahydrofuran, 1,4-dioxane, acetone, or a mixture thereof. The reaction temperature is not critical and the reaction is usually carried out under from cooling to heating, preferably at 0° C. to 30° C.

In the reaction of step (b), the nitrile compound (IV) produced in step (a) is reacted with the compound of formula (VI) to produce the compound of (III). The reaction of the compound of formula (IV) with the compound of formula (VI) can preferably carried out in the presence of a reaction-inert solvent. The solvent which can preferably be used for this purpose includes acetone, 1,4-dioxane, acetonitrile, chloroform, dichloromethane, hexamethylphosphoramide, dichloroethane, tetrahydrofuran, ethyl acetate, dimethylsulfoxide, N,N-dimethylformamide, pyridine, or a mixture thereof.

If necessary, the reaction of step (b) can be carried out in the presence of an acid acceptor. The acid acceptor which can preferably be used for this purpose includes an inorganic base, for example, hydroxide, carbonate or bicarbonate of an alkali metal or an alkaline earth metal such as sodium hydroxide, potassium hydroxide, sodium carbonate, potassium carbonate, magnesium carbonate, sodium bicarbonate, etc. or an organic base, for example, triethylamine, trimethylamine, pyridine, N,N-diisopropylethylamine, etc. Particularly, triethylamine or N,N-diisopropylethylamine is most preferably used as the acid acceptor.

The reaction of step (b) can, if appropriate, be carried out in the presence of a condensing agent. The condensing agent which can preferably be used includes a carbodiimide compound such as N,N-diethylcarbodiimide, 1-(3-dimethylaminopropyl)-3-ethylcarbodiimide hydrochloride, N,N-dicyclohexylcarbodiimide, etc.

Although the reaction temperature and time are not critical, the reaction is usually carried out under from cooling to heating for 2 to 24 hours, preferably at 0° C. to 70° C. for 4 to 15 hours.

Thereafter, in step (c), the compound of formula (III) produced in step (b) is reacted with the alcohol compound of formula (VII) in the presence of hydrogen halide to produce the compound of formula (II). In this reaction, hydrogen chloride, hydrogen bromide, etc. can be used as hydrogen halide, with hydrogen chloride (HCl) being particularly preferably used. In this reaction, when the alcohol compound of formula (VII) is employed in an excessive amount, it can also be used as a solvent. If appropriate, this reaction may also be carried out in the presence of a reaction-inert solvent such as chloroform, dichloromethane, benzene, diethyl ether, etc. Although the reaction temperature and time are not critical, the reaction is usually carried out under from cooling to heating for 2 to 48 hours, preferably at 0° C. to 30° C. for 12 to 24 hours.

In step (d), the compound of formula (III) produced in step (c) is reacted with ammonia to produce the desired compound of formula (I). This reaction is usually carried out in a solvent, for example, $C_1$–$C_4$ alcohol such as ethanol, propanol, etc., aliphatic ether such as diethyl ether, etc., halogenated hydrocarbon such as chloroform, etc., aprotic solvent such as benzene, etc., N,N-dimethylformamide, dimethylsulfoxide, etc., or a mixture thereof. Particularly, $C_1$–$C_4$ alcohol solvent such as ethanol is preferably used. Although the reaction temperature and time in this reaction are not critical, the reaction of step (d) is usually carried out under from cooling to heating for 2 to 72 hours, preferably at 0° C. to 30° C. for 20 to 40 hours.

The compound of formula (I) prepared by the above method according to the present invention can be converted into a salt as mentioned above according to a conventional manner. The compound of formula (I) and its salts thereby produced can be separated and purified by a conventional work-up procedure, for example, column chromatography, recrystallization, etc.

All the compound of formula (V) used as the starting material and the compounds of formulas (II), (III) and (IV) produced as the intermediates in the method for preparation of the compound of formula (I) according to the present invention are novel compounds and therefore, encompassed within the scope of the present invention. The compound of formula (V) used as the starting material in the method of the present invention can be prepared by the two method as shown in the following reaction scheme.

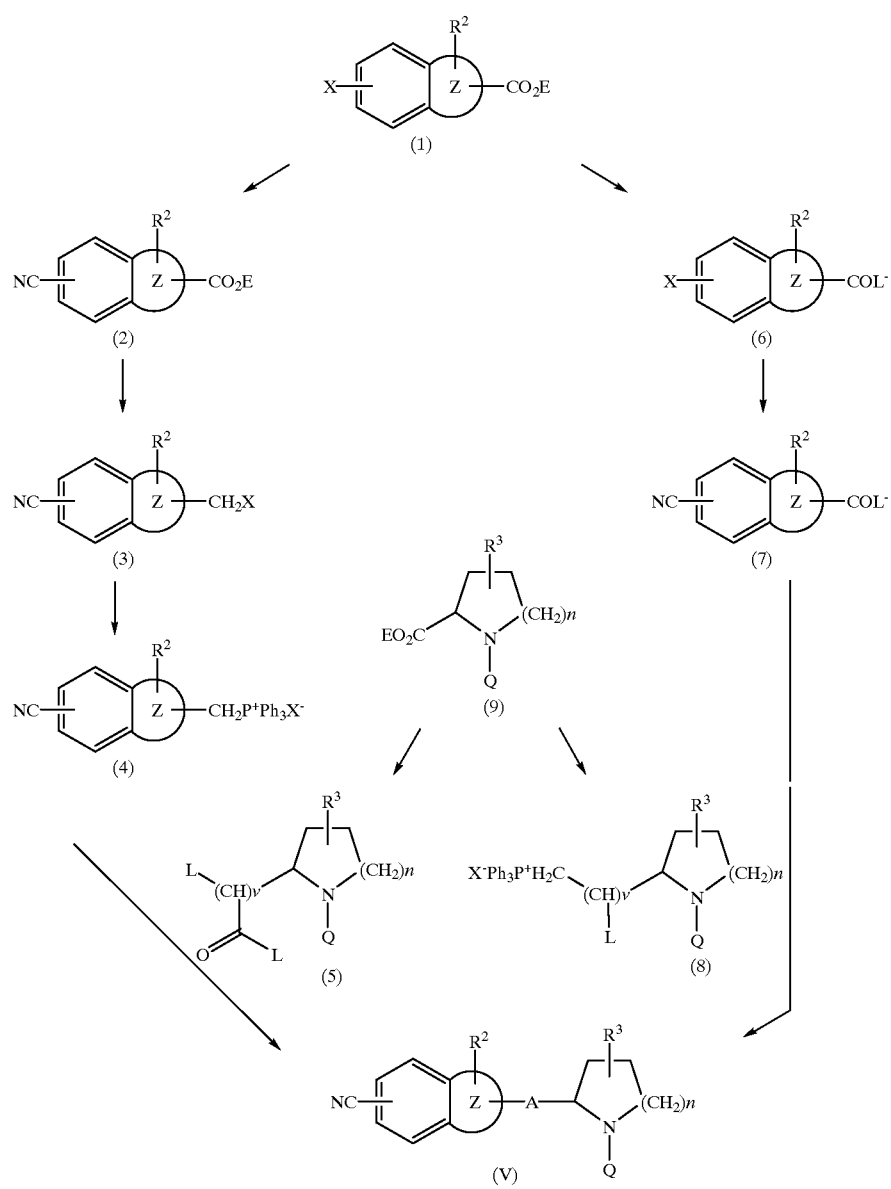

In the above reaction scheme,

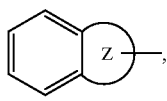

A, $R^2$, $R^3$ and n are defined as in formula (I);

L represents hydrogen, alkyl, alkoxycarbonyl or alkoxycarbonylalkyl and in formula (5) two L groups may be same or different;

E represents hydrogen or lower alkyl;

Q represents an amino-protecting group;

X represents halogen; and v denotes an integer of 0 to 2.

The present invention also relates to a thrombin inhibitor composition which contains as an active component a therapeutically effective amount of the compound of formula (I) or its pharmaceutically acceptable salt together with pharmaceutically acceptable carriers. The composition of the present invention exhibits potent thrombin inhibitory activity and can therefore be used as an agent for prevention and treatment of thrombosis.

The compound of formula (I) according to the present invention is preferable since it is effective even when orally administered.

For clinical purposes, an effective daily dosage of the compound according to the present invention may generally be in the range of 0.1 to 30 mg per kg of body weight, and preferably in the range of 0.5 to 10 mg per kg of body weight. A dosage suitable for an individual subject can appropriately be determined by a specialist depending on a kind of the compound of formula (I) to be applied, weight, sex, health and nutritional condition of the patient, time and method of administration, excretion rates, a kind of medicines to be administered in combination with the compound of formula (I) and severity of disease.

The compound of the present invention may be administered either orally or by injection, depending on the dosage and the therapeutic effect desired.

Orally administrable solid preparations may be in the form of capsules, tablets, pills, powders and granules, with capsule and tablet preparations being preferable. The tablets and pills can preferably be applied to enteric coating. The solid dosage form can be prepared by intimately mixing the compound of formula (I) according to the present invention with carriers, for example, one or more inert diluents such as sucrose, lactose, starch, etc., lubricants such as magnesium stearate, disintegrating agents, binders, etc.

As mentioned above, the compositions containing the compound of formula (I) according to the present invention are characterized by their superior effect even when orally administered. These has been demonstrated through pharmacokinetic experiments using rats and dogs as the test animals, in which the active compound is shown to be retained in blood for a long time when the composition is orally administered. The compound of the present invention is, therefore, more useful than thrombin inhibitors disclosed in the prior art because it can be effectively used in the form of an oral preparation.

The composition containing the compound of formula (I) according to the present invention can also be formulated in the form of an injectable preparation, for example, as a sterilized injectable aqueous or oily suspension using suitable dispersing agents, wetting agents or suspending agents. Aqueous solvents which can be used for this purpose include water, Ringer's solution or isotonic NaCl solution. Sterilized fixing oils may also be used as a solvent or suspending agent. Non-irritable fixing oils including mono-, di-glycerides can be used for this purpose, and fatty acids such as oleic acid may be used in injectable preparations.

In addition, according to the results of experiment, it has been identified that the compound of formula (I) according to the present invention exhibits potent thrombin inhibitor activity without acute toxicity in mammals, such as rats and dogs.

Although the present invention is specifically illustrated by the following examples, the present invention is not in any manner limited by these examples.

EXAMPLE 1

Synthesis of 1-ethyl-2-[2-((S-1-benzylpyrrolidin-2-yl) ethyl]indole-6-carbonitrile (Compound 1)

a) Synthesis of 4-methyl-3-nitrobenzenecarbonitrile

In a 250 ml flask, 10 g of 4-methylbenzenecarbonitrile was dissolved in 30 ml of concentrated sulfuric acid and then cooled to 0° C. 7 ml of nitric acid mixed with 10 ml of concentrated sulfuric acid was slowly added thereto over one hour at −2° C. to 0° C. The reaction solution was poured into ice water and then stirred. The resulting precipitate was filtered, washed three times with water and then dried. The residue was purified with silica gel column chromatography [eluent: ethyl acetate/n-hexane(1:3)]. The fractions containing the desired product were combined and then evaporated to obtain 11.2 g of the title compound as a white solid.

$^1$H NMR(CDCl$_3$, ppm): δ8.30(s, 1H), 7.80(d, 1H), 7.53(d, 1H), 2.7(s, 3H)

b) Synthesis of ethyl 3-(4-cyano-2-nitrophenyl)-2-sodiumprop-2-enoate

To a 500 ml flask, 2.51 g of sodium and 60 ml of tetrahydrofuran were added and 30 ml of ethanol was then added thereto. The mixture was stirred at room temperature until sodium was completely dissolved. A solution of 14.8 ml of diethyl oxalate in tetrahydrofuran was slowly added thereto and the mixture was stirred for 10 minutes at room temperature. 16 g of 4-methyl-3-nitrobenzenecarbonitrile dissolved in tetrahydrofuran was added thereto and the mixture was stirred for 18 hours at room temperature. The reaction solution was evaporated and ether was added to the residue. The resulting precipitate was filtered, washed three times with ether and then dried to obtain 26.4 g of the title compound as a brown solid.

c) Synthesis of ethyl 6-cyanoindole-2-carboxylate 26 g of ethyl 3-(4-cyano-2-nitrophenyl)-2-sodiumprop-2-enoate and 59.8 g of Zn were introduced into a 500 ml flask and 200 ml of acetic acid was added thereto. The mixture was stirred for 2 hours at room temperature and then for 4 hours at 60~70° C. The reaction solution was evaporated, and the residue was purified with silica gel column chromatography [eluent: ethyl acetate/n-hexane(1:3)]. The fractions containing the desired product were combined and then evaporated to obtain 4.16 g of the title compound as a yellow solid.

$^1$H NMR(CDCl$_3$, ppm): δ7.82(m, 2H), 7.42(d, 1H), 7.29 (s, 1H), 4.49(m, 2H), 1.47(t, 3H)

d) Synthesis of ethyl 6-cyano-1-ethylindole-2-carboxylate

In a 1 l flask, 23.5 g of ethyl 6-cyanoindole-2-carboxylate was dissolved in 300 ml of dimethylformamide, and 6.6 g of 60% NaH was slowly added thereto at 0° C. 17.6 ml of iodoethane was then added thereto at −10~0° C. and the mixture was stirred for 2 hours at room temperature. The reaction solution was cooled and, after adding ice, diluted with water and then extracted three times with ethyl acetate. The organic extracts were combined, dried over MgSO$_4$ and then evaporated. The residue was purified with silica gel column chromatography [eluent: ethyl acetate/n-hexane (1:3)]. The fractions containing the desired product were combined and then evaporated to obtain 26.2 g of the title compound as a yellow solid.

$^1$H NMR(CDCl$_3$, ppm): δ7.77 (m, 2H), 7.34(m, 2H), 4.64(m, 2H), 4.42(m, 2H), 1.43(m, 6H)

e) Synthesis of 1-ethyl-2-(hydroxymethyl)indole-6-carbonitrile

In a 1 l flask, 26.27 g of ethyl 6-cyano-1-ethylindole-2-carboxylate and 0.91 g of sodium bicarbonate were dissolved with 300 ml of tetrahydrofuran and then cooled to 0° C. To this mixture was added CaI$_2$.H$_2$O and then slowly added NaBH$_4$. The reaction mixture was stirred while slowly warming from 0° C. to room temperature with stirring. After examined by TLC, ice and a catalytic amount of acetic acid were added thereto at 0° C. and the mixture was stirred. The reaction solution was evaporated to remove tetrahydrofuran, and the residue was diluted with water and extracted three times with ethyl acetate. The organic extracts were combined, dried over MgSO$_4$ and then evaporated. The residue was purified with silica gel column chromatography [eluent: ethyl acetate/n-hexane(1:2)]. The fractions containing the desired product were combined and then evaporated to obtain 18.2 g of the title compound as a white solid.

$^1$H NMR(CDCl$_3$, ppm): δ7.63(m, 2H), 7.26(m, 1H), 6.43 (s, 1H), 4.83(s, 2H), 4.29(m, 2H), 1.41(t, 3H)

f) Synthesis of 6-cyano-1-ethylindole-2-methyl triphenylphosphonium bromide

In a 500 ml flask, 18.2 g of 1-ethyl-2-(hydroxymethyl) indole-6-carbonitrile was dissolved in 200 ml of dichloromethane and then cooled to 0° C. 3.45 ml of PBr$_3$ was slowly added thereto, and the mixture was stirred for 4 hours at room temperature. dichloromethane was then added and the reaction mixture was washed with aqueous Na$_2$CO$_3$ solution, diluted with water and then extracted three times with dichloromethane. The organic extracts were combined, dried over MgSO$_4$ and then evaporated to obtain 6-cyano-1-ethyl-2-bromomethyl indole. The resulting product was dissolved in 200 ml of toluene and 30.9 g of triphenylphosphine was added thereto. The mixture was stirred for 10 hours at refluxing temperature and then cooled to room temperature. To this reaction solution was added diethyl ether, and the resulting precipitate was then filtered, washed several times with diethyl ether and dried to obtain 29 g of the title compound as a pale brown solid.

g) Synthesis of (S)-methyl pyrrolidine-2-carboxylate

In a 250 ml flask, 10 g of L-proline was dissolved in 150 ml of methanol, and HCl gas was bubbled therein at 0° C. for 2 hours to saturate the solution. The reaction solution was then stirred for 5 hours at room temperature and evaporated to remove the solvent, thereby obtain 11.2 g of the title compound as a colorless oil.

$^1$H NMR(CDCl$_3$, ppm): δ4.50(m, 1H), 3.86(s, 3H), 3.52 (m, 2H), 2.48(m, 1H), 2.20(m, 3H)

MS: 130(M+1)$^+$, 116 h) Synthesis of 1-tert-butyl-(S)-2-(methoxycarbonyl) pyrrolidine carboxylate:

In a 500 ml flask, 11.2 g of (S)-methyl pyrrolidine-2-carboxylate was dissolved in 200 ml of dichloromethane and 12 ml of triethylamine was added, and the mixture was then stirred for 5 minutes. 20.9 g of (Boc)$_2$O dissolved in dichloromethane was added thereto at 0° C., and the reaction mixture was stirred for 4 hours at room temperature, diluted with water and extracted three times with dichloromethane. The organic extracts were combined, dried over MgSO$_4$ and then evaporated to obtain 19.9 g of the title compound as a colorless oil.

$^1$H NMR(MeOH-d$_4$, ppm): δ4.20(m, 1H), 3.68(s, 3H), 3.37(m, 2H), 2.22 (m, 1H), 1.89(m, 3H), 1.41(m, 9H)

i) Synthesis of 1-tert-butyl-(S)-2-formylpyrrolidine carboxylate:

In a 500 ml flask, 9.8 g of 1-tert-butyl-(S)-2-(methoxycarbonyl)pyrrolidine carboxylate was dissolved in 200 ml of toluene and 85.5 ml of DIBAL-H (diisobutylaluminum hydride, 1.0M in toluene) was slowly added over 1.5 hour while cooling to −78° C. 15 ml of methanol was then added thereto, and the mixture was stirred for 30 minutes at room temperature. To this solution, aqueous solution of Rochell's salt (potassium sodium tartrate tetrahydrate) was added, and the reaction solution was stirred for about one hour at room temperature and then extracted with dichloromethane. The organic extracts were combined, dried over MgSO$_4$ and evaporated. The residue was purified with silica gel column chromatography [eluent: ethyl acetate/n-hexane(1:3)]. The fractions containing the desired product were combined and then evaporated to obtain 8 g of the title compound as a colorless oil.

j) Synthesis of 1-tert-butyl-(S)-2-[2-(6-cyano-1-ethylindol-2-yl)vinyl]pyrrolidine carboxylate:

In a 500 ml flask, 17.4 g of 6-cyano-1-ethylindole-2-methyl triphenylphosphonium bromide and 6.6 g of 1-tert-butyl-(S)-2-formylpyrrolidine carboxylate were dissolved in a mixed solvent of tetrahydrofuran/ethanol (1:1), and 6.4 ml of 1,8-diazabicyclo[5.4.0]undec-7-ene was added thereto. The reaction solution was stirred for 15 hours at room temperature and evaporated to remove the solvent. The residue was purified with silica gel column chromatography [eluent: ethyl acetate/n-hexane(1:3)]. The fractions containing the desired product were combined and then evaporated to obtain 7.8 g of the title compound as a yellow oil.

k) Synthesis of 1-tert-butyl-(S)-2-[2-(6-cyano-1-ethylindol-2-yl)ethyl]pyrrolidine carboxylate:

In a 500 ml flask, 13 g of 1-tert-butyl-(S)-2-[2-(6-cyano-1-ethylindol-2-yl)vinyl]pyrrolidine carboxylate was dissolved in 250 ml of ethanol, and 4 g of 10% palladium on activated carbon was slowly added thereto. Hydrogen gas was bubbled into the reaction solution and the mixture was stirred for 3 hours at room temperature. The reaction solvent was filtered through a celite and evaporated to remove the solvent. The residue was purified with gel column chromatography [eluent: ethyl acetate/n-hexane(1:3)]. The fractions containing the desired product were combined and then evaporated to obtain 12 g of the title compound as a brown oil.

$^1$H NMR(CDCl$_3$, ppm): δ7.60(m, 2H), 7.28(m, 1H), 6.36 (s, 1H), 4.15(m, 2H), 3.94(m, 1H), 3.72(m, 1H), 3.38 (m, 3H), 2.76(t, 2H), 1.46(s, H), 1.39(m, 3H)

l) Synthesis of 1-ethyl-2-[2-((S)-pyrrolidin-2-yl)ethyl] indole-6-carbonitrile (Compound I-a):

In a 250 ml flask, 3.7 g of 1-tert-butyl-(S)-2-[2-(6-cyano-1-ethylindol-2-yl)ethyl]pyrrolidine carboxylate was dissolved in 100 ml of dichloromethane, and 18.2 ml of trifluoroacetic acid was slowly added thereto at 0° C. The reaction mixture was stirred for about 2 hours at room temperature, and after adding dichloromethane, then diluted with water and washed three times with saturated aqueous NaHCO$_3$ solution. The aqueous layer was extracted three times with dichloromethane. The organic extracts were combined, dried over MgSO$_4$ and then evaporated. The residue was purified with silica gel column chromatography [eluent: dichloromethane/methanol(3:1)]. The fractions containing the desired product were combined and then evaporated to obtain 2.2 g of the title compound as a pale yellow foam.

$^1$H NMR(CDCl$_3$, ppm): δ7.48(m, 2H), 7.28(m, 1H), 6.33 (s, 1H), 4.03(m, 2H), 3.58(m, 1H), 3.27(m, 2H), 2.85 (m, 2H), 2.35(m, 1H), 2.11(m, 3H), 2.00(m, 1H), 1.80(m, 1H), 1.27(t, 3H), m) Synthesis of 1-ethyl-2-[2-((S)-1-benzylpyrrolidin-2-yl) ethyl]indole-6-carbonitrile:

66 mg of the compound I-a obtained in the above l) was dissolved in dichloromethane and then cooled to 0° C. To this solution, 46 μl of triethylamine was added and 38 μl of benzyl chloride was then slowly added. The reaction mixture was stirred for 4 hours at room temperature and then diluted with excess of dichloromethane. The organic layer was washed with water, dried over MgSO$_4$ and filtered under reduced pressure. The filtrate was concentrated and the concentrate was purified with silica gel column chromatography [eluent: dichloromethane/methanol(10:1)]. The fractions containing the desired product were combined and evaporated to obtain 39 mg of the title compound.

n) Synthesis of 1-ethyl-2-[2-((S)-1-benzylpyrrolidin-2-yl) ethyl]indole-6-carboxamidine:

39 mg of 1-ethyl-2-[2-((S)-1-benzylpyrrolidin-2-yl)ethyl] indole-6-carbonitrile was dissolved in ethanol and cooled to 0° C. HCl gas was bubbled for 45 minutes into the solution, and the reaction solution was stirred at room temperature overnight and concentrated under reduced pressure to remove the solvent. The residue was dissolved in ethanol and ammonia gas was bubbled into the solution for one hour at 0° C. The reaction solution was stirred overnight at room temperature and then distilled under reduced pressure. The residue was purified with column chromatography [eluent: dichloromethane/methanol(4:1)] on NH-DM1020 silica to obtain 32 mg of the title compound a pale yellow solid.

$^1$H NMR(MeOH-d$_4$, ppm): δ7.93 (s, 1H), 7.66(d, 1H, J=8.41 Hz), 7.44(d, 1H, J=8.41 Hz), 7.34–7.27(m, 5H), 6.40(s, 1H), 4.28(q, 2H), 4.07(d, 1H), 2.95–2.88(m, 3H), 2.60(m, 1H), 2.31–1.90(m, 4H), 1.80–1.55 (m, 5H), 1.40(t, 3H), J=7.21 Hz)

EXAMPLE 2

Synthesis of Ethyl 2-[(S)-2-[2-(6-amidino-1-methylindol-2-yl)ethyl]pyrrolidinyl]-2-phenylacetate (Compound 2)

a) Synthesis of 6-cyano-1-methylindole-2-methyl triphenyl phosphonium bromide

The reaction was carried out according to the same procedure as Examples 1-a) through 1-f), except that iodomethane was used in place of iodoethane in Example 1-d), to obtain 15 g of the title compound as a pale brown solid.

$^1$H NMR(DMSO-d$_6$, ppm): δ8.00(s, 1H), 7.92(m, 3H), 7.84–7.68(m, 12H), 7.62(d, 1H, J=8.24 Hz), 7.35(d, 1H, J=8.24 Hz), 6.28(s, 1H), 5.57 (d, 2H, J=15.2 Hz), 3.19(s, 3H)

b) Synthesis of 1-methyl-2-[2-((S)-pyrrolidin-2-yl)ethyl]-indole-6-carbonitrile (Compound I-b)

6-Cyano-1-methylindole-2-methyl triphenylphosphonium bromide obtained in the above a) was reacted according to the same procedure as Example 1-l) to obtain 6.4 g of the title compound as a pale yellow foam.

$^1$H NMR(MeOH-d$_4$, ppm): δ7.83(s, 1H), 7.62(d, 1H, J=8.24 Hz), 7.30(d, 1H, J=8.24 Hz), 6.47(s, 1H), 3.80 (s, 3H), 3.64(m, 1H), 3.32(m, 2H), 3.00(m, 2H), 2.41–1.98(m, 5H), 1.80(m, 1H)

c) Synthesis of ethyl 2-[(S)-2-[2-(6-cyano-1-methylindol-2-yl)ethyl]pyrrolidinyl]-2-phenylacetate 90 mg of the compound I-b obtained in the above b) and 86 mg of ethyl-2-bromo-2-phenylacetate were treated according to the same procedure as Example 1-m) to obtain 85 mg of the title compound as a pale yellow solid.

d) Synthesis of ethyl 2-[(S)-2-[2-(6-amidino-1-methylindol-2-yl)ethyl]pyrrolidinyl]-2-phenylacetate 81 mg of ethyl 2-[(S)-2-[2-(6-cyano-1-methylindol-2-yl) ethyl]pyrrolidinyl]-2-phenylacetate obtained in the above c) was treated according to the same procedure as Example 1-n) to obtain 19 mg of the title compound as a pale yellow solid.

$^1$H NMR(MeOH-d$_4$, ppm): δ7.82(d, 1H, J=11.06 Hz), 7.52(d, 1H, J=8.1 Hz), 7.32(m, 3H), 7.19(m, 3H), 6.10(s, 1H), 4.36(s, 1H), 4.00(m, 2H), 1.95(m, 2H), 1.74–1.45(m, 6H), 1.06(m, 3H)

EXAMPLE 3

Synthesis of 2-[(S)-2-[2-(6-amidino-1-methylindol-2-yl)ethyl]pyrrolidinyl]-2-phenylacetic Acid (Compound 3)

13 g of ethyl 2-[(S)-2-[2-(6-amidino-1-methylindol-2-yl) ethyl]-pyrrolidinyl]-2-phenylacetate obtained in Example 2 was dissolved in 5 ml of 35% hydrochloric acid solution, and the resulting solution was heated to 60° C. and stirred for 1.5 hours, and then stirred at room temperature overnight. The reaction solvent was removed by distillation under reduced pressure. The residue was purified with column chromatography [eluent: dichloromethane/methanol (2:3)] on NH-DM1020 silica. The fractions containing the desired product were combined and then distilled under reduced pressure to obtain 6.2 mg of the title compound as a pale yellow solid.

$^1$H NMR(MeOH-d$_4$, ppm): δ7.75(s, 1H), 7.59–7.51(m, 1H), 7.31–7.20(m, 5H), 6.33(s, 1H), 4.13(s, 1H), 3.74 (s, 3H), 3.61(s, 1H), 2.98(m, 2H), 2.89(m, 3H), 2.75(m, 2H), 2.40(m, 1H), 2.35–2.05(m, 3H), 1.80–1.77(m, 6H)

EXAMPLE 4

Synthesis of 1-methyl-2-[2-[(S)-1-(1-naphthylmethyl) pyrrolidin-2yl]ethyl]indole-6-carboxamidine (Compound 4)

a) Synthesis of 1-methyl-2-[2-[(S)-1-(1-naphthylmethyl) pyrrolidin-2-yl]ethyl]indole-6-carbonitrile 89 mg of the compound I-b obtained in Example 2-b), 127 mg of 1-naphthalenemethanol and 148 mg of triphenylphosphine were dissolved in chloroform, and 104 μl of DEAD (diethylazodicarboxylate) was slowly added thereto while stirring at room temperature. The mixture was stirred at room temperature overnight and distilled under reduced pressure to remove the solvent. The residue was purified with silica gel column chromatography [eluent: n-hexane/methanol(1:1)]. The fraction containing the desired product was distilled under reduced pressure to obtain 33 mg of the title compound.

b) Synthesis of 1-methyl-2-[2-(S)-1-(1-naphthylmethyl) pyrrolidin-2-yl]ethyl]indole-6-carboxamide 30 mg of the compound obtained in the above a) was treated according to the same procedure as Example 1-n) to obtain 11 mg of the title compound as a yellow solid.

$^1$H NMR(MeOH-d$_4$, ppm): δ8.20(m, 1H), 7.76(m, 2H), 7.68(d, 1H, J=8.66 Hz), 7.52(d, 1H, J=8.21 Hz), 7.37–7.22(m, 5H), 6.21(s, 1H), 4.37(d, 1H), 3.65(m, 1H), 3.55(m, 1H), 2.10–1.90(m, 5H), 1.66–1.61 (m, 6H)

EXAMPLE 5

Synthesis of 1-methyl-2-[2-[(S)-1-(2-naphthylmethyl) pyrrolidin-2-yl]ethyl]indole-6-carboxamidine (Compound 5)

a) Synthesis of 1-methyl-2-[2-[(S)-1-(2-naphthylmethyl) pyrrolidin-2-yl]ethyl]indole-6-carbonitrile In a 25 ml flask, 70 mg of the compound I-b obtained in Example 2-b) and 54 mg of 2-naphthalenemethanol were dissolved in 5 ml of tetrahydrofuran. To the resulting solution, 105 mg of triphenylphosphine was added and 0.08 ml of DEAD was then added at room temperature. The mixture was stirred for about 40 hours at room temperature and then evaporated to remove the solvent. The residue was purified with silica gel column chromatography [eluent: ethyl acetate /methanol(10:1)]. The fractions containing the desired product were combined and then evaporated to obtain 20 mg of the title compound as a pale yellow solid.

$^1$H NMR(MeOH-$d_4$, ppm): δ7.81(m, 1H), 7.69(m, 4H), 7.52(m, 1H), 7.47 (m, 3H), 7.28(d, 1H), 6.30(s, 1H), 4.14(d, 1H), 3.60(s, 3H), 3.57(d, 1H), 2.99(m, 1H), 2.88(m, 1H), 2.76(m, 1H), 2.63(m, 1H), 2.40(m, 1H), 2.14(m, 2H), 1.79(m, 4H)

b) Synthesis of 1-methyl-2-[-2-[(S)-1-(2-naphthylmethyl) pyrrolidin-2-yl]ethyl]indole-6-carboxamidine 18 mg of the compound obtained in the above a) was treated according to the same procedure as Example 1-n) to obtain 10 mg of the title compound as a pale yellow solid.

$^1$H NMR(MeOH-$d_4$, ppm): δ7.76–7.62(m, 5H), 7.51(d, 1H), 7.35(m, 4H), 6.24(s, 1H), 4.06(d, 1H), 3.60(s, 3H), 3.45(d, 1H), 2.86(m, 1H), 2.72(m, 2H), 2.53(m, 1H), 2.27(m, 1H), 2.04(m, 2H), 1.69(m, 4H)

EXAMPLE 6

Synthesis of 1-methyl-2-[2-[(S)-1-(benzo[d]1,3-dioxolen-5-yl-methyl)pyrrolidin-2-yl]ethyl]indole-6-carboxamidine (Compound 6)

a) Synthesis of 1-methyl-2-[2-[(S)-1-(benzo[d]1,3-dioxolen-5-ylmethyl)pyrrolidin-2-yl]ethyl]indole-6-carbonitrile In a 100 ml flask, 100 mg of the compound I-b obtained in Example 2-b) and 66 mg of piperonyl alcohol were reacted according to the same procedure as Example 5-a) to obtain 40 mg of the title compound as a pale yellow solid.

$^1$H NMR(CDCl$_3$, ppm): δ7.56(m, 2H), 7.31(d, 1H), 6.83 (s, 1H), 6.72(m, 2H), 6.32(d, 1H), 5.91(s, 2H), 3.92(d, 1H), 3.69(s, 3H), 3.21(d, 1H), 2.98(m, 1H), 2.86–2.74 (m, 2H), 2.54(m, 1H), 2.19(m, 1H), 2.03(m, 2H), 1.77(m, 3H), 1.73(m, 1H)

b) Synthesis of 1-methyl-2-[2-[(S)-1-(benzo[d]1,3-dioxolen-5-ylmethyl)pyrrolidin-2-yl]ethyl]indole-6-carboxamidine 40 mg of the compound obtained in the above a) was treated according to the same procedure as Example 1-n) to obtain 16 mg of the title compound as a pale yellow solid.

$^1$H NMR(CDCl$_3$, ppm): δ7.89(m, 1H), 7.39(m, 2H), 6.79 (s, 1H), 6.69(m, 2H), 6.14(s, 1H), 5.89(s, 2H), 3.88(d, 1H), 3.57(s, 3H), 3.11(d, 1H), 2.91(m, 1H), 2.71–2.58 (m, 2H), 2.45(m, 1H), 2.09(m, 1H), 1.98(m, 2H), 1.68(m, 3H), 1.54(m, 1H)

MS: 405(M+1)$^+$, 271, 202, 135

EXAMPLE 7

Synthesis of Methyl 3-[[(S)-2-[2-(6-amidino-1-methylindol-2-yl)ethyl]pyrrolidin-2-yl]methyl]benzo[b]thiophene-2-carboxylate (Compound 7)

a) Synthesis of methyl 3-[[(S)-2-[2-(6-cyano-1-methylindol-2-yl)ethyl]pyrrolidin-2-yl]methyl]benzo[b]thiophene-2-carboxylate 80 mg of the compound I-b obtained in Example 2-b) was dissolved in dichloromethane and cooled to 0° C. To this solution, 59 μl, of triethylamine was added and 110 g of methyl 3-bromomethylbenzo[b]thiophene-2-carboxylate was slowly added. The reaction mixture was stirred for 3.5 hours at room temperature and diluted with excess of dichloromethane. The organic layer was washed with water, dried over MgSO$_4$ and then filtered under reduced pressure. The filtrate was then concentrated. The concentrate was purified with silica gel column chromatography [eluent: n-hexane/ethyl acetate(1:1)]. The fractions containing the desired product were combined and then evaporated to obtain 80 mg of the title compound as a white solid.

b) Synthesis of methyl 3-[[(S)-2-[2-(6-amidino-1-methylindol-2-yl)ethyl]pyrrolidin-2-yl]methyl]benzo[b]thiophene-2-carboxylate 80 mg of the compound obtained in the above a) was dissolved in 5 ml of methanol and cooled to 0° C. HCl gas was bubbled into the solution for 50 minutes and the reaction solution was stirred at room temperature overnight and concentrated under reduced pressure to remove the solvent. The residue was dissolved in 5 ml of methanol, and ammonia gas was bubbled for one hour at 0° C. into the solution. The reaction solution was stirred at room temperature overnight and then distilled under reduced pressure. The residue was purified with column chromatography [eluent: dichloromethane/methanol(4:1)] on NH-DM1020 silica to obtain 22 mg of the title compound as a pale yellow solid.

$^1$H NMR(MeOH-$d_4$, ppm): δ8.13(d, 1H, J=8.06 Hz), 7.88(s, 1H), 7.62(d, 1H, J=8.34 Hz), 7.47–7.37(m, 3H), 6.30(s, 1H), 4.55(d, 1H, J=12.4 Hz), 4.07(d, 1H, J=12.4 Hz), 3.83(s, 3H), 3.67(s, 3H), 2.83–2.67 (m, 4H), 2.26(m, 1H), 2.15–2.05(m, 2H), 1.69–1.57(m, 4H)

EXAMPLE 8

Synthesis of 3-[[(S)-2-[2-(6-amidino-1-ethylindol-2-yl)ethyl]pyrrolidin-2-yl]methyl]benzo[b]thiophene-2-carboxamide (Compound 8)

1.46 g of the compound I-a obtained in Example 1-l) was treated according to the same procedure as Example 7-a) to obtain 1.38 g of the white solid product, which was then treated according to the same procedure as Example 7-b) to obtain 930 mg of the title compound as a pale yellow solid.

$^1$H NMR(MeOH-$d_4$, ppm): δ7.95(d, 1H), 7.79(d, 1H), 7.73(m, 1H), 7.48(d, 1H), 7.33(m, 3H), 6.09(s, 1H), 4.22(d, 1H), 3.99(m, 2H), 3.92(d, 1H), 2.85(m, 1H), 2.68–2.61(m, 4H), 2.39(m, 1H), 2.15(m, 1H), 1.95(m, 1H), 1.74–1.58(m, 4H), 1.86(t, 3H)

EXAMPLE 9

Synthesis of 3-[[(S)-2-[2-(6-amidino-1-methylindol-2-yl)ethyl]pyrrolidin-2-yl]methyl]benzo[b]thiophene-2-carboxamide (Compound 9)

80 mg of 3-[[(S)-2-[2-(6-cyano-1-methylindol-2-yl)ethyl]pyrrolidin-2-yl]methyl]benzo[b]thiophene-2-carboxamide was treated according to the same procedure as Example 7-b) to obtain 36 mg of the title compound as a pale yellow solid.

$^1$H NMR(MeOH-d$_4$, ppm): δ7.90(d, 1H, J=7.5 Hz), 7.77 (d, 1H, J=7.42 Hz), 7.71(s, 1H), 7.47(d, 1H, J=8.36 Hz), 7.33–7.24(m, 3H), 6.10(s, 1H), 4.19(d, 1H, J=12.99 Hz), 4.14(d, 1H, J=7.58 Hz), 3.49(s, 1H), 2.85 (m, 1H), 2.71–2.60(m, 3H), 2.40(m, 1H), 1.92(m, 1H), 1.73–1.58(m, 4H)

EXAMPLE 10

Synthesis of 1-methyl-2-[2-[(S)-1-[[2-(N-methylcarbamoyl)benzo[b]thiophene-3-yl]methyl] pyrrolidin-2-yl]ethyl]indole-6-carboxamidine (Compound 10)

a) Synthesis of N-methyl [3-[[(S)-2-[2-(6-cyano-1-methylindol-2-yl)ethyl]pyrrolidinyl]methyl]benzo[b] thiophen-2-yl]formamide Methyl 3-[[(S)-2-[2-(6-cyano-1-methylindol-2-yl)ethyl] pyrrolidinyl]methyl]benzo[b]thiophene-2-carboxylate was dissolved in methanol solution of 40% methylamine and then stirred for 2 hours at room temperature. The reaction solution was evaporated to obtain the residue which was then purified with silica gel column chromatography [eluent: dichloromethane/ethyl acetate(2:1)] to obtain 70 mg of the title compound as a white foam.

$^1$H NMR(CDCl$_3$, ppm): δ10.64(d, 1H, J=4.83 Hz), 7.88 (d, 1H), 7.80(d, 1H), 7.55(d, 2H, J=8.19 Hz), 7.40(m, 1H), 7.35–7.31(m, 2H), 6.22(s, 1H), 4.18(d, 1H), 3.87 (d, 1H), 3.50(s, 3H), 3.02(d, 3H), 2.99(m, 1H), 2.77–2.70(m, 3H), 2.45(m, 1H), 2.13(m, 1H), 2.07(m, 1H), 1.85–1.82(m, 2H), 1.68–1.63(m, 2H)

b) Synthesis of 1-methyl-2-[2-[(S)-1-[[2-(N-methylcarbamoyl)benzo[b]thiophen-3-yl]methyl] pyrrolidin-2-yl]ethyl]indole-6-carboxamidine 35 mg of the compound obtained in the above a) was treated according to the same procedure as Example 1-n) to obtain 25 mg of the title compound.

$^1$H NMR(CDCl$_3$, ppm): δ10.67(d, 1H, J=4.17 Hz), 8.08(s, 1H), 7.81–7.76 (m, 2H), 7.49–7.45(m, 2H), 7.37–7.32 (m, 2H), 6.10(s, 1H), 4.04(d, 1H), 3.57(s, 3H), 2.93(d, 3H), 2.86(brs, 1H), 2.65(m, 3H), 2.33(m, 1H), 2.20–2.17(m, 1H), 2.02–1.96(m, 1H), 1.77–1.73(m, 2H), 1.58–1.54(m, 2H)

EXAMPLE 11

Synthesis of 1-methyl-2-[2-[(S)-1-[(4-methoxyphenyl)carbonyl]pyrrolidin-2-yl]ethyl] indole-6-carboxamidine (Compound 11)

a) Synthesis of 1-methyl-2-[2-[(S)-1-[(4-methoxyphenyl) carbonyl]pyrrolidin-2-yl]ethyl]indole-6-carbonitrile 70 mg of the compound I-b obtained in Example 2-b) and 67 mg of p-methoxybenzoic acid were dissolved in dichloromethane, and 119 mg of WSCIHCl (1-ethyl-3-(3-dimethylaminopropyl)carbodiimide hydrochloride) was added thereto. The reaction mixture was stirred for 2.5 hours at room temperature, and water was added thereto. The reaction solution was extracted two times with dichloromethane. The extracts were combined, dried over MgSO$_4$ and then concentrated. The residue was purified with silica gel column chromatography [eluent: dichloromethane/ methanol(50:1)] to obtain 78 mg of the title compound as a white solid.

$^1$H NMR(CDCl$_3$, ppm): δ7.54–7.45(m, 2H), 7.26(d, 1H), 7.20–7.13(dd, 2H), 6.90–6.80(dd, 2H), 6.39(s, 1H), 4.29–4.18(brs, 1H), 3.78(s, 3H), 3.66(s, 3H), 3.50(t, 2H), 2.79(t, 2H), 2.20–2.33(m, 1H), 1.97(m, 3H), 1.74 (m, 2H)

b) Synthesis of 1-methyl-2-[2-[(S)-1-[(4-methoxyphenyl) carbonyl]pyrrolidin-2-yl]ethyl]indole-6-carboxamidine:

78 mg of the compound obtained in the above a) was treated according to the same procedure as Example 1-n) to obtain 26 mg of the title compound as a yellowish white solid.

$^1$H NMR(MeOH-d$_4$, ppm): δ7.76(s, 1H), 7.48(d, 1H), 7.06(d, 2H), 6.77(d, 2H), 6.33(s, 1H), 4.13–4.05(brs, 1H), 3.65(s, 3H), 3.49(s, 3H), 3.54–3.40(m, 2H), 2.82–2.75(m, 2H), 2.25–1.60(m, 6H)

EXAMPLE 12

Synthesis of 1-methyl-2-[2-[(S)-1-[(3,4-dimethoxyphenyl)carbonyl]pyrrolidin-2-yl]indole-6-carboxamidine (Compound 12)

a) Synthesis of 1-methyl-2-[2-[(S)-1-[(3,4-dimethoxyphenyl)carbonyl]-pyrrolidin-2-yl]ethyl]indole-6-carbonitrile:

50 mg of the compound I-b obtained in Example 2-b) and 52 mg of 3,4-dimthoxybenzoic acid were reacted according to the same procedure as Example 11-a) to obtain 53 mg of the title compound as a white solid.

$^1$H NMR(MeOH-d$_4$, ppm): δ7.77(s, 1H), 7.54(d, 1H), 7.25(d, 1H), 7.10(s, 2H), 7.00(d, 1H), 6.50(s, 1H), 4.38–4.25(brs, 1H), 3.83(s, 3H), 3.78(s, 3H), 3.65–3.50 (m, 2H), 2.97–2.87(m, 2H), 2.28–1.60(m, 6H) ps b) Synthesis of 1-methyl-2-[2-[(2S)-1-[(3,4-dimethoxyphenyl)carbonyl]pyrrolidin-2-yl]ethyl] indole-6-carboxamidine:

42 mg of the compound obtained in the above a) was treated according to the same procedure as Example 1-n) to obtain 21 mg of the title compound as a yellowish green solid.

$^1$H NMR(CDCl$_3$, ppm): δ7.47–7.40(d, 1H), 7.32–7.20(m, 1H), 7.09(brs, 2H), 6.83–6.81(br, 1H), 6.24(s, 1H), 4.33(brs, 1H), 3.89(s, 3H), 3.86(s, 3H), 3.73(bs, 2H), 3.48(s, 3H), 2.79(brs, 2H), 2.22–1.60(m, 6H)

EXAMPLE 13

Synthesis of 1-methyl-2-[2-[(S)-1-(2-phenylacetyl) pyrrolidin-2-yl]ethyl]indole-6-carboxamidine (Compound 13)

500 mg of the compound I-b obtained in Example 2-b) was dissolved in 10 ml of dichloromethane, and 460 μl of triethylamine and 0.35 ml of phenylacetyl chloride were added thereto. The reaction mixture was treated according to the same procedure as Example 1-m) to obtain 430 mg of 1-methyl-2-[2-[(S)-1-(2-phenylacetyl)pyrrolidin-2-yl] ethyl]-indole-6-carbonitrile, which was then treated according to the same procedure as Example 1-n) to obtain 267 mg of the title compound.

$^1$H NMR(MeOH-d$_4$, ppm): δ7.92(m 1H), 7.66(m, 1H), 7.61(m, 1H), 7.36–7.28(m, 5H), 6.46(s, 1H), 4.21(m, 1H), 3.85(s, 3H), 3.77(m, 2H), 3.60(t, 3H, J=6.60 Hz), 2.84(m, 2H), 2.27(m, 1H), 1.99–1.82(m, 6H)

EXAMPLE 14

Synthesis of 1-ethyl-2-[2-[(S)-1-(2-phenylacetyl)-pyrrolidin-2-yl]ethyl]indole-6-carboxamidine (Compound 14)

a) Synthesis of 1-ethyl-2-[2-[(2S)-1-(2-phenylacetyl)pyrrolidin-2-yl]-ethyl]indole-6-carbonitrile:

80 mg of the compound I-a obtained in Example 1-l) was dissolved in dichloromethane and then cooled to 0° C. To this solution, 56 µl of triethylamine was added and 53 µl of phenylacetyl chloride was then slowly added. The reaction mixture was stirred for 4 hours at room temperature and then diluted with excess of dichloromethane. The organic layer was washed with water, dried over MgSO$_4$ and filtered under reduced pressure. The filtrate was concentrated. The concentrate was then purified with silica gel column chromatography [eluent: dichloromethane/methanol(10:1)]. The fractions containing the desired product were combined and evaporated to obtain 81 mg of the title compound as a pale yellow solid.

b) Synthesis of 1-ethyl-2-[2-[(S)-1-(2-phenylacetyl)pyrrolidin-2-yl]ethyl]-indole-6-carboxamidine:

80 mg of the compound obtained in the above a) was treated according to the same procedure as Example 1-n) to obtain 60 mg of the title compound as a pale yellow solid.

$^1$H NMR(MeOH-d$_4$, ppm): δ7.81(m 1H, J=7.15 Hz), 7.53(d, 1H, J=8.33 Hz), 7.30(d, 1H, J=8.33 Hz), 7.22–7.13(m, 4H), 6.36(s, 1H), 4.14 (m, 3H), 3.62(d, 1H), 3.49(m, 2H), 2.73(t, 2H, J=8.13 Hz), 2.15(m, 1H), 1.93–1.86(m, 5H), 1.26(t, 3H, J=7.15 Hz)

EXAMPLE 15

Synthesis of 1-ethyl-2-[2-(S)-1-[2-(3-chlorophenyl)acetyl]pyrrolidin-2-yl]ethyl]indole-6-carboxamidine (Compound 15)

70 mg of the compound I-a obtained in Example 1-l) and 67 mg of 3-chlorophenylacetic acid were treated according to the same procedure as Example 11-a) to obtain 40 mg of the pale yellow oily product. 38 mg of this product was then treated according to the same procedure as Example 1-n) to obtain 18 mg of the title compound as a pale yellow solid.

$^1$H NMR(CDCl$_3$, ppm): δ7.84(s, 1H), 7.41(d, 1H, J=8.24 Hz), 7.16–7.12(m, 4H), 7.06(m, 1H), 6.27(s, 1H), 4.15–4.10(m, 3H), 3.54(s, 2H), 3.49–3.42(m, 2H), 2.70–2.65(m, 2H), 2.24–2.20(m, 1H), 1.97–1.89 (m, 3H), 1.71–1.63(m, 2H), 1.25(t, 3H, J=7.00 Hz)

EXAMPLE 16

Synthesis of 1-ethyl-2-[2-[(S)-1-[2-(3-hydroxyphenyl)acetyl]pyrrolidin-2-yl]ethyl]indole-6-carboxamidine (Compound 16)

a) Synthesis of 2-[3-(1,1,2,2-tetramethyl-1-silapropoxy)phenyl]acetic acid:

1 g of 3-hydroxyphenylacetic acid was dissolved in 10 ml of N,N-dimethylformamide, and 3.97 g of TBDMSCl (terbutyl dimethylsilyl chloride) and 2.69 g of imidazole were added thereto. The reaction mixture was stirred for 14 hours at room temperature and then for 4 hours at 35° C. The reaction solution was diluted with 150 ml of dichloromethane and then washed with saturated saline and 0.7N cold HCl solution. The organic layer was washed again with saturated saline, dried over sodium sulfate and filtered. The filtrate was concentrated. The residue was then dissolved in 20 ml of methanol and 8 ml of tetrahydrofuran, and aqueous K$_2$CO$_3$ solution (400 mg/8 ml) was added thereto. The reaction mixture was stirred for 1.5 hours at room temperature and then concentrated. To the residue was added saturated saline and the reaction solution was acidified with 10% aqueous citric acid solution to pH 4 and extracted with dichloromethane (100 ml×2). The organic layer was washed with saturated saline, dried over sodium sulfate and then filtered. The filtrate was concentrated. The residue was then purified with silica gel column chromatography [eluent: n-hexane/ethyl acetate(1:1)] to obtain 1.69 g of the title compound as a pale yellow oil.

$^1$H NMR(CDCl$_3$, ppm): δ7.02–6.95(m, 1H), 6.73–6.69 (m, 1H), 6.59–6.53 (m, 2H), 3.40(s, 2H), 0.79(s, 9H), 0.01(s, 6H)

b) Synthesis of 1-ethyl-2-[2-[(S)-1-[2-[3-(1,1,2,2-tetramethyl-1-silapropoxy)phenyl]acetyl]pyrrolidin-2-yl]ethyl]indole-6-carbonitrile:

300 mg of the compound obtained in the above a) was treated according to the same procedure as Example 11-a) to obtain 170 mg of the title compound as a colorless oil.

$^1$H NMR(CDCl$_3$, ppm): δ7.42–7.36(m, 2H), 7.12–7.09 (m, 1H), 7.02–6.97 (m, 1H), 6.71–6.68(m, 1H), 6.61–6.54(m, 2H), 6.23(s, 1H), 4.13 (brs, 1H), 3.95(q, 2H), 3.45(s, 2H), 3.31–3.27(m, 2H), 2.60(t, 2H), 2.20–2.11(m, 1H), 1.81–1.74(m, 3H), 1.57–1.55(m, 2H), 1.18(t, 3H, J=7.20 Hz), 0.78(s, 9H), 0.01(s, 6H)

c) Synthesis of 1-ethyl-2-[2-[(S)-1-[2-(3-hydroxyphenyl)acetyl]pyrrolidin-2-yl]ethyl]indole-6-carbonitrile:

170 mg of the compound obtained in the above b) was dissolved in 10 ml of tetrahydrofuran and then cooled to 0° C. To the resulting solution was added 1.65 ml of 1.0M tetrabutylammonium fluoride solution, and the mixture was stirred for 45 minutes at the same temperature. After adding saturated saline, the reaction solution was extracted with ethyl acetate, and the organic layer was dried over sodium sulfate and filtered. The filtrate was concentrated. The residue was purified with silica gel column chromatography [eluent: dichloromethane/ethyl acetate (1:1)] to obtain 120 mg of the title compound as a colorless oil.

$^1$H NMR(CDCl$_3$, ppm): δ8.66(brs, 1H), 7.35–7.29(m, 2H), 7.12–7.07(m, 1H), 7.00–6.93(m, 2H), 6.60–6.50 (m, 2H), 6.13(s, 1H), 4.13(brs, 1H), 3.87(m, 2H), 3.39(s, 2H), 3.31(m, 2H), 2.57–2.54(m, 2H), 2.12–2.09 (m, 1H), 1.77–1.74(m, 3H), 1.58–1.43(m, 2H), 1.09(t, 3H)

d) Synthesis of 1-ethyl-2-[2-[(S)-1-[2-(3-hydroxyphenyl)acetyl]pyrrolidin-2-ethyl]indole-6-carboxamidine:

70 mg of the compound obtained in the above c) was treated according to the same procedure as Example 1-n) to obtain 55 mg of the title compound as a pale yellow solid.

$^1$H NMR(CDCl$_3$, ppm): δ7.80(d, 1H), 7.54(d, 1H), 7.33 (dd, 1H), J=8.35 Hz, J=1.75 Hz), 7.01(t, 1H), 6.60(m, 3H), 6.38(s, 1H), 4.18–4.14(m, 3H), 3.53–3.47(m, 4H), 2.73(t, 2H), 2.17–2.11(m, 1H), 1.92–1.73(m, 5H), 1.27 (t, 3H)

EXAMPLE 17

Synthesis of 1ethyl-2-[2-[(S)-1-[2-[3-(carbamoylmethoxy)phenyl]acetyl]pyrrolidin-2-yl]ethyl]indole-6-carboxamidine (Compound 18)

a) Synthesis of ethyl 2-[3-[2-[(S)-2-[2-(6-cyano-1-ethyl]indole-2-yl)ethyl]pyrrolidin-2-yl]-2-oxoethyl]phenoxy]acetate:

58 mg (0.146 mmole) of 1-ethyl-2-[2-[(S)-1-[2-(3-hydroxyphenyl)acetyl]pyrrolidin-2-yl]ethyl]indole-6-carbonitrile obtained in Example 16-c) and 26 µl of ethyl bromoacetate were dissolved in 5 ml of dimethylformamide and then cooled to 0° C. After adding NaH, the reaction mixture was stirred for 30 minutes at the same temperature and then for one hour at room temperature. 5 ml of water was added, and the reaction solution was extracted with ethyl acetate. The organic layer was washed with saturated saline, dried over sodium sulfate and then filtered. The filtrate was concentrated, and the residue was purified with silica gel column chromatography [eluent: dichloromethane/ethyl acetate(1:1)] to obtain 53 mg of the title compound as a colorless oil.

$^1$H NMR(CDCl$_3$, ppm): δ7.42–7.37(m, 2H), 7.13–7.04 (m, 2H), 6.76–6.70 (m, 2H), 6.63(m, 1H), 6.24(s, 1H), 4.43(s, 2H), 4.12–4.04(m, 3H), 3.96(m, 2H), 3.46(s, 2H), 3.33(m, 2H), 2.60(t, 2H), 2.21–2.14(m, 1H), 1.82–1.77(m, 3H), 1.58–1.54(m, 2H), 1.19–1.09(m, 6H)

b) Synthesis of 1-ethyl-2-[2-[(S)-1-[2-[3-(carbamoylmethoxy)phenyl]-acetyl]pyrrolidin-2-yl]ethyl]indole-6-carboxamidine:

38 mg of the compound obtained in the above a) was treated according to the same procedure as Example 1-n) to obtain 18 mg of the title compound as a pale yellow solid.

$^1$H NMR(CDCl$_3$, ppm): δ7.18(d, 1H), 7.54(d, 1H), 7.32 (m, 1H), 7.16(t, 1H), 6.83–6.78(m, 3H), 6.38(s, 1H), 4.37(s, 2H), 4.21–4.13(m, 3H), 3.60(d, 2H), 3.52–3.48 (m, 2H), 2.74(t, 2H), 2.18–2.13(m, 1H), 1.97–1.86(m, 3H), 1.79–1.75(m, 2H), 1.26(t, 3H)

EXAMPLE 18

Synthesis of 2-[3-[2-[(S)-2-[2-(6-amidino-1-ethyl-indol-2-yl)ethyl]pyrrolidin-2-yl]-2-oxoethyl]phenoxy]acetic acid (Compound 19)

7 mg of 1-ethyl-2-[2-(S)-1-[2-[3-(carbamoylmethoxy)phenyl]acetyl]pyrrolidin-2-yl]ethyl]indole-6-carboxamidine obtained in Example 17 was dissolved in 0.5 ml of acetic acid and 1 ml of 3N HCl solution, and the resulting solution was heated to refluxing temperature and stirred for 3 hours under refluxing. The reaction solution was concentrated to remove the solvent and the residue was then purified with column chromatography [eluent: ethyl acetate/methanol (1:1)] on NH-DM1020 silica to obtain 4 mg of the title compound as a pale yellow solid.

$^1$H NMR(CDCl$_3$, ppm): δ7.78(s, 1H), 7.50(d, 1H, J=7.58 Hz), 7.35–7.28(m, 1H), 7.12–7.06(m, 1H), 6.75–6.69 (m, 3H), 6.33(s, 1H), 4.24(s, 2H), 4.15–4.06(m, 3H), 3.58–3.47(m, 4H), 2.69–2.65(m, 2H), 2.14–2.09 (m, 1H), 1.94–1.88(m, 3H), 1.80–1.73(m, 2H), 1.22(t, 3H)

EXAMPLE 19

Synthesis of 1ethyl-2-[2-[(S)-1-[2-[3-(trifluoromethyl)phenyl]acetyl]pyrrolidin-2-yl]ethyl]indole-6-carboxamidine (Compound 20)

100 mg of the compound I-a obtained in Example 1-l) and 120 mg of 3-(trifluoromethyl)phenylacetic acid were reacted according to the same procedure as Example 11-a) to obtain 80 mg of the product, which was then treated according to the same procedure as Example 1-n) to obtain 34 mg of the title compound as a pale yellow solid.

$^1$H NMR(MeOH-d$_4$, ppm): δ7.94(m, 1H), 7.65–7.45(m, 6H), 6.46(s, 1H), 4.28(m, 3H), 3.82(m, 1H), 3.46(m, 2H), 2.87(t, 2H), 2.30(m, 1H), 2.05(m, 4H), 1.91–1.82 (m, 2H), 1.36(m, 3H)

EXAMPLE 20

Synthesis of 1ethyl-2-[2-[(S)-1-[2-(2-nitrophenyl)acetyl]pyrrolidin-2-yl]ethyl]indole-6-carboxamidine (Compound 21)

270 mg of the compound I-a obtained in Example 1-l) and 250 mg of 2-nitrophenylacetic acid were reacted according to the same procedure as Example 11-a) to obtain 180 mg of the white solid product. 60 mg of the resulting product was then treated according to the same procedure as Example 1-n) to obtain 30 mg of the title compound as a pale yellow solid.

$^1$H NMR(MeOH-d$_4$, ppm): δ800(d, 1H), 7.76(m, 1H), 7.54–7.33(m, 5H), 6.31(s, 1H), 4.14(m, 3H), 3.96(m, 2H), 3.61(m, 2H), 2.72(t, 2H), 1.98–1.90(m, 6H), 1.80 (m, 2H), 1.26(t, 3H)

EXAMPLE 21

Synthesis of 1-ethyl-2-[2-[2-[(S)-1-[2-[2-(methylsulfonylamino)phenyl]acetyl]pyrrolidin-2-yl]ethyl]indole-6-carboxamidine (Compound 22)

110 mg of 1-ethyl-2-[2-[(S)-1-2-(2-nitrophenyl)acetyl]pyrrolidin-2-yl]ethyl]indole-6-carbonitrile was dissolved in 10 ml of ethanol, and 15 mg of 10% Pd/C was added thereto. The reaction mixture was stirred for 4 hours in hydrogen atmosphere at room temperature under normal pressure and then filtered under reduced pressure. The filtrate was distilled under reduced pressure and dried to obtain 110 mg of the product. To 70 mg of the resulting product thus obtained was added 3 ml of pyridine and methanesulfonyl chloride was then slowly added thereto at 0° C. The reaction mixture was stirred for 3 hours at 0° C., and excess of ethyl acetate was added thereto. The organic layer was washed three times with water and 1N aqueous HCl solution, dried over sodium sulfate and then filtered under reduced pressure. The filtrate was distilled under reduced pressure. The residue was purified with silica gel column chromatography [eluent: n-hexane/ethyl acetate(1:2)]. The fractions containing the desired product were combined and distilled under reduced pressure to obtain 80 mg of the white foamy product. 74 mg of the product thereby obtained was treated according to the same procedure as Example 1-n) to obtain 34 mg of the title compound as a pale yellow solid.

$^1$H NMR(MeOH-d$_4$, ppm): δ7.81(m, 1H), 7.53(d, 1H), 7.29(m, 2H), 7.16 (m, 2H), 7.03(t, 1H), 6.37(s, 1H), 4.19–4.12(m, 3H), 3.75(d, 1H), 3.59(m, 2H), 2.84(s, 3H), 2.74(t, 2H), J=8.09 Hz), 1.96–1.91(m, 4H), 1.77(m, 2H), 1.25(t, 3H)

EXAMPLE 22

Synthesis of ethyl 2-[2-[(S)-2-[2-(6-amidino-1-ethylindol-2-yl)ethyl]pyrrolidin-2yl]-2-oxoethyl]benzoate (Compound 23)

a) Synthesis of 2-[2-[(S)-2-[2-(6-cyano-1-ethylindol-2-yl)ethyl]pyrrolidinyl]-2-oxoethyl]benzoic acid:

985 mg of the compound I-a obtained in Example 1-l) was dissolved in 40 ml of ethanol, and 956 mg of 75% homophthalic anhydride and 1.05 ml of triethylamine were added thereto. The resulting solution was stirred for one hour at room temperature and distilled under reduced pressure to remove ethanol. To the residue was added water. The mixture was extracted with dichloromethane. The organic layer was then washed with 1N-HCl and water, dried over sodium sulfate, and then filtered. The filtrate was distilled under reduced pressure to obtain 1.57 g of the title compound as a yellow foamy solid.

$^1$H NMR(CDCl$_3$, ppm): δ7.95(dd, 1H, J=7.80 Hz, 1.30 Hz), 7.50–7.44(m, 2H), 7.37–7.34(m, 2H), 7.17–7.25 (m, 2H), 6.33(s, 1H), 4.28(s, 2H), 4.06–3.98(m, 3H), 3.94–3.91(m, 2H), 3.75–3.71(m, 2H), 2.24–2.21 (m, 1H), 2.10–2.05(m, 3H), 1.79–1.72(m, 2H), 1.25–1.21 (m, 3H)

b) Synthesis of ethyl 2-[2-[(S)-2-[2-(6-amidino-1-ethylindol-2yl)ethyl]pyrrolidin-2-yl]-2-oxoethyl]benzoate:

150 mg of the compound obtained in the above a) was treated according to the same procedure as Example 1-n) to obtain 50 mg of the title compound as a pale yellow solid.

$^1$H NMR(MeOH-d$_4$, ppm): δ7.87(dd, 1H, J=7.85 Hz, 1.40 Hz), 7.76(s, 1H), 7.48(d, 1H, J=8.30 Hz), 7.39(d, 1H, J=1.50 Hz), 7.30–7.25(m, 2H), 1.78–1.15(m, 1H), 6.32 (s, 1H), 4.14–4.09(m, 5H), 3.93(d, 2H, J=7.96 Hz), 3.58–3.55(m, 2H), 2.74–2.71(m, 2H), 2.14–2.11(m, 1H), 1.96–1.93(m, 3H), 1.83–1.80(m, 2H), 1.19–1.11 (m, 6H)

ES-MS: 475(M+1)$^+$

EXAMPLE 23

Synthesis of 2-[2-[(S)-2-[2-(6-amidino-1-ethylindol-2-yl)ethyl]pyrrolidinyl]-2-oxoethyl]benzoic acid (Compound 24)

150 mg of 2-[2-[(S)-2-[2-(6-cyano-1-ethylindol-2-yl)ethyl]pyrrolidinyl]-2-oxoethyl]benzoic acid obtained in Example 22-a) was treated according to the same procedure as Example 1-n) to obtain 28 mg of the title compound as a pale yellow solid.

$^1$H NMR(MeOH-d$_4$, ppm): δ7.68(s, 1H, J=7.60 Hz), 7.62(dd, 1H, J=7.60 Hz, 2.00 Hz), 7.43(d, 1H, J=8.30 Hz), 7.22–7.15(m, 4H), 6.37(s, 1H). 4.15–4.10(m, 4H), 3.85(d, 1H, J=15.80 Hz), 3.54–3.51(m, 2H), 2.77–2.74 (m, 2H), 2.21–2.16(m, 1H), 1.98–1.93(m, 3H), 1.82–1.78 (m, 2H), 1.28–1.22(m, 3H)

ES-MS: 447(M+1)$^+$

EXAMPLE 24

Synthesis of 1-ethyl-2-[2-[(S)-1-(2-cyclopentyl-2-phenylacetyl)pyrrolidin-2-yl]ethyl]indole-6-carboxamidine (Compound 30)

a) Synthesis of 2-cyclopentyl-2-phenylacetyl chloride:

In a 100 ml flask, 0.2 g of 2-cyclopentyl-2-phenylacetic acid was introduced and 8 ml of thionyl chloride was slowly added thereto at 0° C. The reaction mixture was stirred for 4 hours at 70 ° C. and then evaporated under reduced pressure to remove the solvent. The residue was dried under reduced pressure to obtain 0.2 g of the title compound as a brown oil.

b) Synthesis of 1-ethyl-2-[2-[(S)-1-(2-cyclopentyl-2-phenylacetyl)pyrrolidin-2-ethyl]indole-6-carbonitrile:

300 mg of the compound I-a obtained in Example 1-l) and 30 mg of 2-cyclo-pentyl-2-phenylacetyl chloride were treated according to the same procedure as Example 1-m) to obtain 30 mg of the title compound as a yellow oil.

$^1$H NMR(CDCl$_3$, ppm): δ7.53(m, 2H), 7.36–7.21(m, 6H), 6.28(s, 1H), 4.33(m, 1H), 4.13(m, 2H), 3.59(m, 1H), 3.38–3.30(m, 2H), 2.64(m, 3H), 2.07–1.92(m, 6H), 1.62(m, 6H), 1.26(m, 3H), 1.09(m, 2H)

c) Synthesis of 1-ethyl-2-[2-[(S)-1-(2-cyclopentyl-2-phenylacetyl)pyrrolidin-2-yl]ethyl]indole-6-carboxamidine:

26 mg of the compound obtained in the above b) was treated according to the same procedure as Example 1-n) to obtain 20 mg of the title compound as a pale yellow solid.

$^1$H NMR(CDCl$_3$, ppm): δ8.03(s, 1H), 7.40–7.18(m, 7H), 6.16(s, 1H), 4.27(m, 1H), 4.10 (m, 2H), 3.55(m, 1H), 3.37–3.28(m, 2H), 2.58(m, 3H), 2.01–1.90(m, 6H), 1.57(m, 6H), 1.25(m, 3H), 1.07(m 2H)

EXAMPLE 25

Synthesis of 1ethyl-2-[2-[(S)-1-(2-hydroxy-2-phenylacetyl)pyrrolidin-2-yl]ethyl]indole-6-carboxamidine (Compound 31)

250 mg of the compound I-a obtained in Example 1-l) and 140 mg of benzoylformic acid were dissolved in 10 ml of dichloromethane, and 358 mg of WSCIHCl was then slowly added thereto at 0° C. The reaction mixture was stirred at room temperature overnight, and excess of dichloromethane was added thereto. The organic layer was washed with water, dried over anhydrous magnesium sulfate and then filtered under reduced pressure. The filtrate was distilled under reduced pressure. The residue was purified with silica gel column chromatography [eluent: n-hexane/ethyl acetate (2:1)]. The fractions containing the desired product were combined and distilled under reduced pressure to obtain 83 mg of the product, which was then dissolved in 5 ml of methanol, and 16 mg of NaBH$_4$ was added at room temperature thereto. The mixture was stirred for one hour and then distilled under reduced pressure to remove the reaction solvent. The residue was purified with silica gel column chromatography [eluent: n-hexane/ethyl acetate(1:1)]. The fractions containing the desired product were combined and then distilled under reduced pressure to obtain 15 mg of the white solid product, which was then treated according to the same procedure as Example 1-n) to obtain 7 mg of the title compound as a pale yellow solid.

$^1$H NMR(MeOH-d$_4$, ppm): δ7.81(m, 1H), 7.55(d, 1H), 7.34–7.23(m, 6H), 6.41(s, 1H), 4.23(m, 2H), 4.10(m, 1H), 3.49(m, 2H), 3.10(m, 1H), 2.78(t, 2H), 2.25(m, 1H), 1.91(m, 1H), 1.79–1.72(m, 5H, 1.30(t, 3H)

EXAMPLE 26

Synthesis of 1-methyl-2-[2-[(S)-2-[(R)-2-acetylamino-2-(4-hydroxyphenyl)acetyl]pyrrolidin-2-yl]ethyl]indole-6-carboxamidine (Compound32)

1.00 g of the compound I-b obtained in Example 2-b) and 1.1 g of (R)-2-(acetylamino)-2-(4-acetyloxyphenyl)acetic acid were treated according to the same procedure as Example 11 -a) to obtain 1.67 g of 4-[2-[(S)-2-[2-(6cyano-1-methylindol-2-yl)ethyl]pyrrolidinyl]-(R)-1-acetylamino-2-oxoethyl]phenyl acetate. 96 mg of the compound thereby obtained was treated according to the same procedure as Example 1-n) to obtain 48 mg of the title compound as a pale yellow solid.

$^1$H NMR(MeOH-d$_4$, ppm): δ7.80(s, 1H), 7.52(d, 1H, J=8.25 Hz), 7.32(d, 1H, J=8.33 Hz), 7.08(d, 2H, J=8.46 Hz), 6.62(d, 2H, J=9.42 Hz), 6.36 (s, 1H), 4.09(brs, 1H), 3.70(s, 3H), 1.86(s, 3H)

EXAMPLE 27

Synthesis of 1ethyl-2-[2-[(S)-1-((R)-2-methylsulfonylamino-2-phenylacetyl)pyrrolidin-2-yl]ethyl]indole-6-carboxamidine (Compound 37)

1.00 g of (R)-(-)-2-phenylglycine, 10 ml of 1,4-dioxane and 10 ml of 2N aqueous NaOH solution were mixed, and 1.73 g of (BOC)$_2$O was slowly added at 0° C. The reaction mixture was stirred overnight at room temperature and distilled under reduced pressure to remove 1,4-dioxane. To the residue were added 50 ml of water and 5 ml of aqueous NH$_4$OH solution. The aqueous layer was washed with dichloromethane, acidified with c-HCl, and then extracted with ethyl acetate. The extract was dried over sodium sulfate and distilled under reduced pressure to obtain 1.6 g of liquid (R)-2-[(tert-butoxy)carbonylamino]-2-phenylacetic acid. 507 mg of (R)-2-[tert-butoxy)carbonylamino]-2-phenylacetic acid and 450 mg of 1-ethyl-2-[((S)-pyrrolidin-2-yl)ethyl]indole-6-carbonitrile were then treated according to the same procedure as Example 11-a) to obatin the product, which was then dissolved in dichloromethane. To the resulting solution, 4 ml of trifluoroacetic acid was added. The reaction solution was stirred overnight at room temperature and extracted with excess of dichloromethane. The oragnic layer was neutralized with aqueous NaHCO₃ solution and then extracted with dichloromethane. The extract was dried over MgSO₄ and filtered under reduced pressure. The filtrate was then distilled under reduced pressure. The remaining residue was purified with silica gel column chromatography [eluent: dichloromethane/methanol(10:1)]. The fractions containing the desired product were combined and then distilled under reduced pressure to obtain 290 mg of the white solid product. 80 mg of the resulting product 1-ethyl-2-[2-[(S)-1-((R)-2-amino-2-2-phenylacetyl)pyrrolidin-2-yl]ethyl]indole-6-carbonitrile was dissolved in 5 ml of dichloromethane, and triethylamine (0.299 mmole) and methanesulfonyl chloride (0.299 mmole) were added at 0° C. thereto. The reaction mixture was stirred for 3 hours at 0° C. and excess of dichloromethane was added thereto. The organic layer was washed with water, dried over Na₂SO₄ and then filtered under reduced pressure. The filtrate was evaporated under reduced pressure. The residue was purified with silica gel column chromatography [eluent: n-hexane/ethyl acetate(1:2)] to obtain 90 mg of the white foamy solid product. Finally, 70 mg of the resulting compound, 1-ethyl-2-[2-(S)-1-((R)-2-methylsulfonylamino- 2-phenylacetyl) pyrrolidin-2-yl]ethyl]indole-6-carbonitrile was treated according to the same procedure as Example 1-n) to obtain 28 mg of the title compound as a pale yellow solid.

¹H NMR(MeOH-d₄, ppm): δ7.81(s, 1H), 7.55(d, 1H, J=8.08 Hz), 7.37–7.19(m, 6H), 6.39(s, 1H), 5.21(s, 1H), 4.23–4.12(m, 3H), 3.62(m, 1H), 3.12(m, 1H), 2.80(t, 2H), 2.68(s, 3H), 2.25(m, 1H), 1.93(m, 2H), 1.81–1.74(m, 6H), 1.30(t, 3H)

EXAMPLE 28

Synthesis of ethyl 2-[[(R)-2-[2-[(S)-2-[2-(6-amidino-1ethylindol-2-yl)ethyl]pyrrolidinyl]-2-oxo1-phenyl]ethyl]amino]acetate (Compound 38 )

192 mg of 1-ethyl-2-[2-[(S)-2-((R)-2-amino-2-phenylacetyl)pyrrolidin-2-yl]ethyl]indole-6-carbonitrile obtained in Example 27 and 120 mg of ethyl bromoacetate were treated according to the same procedure as Example 1-m) to obtain 129 mg of ethyl 2-[[(R)-2-[2-[(S)-2-[2-(6-cyano-1-ethylindol-2yl)ethyl]pyrrolidinyl]-2-oxo-1-phenylethyl]amino]acetate. 120 mg of the resulting compound was treated according to the same procedure as Example 1-n) to obtain 34 mg of the title compound as a pale yellow solid.

¹H NMR(MeOH-d₄, ppm): δ7.81(s, 1H), 7.54(t, 1H), 7.48–7.22(m, 6H), 6.39(s, 1H), 4.52(s, 1H), 4.21(m, 2H), 4.06–4.01(m, 2H), 3.56(m, 2H), 3.05(m, 1H), 2.78(m, 2H), 2.25(m, 1H), 1.80–1.68(m, 7H), 1.29(t, 3H), J=7.10 Hz), 1.13(m, 3H)

EXAMPLE 29

Synthesis of 1ethyl-2-[2-[(S)-1-[(R)-2-(carbamoylmethylamino)-2-phenylacetyl]pyrrolidin-2-yl]ethyl]indole-6-carboxamidine (Compound 39)

129 mg of ethyl 2-[[(R)-2-[2-[(S)-2-[2-(6-cyano-1-ethylindol-2-yl)ethyl]pyrrolidinyl]-2-oxo-1-phenyl]ethyl]amino]acetate obtained in Example 28 was treated according to the same procedure as Example 1-n) to obtain 40 mg of the title compound as a pale yellow solid.

¹H NMR(MeOH-d₄, ppm): δ7.81(s, 1H), 7.50(m, 1H), 7.34–7.13(m, 6H), 6.39(s, 1H), 4.46(s, 1H), 4.21(d, 2H), 4.08(m, 1H), 3.60(m, 1H), 3.24–2.97(m, 3H), 2.77(t, 2H, J=7.58 Hz), 2.30(m, 1H), 1.92(m, 2H), 1.80–1.68(m, 5H), 1.28(t, 3H), J=6.93 Hz)

EXAMPLE 30

Synthesis of 2-[[(R)-2-[2-(S)-2-[2-(6-amidino-1-ethylindol-2-yl)ethyl]pyrrolidinyl]-2-oxo-1-phenylethyl]amino]acetic acid (Compound 40 )

To 20 mg of ethyl 2-[[(R)-2-[2-[(S)-2-[2-(6-amidino-1-ethylindol-2-yl)ethyl]pyrrolidinyl]-2-oxo-1-phenyl]ethyl] amino]acetate obtained in Example 28 was added concentrated HCl solution, and the reaction solution was stirred overnight while heating to 50–44° C. and then distilled under reduced pressure to remove the solvent. The residue was purified with column chromatography [eluent: methanol] on NH-DM1020 silica to obtain 14 mg of the title compound as a white solid.

¹H NMR(MeOH-d₄, ppm): δ7.77(s, 1H), 7.46(t, 1H, J=7.58 Hz), 7.36–7.21(m, 6H), 6.33(s, 1H), 4.51(s, 1H), 4.20–4.08(m, 4H), 3.02(m, 2H), 2.76(t, 3H), J=7.90 Hz), 2.25(m, 1H), 1.91(m, 2H), 1.77–1.68(m, 5H), 1.26(m, 3H)

EXAMPLE 31

Synthesis of 1-methyl-2-[2-[(S)-1-(2-cyclopentylacetyl)pyrrolidin-2yl]ethyl]indole-6-carboxamidine (Compound 42 )

a) Synthesis of 1-methyl-2-[2-[(S)-1-(2-cyclopentylacetyl) pyrrolidin-2-yl]ethyl]indole-6-carbonitrile:

100 mg of the compound I-b obtained in Example 2-b) and 0.055 ml of cyclopentylacetic acid were reacted according to the same procedure as Example 11-a) to obtain 32 mg of the title compound as a pale yellow solid.

¹H NMR(CDCl₃, ppm): δ7.57(m, 2H), 7.29(m, 1), 6.40(s, 1H), 4.25(d, 1H), 3.71(s, 3H), 3.48(m, 2H), 2.80(t, 2H), 2.28(m, 4H), 1.98(m, 4H), 1.88 (m, 2H), 1.75(m, 2H), 1.59(m, 3H), 1.16(m, 2H)

b) Synthesis of 1-methyl-2-[2-[(S)-1-(2-cyclopentylacetyl) pyrrolidin-2-yl]ethyl]indole-6-carboxamidine:

32 mg of the compound obtained in the above a) was treated according to the same procedure as Example 1-n) to obtain 20 mg of the title compound as a pale yellow solid.

¹H NMR(CDCl₃, ppm): δ7.95(s, 1H), 7.27(m, 2H), 7.13–6.84(br, 2H), 6.12 (s, 1H), 4.03(m, 1H), 3.56(s, 3H), 3.33(m, 2H), 2.55(m, 2H), 2.13 (m, 4H), 1.84–1.70(m, 6H), 1.52–1.40(m, 5H), 1.03(m, 2H)

ES-MS: 380(M+1)⁺

EXAMPLE 32

Synthesis of 1ethyl-2-[2-[(S)-1-(2-cyclopentylacetyl)pyrrolidin-2-yl]ethyl]indole-6-carboxamidine (Compound 43 )

a) Synthesis of 1ethyl-2-[2-[(S)-1-(2-cyclopentylacetyl) pyrrolidin-2-yl]ethyl]indole-6-carbonitrile:

100 mg of the compound I-a obtained in Example 1-l) and 0.052 ml of cyclopentylacetic acid were reacted according to the same procedure as Example 11-a) to obtain 30 mg of the title compound as a pale yellow solid.

¹H NMR(CDCl₃, ppm): δ7.56(m, 2H), 7.29(m, 1H), 6.40 (s, 1H), 4.28(m, 1H), 4.15(m, 2H), 3.50(m, 2H), 2.79(t, 2H), 2.30(m, 4H), 1.98 (m, 3H), 1.87(m, 2H), 1.75(m, 2H), 1.59(m, 4H), 1.35(m, 3H), 1.18(m, 2H)

b) Synthesis of 1-ethyl-2-[2-[(S)-1-(2-cyclopentylacetyl) pyrrolidin-2-yl]ethyl]indole-6-carboxamidine:

29 mg of the compound obtained in the above a) was treated according to the same procedure as Example 1-n) to obtain 19 mg of the title compound as a pale yellow solid.

$^1$H NMR(CDCl$_3$, ppm): δ8.06(m, 1H), 7.37(m, 2H), 6.91–6.52(br, 4H), 6.22(s, 1H), 4.17(m, 3H), 3.43(m, 2H), 2.67(m, 2H), 2.25(m, 4H), 1.94–1.71(m, 7H), 1.56(m, 4H), 1.21(m, 3H), 1.13(m, 2H)
ES-MS: 394(M+1)$^+$

EXAMPLE 33

Synthesis of ethyl 3-[(S)-2-[2-(6-aminido-1-ethylindol-2-yl)ethyl]pyrrolidinyl]-2-cyclopentyl-3-oxopropanoate (Compound 44)

a) Synthesis of ethyl 3-[(S)-2-[2-(6-cyano-1-ethylindol-2-yl)ethyl]pyrrolidinyl]-2-cyclopentyl-3-oxopropanoate:

In a 100 ml flask, 1g of the compound I-a) obtained in Example 1-l) and 1 g of α-ethylcarboxylate cyclopentane acetyl chloride were introduced and reacted according to the same procedure as Example 1-n) to obtain 0.5 g of the title compound as a pale brown oil.

$^1$H NMR(CDCl$_3$, ppm): δ7.56(m, 2H), 6.40(m, 1H), 4.31 (m, 1H), 4.17(m, 4H), 3.70(m, 1H), 3.59(m, 1H), 3.30(d, 1H), 2.81(m, 2H), 2.68(m, 1H), 2.28(m, 1H), 2.02(m, 5H), 1.77(m, 2H), 1.61(m, 5H), 1.35(m, 3H), 1.22(m, 3H), 1.09(m, 1H)

b) Synthesis of ethyl 3-[(S)-2-[2-(6-amidino-1-ethylindol-2-yl)ethyl]pyrrolidinyl]-2-cyclopentyl-3-oxopropanoate:

0.4 g of the compound obtained in the above a) was treated according to the same procedure as Example 1-n) to obtain 0.31 g of the title compound as a pale yellow solid.

$^1$H NMR(CDCl$_3$, ppm): δ7.98(m, 1H), 7.47(m, 1H), 7.33 (m, 1H), 6.30(s, 1H), 4.16(m, 5H), 3.69–3.56(m, 2H), 3.30(d, 1H), 2.73(m, 3H), 2.25 (m, 1H), 1.98(m, 5H), 1.72–1.58(m, 7H), 1.31–1.21(m, 6H), 1.03(m, 1H)
ES-MS: 466(M+1)$^+$

EXAMPLE 34

Synthesis of 3-[(S)-2-[2-(6-amidino-1-ethylindol-2-yl)ethyl]pyrrolidinyl]-2-cyclopentyl-3-oxopropanoic acid (Compound 45)

In a 50 ml flask, 80 mg of ethyl 3-[(S)-2-[2-(6-amidino-1-ethylindol-2 -yl)ethyl]pyrrolidinyl]-2-cyclopentyl-3-oxopropanoate obtained in Example 33 was dissolved in 20 ml of ethanol, and 10 ml of 2N NaOH was added thereto. The reaction mixture was stirred for 10 hours at room temperature, neutralized with 10% aqueous citric acid solution, and then distilled under reduced pressure to remove the solvent. The residue was then purified with column chromatography [eluent: ethyl acetate/methanol (5:1)] on NH-DM1020 silica to obtain 51 mg of the title compound as a yellowish white solid.

$^1$H NMR(MeOH-d$_4$, ppm): δ7.87(s, 1H), 7.60(d, 1H), 7.38(d, 1H), 6.44(s, 1H), 4.28(m, 2H), 3.87(m, 1H), 3.65(m, 1H), 3.19(d, 1H), 2.89(m, 3H), 2.59(m, 1H), 2.24(m, 1H), 2.03(m, 5H), 1.84(m, 4H), 1.59(m, 4H), 1.32(m, 3H)
IR(KBr): 3420, 2890, 1620 cm$^{-1}$
ES-MS: 439(M+1)$^+$, 462(M+Na)

EXAMPLE 35

Synthesis of 1ethyl-2-[2-[(S)-1-(2-cyclohexylacetyl) pyrrolidin-2 -yl]ethyl]indole-6-carboxamidine (Compound 46 )

a) Synthesis of 1ethyl-2-[2-[(S)-1-(2-cyclohexylacetyl) pyrrolidin-2-yl]ethyl]indole-6-carbonitrile:

100 mg of the compound I-a obtained in Example 1-l) and 88 mg of cyclohexylacetic acid were reacted according to the same procedure as Example 11-a) to obtain 60 mg of the title compound as a pale yellow solid.

$^1$H NMR(CDCl$_3$, ppm): δ7.56(m, 2H), 7.30(m, 1H), 6.40 (s, 1H), 4.28(m, 1H), 4.15(m, 2H), 3.47(t, 2H), 2.79(t, 2H), 2.28(m, 1H), 2.17(m, 1H), 1.99(m, 4H), 1.74–1.67 (m, 7H), 1.38(m, 4H), 1.26(m, 3H), 0.94(m, 2H)

b) Synthesis of 1ethyl-2-[2-[(S)-1-(2-cyclohexylacetyl) pyrrolidin-2-yl]ethyl]indole-6-carboxamidine:

50 mg of the compound obtained in the above a) was treated according to the same procedure as Example 1-n) to obtain 40 mg of the title compound as a pale yellow solid.

$^1$H NMR(CDCl$_3$, ppm): δ8.02(s, 1H), 7.73–7.54(br, 2H), 7.43(m, 2H), 6.25(s, 1H), 4.13(m, 3H), 3.48(m, 2H), 2.68(m, 2H), 2.21(m, 1H), 2.13(m, 1H), 1.92(m, 4H), 1.69–1.63(m, 7H), 1.27(m, 7H), 0.93(m, 2H)
ES-MS: 409(M+1)$^+$

EXAMPLE 36

Synthesis of 1-ethyl-2-[2-[(S)-[1-(3-phenylpropanoyl)pyrrolidin-2yl]ethyl]indole-6-carboxamidine (Compound 50)

60 mg of the compound I-a obtained in Example 1-l) and 40 mg of 3-phenylpropanoic acid were reacted according to the same procedure as Example 11-a) to obtain 55 mg of the product, which was then treated according to the same procedure as Example 1-n) to obtain 40 mg of the title compound.

$^1$H NMR(CDCl$_3$, ppm): δ8.08(m, 1H), 7.61(m, 1H), 7.44 (m, 1H), 7.34–7.17(m, 5H), 6.28(s, 1H), 4.19(m, 3H), 3.36–2.95(m, 2H), 2.92(t, 2H), 2.86(m, 4H), 2.69(m, 2H), 2.54(t, 2H), 2.27(m, 1H), 1.73–1.63 (m, 2H)

EXAMPLE 37

Synthesis of 1methyl-2-[2-[(S)-1-((R)-2-acetylamino-3-phenylpropanoyl)pyrrolidin-2-yl] ethyl]indole-6-carboxamide (Compound 53)

1.00 g of the compound I-b obtained in Example 2-b) and 1.00 g of (2)-2-acetylamino-3-phenylpropanoic acid were treated according to the same procedure as Example 11-a) to obtain 1.37 g of N-[(R)-2-[(S)-2-[2-(6-cyano-1-methylindol-2-yl)ethyl]pyrrolidinyl]-2-oxo-1-benzylethyl]-ethanamide. 78 mg of the compound thereby obtained was treated according to the same procedure as Example 1-n) to obtain 32 mg of the title compound as a pale yellow solid.

$^1$H NMR(MeOH-d$_4$, ppm): δ7.79(s, 1H), 7.48(d, 1H), 7.18(d, 1H), 7.14(m, 5H), 6.31(s, 1H), 4.20–3.90(brs, 1H), 3.66(s, 3H), 2.84(s, 3H)

EXAMPLE 38

Synthesis of 1-ethyl-2-[2-[(S)-1-(2-cyclopropylaminoacetyl)pyrrolidin-2-yl]ethyl] indole-6-carboxamidine (Compound 57)

150 mg of the compound I-b in Example 2-b) was reacted with 96 mg of chloroacetyl chloride under the same conditions as Example 1-m) to obtain the product, which was then dissolved in N,N-dimethylformamide. To the resulting solution were added 50 mg of cyclopropylamine and $K_2CO_3$. The reaction mixture was stirred overnight at room temperature and extracted with ethyl acetate. The extract was dried over $MgSO_4$ and then filtered. The filtrate was concentrated under reduced pressure to obtain the residue, which was then purified with silica gel column chromatography [eluent: ethyl acetate/n-hexane (4:1)] to obtain 120 mg of the pale yellow solid product, 1-ethyl-2-[2-(S)-1-(2-cyclopropylaminoacetyl)pyrrolidin-2-yl]ethyl]indole-6-carbonitrile. The product thereby obtained was treated according to the same procedure as Example 1-n) to obtain 45 mg of the title compound as a pale yellow solid.

ES-MS: 382(M+1)$^+$

EXAMPLE 39

Synthesis of 1-ethyl-2-[2-[(S)-1-[2-[cyclopropyl (methylsulfonyl)amino]acetyl]pyrrolidin-2-yl]ethyl] indole-6-carboxamidine (Compound 58)

100 mg of 1-ethyl-2-[2-[(S)-1-(2-cyclopropylaminoacetyl)pyrrolidin-2-yl]ethyl]indole-6-carbonitrile obtained in Example 38 was reacted with 60 mg of methanesulfonyl chloride in 2 ml of pyridine to obtain 90 mg of the product, which was then treated according to the same procedure as Example 1-n) to obtain 55 mg of the title compound as a pale yellow solid.

ES-MS: 460(M+1)$^+$

EXAMPLE 40

Synthesis of ethyl 2-[[2-[(S)-2-[2-(6-amidino-1-methylindol-2-yl)ethyl]pyrrolidinyl]-2-oxoethyl] cyclopropylamino]acetate (Compound 59)

300 mg of the compound I-b obtained in Example 2-b) was reacted according to the same procedure as Example 38 to obtain 290 mg of 1-methyl-2-[2-[(S)-1-(2-cyclopropylaminoacetyl)pyrrolidin-2-]ethyl]indole-6-carbonitrile, which was then reacted with 170 mg of ethyl 2-bromoacetate according to the same procedure as Example 1-m) to obtain 250 mg of the yellow solid product. The resulting product was then treated according to the same procedure as Example 1-n) to obtain 85 mg of the title compound as a pale yellow solid.

$^1$H-NMR(MeOH-d$_4$, ppm): δ7.80(d, 1H), J=3.28 Hz), 7.56–7.51(m, 1H), 7.32(d, 1H, J=8.32 Hz), 6.36(s, 1H), 4.08–3.93(m, 5H), 3.71(s, 3H), 3.37–3.34(m, 4H), 2.74–2.61(m, 3H), 2.18–2.11(m, 1H), 1.92(m, 1H), 1.80–1.77(m, 2H), 0.82–0.78(m, 3H), 0.58–0.65(m, 3H), 0.36 (m, 1H)

EXAMPLE 41

Synthesis of ethyl 2-[[2-[(S)-2-[2-(6-amidino-1-methylindol-2yl)ethyl]pyrrolidinyl]-2-oxoethyl] cyclopentylamino]acetate (Compound 60 )

100 mg of 1methyl-2-[2-[(S)-1-(2-cyclopropylaminoacetyl)pyrrolidin-2yl]ethyl]indole-6-carbonitrile obtained in Example 40 and 60 mg of cyclopentylamine were reacted according to the same procedure as Example 38 to obtain 95 mg of the yellow solid product, which was then reacted with ethyl 2-bromoacetate according to the same procedure as Example 1-m) to obtain 70 mg of the pale yellow solid product. The resulting product was then treated according to the same procedure as Example 38 to obtain 48 mg of the title compound as a pale yellow solid.

$^1$H NMR (MeOH-d$_4$, ppm): δ 7.80 (s, 1H), 7.54–7.51 (m, 1H), 7.35–7.31 (m, 1H), 6.37 (s, 1H), 4.58 (m, 2H), 4.38–4.31 (m, 1H), 4.08–4.02 (m, 2H), 3.91 (m, 2H), 3.71 (s, 3H), 3.65–3.61 (m, 1H), 3.45–3.40 (m, 2H), 2.79–2.73 (m, 2H), 2.13–2.08 (m, 1H), 1.93 (m, 3H), 1.80–1.77 (m, 4H), 1.57 (br, 2H), 1.41 (br, 4H), 0.82–0.78 (m, 3H)

EXAMPLE 42

Synthesis of ethyl 2-[[2-[(S)-2-[2-(6-amidino-1-methylindol-2-yl)ethyl]pyrrolidinyl]-2-oxoethyl] benzylamino]acetate (Compound 61)

150 mg of the compound I-b obtained in Example 2-b) was treated according to the same procedure as Example 1-m) to obtain the product, to which 70 mg of ethyl 2-(benzylamino)acetate, 101 mg of $K_2CO_3$ and 2.5 ml of dimethylformamide were added. The resulting mixture was stirred overnight at room temperature and extracted with ethyl acetate. The extract was dried over $MgSO_4$ and filtered. The filtrate was then concentrated under reduced pressure. The residue was purified with silica gel column chromatography [eluent: ethyl acetate/n-hexane (4:1)] to obtain 120 mg of the pale yellow solid product, which was treated according to the same procedure as Example 1-n) to obtain 45 mg of the title compound as a pale yellow solid.

$^1$H NMR (MeOH-d$_4$, ppm): δ 7.77–7.31 (m, 4H), 7.28–7.19 (m, 4H), 6.37 (s, 1H), 4.89–4.45 (m, 6H), 4.16–3.93 (m, 3H), 3.69 (d, 3H, J=8.84 Hz), 3.44–3.37 (m, 2H), 2.81–2.75 (m, 2H), 2.18–1.71 (m, 6H), 0.82–0.77 (m, 3H)

ES-MS: 504 (M+1)$^+$

EXAMPLE 43

Synthesis of ethyl 2-[[2-[(S)-2-[2-(6-amidino-1-ethylindol-2-yl)ethyl]pyrrolidinyl]-2-oxoethyl] cyclopropylamino]acetate (Compound 62)

a) Synthesis of 1-ethyl-2-[2-((S)-1-2-chloroacetylpyrrolidin-2-yl)ethyl]-indole-6-carbonitrile:

300 mg of the compound I-a obtained in Example 1-l) and 130 mg of chloroacetyl chloride were reacted according to the same procedure as Example 1-m) to obtain 351 mg of the title compound.

$^1$H NMR (CDCl$_3$, ppm): δ 7.65–7.55 (m, 2H), 7.40–7.30 (m, 1H), 6.45 (s, 1H), 4.40–4.30 (m, 1H), 4.25–4.20 (q, 2H), 4.10 (s, 2H), 3.70–3.55 (m, 2H), 2.90–2.80 (t, 2H), 2.40–2.30 (m, 1H), 2.20–1.95 (m, 4H), 1.90–1.75 (m, 1H), 1.45–1.35 (t, 3H)

b) Synthesis of ethyl 2-[[2-[(S)-2-[2-(6-cyano-1-ethylindol-2-yl)ethyl]pyrrolidinyl]-2-oxoethyl] cyclopropylamino]acetate:

351 mg of the compound obtained in the above a) was dissolved in dimethylformamide, and 3.06 mg of $K_2CO_3$ and 238 mg of N-ethylacetatocyclopropylamine were added. The reaction mixture was stirred overnight at room temperature and extracted with ethyl acetate. The extract was dried over $MgSO_4$ and filtered, and the filtrate was then concentrated under reduced pressure. The residue was purified with silica gel column chromatography [eluent: ethyl acetate/n-hexane (4:1)] to obtain 373 mg of the title compound as an oil.

$^1$H NMR (CDCl$_3$, ppm): δ 7.65–7.55 (m, 2H), 7.30–7.20 (m, 1H), 6.50–6.40 (m, 1H), 4.35–4.10 (m, 6H), 3.75–3.40 (m, 6H), 2.90–2.80 (m, 2H), 2.50–2.30 (m, 1H), 2.20–1.95 (m, 1H), 1.45–1.25 (m, 1H), 0.95–0.70 (m, 2H), 0.55–0.50 (m, 2H)

c) Synthesis of ethyl 2-[[2-[(S)-2-[2-(6-amidino-1-ethylindol-2-yl)ethyl]pyrrolidinyl]-2-oxoethyl]cyclopropylamino]acetate:

55 mg of the compound obtained in the above b) was treated according to the same procedure as Example 1-n) to obtain 24 mg of the title compound.

$^1$H NMR (CDCl$_3$, ppm): δ 7.70 (m, 1H), 7.40 (m, 1H), 7.20 (m, 1H), 6.25 (s, 1H), 4.55–4.40 (d, 1H), 4.20–3.80 (m, 5H), 3.50–3.10 (m, 6H), 2.80–2.70 (m, 2H), 2.20–1.65 (m, 6H), 1.20–1.00 (m, 6H), 0.75–0.65 (m, 4H)

EXAMPLE 44

Synthesis of 2-[[2-[(S)-2-[2-(6-amidino-1-ethylindol-2-yl)ethyl]pyrrolidinyl]-2-oxoethyl] cyclopropylamino]acetic acid (Compound 63)

40 mg of ethyl 2-[[2-[(S)-2-[2-(6-amidino-1-ethylindol-2-yl)ethyl]pyrrolidinyl]-2-oxoethyl]cyclopropylamino] acetate obtained in Example 43 was dissolved in 50 ml of ethanol, and 2 ml, of 2N NaOH was added thereto. The reaction mixture was stirred for 2 hours and then evaporated under reduced pressure to remove the solvent. The residue was purified with column chromatography [eluent: ethanol] on NH—DM 1020 silica to obtain 25 mg of the title compound as a pale yellow solid.

$^1$H NMR (MeOH-d$_4$, ppm): δ 7.81–7.30 (m, 3H), 6.37 (s, 1H), 4.22–4.04 (m, 3H), 3.56–3.43 (m, 4H), 3.28 (s, 2H), 2.81–2.67 (m, 2H), 2.37 (m, 1H), 2.23–1.70 (m, 6H), 1.30–1.22 (m, 3H), 0.64–0.25 (m, 4H)

ES-MS: 440 (M+1)$^+$

EXAMPLE 45

Synthesis of ethyl 2-[[2-[(S)-2-[2-(6-amidino-1-ethylindol-2-yl)ethyl]pyrrolidinyl]-1-methyl-2-oxoethyl]cyclo-propylamino]acetate (Compound 64)

a) Synthesis of ethyl 2-[[2-[(S)-2-[2-(6-cyano-1-ethylindol-2-yl)ethyl]pyrrolidinyl]-1-methyl-2-oxoethyl]cyclopropylamino]acetate:

500 mg of 1-ethyl-2-[((S)-1-2-bromopropanoylpyrrolidin-2-yl)ethyl]indole-6-carbonitrile and cyclopropylamine were dissolved in dry N,N-dimethylformamide, and 104 mg of NaHCO$_3$ and 20.4 mg of KI were added thereto. The reaction mixture was heated under refluxing for one hour and, after water was added, extracted with ethyl acetate. The extract was dried and distilled under reduced pressure. The residue was purified with silica gel column chromatography [eluent: dichloromethane/methane (20:1)] to obtain the title compound in a quantitative yield.

b) Synthesis of ethyl 2-[[2-[(S)-2-[2-(6-cyano-1-ethylindol-2-yl)ethyl]pyrrolidinyl]-1-methyl-2-oxoethyl]cyclopropylamino]acetate:

467 mg of ethyl 2-[[2-[(S)-2-[2-(6-cyano-1-ethylindol-2-yl)ethyl]pyrrolidinyl]-1-methyl-2-oxoethyl]cyclopropylamino]acetate was dissolved in 15 ml of acetonitrile, and diisopropylethylamine and ethyl-2-bromoacetate were added thereto. The reaction mixture was heated to 70° C. and stirred for 4 hours. The reaction solution was concentrated under reduced pressure to obtain the residue, which was then purified with silica gel column chromatography [eluent: dichloromethane/methanol (20:1)] to obtain 538 mg of the title compound as a pale yellow oil.

$^1$H NMR (CDCl$_3$, ppm): δ 7.79 (s, 1H), 7.58 (d, 1H, J=8.10 Hz), 7.28 (d, 1H, J=7.96 Hz), 6.45 (s, 1H), 4.35–3.90 (m, 8H), 3.60–3.40 (m, 3H), 2.84 (m, 2H), 2.38–1.70 (m, 8H), 1.42–1.13 (m, 9H), 0.48 (m, 3H),

ES-MS: 465 (M+1)$^+$ c) Synthesis of ethyl 2-[[2-[(S)-2-[2-(6-amidino-1-ethylindol-2-yl)ethyl]-pyrrolidinyl]-1-methyl-2-oxoethyl]cyclopropylamino]acetate:

500 mg of ethyl 2-[[2-[(S)-2-[2-(6-cyano-1-ethylindol-2-yl)ethyl]pyrrolidinyl]-1-methyl-2-oxoethyl] cyclopropylamino]acetate obtained in the above b) was treated according to the same procedure as Example 1-n) to obtain 114 mg of the title compound.

$^1$H NMR (MeOH-d$_4$, ppm): δ 7.89 (s, 1H), 7.61 (d, 1H, J=8.29 Hz), 7.42 (d, 1H, J=8.22 Hz), 6.44 (s, 1H), 4.40–3.91 (m, 6H), 3.70–3.40 (m, 4H), 2.84 (m, 2H), 2.40–1.70 (m, 8H), 1.41 (t, 3H), 1.23 (m, 6H), 0.50 (m, 3H)

ES-MS: 482 (M+1)$^+$

EXAMPLE 46

Synthesis of 2-[[2-[(S)-2-[2-(6-amidino-1-ethylindol-2-yl)ethyl]pyrrolidinyl]-1-methyl-2-oxoethyl]cyclopylamino]acetic acid (Compound 65)

32 mg of ethyl 2-[[2-[(S)-2-[2-(6-amidino-1-ethylindol-2-yl)ethyl]pyrrolidinyl]-1-methyl-2-oxoethyl] cyclopropylamino]acetate was treated according to the same procedure as Example 44 to obtain 27 mg of the title compound as a yellowish white solid.

$^1$H NMR (MeOH-d$_4$, ppm): δ 7.82 (s, 1H), 7.52 (d, 1H), 7.32 (d, 1H), 6.36 (s, 1H), 4.30–3.80 (m, 6H), 3.51–3.12 (m, 3H), 2.73 (m, 2H), 2.30–1.60 (m, 6H), 1.26 (t, 3H), 1.13 (m, 3H), 0.62–0.25 (m, 4H)

ES-MS: 454 (M+1)$^+$

EXAMPLE 47

Synthesis of ethyl 2-[[2-[(S)-2-[2-(6-amidino-1-ethylindol-2-yl)ethyl]pyrrolidinyl]-(1R)-1-methyl-2-oxoethyl]amino]acetate (Compound 66)

a) Synthesis of N-[2-[(S)-2-[2-(6-cyano-1-ethylindol-2-yl)ethyl]pyrrolidinyl]-(1R)-1-methyl-2-oxoethyl](tert-butoxy)formamide:

406 mg of the compound I-a obtained in Example 1-l) and 316 mg of N-(tert-butoxy)carbonyl-D-alanine were reacted according to the same procedure as Example 11-a) to obtain 290 mg of the title compound as a white solid.

$^1$H-NMR (CDCl$_3$, ppm): δ 7.61–7.54 (m, 2H), 7.30 (m, 1H), 6.42 (s, 1H), 5.37 (d, 1H, J=8.44 Hz), 4.47–4.39 (m, 1H), 4.20–4.11 (m, 3H), 3.74–3.40 (m, 2H), 2.79 (t, 2H, J=7.91 Hz), 2.39–1.77 (m, 6H), 1.43 (s, 9H), 1.37 (t, 3H, J=7.23 Hz), 1.25 (d, 3H, J=7.13 Hz)

b) Synthesis of ethyl 2-[[2-[(S)-2-[2-(6-cyano-1-ethylindol-2-yl)ethyl]pyrrolidinyl]-(1R)-1-methyl-2-oxoethyl]amino]ethanoate:

274 mg of the compound obtained in the above a) was treated according to the same procedure as Example 1-l) to obtain the pale yellow solid product, which was then reacted with 0.076 ml of ethyl 2-bromoacetate under the same conditions as Example 1-m) to obtain 187 mg of the title compound as a pale yellow oil.

$^1$H NMR (CDCl$_3$, ppm) δ 7.62–7.55 (m, 2H), 7.30 (m, 1H), 6.43 (s, 1H), 4.26 (brs, 1H), 4.21–4.13 (m, 4H), 3.50, 3.64 (m, 3H), 3.41 (d, 1 Ha, J=16.68 Hz), 3.25 (d, 1Hb, J=16.70 Hz), 2.81 (t, 2H, J=8.00 Hz), 2.41–1.71 (m, 6H), 1.37 (t, 3H, J=7.21 Hz), 1.27–1.23 (m, 6H)

c) Synthesis of ethyl 2-[[2-[(S)-2-[2-(6-amidino-1-ethylindol-2-yl)ethyl]pyrrolidinyl]-(1R)-1-methyl-2-oxoethyl]amino]acetate:

183 mg of the compound obtained in the above b) was treated according to the same procedure as Example 1-n) to obtain 144 mg of the title compound as a pale yellow solid.

$^1$H NMR (MeOH-d$_4$, ppm): δ 7.81 (s, 1H), 7.60–7.32 (m, 2H), 6.40 (s, 1H), 4.22–4.01 (m, 5H), 3.86–3.72 (m, 1H), 3.59–3.27 (m, 4H), 2.84–2.68 (m, 2H), 2.26–1.77 (m, 6H), 1.30 (t, 3H, J=7.13 Hz), 1.15–1.06 (m, 6H)

IR (KBr) cm$^{-1}$: 3400, 2970, 1720, 1660, 1625, 1520, 1460

ES-MS: 442 (M+1)$^+$

EXAMPLE 48

Synthesis of 2-[[2-[(S)-2-[2-(6-amidino-1-ethylindol-2-yl)ethyl]pyrrolidinyl]-(1R)-1-methyl-2-oxoethyl]amino]acetic acid (Compound 67)

130 mg of ethyl 2-[[2-[(S)-2-[2-(6-amidino-1-ethylindol-2-yl)ethyl]pyrrolidinyl]-(R)-1-methyl-2-oxoethyl]amino] acetate was treated according to the same procedure as Example 44 to obtain 60 mg of the title compound as a pale yellow solid.

$^1$H NMR (MeOH-d$_4$, ppm): δ 7.76 (s, 1H), 7.57–7.27 (m, 2H), 6.35 (s, 1H), 4.21–4.06 (m, 3H), 3.66–3.40 (m, 3H), 3.01 (s, 2H), 2.82–2.73 (m, 2H), 2.27–1.71 (m, 6H), 1.27 (t, 3H, J=7.08 Hz), 1.13–1.05 (m, 3H)

ES-MS: 414 (M+1)$^+$

EXAMPLE 49

Synthesis of ethyl 2-[[2-[(S)-2-[2-(6-amidino-1-ethylindol-2-yl)ethyl]pyrrolidinyl]-(1R)-1-hydroxymethyl-2-oxoethyl]amino]acetate (Compound 69)

a) Synthesis of N-[2-[[(S)-2-[2-(6-Cyano-1-ethylindol-2-yl)ethyl)pyrrolidinyl]-(R)-1-hydroxymethyl-2-oxoethyl]-(1,1-dimethylethyloxy)methanamide:

412 mg of the compound I-a obtained in Example 1-l) and 348 mg of N-(tert-butoxy)carbonyl-D-serine were reacted under the same conditions as Example 11-a) to obtain 110 mg of the title compound as a viscous oil.

$^1$H NMR (CDCl$_3$, ppm): δ 7.61–7.54 (m, 2H), 7.30 (m, 1H), 6.41 (s, 1H), 5.55 (brs, 1H), 4.49 (m, 1H), 4.28–4.13 (m, 3H), 3.90–3.52 (m, 4H), 3.22 (brs, 1H), 2.82–2.75 (m, 2H), 2.40–1.77 (m, 6H), 1.44 (s, 9H), 1.38 (t, 3H, J=8.76 Hz)

b) Synthesis of ethyl 2-[[2-[(S)-2-[2-(6-cyano-1-ethylindol-2-yl)ethyl]-pyrrolidinyl]-(1R)-1-hydroxymethyl-2-oxoethyl]amino]ethanoate:

109 mg of the compound obtained in the above a) was treated according to the same procedure as Example 1-l) to obtain the pale yellow solid product, which was then reacted with 0.029 ml of ethyl 2-bromoacetate under the same conditions as Example 1-m) to obtain 20 mg of the title compound as a pale yellow oil.

$^1$H NMR (CDCl$_3$, ppm): δ 7.62–7.55 (m, 2H), 7.30 (m, 1H), 6.41 (s, 1H), 4.87–4.38 (m, 2H), 4.31–4.11 (m, 6H), 3.93–3.46 (m, 4H), 2.77 (m, 2H), 2.38–1.73 (m, 6H), 1.40–1.25 (m, 6H)

c) Synthesis of ethyl 2-[[2-[(S)-2-[2-(6-amidino-1-ethylindol-2-yl)ethyl]pyrrolidinyl]-(1R)-1-hydroxymethyl-2-oxoethyl]amino]acetate:

20 mg of the compound obtained in the above b) was treated according to the same procedure in Example 1-n) to obtain 10 mg of the title compound as a pale yellow solid.

$^1$H NMR (MeOH-d$_4$, ppm): δ 7.70 (s, 1H), 7.38 (m, 2H), 6.27 (s, 1H), 4.21–4.14 (m, 5H), 3.57–3.47 (m, 6H), 3.22–2.72 (m, 4H), 2.29–1.70 (m, 6H), 1.35 (t, 3H, J=7.09 Hz), 1.25 (t, 3H, J=7.14 Hz)

ES-MS: 458 (M+1)$^+$

EXAMPLE 50

Synthesis of ethyl 4-[(S)-2-[2-(6-amidino-1-ethylindol-2-yl)ethyl]pyrrolidinyl]-3-cyclopropylamino-4-oxobutanoate (Compound 72)

a) Synthesis of N-[2-[(S)-2-[2-(6-cyano-1-ethylindol-2-yl)ethyl]pyrrolidinyl]-2-oxoethyl]-N-cyclopropyl(1,1-dimethylethyloxy)methanamide:

375 mg of 2-[2-((S)-1-2-chloroacetylpyrrolidin-2yl) ethyl]-1-ethylindole-6-carbonitrile and 188 mg of N-butyloxycarbonylcyclopropylamine were reacted under the same conditions as Example 45-b) to obtain 413 mg of the title compound as a white solid.

$^1$H NMR (CDCl$_3$, ppm): δ 7.61–7.53 (m, 2H), 7.30 (m, 1H), 6.36 (s, 1H), 4.31 (brs, 1H), 4.15 (q, 2H, J=7.28 Hz), 3.93 (brs, 2H), 3.54–3.37 (m, 2H), 2.81–2.76 (m, 3H), 2.58–1.75 (m, 6H), 1.47 (s, 9H), 1.35 (t, 3H, J=7.28 Hz), 0.75–0.62 (m, 4H)

b) Synthesis of ethyl 4-[(S)-2-[2-(6-cyano-1-ethylindol-2-yl)ethyl]pyrrolidinyl]-3-[N-cyclopropyl-(1,1-dimethylethyloxy)carbonylamino]-4-oxobutanoate:

413 mg of the compound obtained in the above a) was dissolved in 8 ml of tetrahydrofuran and cooled to −78° C. To this solution was slowly added dropwise 0.489 ml of 2M LDA (lithium diisopropylamide) solution. The reaction mixture was then stirred for 40 minutes. 0.108 ml of ethyl bromoacetate was added dropwise thereto, and the mixture was stirred for 2 hours at −30° C. After 0.5 ml of water was added dropwise, the reaction solution was evaporated under reduced pressure, diluted with 150 ml of dichloromethane, washed with 50 ml of water, dried over sodium sulfate, and then filtered. The filtrate was evaporated under reduced pressure. The residue was purified with silica gel column chromatography [eluent: ethyl acetate/n-hexane (1:1)]. The fractions containing the pure desired product were combined and then evaporated under reduced pressure to obtain 167 mg of the title compound as a white solid.

$^1$H NMR (CDCl$_3$, ppm): δ 7.59–7.54 (m, 2H), 7.29 (m, 1H), 6.37 (s, 1H), 5.11 (brs, 1H), 4.19–4.09 (m, 5H), 3.64–3.33 (m, 2H), 3.22–3.12 (m, 1H), 2.78 (t, 2H, J=8.00 Hz), 2.61–2.52 (m, 1H), 2.36–1.70 (m, 7H), 1.47 (s, 9H), 1.35 (t, 3H, J=7.19 Hz), 1.23 (t, 3H, J=7.10 Hz), 0.75–0.61 (m, 4H)

c) Synthesis of ethyl 4-[-(S)-2-[2-(6-amidino-1-ethylindol-2-yl)ethyl]pyrrolidinyl]-3-(cyclopropylamino)-4-oxobutanoate:

165 mg of the compound obtained in the above b) was treated according to the same procedure as Example 1-n) to obtain 33 mg of the title compound as a pale yellow solid.

$^1$H NMR (MeOH-d$_4$, ppm): δ 7.77 (s, 1H), 7.52–7.30 (m, 2H), 6.33 (s, 1H), 4.23–4.14 (m, 3H), 4.01–3.84 (m, 3H), 3.73–3.46 (m, 2H), 2.85–2.48 (m, 4H), 2.12–1.71 (m, 7H), 1.29 (t, 3H, J=7.14 Hz), 1.11–1.05 (m, 3H), 0.40–0.22 (m, 4H)

ES-MS: 468 (M+1)$^+$

EXAMPLE 51

Synthesis of 4-[(S)-2-[2-(6-amidino-1-ethylindol-2-yl)ethyl]pyrrolidinyl]-3-cyclopropylamino-4-oxobutanoic acid (Compound 73)

26 mg of ethyl 4-[(S)-2-[2-(6-amidino-1-ethylindol-2-yl) ethyl]pyrrolidinyl]-3-cyclopropylamino-4-oxobutanoate was treated according to the same procedure as Example 44 to obtain 16 mg of the title compound as a pale yellow solid.

$^1$H NMR (MeOH-d$_4$, ppm): δ 7.57 (s, 1H), 7.31–7.06 (m, 2H), 6.27 (s, 1H), 4.22 (brs, 1H), 4.13–4.05 (m, 2H), 3.94–3.82 (m, 2H), 3.74–3.66 (m, 1H), 2.79–2.71 (m, 2H), 2.46 (m, 2H), 2.05–1.82 (m, 7H), 1.22 (t, 3H, J=7.13 Hz), 0.36–0.31 (m, 4H)

ES-MS: 440 (M+1)$^+$

EXAMPLE 52

Synthesis of ethyl 2-[2-[(S)-2-[2-(6-amidino-1-methylindol-2-yl)ethyl]pyrrolidinyl]-N-cyclopentylacetylamino]-acetate (Compound 75)

100 mg of the compound I-b obtained in Example 2-b) and 98 mg of ethyl 2-(2-chloro-N-cyclopentylacetylamino) acetate were reacted under the same conditions as Example 42 to obtain the pale yellow solid product, which was then treated according to the same procedure as Example 1-n) to obtain 20 mg of the title compound as a pale yellow solid.

$^1$H NMR (MeOH-d$_4$, ppm): δ 7.81–7.32 (m, 3H), 6.31 (m, 1H), 4.52–4.43 (m, 1H), 4.04–3.96 (m, 2H), 3.80–3.48 (m, 4H), 3.85 (s, 3H), 3.11–2.66 (m, 4H), 2.55–1.03 (m, 15H), 0.80 (t, 3H, J=6.94 Hz)

ES-MS: 482 (M+1)$^+$

EXAMPLE 53

Synthesis of 1-methyl-2-[2-[(S)-1-(2-naphthylsulfonyl)pyrrolidin-2-yl]ethyl]indole-6-carboxamidine (Compound 77)

a) Synthesis of 1-methyl-2-[2-[(S)-1-(2-naphthylsulfonyl)pyrrolidin-2-yl]ethyl]indole-6-carbonitrile:

In a 25 ml flask, 30 mg of 1-methyl-2-((S)-2-pyrrolidin-2-ylethyl)indole- 6-carbonitrile and 36 mg of 2-naphthalenesulfonyl chloride were dissolved in 3 ml of dichloromethane, and 0.055 ml of triethylamine was added at room temperature. The reaction mixture was stirred for 2 hours, diluted with water and then extracted three times with dichloromethane. The extracts were combined, dried over MgSO$_4$ and then evaporated. The residue was purified with silica gel column chromatography [eluent: ethyl acetate/n-hexane (1:3)]. The fractions containing the pure desired product were combined and then evaporated to obtain 26.9 mg of the title compound as a pale yellow solid.

$^1$H NMR (CDCl$_3$, ppm): δ 8.26 (s, 1H), 7.88 (m, 2H), 7.78 (m, 1H), 7.73 (d, 1H), 7.70 (m, 2H), 7.64 (m, 1H), 7.59 (m, 1H), 7.34 (d, 1H), 6.39 (s, 1H), 3.79 (m, 1H), 3.74 (s, 3H), 3.50 (m, 1H), 3.34 (m, 1H), 2.93 (m, 2H), 2.28 (m, 1H), 1.99 (m, 1H), 1.83 (m, 1H), 1.65 (m, 2H), 1.58 (m, 1H)

b) Synthesis of 1-methyl-2-[2-[(S)-1-(2-naphthylsulfonyl)pyrrolidin-2-yl]ethyl]indole-6-carboxamidine:

27 mg of the compound obtained in the above a) was treated according to the same procedure as Example 1-n) to obtain 14 mg of the title compound as a yellowish white solid.

$^1$H NMR (MeOH-d$_4$, ppm): δ 8.11 (s, 1H), 7.89–7.82 (m, 3H), 7.64 (d, 1H), 7.61–7.44 (m, 4H), 7.43 (d, 1H), 6.37 (s, 1H), 3.77 (s, 3H), 3.63 (m, 1H), 3.37 (m, 1H), 3.25 (m, 1H), 2.85 (m, 2H), 2.23 (m, 1H), 1.91 (m, 1H), 1.80 (m, 1H), 1.59 (m, 2H), 1.36 (m, 1H),

ES-MS: 461 (M+1)$^+$

EXAMPLE 54

Synthesis of 1-methyl-2-[2-((S)-1-naphthylsulfonylpyrrolidin-2-yl)ethyl]indole-6-carboxamidine (Compound 79)

a) Synthesis of 1-methyl-2-[2-((S)-1-naphthylsulfonylpyrrolidin-2-yl)ethyl]indole-6-carbonitrile:

53 mg of 1-naphthalenesulfonyl chloride was treated according to the same procedure as Example 53-a) to obtain 55 mg of the title compound as a pale yellow solid.

$^1$H NMR (CDCl$_3$, ppm): δ 8.79 (d, 1H), 8.12 (d, 1H), 7.98 (d, 1H), 7.99 (d, 1H), 7.54 (m, 4H), 7.40 (m, 1H), 7.32 (m, 1H), 6.25 (s, 1H), 3.99 (m, 1H), 3.57 (s, 3H), 3.47–3.40 (m, 2H), 2.74 (m, 2H), 2.11 (m, 1H), 1.87–1.81 (m, 3H), 1.66 (m, 2H)

b) Synthesis of 1-methyl-2-[2-[(S)-1-naphthylsulfonylpyrrolidin-2-yl)ethyl]indole-6-carboxamidine:

51 mg of the compound obtained in the above a) was treated according to the same procedure as Example 1-n) to obtain 25 mg of the title compound as a yellowish white solid.

$^1$H NMR (MeOH-d$_4$, ppm): δ 8.77 (d, 1H), 8.06 (m, 2H), 7.95 (m, 2H), 7.67 (d, 1H), 7.58 (m, 1H), 7.52–7.40 (m, 3H), 6.33 (s, 1H), 3.94 (m, 1H), 3.73 (s, 3H), 3.50–3.42 (m, 2H), 2.82 (m, 2H), 2.14 (m, 1H), 1.90 (m, 2H), 1.74 (m, 2H), 1.64 (m, 1H)

EXAMPLE 55

Synthesis of 1-methyl-2-[2-((S)-1-acetylpyrrolidin-2-yl)ethyl]indole-6-carboxamidine (Compound 81)

490 mg of 1-methyl-2-[2-((S)-1-acetylpyrrolidin-2-yl) ethyl]indole-6-carbonitrile was treated according to the same procedure as Example 1-n) to obtain 24 mg of the title compound.

$^1$H NMR (CDCl$_3$, ppm): δ 7.99 (s, 1H), 7.33 (m, 2H), 6.12 (s, 1H), 4.01 (bs, 1H), 3.54 (s, 3H), 3.45–3.20 (m, 2H), 2.54 (bs, 2H), 2.20–1.40 (m, 6H), 1.97 (s, 3H)

EXAMPLE 56

Synthesis of 1-methyl-2-[2-[(S)-1-(2-phenylsulfonylacetyl)pyrrolidin-2-yl]ethyl]indole-6-carboxamidine (Compound 82)

a) Synthesis of 1-methyl-2-[2-[(S)-1-(2-phenylsulfonylacetyl)pyrrolidin-2-yl]ethyl]indole-6-carbonitrile 70 mg of the compound I-b obtained in Example 2-b) and 81 mg of phenylsulfonylacetic acid were reacted according to the same procedure as Example 11-a) to obtain 12 mg of the title compound as a yellow oil.

$^1$H NMR (CDCl$_3$, ppm): δ 7.94–7.91 (m, 2H), 7.65 (d, 1H, J=7.50 Hz), 7.57–7.51 (m, 4H), 7.29 (d, 1H), 6.37 (s, 1H), 4.23–4.10 (m, 3H), 3.68 (s, 3H), 3.75–3.66 (m, 2H), 2.80 (t, 3H, J=8.00 Hz), 2.22–1.79 (m, 6H)

b) Synthesis of 1-methyl-2-[2-[(S)-1-(2-phenylsulfonylacetyl)pyrrolidin-2-yl]ethyl]indole-6-carboxamidine:

12 mg of the compound obtained in the above a) was treated according to the same procedure as Example 1-n) to obtain 4 mg of the title compound as a pale yellow solid.

$^1$H NMR (CDCl$_3$, ppm): δ 7.98–7.93 (m, 3H), 7.74–7.62 (m, 4H), 7.47 (d, 1H, J=8.30 Hz), 6.47 (s, 1H), 4.15 (bs, 1H), 3.82 (s, 3H), 3.66–3.62 (m, 2H), 3.33 (s, 2H), 2.89 (t, 2H), 2.20–1.84 (m, 6H)

EXAMPLE 57

Synthesis of 1-ethyl-2-[2-[(S)-1-(R)-pyrrolidin-2-ylcarbonyl)pyrrolidin-2-yl]ethyl]indole-6-carboxamidine (Compound 83)

a) Synthesis of tert-butyl-(R)-[[(S)-2-[2-(6-cyano-1-ethylindol-2-yl)ethyl]pyrrolidinyl]carbonyl]pyrrolidine carboxylate:

17 g of 1-ethyl-2-[((S)-pyrrolidin-2-yl)ethyl]indole-6-carbonitrile and 17.8 g of (R)-N-(tert-butoxycarbonyl) proline were dissolved in dichloromethane, and 18.3 g of WSCIHCl was added thereto. The reaction mixture was stirred for 2.5 hours at room temperature and, after water was added, extracted two times with dichloromethane. The extracts were combined, dried over MgSO$_4$ and then concentrated. The residue was purified with silica gel column chromatography [eluent: dichloromethane/methanol (50:1)] to obtain 24 g of the title compound as a white foam.

ES-MS: 465 (M+1)$^+$ $^1$H NMR (CDCl$_3$, ppm): δ 7.60–7.51 (m, 2H), 7.32–7.24 (m, 1H), 6.41–6.33 (m, 1H), 4.52–4.47 (m, 1H), 4.40–4.28 (m, 1H), 4.16 (q, J=7.20 Hz, 2H), 3.79–3.62 (m, 2H), 3.50–3.44 (m, 2H), 2.83–2.79 (m, 2H), 2.15–1.85 (m, 10H), 1.43–1.40 (m, 9H), 1.35 (t, J=7.20 Hz, 3H)

b) Synthesis of 1-ethyl-2-[2-[(S)-[1-((R)-pyrrolidin-2-yl) carbonyl]pyrrolidin-2-yl]ethyl]indole-6-carbonitrile (Compound II-a):

24 mg of the compound obtained in the above a) was treated according to the same procedure as Example 1-l) to obtain 11 g of the title compound as a white foam.

$^1$H NMR (CDCl$_3$, ppm): δ 7.60–7.56 (m, 2H), 7.31–7.26 (m, 1H), 6.43 (s, 1H), 4.41–4.37 (m, 1H), 4.20–4.13 (m, 3H), 3.64–3.61 (m, 1H), 3.41–3.34 (m, 3H), 2.81–2.78 (m, 2H), 2.43–2.38 (m, 2H), 2.17–1.82 (m, 8H), 1.38 (t, J=7.20 Hz, 3H)

c) Synthesis of 1-ethyl-2-[2-[(S)-1-((R)-pyrrolidin-2-ylcarbonyl)pyrrolidin-2-yl]ethyl]indole-6-carboxamidine:

50 mg of the compound II-a obtained in the above b) was treated according to the same procedure as Example 1-n) to obtain 27 mg of the title compound as a pale yellow solid.

$^1$H NMR (MeOH-d$_4$, ppm): δ 7.81 (s, 1H), 7.59–7.31 (m, 2H), 6.39 (s, 1H), 4.21–4.05 (m, 3H), 3.68–3.46 (m, 3H), 3.10–2.66 (m, 4H), 2.27–1.52 (m, 10H), 1.30 (t, 3H, J=7.15 Hz)

IR (KBr) cm$^{-1}$: 3480, 1650, 1025

ES-MS: 382 (M+1)$^+$

EXAMPLE 58

Synthesis of ethyl 2-[(R)-2-[[(S)-2-[2-(6-amidino-1-methylindol-2-yl)ethyl]pyrrolidinyl]carbonyl] pyrrolidinyl]acetate (Compound 84)

a) Synthesis of 1-methyl-2-[(2S)-[1-((2R)-pyrrolidin-2-yl)carbonyl]pyrrolidin-2-yl]ethyl]indole-6-carbonitrile (Compound II-b):

300 mg of the compound I-b obtained in Example 2-b) was treated according to the same procedure as Examples 57-a) and 57-b) to obtain 200 mg of the title compound as a white foam.

$^1$H NMR (CDCl$_3$, ppm): δ 7.63 (s, 1H), 7.38 (d, 1H), 7.10 (d, 1H), 6.30 (s, 1H), 4.25 (t, 3H), 4.10–4.00 (m, 1H), 3.65 (s, 3H), 3.45–3.20 (m, 2H), 2.80–2.70 (m, 2H), 2.45–2.30 (m, 1H), 2.30–2.15 (m, 1H), 2.1–1.6 (m, 1H)

b) Synthesis of methyl 2-[(R)-2-[[(S)-2-[2-(6-cyano-1-methylindol-2-yl)ethyl]pyrrolidinyl]carbonyl]pyrrolidinyl] acetate:

50.0 mg of the compound II-b obtained in the above a) was dissolved in dichloromethane and then cooled to 0° C. 24 μl of triethylamine was added thereto, and after 20 minutes, 16 μl of methyl bromoacetate was added dropwise. After 20 minutes, water was added and the reaction solution was extracted two times with dichloromethane. The extracts were combined, dried over MgSO$_4$ and then concentrated. The residue was purified with silica gel column chromatography [eluent: dichloromethane/methanol (20:1)] to obtain 28 mg of the title compound as a colorless liquid.

$^1$H NMR (CDCl$_3$, ppm): δ 7.56–7.48 (m, 2H), 7.32 (m, 1H), 6.44 (s, 1H), 4.28–4.15 (bs, 1H), 3.86 (m, 1H), 3.72 (s, 3H), 3.67 (s, 3H), 3.50 (m, 2H), 2.82 (m, 4H), 2.37–1.60 (m, 12H)

c) Synthesis of ethyl 2-[(R)-2-[[(S)-2-[2-(6-amidino-1-methylindol-2-yl)ethyl]pyrrolidinyl]carbonyl]pyrrolidinyl] acetate:

26 mg of the compound obtained in the above b) was dissolved in 15 ml of ethanol solution saturated with HCl gas. The reaction solution was allowed to stand at room temperature for one day and then concentrated under reduced pressure. The remaining HCl was removed for 5 hours by means of a vacuum pump. The dried product was then dissolved in 15 ml of ethanol solution saturated with NH$_3$ gas. After one day, the reaction solution was concentrated under reduced pressure. The residue was purified with column chromatography [eluent: ethyl acetate/methanol (1:1)] on NH—DM1020 silica to obtain 12 mg of the title compound as a yellowish white solid.

$^1$H NMR (MeOH-d$_4$, ppm): δ 7.94 (s, 1H), 7.68 (d, 1H), 7.47 (d, 1H), 6.52 (s, 1H), 4.30 (bs, 1H), 3.92 (m, 1H), 3.80–3.50 (m, 7H), 3.28 (m, 1H), 3.15–2.90 (m, 3H), 2.40–1.75 (m, 12H), 1.25 (t, 3H)

EXAMPLE 59

Synthesis of ethyl 2-[(R)-2-[[2-[2-(6-amidino-1-ethylindol-2-yl)ethyl]azetidinyl]carbonyl] pyrrolidinyl]acetate (Compound 85)

a) Synthesis of methyl (S)-2-azetidine carboxylate:

900 mg of azetidine-(S)-2-carboxylic acid was treated according to the same procedure as Example 1-g) to obtain 1 g of the title compound as a colorless oil.

b) Synthesis of methyl (S)-2-(tert-butoxycarbonyl)-2-azetidine carboxylate:

1 g of the compound obtained in the above a) was treated according to the same procedure as Example 1-h) to obtain 1.8 g of the title compound as a colorless oil.

$^1$H NMR (CDCl$_3$, ppm): δ 4.61 (m, 1H), 4.02 (m, 1H), 3.89 (m, 1H), 3.77 (s, 3H), 2.50 (m, 1H), 2.17 (m, 1H), 1.42 (s, 9H)

c) Synthesis of tert-butyl (S)-2-formylazetidine carboxylate:

1.7 g of the compound obtained in the above b) was treated according to the same procedure as Example 1-i) to obtain 1.4 g of the title compound as a colorless oil.

$^1$H NMR (CDCl$_3$, ppm): δ 4.45 (m, 1H), 3.92–3.77 (m, 2H), 3.50 (m, 1H), 2.30–2.08 (m, 2H), 1.42 (s, 9H)

ES-MS: 187 (M+2)$^+$ d) Synthesis of tert-butyl (S)-2-[2-(6-cyano-1-ethylindol-2-yl)vinyl]azetidine carboxylate:

3.8 g of 6-cyano-1-ethylindole-2-methyl triphenylphosphonium bromide and 1.3 g of tert-butyl (S)-2- formylazetidine carboxylate obtained in the above c) were treated according to the same procedure as Example 1-j) to obtain 1.7 g of the title compound as a pale yellow solid.

$^1$H NMR (CDCl$_3$, ppm): δ 7.60 (m, 2H), 7.28 (m, 1H), 6.70 (s, 1H), 6.61 (s, 1H), 6.55 (d, 1H), 4.88 (m, 1H), 4.21 (q, 2H, J=7.2 Hz), 3.92 (m, 2H), 2.49 (m, 1H), 2.10 (m, 1H), 1.43 (m, 9H), 1.38 (m, 3H)

e) Synthesis of tert-butyl (S)-2-[2-(6-cyano-1-ethylindol-2-yl)ethyl]azetidine carboxylate:

1.6 g of the compound obtained in the above d) was treated according to the same procedure as Example 1-k) to obtain 1.2 g of the title compound as a yellow oil.

$^1$H NMR (CDCl$_3$, ppm): δ 7.59 (m, 2H), 7.28 (m, 1H), 6.35 (s, 1H), 4.36 (m, 1H), 4.14 (q, 2H, J=7.2 Hz), 3.86 (m, 2H), 2.83 (m, 2H), 2.33 (m, 2H), 2.10 (m, 1H), 1.92 (m, 1H), 1.46 (s, 9H), 1.35 (t, 3H, J=7.2 Hz)

f) Synthesis of 2-[2-((S)-2-azetidinyl)ethyl]-1-ethylindole-6-carbonitrile:

1.1 g of the compound obtained in the above e) was treated according to the same procedure as Example 1-l) to obtain 0.75 g of the title compound as a pale yellow solid.

g) Synthesis of tert-butyl (R)-2-[[(S)-2-[2-(6-cyano-1-ethylindol-2-yl)ethyl]azetidinyl]carbonyl]pyrrolidine carboxylate:

730 mg of the compound obtained in the above f) was treated according to the same procedure as Example 11-a) to obtain 920 mg of the title compound as a yellowish white oil.

$^1$H NMR (CDCl$_3$, ppm): δ 7.54 (m, 2H), 7.28 (m, 1H), 6.35 (s, 1H), 4.54 (m, 1H), 4.10 (m, 3H), 3.53 (m, 1H), 2.93 (m, 1H), 2.48 (m, 1H), 2.30 (m, 2H), 2.07 (m, 4H), 1.87 (m, 2H), 1.44 (s, 9H), 1.35 (t, 3H, J=7.1 Hz)

h) Synthesis of 1-ethyl-2-[2-[(S)-1-((R)-pyrrolidin-2-ylcarbonyl)-2-acetidinyl]ethyl]indole-6-carbonitrile:

900 mg of the compound obtained in the above g) was treated according to the same procedure as Example 1-l) to obtain 660 mg of the title compound as a pale yellow solid.

$^1$H NMR (CDCl$_3$, ppm): δ 7.56 (m, 2H), 7.29 (m, 1H), 6.35 (s, 1H), 4.53 (m, 1H), 4.15 (q, 2H, J=7.1 Hz), 4.04 (m, 1H), 3.63 (m, 1H), 3.20 (m, 1H), 2.88 (m, 3H), 2.49 (m, 2H), 2.02 (m, 3H), 1.82 (m, 2H), 1.70 (m, 1H), 1.36 (t, 3H, J=7.1 Hz)

i) Synthesis of ethyl 2-[(R)-2-[[(S)-2-[2-(6-cyano-1-ethylindol-2-yl)ethyl]azetidinyl]carbonyl]pyrrolidinyl]acetate:

650 mg of the compound obtained in the above h) and 0.31 ml of ethyl 2-bromoacetate were treated according to the same procedure as Example 1-m) to obtain 690 mg of the title compound as a pale yellow oil.

$^1$H NMR (CDCl$_3$, ppm): δ 7.56 (m, 2H), 7.29 (m, 1H), 6.36 (s, 1H), 4.55 (m, 1H), 4.16 (m, 5H), 3.51 (m, 2H), 3.20 (m, 1H), 2.92–2.75 (m, 3H), 2.46 (m, 2H), 2.09 (m, 2H), 1.92 (m, 4H), 1.36 (t, 3H, J=7.1 Hz), 1.25 (m, 3H)

j) Synthesis of ethyl 2-[(2)-2-[[(S)-2-[2-(6-amidino-1-ethylindol-2-yl)ethyl]azetidinyl]carbonyl]pyrrolidinyl]acetate:

680 mg of the compound obtained in the above i) was treated according to the same procedure as Example 1-n) to obtain 90 mg of the title compound as a pale yellow solid.

$^1$H NMR (CDCl$_3$, ppm): δ 7.61 (m, 1H), 7.53 (m, 1H), 7.32 (m, 1H), 6.33 (s, 1H), 5.08–4.65 (br, 2H), 4.54 (m, 1H), 4.17 (m, 5H), 3.69 (m, 1H), 3.48 (m, 2H), 3.41 (m, 1H), 3.19 (m, 1H), 2.88–2.73 (m, 3H), 2.45 (m, 2H), 2.13 (m, 2H), 1.90 (m, 4H), 1.36 (t, 3H), 1.24 (t, 3H)

IR (KBr): 3250, 2900, 1720, 1620, 1460 cm$^{-1}$

ES-MS: 454 (M+1)$^+$, 477 (M+Na)

EXAMPLE 60

Synthesis of ethyl 2-[(R)-2-[[(S)-2-[2-(6-amidino-1-ethylindol-2-yl)ethyl]pyrrolidinyl]carbonyl] pyrrolidinyl]acetate (Compound 86)

a) Synthesis of methyl 2[(R)-2-[[(S)-2-[2-(6-cyano-1-ethylindol-2-yl)ethyl]pyrrolidinyl]carbonyl]pyrrolidinyl] acetate:

615 mg of the compound II-a obtained in Example 57-b) was dissolved in dichloromethane, and 0.39 ml of triethylamine was added thereto at room temperature. After 20 minutes, 280 mg of methyl bromoacetate was added dropwise thereto. After 20 minutes, water was added and the reaction mixture was extracted three times with dichloromethane. The extracts were combined, dried over MgSO$_4$ and then concentrated. The residue was purified with silica gel column chromatography [eluent: dichloromethane/ methanol (50:1)] to obtain 406 mg of the title compound as a colorless liquid.

$^1$H NMR (CDCl$_3$, ppm): δ 7.60–7.47 (m, 2H), 7.29 (s, 1H), 6.44 (s, 1H), 4.25 (bs, 1H), 4.20–4.10 (m, 2H), 3.83 (bs, 1H), 3.67 (s, 3H), 3.60–3.43 (m, 2H), 3.25–3.17 (m, 1H), 2.88–2.72 (m, 3H), 2.38–1.62 (m, 12H), 1.36 (t, 3H)

b) Synthesis of ethyl 2-[(R)-2-[[(S)-2-[2-(6-amidino-1-ethylindol-2-yl)ethyl]pyrrolidinyl]carbonyl]pyrrolidinyl] acetate:

406 mg of the compound obtained in the above a) was dissolved in 30 ml of ethanol solution saturated with HCl gas. The reaction solution was allowed to stand at room temperature for 2 days and then concentrated under reduced pressure. The remaining HCl was removed for 5 hours by means of a vacuum pump. The dried product was then dissolved in 30 ml of ethanol solution saturated with NH$_3$ gas. After 2 days, the reaction solution was concentrated under reduced pressure and the residue thereby obtained was purified with column chromatography [eluent: ethyl acetate/ methanol (1:1)] on NH—DM1020 silica to obtain 246 mg of the title compound as a white foamy solid.

$^1$NMR (MeOH-d$_4$, ppm): δ 7.88 (s, 1H), 7.57 (d, 1H), 7.40 (d, 1H), 6.47 (s, 1H), 4.43–4.18 (m, 3H), 4.18–4.03 (m, 2H), 3.78 (m, 1H), 3.74–3.45 (m, 4H), 2.70 (m, 2H), 2.12–1.60 (m, 12H), 1.35 (t, 3H), 1.18 (t, 3H)

EXAMPLE 61

Synthesis of ethyl 2-[(R)-2-[[(S)-2-[2-(6-amidino-1-ethylindol-2-yl)ethyl]piperidyl]carbonyl] pyrrolidinyl]acetate (Compound 87)

a) Synthesis of tert-butyl (S)-2-(methoxycarbonyl) piperidine carboxylate:

In a 100 ml flask, 5 g of 1-((tert-butyl)oxycarbonyl) piperidine-(S)-2-carboxylic acid and 3.2 g of NaHCO$_3$ were dissolved in 50 ml of N,N-dimethylformamide, and 1.8 ml of iodomethane was added thereto. The reaction solution was stirred for 8 hours at room temperature. After adding water, the reaction solution was extracted two times with ethyl acetate. The extracts were combined, dried over MgSO$_4$ and evaporated to obtain 4.5 g of the title compound as a pale yellow oil.

$^1$H NMR(CDCl$_3$, ppm): δ4.94–4.73(brs, 1H), 3.97(br, 1H), 3.73(s, 3H), 2.95–2.88(br, 1H), 2.21(m, 1H), 1.65(m, 3H), 1.45(br, 9H), 1.25(m, 2H)

b) Synthesis of tert-butyl (S)-2-formylpiperidine carboxylate:

3 g of tert-butyl (S)-2-(methoxycarbonyl)piperidine carboxylate obtained in the above a) was treated according to the same procedure as Example 1-i) to obtain 2 g of the title compound as a colorless oil.

$^1$H NMR(CDCl$_3$, ppm): δ9.59 (s, 1H), 4.58(br, 1H), 4.08–3.89(br, 1H), 2.91(br, 1H), 2.14(m, 1H), 1.66(m, 3H), 1.46(br, 9H), 1.25(m, 2H)

c) Synthesis of tert-butyl (S)-2-[2-(6-cyano-1-ethylindol-2-yl)vinyl]-piperidine carboxylate:

4 g of 6-cyano-1-ethylindole-2-methyl triphenylphosphonium bromide and 1.9 g of tert-butyl (S)-2-formylpiperidinecarboxylate obtained in the above b) were treated according to the same procedure as Example 1-m) to obtain 1.8 g of the title compound as a pale yellow solid.

$^1$H NMR(CDCl$_3$, ppm): δ7.60(m, 2H), 7.29 (m, 1H), 6.62(m, 1H), 6.43(m, 1H), 6.27(m, 1H), 5.39(m, 1H), 4.18 (m, 2H), 4.11(m, 1H), 2.99(m, 1H), 1.79(m, 2H), 1.69(m, 2H), 1.48(m, 2H), 1.34(m, 3H), 1.25(m, 9H)

ES-MS: 380(m+1)$^+$ d) Synthesis of tert-butyl (S)-2-[2-(6-cyano-1-ethylindol-2-yl)ethyl]-piperidine carboxylate;

1.5 g of the compound obtained in the above c) was treated according to the same procedure as Example 1-n) to obtain 1.5 g of the title compound as a brown oil.

$^1$H NMR (CDCl$_3$, ppm): δ7.56(m, 2H), 7.27(m, 1H), 6.35(s, 1H), 4.41(br, 1H), 4.15(m, 2H), 4.02(m, 1H), 2,68(m, 3H), 2.16(m, 1H), 1.83(m, 1H), 1.67–1.61(br, 6H), 1.45(s, 9H), 1.35(t, 3H, J=7.2 Hz)

e) Synthesis of 1-ethyl-2-[2-(2-piperidyl)ethyl]indole-6-carbonitrile:

1.5 g of the compound obtained in the above d) was treated according to the same procedure as Example 1-l) to obtain 1.1 g of the title compound as a pale yellow solid.

$^1$H NMR (CDCl$_3$, ppm): δ7.47(m, 2H), 7.28(m, 1H), 6.31(s, 1H), 4.63–4.51br, 1H, 4.11(q, 2H, J=7.2 Hz), 3.18 (m, 1H), 2.80(m, 3H), 1.95–1.85(m, 4H), 1.62(m, 1H), 1.40(m, 3H), 1.31(t, 3H, J=7.2 Hz)

ES-MS:282(M+1)$^+$ f) Synthesis of tert-butyl (R)-2-[[(2)-2-[2-(6-cyano-1-ethylindol-2-yl)-ethyl]piperidyl]carbonyl]pyrrolidine carboxylate:

1.1 g of the compound obtained in the above e) was treated according to the same procedure as Example 11-a) to obtain 860 mg of the title compound as a pale brown oil.

$^1$H NMR(CDCl$_3$, ppm): δ7.54(m, 2H), 7.26(m, 1H), 6.33 (s, 1H), 4.98(m, 1H), 4.64(m, 1H), 4.16(m, 2H), 3.78 (m, 1H), 3.57(m, 1H), 3.47(m, 1H), 3.21(m, 1H), 2.74(m, 2H), 1.88(m, 3H), 1.73–1.64(br, 5H), 1.45(m, 9H), 1.38(m, 3H)

ES-MS: 479(M+1)$^+$ g) Synthesis of 1-ethyl-2-[2-[(S)-1-((R)-pyrrolidin-2-ylcarbonyl)-2-piperidyl]ethyl]indole-6-carbonitrile:

670 mg of the compound obtained in the above f) was treated according to the same procedure as Example 1-l) to obtain 440 mg of the title compound as a pale yellow solid.

h) Synthesis of ethyl 2-[(R)-2-[[(S)-2-[2-(6-cyano-1-ethylindol-2-yl)-ethyl]piperidyl]carbonyl]pyrrolidinyl]acetate:

430 mg of the compound obtained in the above g) and 0.19 ml of ethyl 2-bromoacetate were treated according to the same procedure as Example 1-m) to obtain 320 mg of the title compound as a pale brown oil.

$^1$H NMR (CDCl$_3$, ppm): δ7.53(m, 2H), 7.29(m, 1H), 6.36(s, 1H), 4.98(br, 1H), 412(m, 5H), 3.92(m, 2H), 3.59(m, 2H), 3.23(m, 1H), 3.06(m, 1H), 2.79–2.62(m, 4H), 2.16(m, 3H), 1.91–1.85(br, 5H), 1.28(m, 3H), 1.21(m, 3H)

ES-MS: 465(M+1)$^+$ i) Synthesis of ethyl 2-[(R)-2-[[(S)-2-[2-(6-amidino-1-ethylindol-2-yl)-ethyl]piperidyl]carbonyl]pyrrolidinyl] acetate:

300 mg of the compound obtained in the above h) was treated according to the same procedure as Example 1-n) to obtain 60 mg of the title compound as a pale yellow solid.

$^1$H NMR(CDCl$_3$, ppm): δ7.88(s, 1H), 7.52(m, 1H, 7.30 (m, 1H), 6.32(s, 1H), 4.97(br, 1H), 4.14(m, 4H), 3.93 (m, 1H), 3.26(m, 1H), 3.11(m, 1H), 2.74(m, 2H), 2.18(br, 2H), 1.86(m, 4H), 1.67(br, 6H), 1.33(m, 3H), 1.23(m, 3H)

IR(KBr): 3430, 2900, 1640 cm$^{-1}$

ES-MS: 482(M+1)$^+$

EXAMPLE 62

Synthesis of 2-[(R)-2-[[(S)-2-[2-(6-amidino-1-ethylindol-2-yl)ethyl]pyrrolidinyl]carbonyl] pyrrolidinyl]acetic acid (Compound 88)

720 mg of ethyl 2-[(R)-2-[[(S)-2-[2-(6-amidino-1-ethylindol-2-yl)-ethyl]pyrrolidinyl]carbonyl]pyrrolidinyl] acetate was treated according to the same procedure as Example 44 to obtain 583 mg of the title compound as a white solid.

$^1$H NMR (MeOH-d$_4$, ppm): δ7.83(s, 1H), 7.55(d, 1H, J=8.34 Hz), 7.25(d, 1H, J=8.36 Hz), 6.36(s, 1H), 4.25–4.03(m, 3H), 3.62(m, 1H), 3.52–3.38(m, 2H), 3.16–3.03(m, 2H), 2.73(m, 2H), 2.37–1.46(m, 12H), 1.24(t, 3H)

ES-MS: 440(M+1)$^+$

IR(KBr): 3200, 1600 cm$^{-1}$

EXAMPLE 63

Synthesis of 2-[(R)-2-[[(S)-2-[2-(6-amidino-1-ethylindol-2-yl)ethyl]piperidyl]carbonyl] pyrrolidinyl]acetic acid (Compound 89)

In a 50 ml flask; 140 mg of ethyl 2-[(R)-2-[[(S)-2-[2-(6-amidino-1-ethylindol-2-yl)ethyl]piperidyl]carbonyl] pyrrolidinyl]acetate was dissolved in 10 ml of ethanol, and 0.5 ml of 2N NaOH was added thereto. The reaction solution was stirred for 3 hours at room temperature and evaporated under reduced pressure to remove the solvent. The residue was purified with column choromatography [eluent: ethyl acetate/methanol (1:1)] on NH-DM1020 silica to obtain 60 mg of the title compound as a yellowish white solid.

$^1$H NMR (MeOH-d$_4$, ppm): δ7.87(m, 1H), 7.59(m, 1H), 7.42(m, 1H), 6.42 (m, 1H), 4.25(m, 2H), 3.64(m, 1H), 3.20(m, 1H), 3.15(m, 1H), 2.78(m, 2H), 2.31(m, 2H), 1.91(br, 2H), 1.77–1.68(br, 6H), 1.36(m, 3H)

IR(KBr):3400, 3000, 1650, 1600 cm$^{-1}$

ES-MS:454(M+1)$^+$, 476(M+Na), 498(M+2Na)

EXAMPLE 64

Synthesis of ethyl 2-[(R)-2-[[(S)-2-[2-(6-amidino-1-ethylindol-2-yl)ethyl]-(S)-4-methylpyrrolidinyl]carbonyl]pyrrolidinyl]acetate (Compound 97)

a) Synthesis of (R)-4-hydroxy-1-(benzyloxycarbonyl)pyrrolidine-2-carboxylic acid:

In a 1 l flash, 25 g of (R)-4-hydroxy-L-proline was dissolved in 350 ml of 4N-NaOH solution and then cooled to −20° C. To the resulting solution was added dropwise 41 ml of benzyl chloroformate and the reaction mixture was stirred for one hour at −20° C. After the reaction is completed, the reaction solution was adjusted to pH 4 with 2N aqueous HCl solution and then extrated two times with ethyl acetate. The organic layers were combined, dried over $MgSO_4$ and evaporated to obtain 31.5 g of the title compound as a white solid.

b) Synthesis of (S)-4-oxo-1-(benzyloxycarbonyl)pyrrolidine-2-carboxylic acid:

In a 500 ml flask, 37.2 g of $CrO_3$ and a small quantity of ice-water were mixed and 30.8 ml of concentrated sulfuric acid was added dropwise thereto. The resulting solution was diluted with water to prepare 140 ml of 8N-chromoic acid. In a 2 l flask; 31.5 g of the compound obtained in the above a) was dissolved in 800 ml of acetone, and 140 ml of 8N-chromoic acid as prepared above was slowly added thereto. The reaction mixture was stirred for 2 hours at room temperature, and methanol was added dropwise to complete the reaction. The resulting precipitate was filtered and the filtrate was evaporated. The residue was extracted two times with chloroform. The organic layers were combined, dried over $MgSO_4$ and then evaporated to obtain 28.4 g of the title compound as a white solid.

$^1$H NMR($CDCl_3$, δ10.0(br, 1H), 7.30(s, 5H), 5.15(m, 2H), 4.90(m, 1H), 5.95(m, 2H), 2.95(m, 1H), 2.65(m, 1H)

ES-MS:264(M+1)$^+$ c) Synthesis of phenylmethyl (S)-4,4-dimethoxy-2-(methoxycarbonyl)-pyrrolidine carboxylate:

In a 100 ml flask, 4.0 g of the compound obtained in the above b) was dissolved in 40 ml of methanol, and 1.08 ml of thionyl chloride was slowly added thereto at 0° C. The reaction mixture was refluxed for 2 hours with stirring. After the reaction was completed, the reaction solution was evaporated under reduced pressure. The residue was extracted twice with ethyl acetate. The organic layers were combined, dried over $MgSO_4$ and then evaporated. The residue was purified with silica gel column chromatography [eluent: ethyl acetate/n-hexane(1:2)]. The fractions containing the desired product were combined and evaporated to obtain 4.2 g of the title compound as a colorless liquid.

$^1$H NMR ($CDCl_3$, ppm): δ7.30(m, 5H), 5.30–5.0(m, 2H), 4.45(m, 1H), 3.80 (s, 2H), 3.55(m, 3H), 3.15(s, 6H), 2.35(m, 1H), 2.20(m, 1H)

ES-MS: 324(M+1)$^+$ d) Synthesis of methyl (S)-4-oxo-1-(benzyloxycarbonyl)pyrrolidone-2-carboxylate:

In a 100 ml flask, 3.0 g of the compound obtained in the above c) was dissolved in 90 ml of acetone and $TsOH.H_2O$ was then added. The reaction mixture was refluxed for 2 hours with stirring. After the reaction was completed, the reaction solution was evaporated under reduced pressure, and the residue was extracted twice with ethyl acetate. The organic layers were combined, dried over $MgSO_4$ and th en evaporated. The residue was purified with silica gel column chromatography [eluent: ethyl acetate/n-hexane(1:2)]. The fractions containing the desired product were combined and evaporated to obtain 3.2 g of the title compound as a colorless liquid.

$^1$H NMR ($CDCl_3$, ppm): δ7.35(m, 5H), 5.20(m, 2H), 4.80(m, 1H), 4.0(s, 2H), 3.80(d, 3H), 2.95(m, 1H), 2.55(dd, 1H, J=18.85 Hz, 2.67 Hz)

ES-MS: 278(M+1)$^+$ e) Synthesis of methyl (S)-4-methylene-1-(benzyloxycarbonyl)pyrrolidine carboxylate:

In a 100 ml flask, 10.0 g of methyltripheylphosphonium bromide was dissolved in 50 ml of tetrahydrofuran, and tBuOK was slowly added thereto. The reaction mixture was stirred for 2 hours. 3.11 g of the compound obtained in the above d) which was dissolved in a small quantity of tetrahydrofuran was slowly added dropwise, and the mixture was stirred for 2 hours. After the reaction was quenched with a small quantity of water, the reaction solution was evaporated under reduced pressure, and the residue was extracted twice with ethyl ether. The organic layers were combined, dried over $MgSO_4$ and then evaporated. The residue was purified with silica gel column chromatography [eluent: ethyl acetate/n-hexane(1:5)]. The fractions containing the desired product were combined and evaporated to obtain 1.5 g of the title compound as a colorless liquid.

$^1$H NMR ($CDCl_3$, ppm): δ7.35(br, 5H), 5.20(m, 2H), 5.0(br, 2H), 4.55(m, 1H), 4.15(br, 2H), 3.65(d, 3H), 3.0(m, 1H), 2.65(d, 1H, J=16.0 Hz)

ES-MS:276(M+1)$^+$ f) Synthesis of methyl (S)-4-methyl-1-[tert-butoxycarbonyl]pyrrolidine-2-carboxylate:

1.5 g of the compound obtained in the above e) was treated according to the same procedure as Example 1-k) to obtain 540 mg of the yellow liquid product, which was then treated according to the same procedure as Example 1-h) to obtain 887 mg of the title compound as a yellow liquid.

$^1$H NMR ($CDCl_3$, ppm): δ4.20(m, 2H), 3.70(br, 3H), 3.0(t, 1H, J=10.05 Hz), 2.40(m, 1H), 2.20(m, 1H), 1.50–1.30(br, 9H), 1.20(m, 1H), 1.0(br, 3H)

ES-MS:224(M+1)$^+$ g) Synthesis of tert-butyl (S)-2-formyl-(S)-4-methylpyrrolidine carboxylate:

880 mg of the compound obtained in the above f) was treated according to the same procedure as Example 1-i) to obtain the title compound as a yellow liquid in a quantitative yield.

h) Synthesis of tert-butyl (S)-2-[2-(6-cyano-1-ethylindol-2-yl)vinyl]-(S)-4-methylpyrrolidine carboxylate:

2.85 g of 6-cyano-1-ethylindole-2-ethyl triphenylphosphonium bromide obtained in Example 1-f) and the compound obtained in the above g) were treated according to the same procedure as Example 1-j) to obtain 800 mg of the title compound as a yellow fluorescent liquid.

$^1$H NMR ($CDCl_3$, ppm): δ7.60(m, 2H), 7.25(m, 1H), 6.65(s, 1H), 6.60–6.40(br, 1H), 6.25(dd, 1H, J=15.63 Hz), 4.40(m, 1H), 4.20 (q, 2H, J=7.24 Hz), 4.0–3.45(m, 2H), 2.45–2.10(m, 2H), 1.60–1.30 (m, 12H), 1.25(m, 1H), 1.05(d, 3H), J=6.51 Hz)

ES-MS: 380(M+1)$^+$ i) Synthesis of tert-butyl (S)-2-[2-(6-cyano-1-ethylindol-2-yl)ethyl]-(S)-4-methylpyrrolidine carboxylate:

800 mg of the compound obtained in the above h) was treated according to the same procedure as Example 1-k) to obtain 710 mg of the title compound as a colorless liquid.

$^1$H NMR ($CDCl_3$, ppm): δ7.55(m, 2H), 7.25(m, 1H), 6.30(s, 1H), 4.15(q, 2H, J=7.24 z), 3.90–3.60(m, 2H), 2.70(m, 3Hz), 2.30(m, 2H), 2.10(m, 1H), 1.85(m, 1H), 1.45(s, 9H), 1.35(t, 3H, J=7.24 Hz), 1.25 (m, 1H), 1.10(d, 3H, J=6.46 Hz)

ES-MS: 382 (M+1)⁺ j) Synthesis of 1-ethyl-2-[2-[(S)-((S)-4-methyl)pyrrolidin-2-yl]ethyl]-indole-6-carbonitrile:

430 mg of the compound obtained in the above i) was treated according to the same procedure as Example 1—1) to obtain 401 mg of the title compound as a pale yellow solid.

$^1$H NMR (CDCl$_3$, ppm): δ7.45(m, 2H), 7.25(m, 1H), 6.25(s, 1H), 4.05 2H, J=7.24 Hz), 3.60 m, 2H), 3.35(m, 1H), 2.90–2.65(m, 3H), 2.40–2.20(m, 3H), 2.15(m, 1H), 1.25(t, 3H, J=7.24 Hz), 1.10(d, 3H, J=6.46 Hz)

ES-MS: 282(M+1)⁺ k) Synthesis of tert-butyl (R)-2-[[(S)-2-[2-(6-cyano-1-ethylindol-2-yl)-ethyl]-(S)-4-methylpyrrolidinyl]carbonyl]pyrrolidine carboxylate:

400 mg of the compound obtained in the above j) was treated according to the same procedure as Example 11-a) to obtain 370 mg of the title compound as a pale yellow solid.

$^1$H NMR (CDCl$_3$, ppm): δ7.55(m, 2H), 7.25(m, 1H), 6.30(m, 1H), 4.40(m, 1H), 4.10(m, 2H), 3.60(m, 2H), 3.40(m, 1H), 3.10(m, 1H), 2.80(m, 3H), 2.60–1.80(m, 6H), 1.80–1.10(m, 13H, J=6.46 Hz), 1.05(d, 3H, J=6.46 Hz)

ES-MS: 479(M+1)⁺ l) Synthesis of 1-ethyl-2-[2-[(S)-4-methyl-1-((R)-pyrrolidin-2-ylcarbonyl)pyrrolidin-(S)-2-yl]ethyl]indole-6-carbonitrile:

270 mg of the compound obtained in the above k) was treated according to the same procedure as Example 1-1) to obtain 220 mg of the title compound as a pale yellow solid.

$^1$H NMR (CDCl$_3$, ppm): δ7.55 (m, 2H), 7.25(m, 1H), 6.40(s, 1H), 4.15(q, 2H, J=7.24 Hz), 3.80(m, 1H), 3.25(m, 1H), 3.0(m, 2H), 2.80(m, 2H), 2.50(m, 1H), 2.20(m, 2H), 2.0–1.60(m, 4H), 1.50–1.20(m, 4H), 1.05 (d, 3H, J=6.46 Hz)

ES-MS: 379(M+1)⁺ m) Synthesis of 1-ethyl-2-[2-[(S)-4-methyl-1-((R)-pyrrolidin-2-ylcarbonyl)pyrrolidin-(S)-2-yl]ethyl]indole-6-carbonitrile:

150 mg of the compound obtained in the above l) was treated according to the same procedure as Example 1-m) to obtain 247 mg of the title compound as a pale yellow solid.

$^1$H NMR(CDCl$_3$, ppm): δ7.55(m, 2H), 7.25(m, 1H), 6.40 (s, 1H), 4.20–4.00 (m, 4H), 3.95–3.75(m, 2H), 3.50(q, 2H), 3.20(m, 1H), 3.0–2.70(m, 4H), 2.60(m, 1H), 2.35 (m, 1H), 2.20–1.70(m, 7H), 1.35(t, 3H, J=7.22 Hz), 1.25(m, 4H), 1.10(d, 3H, J=6.43 Hz)

ES-MS: 4.66(M+1)⁺ n) Synthesis of ethyl 2-[(R)-2-[[(S)-2-[2-(6-amidino-1-ethylindol-2-yl)-ethyl]-(S)-4-methylpyrrolidinyl]carbonyl]pyrrolidinyl]acetate:

240 mg of the compound obtained in the above m) was treated according to the same procedure as Example 1-n) to obtain 71 mg of the title compound as a pale yellow solid.

$^1$H NMR (CDCl$_3$): δ7.80(s, 1H), 7.50(d, 1H), 7.40(d, 1H), 6.40(s, 1H), 4.30–4.10(m, 4H), 3.90–3.70(m, 2H), 3.50 (q, 2H), 3.20(m, 1H), 3.0–2.65(m, 4H), 2.60(m, 1H), 2.30(m, 1H), 2.20–1.70(m, 7H), 1.35(t, 3H, J=7.08 Hz), 1.25(t, 3H, J=7.11 Hz), 1.05(d, 3H, J=6.41 Hz)

ES-MS: 482(M+1)⁺

IR(KBr): 3100, 2950, 1750, 1650 cm⁻¹

EXAMPLE 65

Synthesis of 2-[(R)-2-[[(S)-2-[2-(6-amidino-1-ethylindol-2-yl)ethyl]-(S)-4-methylpyrrolidinyl]carbonyl]pyrrolidinyl]acetic acid (Compound 98)

42 mg of ethyl 2-[(R)-2-[[(S)-2-[2-(6-amidino-1-ethylindol-2-yl)-ethyl]-(S)-4-methylpyrrolidinyl]carbonyl]pyrrolidinyl]acetate obtained in Example 64 was treated according to the same procedure as Example 44 to obtain 27 mg of the title compound as a pale yellow solid.

$^1$H NMR (CD$_3$OD, ppm): δ7.70(s, 1H), 7.40(d, 1H), 7.20(d, 1H), 6.25(s, 1H), 4.20–3.80(m, 3H), 3.65(m, 1H), 3.15–2.50 (m, 6H), 2.50–1.40 (m, 9H), 1.15(m, 3H), 0.95(m, 3H)

ES-MS: 454(M+1)⁺

IR(KBr): 3200, 2950, 2850, 1650 cm⁻¹

EXAMPLE 66

Synthesis of ethyl 2-[(R)-2-[[(S)-2-[2-(6-amidino-1-ethylindol-2-yl)ethyl]-(S)-4-methoxypyrrolidinyl]carbonyl]pyrrolidinyl]acetate (Compound 99)

a) Synthesis of (4R)-4-hydroxy-1-(benzyloxycarbonyl)pyrrolidine-(S)-2-carboxylic acid:

In a 250 ml flask, 10 g of (R)-4-hydroxypyrrolidine-(S)-2-carboxylic acid and 140 ml of 4N NaOH were introduced and cooled to −20° C., and 17 ml of benzyl chloroformate was slowly added. The reaction solution was stirred for one hour at −20° C. and extracted with ethyl ether and water. The ether layer was removed and the aqueous layer was acidified with 2N aqueous HCl solution and then extracted twice with ethyl acetate. The extracts were combined, dried over MgSO$_4$ and then evaporated to obtain 17.3 g of the title compound as a colorless oil.

$^1$H NMR (CDCl$_3$, ppm): δ7.30(m, 5H), 5.17(m, 2H), 4.52(m, 1H), 4.45(m, 1H), 3.60(m, 2H), 2.24(m, 2H)

b) Synthesis of 4-oxo-1-(benzyloxycarbonyl)pyrrolidine-(S)-2-carboxylic acid:

In a 1 l flask, 16 g of the compound obtained in the above a) was dissolved in 600 ml of acetone, and 64 ml of 8N chromic acid was then slowly added at −10° C. The reaction mixture was stirred for 4 hours at −10° C., and 40 ml of methanol was added thereto. The reaction solution was filtered. To the filtrate was added water, and the mixture was extracted twice with chloroform. The extracts were combined, dried over MgSO$_4$ and evaporated. The residue was purified with silica gel column chromatography [eluent: dichloromethane/methanol(10:1)] to obtain 12 g of the title compound as a pale yellow solid.

$^1$NMR (CDCl$_3$, ppm): δ7.34(s, 5H), 5.16(m, 1H), 5.09(m, 1H), 4.69(m, 1H), 3.92(s, 2H), 2.87(m, 1H), 2.64(m, 1H)

ES-MS: 264(M+1)⁺ c) Synthesis of (S)-4-hydroxy-1-benzyloxycarbonyl)pyrrolidine-(S)-2-carboxylic acid:

In a 250 ml flask, 4.6 g of the compound obtained in the above b) was dissolved in 164 ml of methanol, and 2.6 g of NaBH$_4$ dissolved in 11 ml of water was slowly added at −10° C. The reaction solution was stirred for about 2.5 hours at −10° C. to 0° C. and then evaporated to remove methanol. About 100 ml of 2N aqueous NaOH solution was added to the residue and then stirred for 30 minutes at room temperature. The reaction solution was cooled to 0° C., acidified with hydrochloric acid and then extracted twice with ethyl acetate. The extracts were combined, dried over MgSO$_4$ and evaporated. The residue was purified with silica gel column chromatography [eluent: dichloromethane/methanol(3:1)] to obtain 3.2 g of the title compound as a yellowish white solid.

$^1$H NMR (CDCl$_3$, ppm): δ7.30(m, 5H), 6.90(br, 1H), 5.12(m, 2H), 4.43(m, 2H), 3.64(m, 1H), 3.54(m, 1H), 2.21(br, 2H)

ES-MS: 266(M+1)⁺ d) Synthesis of (S)-4-methoxy-1-benzyloxycarbonyl)pyrrolidine-(S)-2-carboxylic acid:

In a 100 ml flask, 3 g of the compound obtained in the above c) was dissolved in 40 ml of tetrahydrofuran, and 0.95 g of 60% NaH was slowly added. The reaction solution was stirred for one hour at room temperature, and 1.48 ml of iodomethane was added. The reaction mixture was stirred for 3 hours at refluxing temperature and then for 10 hours at room temperature, and evaporated. To the residue was added water, and the mixture was acidified with 2N HCl and extracted twice with dichloromethane. The extracts were combined, dried over $MgSO_4$ and then evaporated. The residue was purified with silica gel column chromatography [eluent: dichloromethane/methanol(3:1)] to obtain 3.2 g of the title compound as a pale brown oil.

$^1$H NMR ($CDCl_3$, ppm): δ7.31(m, 5H), 5.17(m, 2H), 4.46(m, 1H), 3.94(m, 1H), 3.64(m, 2H), 3.26(s, 3H), 2.45–2.38(m, 1H), 2.22(m, 1H)

ES-MS: 280(M+1)$^+$, 302(M+Na)

e) Synthesis of phenylmethyl (S)-4-methoxy-(S)-2-(methoxycarbonyl)-pyrrolidine carboxylate:

In a 100 ml flask, 13 ml of methanol was introduced and 0.93 ml of thionyl chloride was slowly added thereto at 0° C. 3.1 g of the compound obtained in the above d) which was dissolved in 11 ml of methanol was added thereto, and the reaction mixture was stirred for 2 hours at refluxing temperture and then evaporated under reduced pressure. The residue was purified with silica gel column chromatography [eluent: n-hexane/ethyl acetate (3:1)] to obtain 2.4 g of the title compound as a colorless oil.

$^1$H NMR($CDCl_3$, ppm): δ7.31(m, 5H), 5.17(m, 2H), 4.45(m, 1H), 3.93(m, 1H), 3.72(m, 2H), 3.67(s, 3H), 3.25(s, 3H), 2.32–2.22(m, 2H)

ES-MS: 294(M+1)$^+$ f) Synthesis of phenylmethyl (S)-2-formyl-(S)-4-methoxypyrrolidine carboxylate:

2.3 g of the compound obtained in the above e) was treated according to the same rocedure as Example 1-i)to obtain 1.4 g of the title compound as a colorless oil.

$^1$NMR ($CDCl_3$, ppm): δ7.33(m, 5H), 5.16(m, 2H), 4.19(m, 1H), 3.92(m, 1H), 3.73(m, 1H), 3.52(m, 1H), 3.22(s, 3H), 2.38(m, 1H), 2.14(m, 1H)

ES-MS: 264(M+1)$^+$ g) Synthesis of phenylmethyl (S)-2-[2-(6-cyano-1-ethylindol-2-yl)vinyl]-(S)-4-methoxypyrrolidine carboxylate:

2.3 g of 6-cyano-1-ethylindole-2-methyl triphenylphosphonium bromide and 1.2 g of phenylmethyl 2-formyl-4-methoxypyrrolidine carboxylate were reacted according to the same procedure as Example 1-j) to obtain 1.7 g of the title compound as a yellow solid.

$^1$H NMR($CDCl_3$, ppm): δ7.58(br, 2H), 7.36–7.21(br, 6H), 6.64(m, 1H), 6.47(m, 1H), 5.14(m, 2H), 4.21(m, 1H), 4.00(m, 2H), 3.68–3.58(br, 2H), 3.34(s, 3H), 2.34(m, 1H), 1.23–1.20(m, 4H)

ES-MS: 452(M+Na)

h) Synthesis of 1-ethyl-2-[2-[(S)-((S)-4-methoxy)pyrrolidin-2-yl]ethyl]-indole-6-carbonitrile:

1.6 g of the compound obtained in the above g) was treated according to the same procedure as Example 1-k) to obtain 500 mg of the title compound as a brown oil.

$^1$H NMR($CDCl_3$, ppm): δ7.58(m, 2H), 7.27(m, 1H), 6.30 (s, 1H), 4.16(q, 2H, J=7.1 Hz), 3.91(m, 1H), 3.28(s, 3H), 3.15(m, 2H), 2.92–2.78(m, 4H), 2.24(m, 1H), 2.02(m, 2H), 1.34(t, 3H, J=7.1 Hz)

ES-MS: 298(M+1)$^+$ i) Synthesis of tert-butyl (R)-2-[[(S)-2-[2-(6-cyano-1ethylindol-2-yl)-ethyl]-(S)-4-methoxypyrrolidinyl]carbonyl]pyrrolidine carboxylate 450 mg of the compound obtained in the above h) was treated according to the same procedure as Example 11-a) to obtain 500 mg of the title compound as a pale brown oil.

$^1$H NMR ($CDCl_3$, ppm):δ7.55(m, 2H), 7.28(m, 1H), 6.39 (m, 1H), 4.37(m, 1H), 4.16(m, 2H), 4.03(m, 1H), 3.62(m, 1H), 3.32(s, 3H), 2.82(m, 2H), 2.12–1.96(br, 4H), 1.85(m, 2H), 1.40(m, 9H), 1.33(m, 3H)

j) Synthesis of 1-ethyl-2-[2-[(S)-4-methoxy-1-((R)-pyrrolidin-2-ylcarbonyl)pyrrolidin-(S)-2-yl]ethyl]indole-6-carbonitrile:

580 mg of the compound obtained in the above i) was treated according to the same procedure as Example 1-l) to obtain 450 mg of the title compound as a pale yellow solid.

$^1$H NMR($CDCl_3$, ppm): δ7.56(m, 2H), 7.32(m, 1H), 6.42 (s, 1H), 4.28(m, 1H), 4.15(m, 2H), 4.01(m, 1H, 3.75(m, 1H), 3.65(m, 1H), 3.33(s, 3H), 3.21(m, 1H), 2.80(m, 2H), 2.45(m, 1H), 2.10(m, 2H), 1.99–1.79(br, 7H), 1.36(m, 3H)

k) Synthesis of ethyl 2-[(R)-2-[[(S)-2-[2-(6-cyano-1-ethylindol-2-yl)-ethyl]-(S)-4-methoxypyrrolidinyl]carbonyl]pyrrolidinyl]acetate:

440 mg of the compound obtained in the above j) and 0.19 ml of ethyl 2-bromoacetate were treated according to the same procedure as example 1-m) to obtain 380 mg of the title compound as a pale yellow oil.

ES-MS: 481(M+1)$^+$ l) Synthesis of ethyl 2-[(R)-2-[[(S)-2-[2-(6-amidino-1-ethylindol-2-yl)-ethyl]-(S)-4-methoxypyrrolidinyl]carbonyl]pyrrolidinyl]acetate:

380 mg of the compound obtained in the above k) was treated according to the same procedure as Example 1-n) to obtain 90 mg of the title compound as a pale yellow solid.

IR(KBr): 3300, 3000, 1750, 1640 cm$^{-1}$

ES-MS: 498(M+1)$^+$

EXAMPLE 67

Synthesis of ethyl-2-[(R)-2-[[(S)-2-[2-(6-amidino-1-ethylindol-2-yl)ethyl]pyrrolidinyl]carbonyl] pyrrolidinyl]propionate (Compound 109)

a) Synthesis of ethyl-2-[(R)-2-[[(S)-2-[2-(6-cyano-1-ethylindol-2-yl)-ethyl]pyrrolidinyl]carbonyl]pyrrolidinyl] propionate:

300 mg (0.823 mmole) of 1-ethyl-2-[2-[(S)-1-[((R)-pyrrolidin-2-yl)carbonyl]pyrrolidin-2-yl]ethyl]indole-6-carbonitrile was dissolved in 15 ml of acetonitrile, and 0.29 ml (1.646 mmole) of diisopropylethylamine and 0.22 ml (1.646 mmole) of ethyl 2-bromopropionate were added thereto. The reaction mixture was heated to 70° C., stirred for 4 hours, and then concentrated under reduced pressure. The residue was purified with silica gel column chromatography [eluent: dichloromethane/methanol(20:1)] to obtain 310 mg of the title compound as a pale yellow oil.

ES-MS: 464 (M+1)$^+$ $^1$H NMR ($CDCl_3$, ppm): δ7.61–7.56(m, 2H), 7.34–7.28 (m, 1H), 6.46(s, 1H), 4.31(br, 1H), 4.21–4.14(m, 4H), 3.80–3.75(m, 1H), 3.61–3.53(m, 3H), 3.23–3.19(m, 1H), 2.86–2.81(m, 3H), 2.34–2.31(m, 1H), 2.01–1.77 (m, 9H), 1.42–1.36(m, 3H), 1.32–1.22(m, 6H)

b) Synthesis of ethyl-2-[(R)-2-[[(S)-2-[2-(6-amidino-1-ethylindol-2-yl) ethyl]pyrrolidinyl]carbonyl]pyrrolidinyl]propionate:

310 mg of the compound obtained in the above a) was treated according to the same procedure as Example 1-n) to obtain 220 mg of the title compound as a pale yellow foam.

$^1$H NMR(MeOH-d$_4$, ppm): δ7.93–7.89(m, 1H), 7.64–7.58(m, 1H), 7.48–7.42(m, 1H), 6.46–6.42(m, 1H), 4.34–4.30(m, 3H), 4.18–4.14(m, 2H), 3.91–3.81(m, 1H), 3.65–3.61(m, 3H), 3.15–3.11(m, 1H), 2.88–2.81 (m, 3H), 2.21–1.85(m, 10H), 1.42–1.27(m, 9H)

IR(KBr): 3300, 2980, 1720, 1680, 1640, 1540 cm$^{-1}$

ES-MS: 482(M+1)$^+$

EXAMPLE 68

Synthesis of ethyl 2-[(R)-2-[[(S)-2-[2-(6-amidino-1-ethylindol-2-yl)ethyl]pyrrolidinyl]carbonyl]pyrrolidinyl]butanoate (Compound 110)

a) Synthesis of ethyl 2-[(R)-2-[[(S)-2-[2-(6-cyano-1-ethylindol-2-yl)-ethyl]pyrrolidinyl]carbonyl]pyrrolidinyl]butanoate:

100 mg of the compound II-a obtained in Example 57-b) and 80 μl of ethyl 2-bromoacetate were reacted according to the same procedure as Example 45-b) to obtain 88 mg of the title compound.

$^1$H NMR(CDCl$_3$, ppm): δ7.58(m, 2H), 7.27(m, 1H), 6.40 (d, 1H), 4.38(m, 1H), 4.15(m, 4H), 3.69(m, 1H), 3.54 (m, 2H), 3.30–3.10(m, 1H), 2.82(m, 3H), 2.30(m, 1H), 2.18–1.55(m, 12H), 1.42–1.17(m, 6H), 0.89(m, 3H)

b) Synthesis of ethyl 2-[(R)-2-[[(S)-2-[2-(6-amidino-1-ethylindol-2-yl)-ethyl]pyrrolidinyl]carbonyl]pyrrolidinyl]butanoate:

88 mg of the compound in the above a) was treated according to the same procedure as Example 1-n) to obtain 24 mg of the title compound.

$^1$H NMR (MeOH-d$_4$, ppm): δ8.00–6.24(m, 4H), 4.24(m, 5H), 3.64(m, 1H), 3.52(m, 2H), 3.41–3.10(m, 3H), 2.83(m, 5H), 2.31(m, 1H), 2.18–1.54(m, 8H), 1.44–1.10(m, 6H), 0.84(m, 3H)

EXAMPLE 69

Synthesis of ethyl 2-[(R)-2-[[(S)-2-[2-(6-amidino-1-ethylindol-2-yl)ethyl]pyrrolidinyl]carbonyl]pyrrolidinyl]hexanoate (Compound 111)

a) Synthesis of ethyl 2-[(R)-2-[[(S)-2-[2-(6-cyano-1-ethylindol-2-yl)-ethyl]pyrrolidinyl]carbonyl]pyrrolidinyl]hexanoate:

135 mg of the compound II-a obtained in Example 57-b) and 155 μl of ethyl 2-bromoacetate were reacted according to the same procedure as Example 45-b) to obtain 112 mg of the title compound.

$^1$H NMR (CDCl$_3$, ppm):δ7.58(m, 2H), 7.28(d, 1H), 6.45 (d, 1H, J=8.20 Hz), 4.30–4.00(m, 6H), 3.71–3.31(m, 3H), 3.25–3.05(m, 1H), 2.82(m, 3H), 2.45–2.20(m, 1H), 2.13–1.55(m, 11H), 1.38–1.12(m, 10H), 0.85(t, 1H)

b) Synthesis of ethyl 2-[(R)-2-[[(S)-2-[2-(6-amidino-1-ethylindol-2-yl)-ethyl]pyrrolidinyl]carbonyl]pyrrolidinyl]hexanoate:

112 mg of the compound obtained in the above a) was treated according to the same procedure as Example 1-n) to obtain 73 mg of the title compound.

$^1$H NMR (MeOH-d$_4$, ppm): δ7.82(s, 1H), 7.62(d, 1H J=11.71 Hz), 7.34(d, 1H, J=7.80 Hz), 6.46 (d, 1H, J=11.14 Hz), 4.40–4.05(m, 6H), 3.75–3.40(m, 3H), 3.30–3.05(m, 1H), 2.99–2.66(m, 3H), 2.50–2.30(m, 1H), 2.13–1.52(m, 11H), 1.50–1.10(m, 10H), 0.90–0.70(m, 3H)

ES-MS: 524(M+1)$^+$

EXAMPLE 70

Synthesis of ethyl-2-[(R)-2-[[(S)-2-[2-(6-amidino-1-ethylindol-2-yl)ethyl]pyrrolidinyl]carbonyl] pyrrolidinyl]-2-phenylacetate (Compound 112)

a) Synthesis of ethyl-2-[(R)-2-[[(S)-2-[2-(6-cyano-1-ethylindol-2-yl)-ethyl]pyrrolidinyl]carbonyl]pyrrolidinyl]-2-phenylacetate:

300 mg of the compound II-a obtained in Example 57-b) ad 300 mg of ethyl 2-bromophenyl acetate were reacted according to the same procedure as Example 45-b) to obtain 300 mg of the title compound as a pale yellow foam.

$^1$H NMR (CDCl$_3$, ppm): δ7.63–7.57(m, 2H), 7.51–7.48 (m, 2H), 7.34–7.29 (m, 4H), 6.43(s, 1H), 4.65(s, 1H), 4.24–4.19(m, 3H), 4.11–4.04(m, 3H), 3.45–3.41(m, 2H), 3.06–3.03(m, 1H), 2.84–2.71(m, 3H), 2.30–2.20 (m, 2H), 1.98–1.82(m, 8H), 1.42(t, J=7.20 Hz, 3H), 1.08(t, J=7.10 Hz, 3H)

ES-MS: 526(M+1)$^+$ b) Synthesis of ethyl-2-[(R)-2-[[(S)-2-[2-(6-amidino-1-ethylindol-2-yl)-ethyl]pyrrolidinyl]carbonyl]pyrrolidinyl]-2-phenylacetate:

130 mg of the compound obtained in the above a) was treated according to the same procedure as Example 1-n) to obtain 80 mg of the title compound as a pale yellow solid.

$^1$H NMR(MeOH-d$_4$, ppm): δ8.04–7.95(m, 1H), 7.78–7.67(m, 1H), 7.50–7.45(m, 2H), 7.31–7.24(m, 4H), 6.51(m, 1H), 4.52(m, 1H), 4.37–4.34(m, 2H), 4.09–4.04(m, 3H), 3.49–3.44(m, 1H), 3.20–3.09(m,2H), 2.98–2.65(m, 4H), 2.20–1.75(m, 10H), 1.47–1.42(m, 3H), 1.13–1.06(m, 3H)

ES-MS: 544(M+1)$^+$

EXAMPLE 71

Synthesis of ethyl 2-[(R)-2-[[(S)-2-[2-(6-amidino-1-ethylindol-2-yl)ethyl]-pyrrolidinyl]carbonyl]-pyrrolidinyl]-2-(3-bromo-4-methoxyphenyl)acetate (Compound 113)

a) Synthesis of ethyl-2-bromo-2-(3-bromo-4-methoxyphenyl)acetate:

4.3 g (0.0259 mole) of 4-methoxyphenylacetic acid was dissolved in 10 ml of thionyl chloride, and the resulting solution was stirred for 18 hours at 70° C. and then cooled to room temperature. To the reaction solution was added 50 ml of carbon tetrachloride and then added 5.54 g (0.0331 mole) of N-bromosuccinimide and 5 drops of 48% aqueous HBr solution. The resulting mixture was stirred for 4 hours at refluxing temperature and filtered to remove the unsoluble materials. 50 ml of ethanol was added to the filtrate and the mixture was stirred for 30 minutes and then evaporated under reduced pressure to remove the solvent. The residue was purified with silica gel column chromatography [eluent: ethyl acetate/n-hexane(1:9)] to obtain 1.5 g of the title compound as a yellow oil.

$^1$H NMR (CDCl$_3$, ppm): δ7.72(d, J=2.23 Hz, 1H), 7.45 (dd, 1H, J=2.22 Hz, 8.50 Hz), 6.93 (d, 1H, J=8.50 Hz), 5.28 (s, 1H), 4.32–4.25(m, 2H), 3.93 (s, 3H), 1.32(t, 3H, J=7.00 Hz)

b) Synthesis of ethyl 2-[(R)-2-[[(S)-2-2-[2-(6-cyano-1-ethylindol-2-yl)-ethyl]pyrrolidinyl]carbonyl]pyrrolidinyl]-2-(3-bromo-4-methoxyphenyl)-acetate:

100 mg of the compound II-a obtained in Example 57-b) and 80 mg of the compound obtained in the above a) were reacted according to the same procedure as Example 1-m) to obtain 170 mg of the title compound as a pale yellow foam.

$^1$H NMR (CDCl$_3$, ppm): δ7.69–7.57(m, 3H), 7.40–7.29 (m, 2H), 6.82(m, 1H), 6.44(m, 1H), 4.60(m, 1H), 4.24–4.21 (m, 3H), 4.09–3.98(m, 3H), 3.78(m, 3H), 3.41–3.37(m, 2H), 3.24–3.05(m, 2H), 2.81–2.75 (m, 2H), 2.21–1.72(m, 10H), 1.45–1.39(m, 3H), 1.24–1.08(m, 3H)

c) Synthesis of ethyl-2-[(R)-2-[[(S)-2-[2-(6-amidino-1-ethylindol-2-yl)-ethyl]pyrrolidinyl]carbonyl]pyrrolidinyl]-2-(3-bromo-4-methoxyphenyl)-acetate:

170 mg of the compound obtained in the above b) was treated according to the same procedure as Example 1-n) to obtain 70 mg of the title compound as a pale yellow solid.

$^1$H NMR(MeOH-d$_4$, ppm): δ7.85–7.75(m, 1H), 7.57–7.42(m, 2H), 7.33–7.29(m, 2H), 6.96–6.78(m, 1H), 6.36–6.33(m, 1H), 4.52(s, 1H), 4.21–4.18(m, 3H), 4.04–3.86(m, 3H), 3.73(m, 3H), 3.22–3.02(m, 2H), 2.91–2.78(m, 2H), 2.65–2.60(m, 2H), 2.10–1.65(m, 10H), 1.33–1.25(m, 3H), 1.09–1.00(m, 3H)

ES-MS: 653(M+1)$^+$

IR(KBr): 3380, 3020, 1740, 1635, 1540 cm$^{-1}$

EXAMPLE 72

Synthesis of 1-ethyl-2-[2-[(S)-1-[[(R)-1-(carbamoylmethyl)pyrrolidin-2-yl]carbonyl]pyrrolidin-2-yl]ethyl]indole-6-carboxamidine (Compound 114)

681 mg of methyl 2-[(R)-2-[[(S)-2-[2-(6-cyano-1-ethylindol-2-yl)ethyl]pyrrolidinyl]carbonyl]pyrrolidinyl] acetate was dissolved in 25 ml of ethanol solution saturated with HCl gas. The resulting solution was allowed to stand for one day at room temperature and then concentrated under reduced pressure. The remaining HCl was removed for 5 hours by means of a vaccum pump. The dried product was dissolved in 25 ml of ethanol solution saturated with NH$_3$ gas, and the resulting solution was allowed to stand for 3 days at room temperature and then concentrated. The residue was purified with column chromatography [eluent: ethyl acetate/ethanol(1:1)] on NH-DM1010 silica to obtain 553 mg of the title compound as a colorless solid.

$^1$H NMR(MeOH-d$_4$, ppm): δ 7.79(s, 1H), 7.53(d, 1H, J=8.42 Hz), 7.32(d, 1H, J=8.72 Hz), 6.40(s, 1H), 4.18 (m, 3H), 3.57(m, 1H), 3.46(m, 4H), 2.84(m, 2H), 2.51-1.7(m, 12H), 1.28(t, 3H)

ES-MS: 439(M+1)$^+$

EXAMPLE 73

Synthesis of 1-ethyl-2-[2-[(S)-1-[[(R)-1-[(N-cyclopropylcarbamoyl)methyl]pyrrolidin-2-yl]carbonyl]pyrrolidin-2-yl]-ethyl]indole-6-carboxamidine (Compound 115)

250 mg of the compound II-a obtained in Example 57-b) and 92 mg of N-cyclopropyl-2-chloroethanamide were reacted under the same conditions as Example 42 to obtain 125 mg of the pale yellow solid product, which was then treated according to the same procedure as Example 1-n) to obtain 93 mg of the title compound as a pale yellow solid.

$^1$H NMR(CDCl$_3$, ppm): δ 8.13(d, 1H, J=3.75 Hz), 7.88(s, 1H), 7.61-7.38(m, 2H), 6.40(s, 1H), 4.27-4.13(m, 3H), 3.56-3.08(m, 3H), 2.90(s, 2H), 2.82(t, 2H, J=6.91 Hz), 2.72-2.65(m, 1H), 2.50-1.67(m, 12H), 1.35 (t, 3H, J32 7.20 Hz), 0.88-0.50(m, 4H)

ES-MS: 479(M+1)$^+$

EXAMPLE 74

Synthesis of ethyl (s)-2-[2-[(R)-2-[[(S)-2-[2-(6-amidino-1-ethylindol-2-yl)ethyl]pyrrolidinyl] carbonyl]pyrrolidinyl]-acetylamino]propanoate (Compound 116)

250 mg of the compound II-a obtained in Example 57-b) and 133 mg of ethyl-(S)-2-(2-chloroacetylamino)propanoate were reacted under the same conditions as Example 42 to obtain 260 mg of the pale yellow solid product, which was then treated according to the same procedure as Example 1-n) to obtain 96 mg of the title compound as a pale yellow solid.

ES-MS: 539(M+1)$^+$

EXAMPLE 75

Synthesis of 1-ethyl-2-[2-[(S)-1-[[(R)-1-(1-carbamoyl-3-hydroxypropyl)pyrrolidin-2-yl]carbonyl]pyrrolidin-2-yl]-ethyl]indole-6-carboxamidine (Compound 117)

a) Synthesis of 1-ethyl-2-[2-[(S)-1-[[(R)-1-(2-oxo-3-oxolanyl)pyrrolidin-2-yl]carbonyl]pyrrolidin-2-yl]ethyl]indole-6-carbonitrile:

700 mg of the compound II-a obtained in Example 57-b) and 500 mg of α-bromo-γ-butyrolactone were reacted according to the same procedure as Example 45-b) to obtain 650 mg of the title compound as a white foam.

$^1$H NMR(CDCl$_3$, ppm): δ 7.58-7.53(m, 2H), 7.30-7.26(m, 1H), 6.46(s, 1H), 4.39-4.34(m, 1H), 4.26(br, 1H), 4.21-4.13(m, 3H), 3.86-3.63(m, 3H), 3.51-3.45(m, 1H), 3.30-3.22(m, 1H), 2.96-2.90(m, 1H), 2.83-2.79(m, 2H), 2.39-2.11(m, 4H), 2.03-1.96(m, 4H), 1.84-1.66(m, 4H), 1.35(t, J=7.30 Hz, 3H)

ES-MS: 449(M+1)$^+$ b) Synthesis of 1-ethyl-2-[2-[(S)-1-[[(R)-1-(1-carbamoyl-3-hydroxy-propyl)pyrrolidin-2-yl]carbonyl]pyrrolidin-2-yl] ethyl]indole-6-carboxamidine:

450 mg of the compound obtained in the above a) was treated according to the same procedure as Example 1-n) to obtain 370 mg of the title compound as a white solid.

$^1$H NMR(MeOH-d$_4$, ppm): δ 7.85-7.79(m, 2H), 7.56-7.52 (m, 1H), 6.41(m, 1H), 4.23-4.18(m, 2H), 4.13-4.10(m, 1H), 3.64-3.59(m, 1H), 3.50-3.31(m, 4H), 3.07-2.87(m, 1H), 2.81-2.76(m, 2H), 2.68-2.61(m, 1H), 2.24-2.08(m, 2H), 1.92-1.71(m, 10H), 1.30(t, J=7.05 Hz, 3H)

ES-MS: 483(M+1)$^+$

IR(KBr): 3340, 3220, 2980, 1680, 1630, 1540 cm$^{-1}$

EXAMPLE 76

Synthesis of 2-[(R)-2-[[(S)-2-[2-(6-amidino-1-ethylindol-2-yl)ethyl]pyrrolidinyl]carbonyl] pyrrolidinyl]-4-hydroxy-butanoic acid (Compound 118)

250 mg of 1-ethyl-2-[2-[(S)-1-[[(R)-1-(1-carbamoyl-3-hydroxy-propyl)pyrrolidin-2-yl]carbonyl]pyrrolidin-2-yl] ethyl]indole-6-carboxamidine was treated according to the same procedure as Example 44 to obtain 180 mg of the title compound as a white solid.

$^1$H NMR(MeOH-d$_4$, ppm): δ 7.80-7.74(m, 1H), 7.56-7.48 (m, 1H), 7.32- 7.26(m,1H), 6.39-6.34(m, 1H), 4.31-

4.03(m, 4H), 3.69-3.64(m, 1H), 3.56-3.29(m, 4H), 3.04-2.96(m, 1H), 2.78(br, 3H), 2.20(br, 1H), 2.01-1.56 (m, 11H), 1.29-1.24(m, 3H)
ES-MS: 484(M+1)$^+$
IR(KBr): 3400, 3000, 1630, 1580 cm$^{-1}$

EXAMPLE 77

Synthesis of 1-[(R)-2-[[(S)-2-[2-(6-amidino-1-ethyl-indol-2-yl)ethyl]pyrrolidinyl]carbonyl]pyrrolidinyl] ethane-1,2-dicarboxylic acid (Compound 123)

a) Synthesis of diethyl-2-[(R)-2-[[(S)-2-[2-(6-cyano-1-ethylindol-2-yl)-ethyl]pyrrolidinyl]carbonyl]pyrrolidinyl] butane-1,4-dioate:

250 mg(0.525 mmole) of ethyl-2-[(R)-2-[[(S)-2-[2-(6-cyano-1-ethyl-indol-2-yl)ethyl]pyrrolidinyl]carbonyl] pyrrolidinyl]acetate was dissolved in 15 ml of tetrahydrofuran and then cooled to −78° C. 0.79 ml of lithium bis(trimethylsilyl)amide (1.0M solution in tetrahydrofuran) was added dropwise thereto, and the reaction mixture was stirred for 30 minutes. 0.09 ml(0.787 mmole) of ethyl bromoacetate diluted with 5 ml of tetrahydrofuran was added dropwise thereto, and the resulting mixture was stirred for one hour. After water was added, the reaction solution thereby obtained was extracted with dichloromethane. The organic layer was dried over sodium sulfate and evaporated under reduced pressure to remove the solvent. The residue was purified with silica gel column chromatography [eluent: dichloromethane/methanol(40:1)] to obtain 180 mg (Yield: 63.9%) of the title compound as a pale yellow foam.

$^1$H NMR(CDCl$_3$, ppm): δ 7.61-7.51(m, 2H), 7.27(dd, 1H, J=1.30 Hz, 8.10 Hz), 6.46(s, 1H), 4.33(br, 1H), 4.21-4.06(m, 6H), 3.95-3.91(m, 1H), 8.84-3.80(m, 1H), 3.67-3.63(m, 1H), 3.49-3.45(m, 1H), 3.17-3.11(m, 1H), 2.99-2.91(m, 1H), 2.82-2.74(m, 3H), 2.60-2.55(m, 1H), 2.38-2.31(m, 1H), 2.02-1.95(m, 5H), 1.81-1.74(m, 4H), 1.38-1.17(m, 9H)
ES-MS: 537(M+1)$^+$ b) Synthesis of 1-[(R)-2-[[(S)-2-[2-(6-amidino-1-ethylindol-2-yl)ethyl]-pyrrolidinyl]carbonyl]pyrrolidinyl] ethane-1,2-dicarboxylic acid:

400 mg of the compound obtained in the above a) was treated according to the same procedure as Example 1-n) to obtain 180 mg of diethyl 2-[(2)-2-[[(2)-2-[2-(6-amidino-1-ethylindole-2-yl)ethyl]pyrrolidinyl]carbonyl]pyrrolidinyl] butane-1,4-dioate, which was then treated according to the same procedure as Example 44 to obtain 120 mg of the title compound as white solid.

$^1$H NMR(MeOH-d$_4$): δ 7.79(s, 1H), 7.51-7.47(m, 1H), 7.32-7.29(m, 1H), 4.42(s, 1H), 4.57(br, 1H), 4.23-4.19 (m, 2H), 3.70(br, 2H), 3.52-3.48(m, 2H), 2.86-2.74(m, 4H), 2.60-2.54(m, 2H), 2.36-2.31(m, 1H), 2.12-2.09(m, 2H), 2.02-1.92(m, 6H), 1.66-1.61(m, 1H), 1.33-1.28(m, 3H)
ES-MS: 498(M+1)$^+$
IR(KBr): 3400, 3000, 1630, 1580 cm$^{-1}$

EXAMPLE 78

Synthesis of 1-ethyl-2-[2-[(S)-1-[[(R)-1-(2-oxo-3-oxolanyl)pyrrolidin-2-yl]carbonyl]pyrrolidin-2-yl] ethyl]indole-6-carboxamidine (Compound 125)

130 mg(0.269 mmole) of 2-[(R)-2-[[(S)-2-[2-(6-amidino-1-ethylindol-2-yl)ethyl]pyrrolidinyl]carbonyl]pyrrolidinyl]-4-hydroxybutanoic acid was dissolved in 5 ml of 3N—HCl, and the resulting solution was stirred for 18 hours at room temperature and then evaporated under reduced pressure to remove the solvent. The residue was purified with column chromatography [eluent: ethyl acetate/methanol(3:1) on NH-DM1020 silica to obtain 70 mg of the title compound as a white solid.

$^1$H NMR(MeOH-d$_4$, ppm): δ 7.79(s, 1H), 7.54-7.51(m, 1H), 7.34-7.30(m, 1H), 6.39(s, 1H), 4.31-4.20(m, 3H), 4.11-4.07(m, 2H), 3.68-3.64(m, 1H), 3.58-3.46(m, 4H), 2.80-2.75(m, 2H), 2.67-2.61(m, 1H), 2.30-2.12(m, 3H), 1.93-1.87(m, 4H), 1.80-1.73(m, 5H), 1.31-1.27(m, 3H)
ES-MS: 466(M+1)$^+$
IR(KBr): 3400, 3020, 1770, 1640, 1540 cm$^{-1}$

EXAMPLE 79

Synthesis of ethyl 4-[(R)-2-[[(S)-2-[2-(6-amidino-1-ethylindol-2-yl)ethyl]pyrrolidinyl]carbonyl] pyrrolidinyl]butanoate (Compound 126)

a) Synthesis of ethyl 4-[(R)-2-[[(S)-2-[2-(6-cyano-1-ethylindol-2-yl)-ethyl]pyrrolidinyl]carbonyl]pyrrolidinyl] butanoate:

400 mg of the compound II-a obtained in Example 57-b) and 0.173 ml of ethyl 4-bromobutanoate were reacted according to the same procedure as Example 45-b) to obtain 453 mg of the title compound as a viscous oil.

$^1$H NMR(CDCl$_3$, ppm): δ 7.59-7.53(m, 2H), 7.29(m, 1H), 6.47(s, 1H), 4.32-4.11(m, 3H), 4.05-3.99(m, 2H), 3.61 (m, 2H), 3.27-3.18(m, 2H), 2.77(m, 2H), 2.66-1.62(m, 16H), 1.36(t, 3H, J=7.18 Hz), 1.17(t, 3H, J=7.14 Hz)

b) Synthesis of ethyl 4-[(R)-2-[[(S)-2-[2-(6-amidino-1-ethylindol-2-yl)ethyl]pyrrolidinyl]carbonyl]pyrrolidinyl] butanoate:

435 mg of the compound obtained in the above a) was treated according to the same procedure as Example 1-n) to obtain 228 mg of the title compound as a pale yellow solid.

$^1$H NMR(MeOH-d$_4$, ppm): δ 7.7(s, 1H), 7.56-7.31(m, 2H), 6.40(s, 1H), 4.21(m, 2H), 4.10(brs, 1H), 3.91-3.80 (m, 2H), 3.63-3.47(m, 2H), 3.08(m, 1H), 2.77(m, 2H), 2.52-1.65(m, 18H), 1.30(t, 3H, J=7.17 Hz), 1.08-0.97 (m, 3H)
IR(KBr): 330, 3000, 1740, 1640, 1540, 1480 cm$^{-1}$
ES-MS: 496(M+1)$^+$

EXAMPLE 80

Synthesis of 4-[(R)-2-[[(S)-2-[2-(6-amidino-1-ethylindol-2-yl)ethyl]pyrrolidinyl]carbonyl] pyrrolidinyl]butanoic acid (Compound 127)

122 mg of ethyl 4-[(R)-2-[[(S)-2-[2-(6-amidino-1-ethylindol-2-yl)-ethyl]pyrrolidinyl]carbonyl]pyrrolidinyl] butanoate was treated according to the same procedure as Example 44 to obtain 89 mg of the title compound as a pale yellow solid.

$^1$H NMR(MeOH-d$_4$, ppm): δ 7.79(s, 1H), 7.59-7.28(m, 2H), 6.38(s, 1H), 4.23-4.07(m, 3H), 3.62-3.50(m, 3H), 3.11(m, 1H), 2.77(m, 2H), 2.57-1.61(m, 18H), 1.28(t, 3H, J=7.14 Hz)
IR(KBr): 3400, 3000, 1700, 1640, 1540, 1480 cm$^{-1}$
ES-MS: 468(M+1)$^+$

EXAMPLE 81

Synthesis of ethyl 5-[(R)-2-[[(S)-2-[2-(6-amidino-1-ethylindol-2-yl)ethyl]pyrrolidinyl]carbonyl]pyrrolidinyl]pentanoate (Compound 128)

a) Synthesis of ethyl 5-[(R)-2-[[(S)-2-[2-(6-cyano-1-ethylindol-2-yl)-ethyl]pyrrolidinyl]carbonyl]pyrrolidinyl]pentanoate:

138 mg of the compound II-a obtained in Example 57-b) and 0.066 ml of ethyl 5-bromovalerate were reacted according to the same procedure as Example 45-b) to obtain 150 mg of the title compound as a brown oil.

$^1$H NMR(CDCl$_3$, ppm): δ 7.62-7.54(m, 2H), 6.46(s, 1H), 4.30-4.04(m, 5H), 3.68-3.51(m, 2H), 3.27-3.16(m, 2H), 2.80(t, 2H, J=7.91 Hz), 2.69-1.59(m, 19H), 1.36(t, 3H, J=7.20 Hz), 1.20(t, 3H, J=7.13 Hz)

b) Synthesis of ethyl 5-[(R)-2-[[(S)-2-[2-(6-amidino-1-ethylindol-2-yl)-ethyl]pyrrolidinyl]carbonyl]pyrrolidinyl]pentanoate:

246 mg of the compound obtained in the above a) was treated according to the same procedure as Example 1-n) to obtain 48 mg of the title compound as a pale yellow solid.

$^1$H NMR(MeOH-d$_4$, ppm): δ 7.78(s, 2H), 7.54-7.30(m, 2H), 6.37(s, 1H), 4.22-3.91(m, 5H), 3.60-3.47(m, 2H), 3.19-3.05(m, 2H), 2.81-2.73(m, 2H), 2.52-1.37(m, 19H), 1.30(t, 3H, J=7.15 Hz), 1.05(t, 3H, J=7.88 Hz)
IR(KBr): 3100, 2990, 1740, 1670, 1630, 1530, 1470 cm$^{-1}$
ES-MS: 510(M+1)$^+$

EXAMPLE 82

Synthesis of 5-[(R)-2-[[(S)-2-[2-(6-amidino-1-ethylindol-2-yl)-ethyl]pyrrolidinyl]carbonyl]pyrrolidinyl]pentanoic acid (Compound 129)

38 mg of ethyl 5-[(R)-2-[[(S)-2-[2-(6-amidino-1-ethylindol-2-yl)-ethyl]pyrrolidinyl]carbonyl]pyrrolidinyl]pentanoate was treated according to the same procedure as Example 44 to obtain 16 mg of the title compound as a pale yellow solid.

$^1$H NMR(MeOH-d$_4$, ppm): δ 7.80(s, 1H), 7.54-7.29(m, 2H), 6.36(s, 1H), 4.27-4.10(m, 3H), 3.65-3.42(m, 2H), 3.19-3.03(m, 2H), 2.82-2.71(m, 2H), 2.57-1.41(m, 19H), 1.29(t, 3H, J=7.19 Hz)
ES-MS: 428(M+1)$^+$

EXAMPLE 83

Synthesis of ethyl 6-[(R)-2-[[(S)-2-[2-(6-amidino-1-ethylindol-2-yl)-ethyl]pyrrolidinyl]carbonyl]pyrrolidinyl]hexanoate (Compound 130)

a) Synthesis of ethyl 6-[(R)-2-[[(S)-2-[2-(6-cyano-1-ethylindol-2-yl)-ethyl]pyrrolidinyl]carbonyl]pyrrolidinyl]hexanoate:

160 mg of the compound II-a obtained in Example 57-b) and 0.086 ml of ethyl 6-bromohexanoate were reacted according to the same procedure as Example 45-b) to obtain 168 mg of the title compound as a brown oil.

$^1$H NMR(CDCl$_3$, ppm): δ 7.61-7.54(m, 2H), 7.30(M, 1H), 6.45(s, 1H), 4.27(brs, 1H), 4.18-4.04(m, 4H), 3.68-3.52 (m, 2H), 3.26-3.17(m, 2H), 2.80(t, 2H, J=7.95 Hz), 2.23(t, 2H, J=7.45 Hz), 2.66-1.25(m, 19H), 1.36(t, 3H, J=7.18 Hz), 1.21(t, 3H, J=7.13 Hz)

b) Synthesis of ethyl 6-[(R)-2-[[(S)-2-[2-(6-amidino-1-ethylindol-2-yl)-ethyl]pyrrolidinyl]carbonyl]pyrrolidinyl]hexanoate:

161 mg of the compound obtained in the above a) was treated according to the same procedure as Example 1-n) to obtain 41 mg of the title compound as a pale yellow solid.

$^1$H NMR(MeOH-d$_4$, ppm): δ 7.78(s, 2H), 7.54-7.30(m, 2H), 6.36(s, 1H), 4.26-3.88(m, 5H), 3.61-3.46(m, 2H), 3.19-3.03(m, 2H), 2.81-2.72(m, 2H), 2.52-1.38(m, 2H), 1.18(t, 3H, J=7.18 Hz), 1.06(t, 3H, J=7.12 Hz)
IR(KBr): 3200, 2970, 1730, 1630, 1530, 1470, 1340 cm$^{-1}$
ES-MS: 524(M+1)$^+$

EXAMPLE 84

Synthesis of 6-[(R)-2-[[(S)-2-[2-(6-amidino-1-ethylindol-2-yl)-ethyl]pyrrolidinyl]carbonyl]pyrrolidinyl]hexanoic acid (Compound 131)

30 mg of ethyl 6-[(R)-2-[[(S)-2-[2-(6-amidino-1-ethylindol-2-yl)-ethyl]pyrrolidinyl]carbonyl]pyrrolidinyl]hexanoate was treated according to the same procedure as Example 44 to obtain 26 mg of the title compound as a pale yellow solid.

$^1$H NMR(MeOH-d$_4$, ppm): δ 7.80(s, 1H), 7.54-7.29(m, 2H), 6.34(s, 1H), 4.27-4.11(m, 3H), 3.66-3.45(m, 2H), 3.18-3.04(m, 2H), 2.82-2.71(m, 2H), 2.50-1.17(m, 21H), 1.28(t, 3H, J=7.15 Hz)
ES-MS: 496(M+1)$^+$

EXAMPLE 85

Synthesis of ethyl 2-[(R,R)-[[(S)-2-[2-(6-amidino-1-ethylindol-2-yl)-ethyl]pyrrolidinyl]carbonyl]-4-methoxypyrrolidinyl lacetate (Compound 135)

a) Synthesis of methyl (R,R)-4-methoxy-1-(tert-butoxycarbonyl)pyrrolidine-2-carboxylate:

500 mg of 4-cis-hydroxy-D-proline was dissolved in 4 ml of methanol, and 0.4 ml of acetyl chloride was added dropwise at 0° C. 0.14 ml of thionyl chloride was added dropwise at room temperature, and the resulting mixture was heated under refluxing for 2 hours with stirring. The reaction solution was cooled to room temperature and then evaporated under reduced pressure to obtain 704 mg of the white solid product, which was then dissolved in 10 ml of dichloromethane. To the resulting solution was added dropwise 1.07 ml of triethylamine at 0° C. and then added 930 mg of (BOC)$_2$O. The reaction mixture was stirred for 2.5 hours at room temperature, diluted with 150 ml of dichloromethane, washed with 30 ml of 2N—HCl solution and 30 ml of water, dried over sodium sulfate and then filtered. The filtrate was then evaporated under reduced pressure to obtain 780 mg of the brown solid, which was dissolved in 15 ml of anhydrous tetrahydrofuran. To the resulting solution was then added 138 mg of NaH, and the mixture was stirred for one hour at room temperature. 0.214 ml of methyliodide was slowly added dropwise thereto, and the reaction mixture was heated under refluxing overnight with stirring. After 1 ml of water was added dropwise, the reaction solution was evaporated under reduced pressure to obtain the residue, which was then diluted with 150 ml of dichloromethane, washed with 50 ml of water, dried over sodium sulfate and then filtered. The residue was purified with silica gel column chromatography [eluent: ethyl acetate/n-hexane(1:3)]. The fractions containing the desired product were combined and then evaporated to obtain 404 mg of the title compound as a viscous oil.

$^1$H NMR(CDCl$_3$, ppm): δ 4.46-4.28(m, 1H), 3.94(brs, 1H), 3.73(s, 3H), 3.63-3.49(m, 2H), 3.30(d, 3H, J=9.48 Hz), 2.41-2.22(m, 1H), 2.11-1.98(m, 1H), 1.44(m, 9H)

b) Synthesis of (R,R)-4-methoxy-1-(tert-butoxycarbonyl)pyrrolidine-2-carboxylic acid:

520 mg of the compound obtained in the above a) was reacted in the presence of methanol solvent under the same conditions as Example 44 to obtain 480 mg of the title compound as a colorless oil.

$^1$H NMR(CDCl$_3$, ppm): δ 4.47-4.34(m, 1H), 3.97(brs, 1H), 3.64-3.49(m, 2H), 3.33(s, 3H), 2.44-2.10(m, 2H), 1.49-1.42(m, 9H)

c) Synthesis of tert-butyl (R,R)-2-[[(S)-2-[2-(6-cyano-1-ethylindol-2-yl)-ethyl]pyrrolidinyl]carbonyl]-4-methoxypyrrolidine carboxylate:

203 mg of the compound I-a obtained in Example 1-l) was reacted with the compound obtained in the above b) according to the same procedure as Example 11-a) to obtain 212 mg of the title compound as a white solid.

$^1$H NMR(CDCl$_3$, ppm): δ 7.58-7.52(m, 2H), 7.30(m, 1H), 6.39(m, 1H), 4.31(m, 1H), 4.21-4.10(m, 2H), 3.97-3.40 (m, 6H), 3.32(s, 3H), 2.88-2.76(m, 2H), 2.58-1.67(m, 8H), 1.45-1.40(m, 9H), 1.35(t, 3H, J=7.11 Hz)

d) Synthesis of 1-ethyl-2-[2-[(S)-1-[((R,R)-4-methoxypyrrolidin-2-yl)-carbonyl]pyrrolidin-2-yl]ethyl]indole-6-carbonitrile:

210 mg of the compound obtained in the above c) was treated according to the same procedure as Example 1-l) to obtain 145 mg of the title compound as a pale yellow solid.

$^1$H NMR(CDCl$_3$, ppm): δ 7.59-7.54(m, 2H), 7.29(m, 1H), 6.40(s, 1H), 42.8(brs, 1H), 4.18-41.0(m, 2H), 4.04-3.93 (m, 2H), 3.67-3.42(m, 2H), 3.31(s, 3H), 3.21(s, 1H), 3.00-2.92(m, 1H), 2.85-2.74(m, 2H), 2.43-1.72(m, 9H), 1.36(t, 3H, J=7.19 Hz)

e) Synthesis of ethyl-2-[(R,R)-[[(S)-2-[2-(6-cyano-1-ethylindol-2-yl)-ethyl]pyrrolidinyl]carbonyl]-4-methoxypyrrolidin-2-yl]acetate:

98 mg of the compound obtained in the above d) was reacted with 30 μl of ethyl 2-bromoacetate according to the same procedure as Example 1-m) to obtain 93 mg of the title compound as a yellow oil.

$^1$H NMR(CDCl$_3$, ppm): δ 7.58-7.53(m, 2H), 7.29(m, 1H), 6.42(s, 1H), 4.31(brs, 1H), 4.20-4.11(m, 4H), 4.08-4.01 (m, 2H), 3.62-3.50(m, 5H), 3.29(s, 3H), 2.82-2.73(m, 3H), 2.35-1.59(m, 8H), 1.35(t, 3H, J=7.24 Hz), 1.26(t, 3H, J=7.13 Hz)

f) Synthesis of ethyl 2-[(R,R)-[[(S)-2-[2-(6-amidino-1-ethylindol-2-yl)-ethyl]pyrrolidinyl]carbonyl]-4-methoxypyrrolidin-2-yl]acetate:

93 mg of the compound obtained in the above e) was treated according to the same procedure as Example 1-n) to obtain 16 mg of the title compound as a pale yellow solid.

$^1$H NMR(MeOH-d$_4$, ppm): δ 7.83(s, 1H), 7.54-7.31(m, 2H), 6.38(s, 1H), 4.21-3.85(m, 7H), 3.58-3.29(m, 5H), 3.18(s, 3H), 2.82-2.73(m, 2H), 2.61(m, 1H), 2.19-1.66 (m, 8H), 1.29(t, 3H, J=6.85 Hz), 1.17-1.08(m, 3H)

ES-MS: 498(M+1)$^+$

EXAMPLE 86

Synthesis of ethyl-2-[(R,R)-[[(S)-2-[2-(6-amidino-1-ethylindol-2-yl)-ethyl]pyrrolidinyl]carbonyl]-4-methoxypyrrolidin-2-yl]acetate (Compound 136)

a) Synthesis of (R,R)-4-hydroxy-1-(benzyloxycarbonyl)pyrrolidine-2-carboxylic acid:

0.81 g of (R,R)-4-hydroxypyrrolidine-2-carboxylic acid was treated according to the same procedure as Example 66-a) to obtain 1 g of the title compound as a colorless oil.

$^1$H NMR(CDCl$_3$, ppm): δ 7.31(m, 5H), 5.19(m, 2H), 4.53(m, 1H), 4.43(m, 1H), 3.60(m, 2H), 2.24(m, 2H)

b) Synthesis of (R,R)-4-methoxy-1-(benzyloxycarbonyl)pyrrolidine-2-carboxylic acid:

1 g of the compound obtained in the above a) was treated according to the same procedure as Example 66-d) to obtain 1.1 g of the title compound as a pale brown oil.

$^1$H NMR(CDCl$_3$, ppm): δ 7.31(m, 5H), 5.16(m, 2H), 4.45(m, 1H), 3.95(m, 1H), 3.64(m, 2H), 3.26(s, 3H), 2.45-2.38(m, 1H), 2.24(m, 1H)

c) Synthesis of phenylmethyl-2-(R,R)-[[(S)-2-[2-(6-cyano-1-ethylindol-2-yl)ethyl]piperidinyl]carbonyl]-4-methoxypyrrolidine carboxylate:

0.92 g of 1-ethyl-2-[2-((S)-2-piperidyl)ethyl]indole-6-carbonitrile and 1.1 g of (R,R)-4-methoxy-1-(benzyloxycarbonyl)pyrrolidine-2-carboxylic acid were treated according to the same procedure as Example 11-a) to obtain 500 mg of the title compound as a yellow oil.

$^1$H NMR(CDCl$_3$, ppm): δ 7.56(m, 2H), 7.35(m, 5H), 7.27(m, 1H), 6.33(s, 1H), 5.09(m, 2H), 4.16(m, 1H), 3.95(m, 2H), 3.66(m, 2H), 3.26(m, 3H), 2.32(m, 2H), 1.41(m, 2H), 1.25(m, 3H)

d) Synthesis of 1-ethyl-2-[2-[(S)-1-[((R,R)-4-methoxypyrrolidin-2-yl)-carbonyl]piperidin-2-yl]ethyl]indole-6-carbonitrile:

480 mg of the compound obtained in the above c) was treated according to the same procedure as Example 1-k) to obtain 270 mg of the title compound as a pale yellow solid.

e) Synthesis of ethyl 2-[(R,R)-[[(S)-2-[2-(6-cyano-1-ethylindol-2-yl)-ethyl]piperidinyl]carbonyl]-4-methoxypyrrolidin-2-yl]acetate:

250 mg of the compound obtained in the above d, and 0.1 ml of ethyl 2-bromoacetate were treated according to the same procedure as Example 1-m) to obtain 200 mg of the title compound as a pale yellow oil.

$^1$H NMR(CDCl$_3$, ppm): δ 7.78(m, 1H), 7.54(m, 1H), 7.33(m, 1H), 6.31(s, 1H), 4.95(br, 1H), 4.12(m, 4H), 3.97(m, 2H), 3.72-3.60(m, 2H), 3.28(m, 3H), 3.02(m, 1H), 2.71(m, 1H), 2.61-2.49(m, 2H), 2.19(m, 1H), 1.30(m, 3H), 1.26-1.19(m, 6H)

f) Synthesis of ethyl 2-[(R,R)-[[(S)-2-[2-(6-amidino-1-ethylindol-2-yl)-ethyl]piperidinyl]carbonyl]-4-methoxypyrrolidin-2-yl]acetate:

190 mg of the compound obtained in the above e) was treated according to the same procedure as Example 1-n) to obtain 50 mg of the title compound as a pale yellow solid.

$^1$H NMR(CDCl$_3$, ppm): δ 7.77(m, 1H), 7.54(m, 1H), 7.33(m, 1H), 6.31(s, 1H), 4.95(br, 1H), 4.15(m, 4H), 3.98-3.87(m, 2H), 3.62(m, 2H), 3.28(m, 3H), 3.05(m, 1H), 2.70(m, 1H), 2.77-2.52(m, 2H), 2.18(br, 1H), 1.84(m, 2H), 1.67(m, 5H), 1.32(m, 3H), 1.24(m, 3H)

IR(KBr): 3400, 2920, 1720, 1630, 1460 cm$^{-1}$

ES-MS: 512(M+1)$^+$

EXAMPLE 87

Synthesis of 1-ethyl-2-[2-[(S)-1-[[(R)-1-(2-hydroxyethyl)pyrrolidin-2-yl]carbonyl]pyrrolidin-2-yl]ethyl]indole-6-carboxamidine (Compound 140)

a) Synthesis of 1-ethyl-2-[2-[(S)-1-[[(R)-1-(2-hydroxyethyl)pyrrolidin-2-yl]carbonyl]pyrrolidin-2-yl]ethyl]indole-6-carbonitrile:

130 mg of the compound II-a obtained in Example 57-b) and 0.1 ml of 2-bromoethanol were treated according to the same procedure as Example 45-b) to obtain 140 mg of the title compound as a yellow oil.

$^1$H NMR(CDCl$_3$, ppm): 7.50(m, 2H), 7.25(s, 1H), 6.34(s, 1H), 4.20(m, 1H), 4.10(t, 3H), 3.52(m, 2H), 3.37(m, 2H), 3.21(m, 2H), 2.76(m, 2H), 2.44(m, 2H), 2.32-1.60 (m, 11H), 1.27(t, 3H)

ES-MS: 409(M+1)$^+$ b) Synthesis of 1-ethyl-2-[2-[(S)-1-[[(R)-1-(2-hydroxyethyl)pyrrolidin-2-yl]carbonyl]pyrrolidin-2-yl] ethyl]indole-6-carboxamidine:

140 mg of the compound obtained in the above a) was treated according to the same procedure as Example 1-n) to obtain 45 mg of the title compound as a pale yellow solid.

$^1$H NMR(MeOH-d$_4$, ppm): δ 7.80(s, 1H), 7.58(m, 1H), 7.34(s, 1H), 6.83(d, 1H), 4.20(m, 1H), 4.05(s, 3H), 3.57(m, 2H), 3.60(m, 2H), 3.47(m, 2H), 3.20(m, 2H), 2.83(m, 2H), 2.65(m, 2H), 2.40-1.80(m, 11H), 1.37(m, 3H)

ES-MS: 426(M+1)$^+$

EXAMPLE 88

Synthesis of 1-ethyl-2-[2-[(S)-1-[[(R)-1-[2-(methylamino)acetyl]pyrrolidin-2-yl]carbonyl] pyrrolidin-2-yl]ethyl]indole-6-carboxamidine (Compound 142)

a) Synthesis of N-[2-[(R)-2-[[(S)-2-[2-(6-cyano-1-ethylindol-2-yl)-ethyl]pyrrolidinyl]carbonyl]pyrrolidinyl]-2-oxoethyl]-N-methyl-(tertbutoxy)formamide:

101 mg of the compound II-a obtained in Example 57-b) and 52 mg of N-(tert-butoxycarbonyl)sarcosine were reacted according to the same procedure as Example 11-a) to obtain 106 mg of the title compound as a white solid.

$^1$H NMR(CDCl$_3$, ppm): δ 7.61-7.52(m, 2H), 7.27(m, 1H), 6.34(s, 1H), 4.67(m, 1H), 4.28-4.12(m, 3H), 3.81-3.44 (m, 6H), 2.88(s, 3H), 2.79(t, 2H), J=7.90 Hz), 2.28-1.73(m, 10H), 1.44(s, 9H), 1.35(t, 3H, J=7.31 Hz)

b) Synthesis of 1-ethyl-2-[2-[(S)-1-[[(R)-1-[2-(methylamino)acetyl] pyrrolidin-2-yl]carbonyl]pyrrolidin-2-yl]ethyl]indole-6-carboxamidine:

103 mg of the compound obtained in the above a) was treated according to the same procedure as Example 1-n) to obtain 46 mg of the title compound as a pale yellow solid.

$^1$H NMR(MeOH-d$_4$, ppm): δ 7.81(s, 1H), 7.55-7.31(m, 2H), 6.37(s, 1H), 4.57(m, 1H), 4.22-4.08(m, 3H), 3.75-3.47(m, 4H), 3.31(s, 2H), 2.77(brs, 2H), 2.27(s, 3H), 2.19-1.77(m, 10H), 1.29(t, 3H, J=7.12 Hz)

IR(KBr): 3440, 1640, 1025 cm$^{-1}$

ES-MS: 453(M+1)$^+$

EXAMPLE 89

Synthesis of 1-ethyl-2-[2-[(S)-1-[[(R)-1-((S)-2-aminopropanoyl)pyrrolidin-2-yl]carbonyl]pyrrolidin-2-yl]ethyl]indole-6-carboxamidine (Compound 143)

a) Synthesis of N-[(1S)-2-[(R)-2-[[(S)-2-[2-(6-cyano-1-ethylindol-2-yl)-ethyl]pyrrolidinyl]carbonyl]pyrrolidinyl]-1-methyl-2-oxoethyl]-tertbutoxy)formamide:

300 mg of the compound II-a obtained in Example 57-b) and 187 mg of (S)-2-[(tert-butoxy)carbonylamino] propanoic acid were reacted according to the same procedure as Example 11-a) to obtain 210 mg of the title compound as a pale yellow solid.

$^1$H NMR(CDCl$_3$, ppm): δ 7.55(m, 2H), 7.24(m, 1H), 6.35(s, 1H), 4.57(m, 1H), 4.49(m, 1H), 4.32(m, 1H), 4.13(m, 2H), 3.79(m, 2H), 3.58-3.43(br, 2H), 2.81(m, 2H), 2.12(m, 4H), 1.42(m, 9H), 1.35(m, 6H)

ES-MS: 356(M+1)$^+$ b) Synthesis of 1-ethyl-2-[2-[(S)-1-[[(R)-1-((S)-2-aminopropanoyl)pyrrolidin-2-yl]carbonyl]pyrrolidin-2-yl] ethyl]indole-6-carboxamidine:

200 mg of the compound obtained in the above a) was treated according to the same procedure as Example 1-n) to obtain 100 mg of the title compound as a yellowish white solid.

$^1$H NMR(CDCl$_3$, ppm): δ 7.80(m, 1H), 7.38(m, 1H), 7.23(m, 1H), 6.15(m, 1H), 4.57(m, 2H), 4.13(br, 3H), 3.83(m, 2H), 3.66(m, 1H), 3.45(m, 2H), 2.71(m, 2H), 2.12(m, 3H), 1.97-1.84(br, 6H), 1.25-1.17(m, 6H)

IR(KBr): 3420, 3000, 1640 cm$^{-1}$

ES-MS: 453(M+1)$^+$

EXAMPLE 90

Synthesis of 1-ethyl-2-[2-[(S)-1-[[(R)-1-(2-aminobutanoyl)pyrrolidin-2-yl]carbonyl]pyrrolidin-2-yl]ethyl]indole-6-carboxamidine (Compound 144)

a) Synthesis of N-[(R)-2-[(S)-2-[2-(6-cyano-1-ethylindol-2-yl)ethyl]-pyrrolidinyl]carbonyl]pyrrolidinyl]-1-ethyl-2-oxoethyl](tert-butoxy) formamide:

400 mg of the compound II-a obtained in Example 57-b) and 270 mg of 3-[(tert-butoxy)carbonylamino]butanoic acid were reacted according to the same procedure as Example 11-a) to obtain 350 mg of the title compound as a yellow oil.

b) Synthesis of 1-ethyl-2-[2-[(S)-1-[[(R)-1-(2-aminobutanoyl)pyrrolidin-2-yl]carbonyl]pyrrolidin-2-yl] ethyl]indole-6-carboxamidine:

340 mg of the compound obtained in the above a) was treated according to the same procedure as Example 1-n) to obtain 190 mg of the title compound as a yellowish white solid.

$^1$H NMR(CDCl$_3$, ppm): δ 7.83(m, 1H), 7.32(m, 1H), 7.16(m, 1H), 6.21(s, 1H), 4.60(m, 2H), 4.18(m, 5H), 3.88(m, 2H), 3.78(m, 2H), 3.64(m, 1H), 3.48(m, 5H), 2.72(m, 3H), 2.16(m, 5H), 1.24(m, 5H), 0.95(m, 3H)

IR(KBr): 3400, 3000, 1640 cm$^{-1}$

ES-MS: 467(M+1)$^+$

EXAMPLE 91

Synthesis of 1-ethyl-2-[2-[(S)-1-[[(R)-1-((S)-2-amino-3-methylbutanoyl)pyrrolidin-2-yl]carbonyl] pyrrolidin-2-yl]-ethyl]indole-6-carboxamidine (Compound 145)

a) Synthesis of N-[(1S)-2-[(R)-2-[[(S)-2-[2-(6-cyano-1-ethylindol-2-yl)-ethyl]-pyrrolidinyl]carbonyl]pyrrolidinyl]-1-isopropyl-2-oxo-ethyl](tert-butoxy)formamide:

250 mg of the compound II-a obtained in Example 57-b) and 298 mg of 3-methyl-(S)-2-[(tert-butoxy)carbonylamino] butanoic acid were reacted according to the same procedure as Example 11-a) to obtain 300 mg of the title compound as a yellowish white solid.

$^1$H NMR(CDCl$_3$, ppm): δ 7.52(m, 2H), 7.30(m, 1H), 6.32(s, 1H), 5.18(m, 1H), 4.54(m, 1H), 4.23-4.14(m, 1H), 4.15(q, 2H), 3.88(m, 2H), 3.68-3.39(m, 2H) 2.82 (m, 2H), 2.71-2.32(m, 10H), 1.38(brs, 9H), 1.34(t, 3H), 0.98(m, 3H), 0.85(m, 4H)

b) Synthesis of 1-ethyl-2-[2-[(S)-1-[[(R)-1-((S)-2-amino-3-methylbutanoyl)pyrrolidin-2-yl]carbonyl] pyrrolidin-2-yl]ethyl]-1-ethylindole-6-carboxamidine:

140 mg of the compound obtained in the above a) was treated according to the same procedure as Example 1-n) to obtain 59 mg of the title compound as a pale yellowish white solid.

¹H NMR(CDCl₃, ppm): δ 7.69(m, 1H), 7.42(m, 1H), 7.22(m, 1H), 6.28(s, 1H), 4.58(m, 1H), 4.33-4.16(m, 2H), 4.11(q, 2H), 3.91-3.72(m, 2H), 3.58-3.38(m, 2H), 2.73(m, 2H), 2.22-1.77(m, 10H), 1.28(t, 3H), 0.89(m, 7H)
ES-MS: 482(M+2)⁺
IR(KBr): 2997, 1642, 1543, 1480 cm⁻¹

EXAMPLE 92

Synthesis of 1-ethyl-2-[2-[(S)-1-[[(R)-1-[(S)-2-(methanesulfonylamino)propanoyl]pyrrolidin-2-yl]carbonyl]pyrrolidin-2-yl]-ethyl]indole-6-carboxamidine (Compound 146)

a) Synthesis of 1-ethyl-2-[2-[(S)-1-[[(R)-1-((S)-2-aminopropanoyl)pyrrolidin-2-yl]carbonyl]pyrrolidin-2-yl]ethyl]indole-6-carbonitrile:

294 mg of N-[(S)-2-[(R)-2-[[(S)-2-[2-(6-cyano-1-ethylindol-2-yl)ethyl]pyrrolidinyl]carbonyl]pyrrolidinyl]-1-methyl-2-oxoethyl](tert-butoxy)formamide was treated according to the same procedure as Example 1-l) to obtain 220 mg of the title compound as a pale yellow solid.

¹H NMR(CDCl₃, ppm): δ 7.56(m, 2H), 7.21(m, 1H), 6.37(s, 1H), 4.58(m, 1H), 4.27(m, 1H), 4.14(q, 2H), 3.82-3.58(m, 3H), 3.42(m, 2H), 2.82(m, 2H), 2.26-1.78 (m, 10H), 1.37(t, 3H), 1.21(t, 3H)

b) Synthesis of 1-ethyl-2-[2-[(S)-1-[[(R)-1-[(S)-2-(methanesulfonylamino)propanoyl]pyrrolidin-2-yl]carbonyl]pyrrolidin-2-yl]-ethyl]indole-6-carbonitrile:

140 mg of the compound obtained in the above a) and 20 μl of methanesulfonyl chloride were reacted according to the same procedure as Example 1-m) to obtain 120 mg of the title compound as a pale yellow solid.

¹H NMR(CDCl₃, ppm): δ 7.59(m, 2H), 7.28(m, 1H), 6.41(s, 1H), 5.13(m, 1H), 4.61(m, 1H), 4.32(m, 1H), 4.14(q, 2H), 3.89-3.75(m, 2H), 3.55-3.48(m, 2H), 2.86 (s, 6H), 2.75(m, 2H), 2.28-1.74(m, 10H), 1.38(m, 6H)
ES-MS: 514(M+1)⁺ c) Synthesis of 1-ethyl-2-[2-[(S)-1-[[(R)-1-((S)-2-(methanesulfonylamino)propanoyl]pyrrolidin-2-yl]carbonyl]pyrrolidin-2-yl]ethyl]indole-6-carboxamidine:

120 mg of the compound obtained in the above b) was treated according to the same procedure as Example 1-n) to obtain 61 mg of the title compound as a pale yellowish white solid.

¹H NMR(CDCl₃, ppm): δ 7.94(m, 1H), 7.41(m, 1H), 7.23(m, 1H), 6.22(s, 1H), 4.61(m, 1H), 4.35(m, 1H), 4.18(m, 3H), 3.92-3.75(m, 2H), 3.56-3.38(m, 2H), 2.86 (s, 3H), 2.68(m, 2H), 2.22-1.71(m, 10H), 1.42(t, 3H), 1.24(m, 3H)
ES-MS: 531(M+1)⁺
IR(KBr): 2998, 1643, 1541, 1342 cm⁻¹

EXAMPLE 93

Synthesis of ethyl 4-[(R)-2-[[(S)-2-[2-(6-amidino-1-ethylindol-2-yl)ethyl]pyrrolidinyl]carbonyl]pyrrolidinyl]-(S)-3-amino-4-oxobutanoate (Compound 147)

a) Synthesis of phenylmethyl-4-[(R)-2-[[(S)-2-[2-(6-cyano-1-ethylindol-2-yl)ethyl]pyrrolidinyl]carbonyl]pyrrolidinyl]-(S)-3-[(tert-butoxy)carbonylamino]-4-oxobutanoate:

0.6 g of the compound II-a obtained in Example 57-b) and 798 mg of (S)-2-[(tert-butoxy)carbonylamino]-3-(benzyloxycarbonyl)propanoic acid were reacted according to the same procedure as Example 11-a) to obtain 1.1 g of the title compound as a yellowish white solid.

¹H NMR(CDCl₃, ppm): δ 7.52(m, 2H), 7.35-7.17(m, 6H), 6.33(s, 1H), 5.26(m, 1H), 4.98(m, 2H), 4.88(m, 1H), 4.47(m, 1H), 4.12(q, 2H), 3.78-3.39(m, 4H), 2.88-2.66 (m, 4H), 2.23-1.71(m, 10H), 1.39(brs, 9H), 1.29(t, 3H)
ES-MS: 682(M+Na⁺), 670(M+1)⁺ b) Synthesis of ethyl 4-[(R)-2-[[(S)-2-[2-(6-amidino-1-ethylindol-2-yl)ethyl]pyrrolidinyl]carbonyl]pyrrolidinyl]-(S)-3-amino-4-oxobutanoate:

1.1 g of the compound obtained in the above a) was treated according to the same procedure as Example 1-n) to obtain 250 mg of the title compound as a yellowish white solid.

¹H NMR(CDCl₃, ppm): δ 7.75(m, 1H), 7.39(m, 1H), 7.22(m, 1H), 6.27(s, 1H), 4.66-4.47(m, 1H), 4.27-3.95 (m, 6H), 3.86-3.37(m, 4H), 2.79-2.42(m, 4H), 2.19-1.73(m, 10H), 1.31-1.19(m, 6H)
ES-MS: 525(M+1)⁺
IR(KBr): 3028, 1768, 1647, 1374 cm⁻¹

EXAMPLE 94

Synthesis of 1-ethyl-2-[2-[(S)-1-[[(R)-1-((S)-2-amino-3-carbamoylpropanoyl)pyrrolidin-2-yl]carbonyl]pyrrolidin-2-yl]ethyl]indole-6-carboxamidine (Compound 148)

1.1 g of phenylmethyl-4-[(R)-2-[[(S)-2-[2-(6-cyano-1-ethylindol-2-yl)ethyl]pyrrolidinyl]carbonyl]pyrrolidinyl]-(S)-3-[(tert-butoxy)carbonylamino]-4-oxobutanoate was treated according to the same procedure as Example 1-n) to obtain 150 mg of the title compound as a white solid.

¹H NMR(CDCl₃, ppm): δ 7.77(m, 1H), 7.48(m, 1H), 7.32(m, 1H), 6.34(s, 1H), 4.49(m, 1H), 4.22-4.07(m, 3H), 3.92(m, 1H), 3.66(m, 2H), 3.38(m, 2H), 2.71(m, 2H), 2.50-2.25(m, 2H), 2.22-1.74(m, 10H), 1.30(t, 3H)
ES-MS: 496(M+1)⁺
IR: 3086, 1637, 1367 cm⁻¹

EXAMPLE 95

Synthesis of 4-[(R)-2-[[(S)-2-[2-(6-amidino-1-ethylindol-2-yl)ethyl]pyrrolidinyl]carbonyl]pyrrolidinyl]-(S)-3-amino-4-oxobutanoic acid (Compound 149)

150 mg of ethyl-4-[(R)-2-[[(S)-2-[2-(6-amidino-1-ethylindol-2-yl)ethyl]pyrrolidinyl]carbonyl]pyrrolidinyl]-(3S)-3-amino-4-oxobutanoate and 50 mg of 2-[2-[(S)-1-[[(R)-1-[((S)-2-amino-3-carbamoyl)propanoyl]pyrrolidin-2-yl]carbonyl]pyrrolidin-2-yl]ethyl]-1-ethylindole-6-carboxamidine were reacted under the same conditions as Example 44 to obtain 145 mg of the title compound as a white solid.

¹H NMR(MeOH-d₄, ppm): δ 7.75(m, 1H), 7.51(m, 1H), 7.30(m, 1H), 6.32 (s, 1H), 4.56–4.28(m, 1H), 4.21–4.08(m, 3H), 3.93(m, 1H), 3.81–3.66(m, 2H), 3.52–3.25(m, 2H), 2.76(m, 2H), 2.54–2.18(m, 2H), 2.12–1.69(m, 10H), 1.28(t, 3H)
ES-MS: 498 (M+2)⁺
IR(KBr): 1632, 1372 cm⁻¹

EXAMPLE 96

Synthesis of 1-ethyl-2-[2-[((S)-1-[[(R)-1-(3-amino-propanoyl)pyrrolidin-2-yl]carbonyl]pyrrolidin-2-yl]ethyl]indole-6-carboxamidine (Compound 155)

a) Synthesis of 2-[2-[(S)-1-[[(R)-1-(3-chloropropanoyl)pyrrolidin-2-yl]-carbonyl]pyrrolidin-2-yl]ethyl]-1-ethylindole-6-carbonitrile 800 mg of the compound II-a obtained in Example 57-b) and 0.475 ml of 3-chloropropionic acid were reacted according to the same procedure as Example 11-a) to obtain 926 mg of the title compound.

$^1$H NMR(CDCl$_3$, ppm): δ 7.61(s, 1H), 7.56(d, 1H, J=8.81 Hz), 7.26(d, 1H, J=8.98 Hz), 6.37(s, 1H), 4.65(m, 1H), 4.28(m, 1H), 4.15(q, 2H), 3.82(m, 2H), 3.71(m, 4H), 3.62–3.40(m, 2H), 2.78(m, 4H), 2.30–1.78 (m, 10H), 1.33(t, 3H)

b) Synthesis of 1-ethyl-2-[2-[(S)-1-[[(R)-1-(3-aminopropanoyl)pyrrolidin-2-yl]carbonyl]pyrrolidin-2-yl]ethyl]indole-6-carboxamidine:

320 mg of the compound obtained in the above a) was treated according to the same procedure as Example 1-n) to obtain 98 mg of the title compound as a pale yellow solid.

$^1$H NMR(MeOH-d$_4$, ppm): δ 7.92(s, 1H), 7.65(d, 1H, J=8.25 Hz), 7.46(d, 1H), 6.49(s, 1H), 4.40–4.16(m, 3H), 3.87(m, 1H), 3.78–3.53(m, 4H), 2.91(m, 4H), 2.89(m, 2H), 2.40–1.80(m, 10H), 1.41(t, 3H)

EXAMPLE 97

Synthesis of 1-ethyl-2-[2-[(S)-1-[[(R)-1-(3-amino-2-methylpropanoyl)pyrrolidin-2-yl]carbonyl]pyrrolidin-2-yl]ethyl]indole-6-carboxamidine (Compound 156)

a) Synthesis of N-(3-[(R)-2-[[(S)-2-[2-(6-cyano-1-ethylindol-2-yl)ethyl]-ethyl]pyrrolidinyl]carbonyl]pyrrolidinyl]-2-methyl-3-oxopropyl](tert-butoxy)formamide:

430 mg of the compound II-a obtained in Example 57-b) and 290 mg of 2-methyl-3-[(tert-butoxy)carbonylamino]propanoic acid were reacted according to the same procedure as Example 11-a) to obtain 270 mg of the title compound as a yellow oil.

$^1$H NMR(CDCl$_3$, ppm): δ 7.57(m, 2H), 7.28(m, 1H), 6.36(d, 1H), 4.62(m, 1H), 4.26(m, 1H), 4.16(m, 2H), 3.47(m, 2H), 3.22(m, 2H), 2.79(m, 2H), 2.15(m, 3H), 1.93(m, 6H), 1.60(m, 9H), 1.27(m, 3H), 1.12(t, 3H)

ES-MS: 550(M+1)$^+$, 573(M+Na)

b) Synthesis of 1-ethyl-2-[2-(S)-1-[[(R)-1-(3-amino-2-methylpropanoyl)pyrrolidin-2-yl]carbonyl]pyrrolidin-2-yl]ethyl]indole-6-carboxamidine 250 mg of the compound obtained in the above a) was treated according to the same procedure as Example 1-n) to obtain 100 mg of the title compound as a pale yellow solid.

$^1$H NMR(CDCl$_3$, ppm): δ 7.89(d, 1H, J=7.00 Hz), 7.32 (m, 1H), 7.18(m, 1H), 6.19(d, 1H, J=8.70 Hz), 4.61(m, 1H), 4.14(m, 2H), 3.85(m, 3H), 3.45(m, 2H), 2.69(m, 2H), 2.19(m, 6H), 1.26(m, 5H), 1.07(m, 3H), 1.02(m, 3H)

IR(KBr): 3420, 1650 cm$^{-1}$

ES-MS: 467(M+1)$^+$

EXAMPLE 98

Synthesis of 1-ethyl-2-[2-[(S)-1-[[(R)-1-(3-amino-butanoyl)pyrrolidin-2-yl]carbonyl]pyrrolidin-2-yl]ethyl]indole-6-carboxamidine (Compound 157)

a) Synthesis of N-[3-[(R)-2-[[(S)-2-[2-(6-cyano-1-ethylindol-2-yl)ethyl]pyrrolidinyl]carbonyl]pyrrolidinyl]-1-methyl-3-oxopropyl](tert-butoxy) formamide:

430 mg of the compound II-a obtained in Example 57-b) and 290 mg of 3-[(tert-butoxy)carbonylamino]butanoic acid were reacted according to the same procedure as Example 11-a) to obtain 260 mg of the title compound as a yellow oil.

$^1$H NMR(CDCl$_3$, ppm): δ 7.57(m, 2H), 7.29(m, 1H), 6.36(s, 1H), 4.62(m, 1H), 4.15(t, 2H, J=7.20 Hz), 4.03(m, 1H), 3.69(m, 2H), 3.47(m, 3H), 2.80(m, 2H), 2.57(m, 2H), 2.16(m, 3H), 1.93(m, 6H), 1.43(m, 9H), 1.37(m, 3H), 1.20(m, 3H)

ES-MS: 550(M+1)$^+$ b) Synthesis of 1-ethyl-2-[2-[(S)-1-[[(R)-1-(3-aminobutanoyl)pyrrolidin-2-yl]carbonyl]pyrrolidin-2-yl]ethyl]indole-6-carboxamidine:

250 mg of the compound obtained in the above a) was treated according to the same procedure as Example 1-n) to obtain 110 mg of the title compound as a pale yellow solid.

$^1$H NMR(CDCl$_3$, ppm): δ 7.87(m, 1H), 7.35(m, 1H), 7.20(m, 1H), 6.21(s, 1H), 4.60(m, 1H), 4.21(m, 4H), 3.85(m, 2H), 2.72(m, 3H), 2.11(br, 6H), 1.98(br, 3H), 1.21(m, 3H), 1.04(m, 3H)

IR(KBr): 3400, 2840, 1650, 1020 cm$^{-1}$

ES-MS: 467(M+1)$^+$

EXAMPLE 99

Synthesis of 1-ethyl-2-[2[(S)-1-[[(R)-1-[3-[(methanesulfonyl)amino]propanoyl]pyrrolidin-2-yl]carbonyl]pyrrolidin-2-yl]ethyl]indole-6-carboxamidine (Compound 158)

a) Synthesis of N-[3-[(R)-2-[[(S)-2-[2-(6-cyano-1-ethylindol-2-yl)ethyl]-pyrrolidinyl]carbonyl]pyrrolidinyl]-3-oxopropyl](tert-butoxy)formamide 500 mg of the compound II-a obtained in Example 57-b) and 290 mg of 3-[(tert-butoxy)carbonylamino]propanoic acid were reacted according to the same procedure as Example 11-a) to obtain 340 mg of the title compound as a yellow oil.

$^1$H NMR(CDCl$_3$, ppm): δ 7.55(m, 2H), 7.26(m, 1H), 6.37(s, 1H), 4.63(m, 1H), 4.28(m, 1H), 4.15(t, 2H, J=7.20 Hz), 3.81(m, 1H), 3.66(m, 2H), 3.41(m, 6H), 2.80(m, 2H), 2.52(m, 2H), 2.18(m, 4H), 1.98(m, 6H), 1.42(m, 9H), 1.32(m, 3H)

ES-MS: 536(M+1)$^+$558(M+Na), 574(M+K)

b) Synthesis of 1-ethyl-2-[2-[(S)-1-[[(R)-1-(3-aminopropanoyl)pyrrolidin-2-yl]carbonyl]pyrrolidin-2-yl]ethyl]indole-6-carbonitrile:

340 mg of the compound obtained in the above a) was treated according to the same procedure as Example 1—1) to obtain 160 mg of the title compound as a yellow oil.

c) Synthesis of 1-ethyl-2-[2-[(S)-1-[[(R)-1-[3-[(methanesulfonyl)amino]propanoyl]pyrrolidin-2-yl]carbonyl]pyrrolidin-2-yl]ethyl]indole-6-carbonitrile:

180 mg of the compound obtained in the above b) and 55 μl of methanesulfonyl chloride were reacted according to the same procedure as Example 1-m) to obtain 100 mg of the title compound as a yellow oil.

$^1$H NMR(CDCl$_3$, ppm): δ 7.56(m, 2H), 7.25(m, 1H), 6.41(s, 1H), 4.62 (m, 1H), 4.24(m, 1H), 4.18(t, 2H, J=7.20 Hz), 3.75(m, 2H), 3.48–3.39(m, 4H), 2.87–2.79 (m, 4H), 2.20(m, 2H), 2.01–1.90(br, 7H), 1.35(m, 3H)

d) Synthesis of 1-ethyl-2-[2-[(S)-1-[[(R)-1-[3-[(methanesulfonyl)amino]propanoyl]pyrrolidin-2-yl]carbonyl]pyrrolidin-2-yl]ethyl]indole-6-carboxamidine:

100 mg of the compound obtained in the above c) was treated according to the same procedure as Example 1-n) to obtain 60 mg of the title compound as a yellowish white solid.

$^1$H NMR(CDCl$_3$, ppm): δ 7.69(s, 1H), 7.54(m, 1H), 7.28(m, 1H), 6.34 (s, 1H), 4.60(m, 1H), 4.21(m, 3H), 3.73(m, 2H), 3.34(m, 2H), 2.83(s, 3H), 2.79(m, 2H), 2.16(m, 4H), 2.02–1.96(br, 4H), 1.33(t, 3H, J=7.10 Hz)

IR(KBr): 3300, 3000, 1640 cm$^{-1}$

ES-MS: 531(M+1)$^+$

EXAMPLE 100

Synthesis of ethyl 4-[(R)-2-[[(S)-2-[2-(6-amindino-1-ethylindol-2-yl)ethyl]pyrrolidinyl]carbonyl]pyrrolidinyl]-(S)-2-amino-4-oxobutanoate (Compound 159)

a) Synthesis of phenylmethyl-4-[(R)-2-[[(S)-2-[2-(6-cyano-1-ethylindol-2-yl)ethyl]pyrrolidinyl]carbonyl]pyrrolidinyl]-(S)-2-[(tert-butoxy)carbonylamino]-4-oxobutanoate:

0.6 g of the compound II-a obtained in Example 57-b) and 0.798 g of (S)-3-[(tert-butoxy)carbonylamino]-3-(benzyloxycarbonyl)propanoic acid were reacted according to the same procedure as Example 11-a) to obtain 1.08 g of the title compound as a pale yellow solid.

$^1$H NMR(CDCl$_3$, ppm): δ 7.51(m, 1H), 7.49(m, 1H), 7.32–7.04(m, 6H), 6.30 (s, 1H), 5.67(m, 1H), 4.86–4.72(m, 2H), 4.59–4.46(m, 1H), 4.27–4.01(m, 3H), 3.83–3.58(m, 2), 3.46–3.37(m, 2H), 3.09–2.66(m, 4H), 2.27–1.69(m, 10H), 1.42(brs, 9H), 1.25(t, 3H)

ES-MS: 692(M+Na$^+$), 670(M+1)$^+$ b) Synthesis of ethyl 4-[(R)-2-[[(S)-2-[2-(6-amidino-1-ethylindol-2-yl)-ethyl]pyrrolidinyl]carbonyl]pyrrolidinyl]-(S)-2-amino-4-oxobutanoate:

1.08 g of the compound obtained in the above a) was treated according to the same procedure as Example 1-n) to obtain 250 mg of the title compound as a pale yellow solid.

$^1$H NMR(CDCl$_3$, ppm): δ 7.77(m, 1H), 7.44(m, 1H), 7.28(m, 1H), 6.28 (s, 1H), 4.62(m, 1H), 4.21(m, 4H), 4.06(q, 2H), 3.90–3.71(m, 2H), 3.61–3.39(m, 2H), 2.71 (m, 4H), 2.28–1.72(m, 10H), 1.32(t, 3H), 1.18(t, 3H)

ES-MS: 525(M+1)$^+$

IR(KBr): 1752, 1648, 1375 cm$^{-1}$

EXAMPLE 101

Synthesis of 1-ethyl-2-[2-[(S)-1-[[(R)-1-((S)-3-amino-3-carbamoylpropanoyl)pyrrolidin-2-yl]carbonyl]pyrrolidin-2-yl]ethyl]indole-6-carboxamidine (Compound 160)

1.08 g of phenylmethyl 4-[(R)-2-[[(S)-2-[2-(6-cyano-1-ethyl-indol-2-yl)ethyl]pyrrolidinyl]carbonyl]pyrrolidinyl]-(S)-[(tert-butoxy)carbonylamino]-4-oxobutanoate was treated according to the same procedure as Example 1-n) to obtain 230 mg of the title compound as a white solid.

$^1$H NMR(MeOH-d$_4$): δ 7.78(m, 1H), 7.49(m, 1H), 7.28 (m, 1H), 6.35(s, 1H), 4.53(m, 1H), 4.19–4.08(m, 3H), 3.76–3.38(m, 5H), 2.81–2.42(m, 4H), 2.25–1.71(m, 10H), 1.28(t, 3H)

ES-MS: 496(M+1)$^+$

IR(KBr): 3098, 1641, 1498, 1365 cm$^{-1}$

EXAMPLE 102

Synthesis of 4-[(R)-2-[[(S)-2-[2-(6-amidino-1-ethylindol-2-yl)ethyl]pyrrolidinyl]carbonyl]pyrrolidinyl]-(S)-2-amino-4-oxobutanoic acid (Compound 161)

170 mg of ethyl-4-[(R)-2-[[(S)-2-[2-(6-amidino-1-ethylindol-2-yl)ethyl]pyrrolidinyl]carbonyl]pyrrolidinyl]-(S)-2-amino-4-oxobutanonte and 130 mg of 1-ethyl-2-[2-[(S)-1-[(R)-1-((S)-3-amino-3-carbamoylpropanoyl)pyrolidin-2-yl]carbonyl]pyrrolidin-2-yl]ethyl]indole-6-carboxamidine were reacted under the same conditions as Example 44 to obtain 170 mg of the title compound as a white solid.

$^1$H NMR(MeOH-d$_4$, ppm): δ 7.75(m, 1H), 7.46(m, 1H), 7.25(m, 1H), 6.31 (s, 1H), 4.52(m, 1H), 4.18–4.05(m, 3H), 3.77–3.38(m, 5H), 2.89–2.39(m, 4H), 2.29–1.70 (m, 10H), 1.26(t, 3H)

ES-MS: 498(M+2)$^+$

IR(KBr): 2980, 1615, 1459, 1381 cm$^{-1}$

EXAMPLE 103

Synthesis of 1-ethyl-2-[2-[(S)-1-[[1-[(R)-1-[3-carbamoyl-(S)-3-[(methanesulfonyl)amino]propanoyl]pyrrolidin-2-yl]carbonyl]pyrrolidin-2-yl]ethyl]indole-6-carboxamidine (Compound 162)

a) Synthesis of phenylmethyl 4-[(R)-2-[[(S)-2-[2-(6-cyano-1-ethylindol-2-yl)ethyl]pyrrolidinyl]carbonyl]pyrrolidinyl]-(S)-2-[(tert-butoxy)carbonylamino]-4-oxobutanoate:

0.3 g of the compound II-a obtained in Example 57-b) and 0.346 g of (S)-3-[(tert-butoxy)carbonylamino]-3-(benzyloxycarbonyl)propanoic acid were reacted according to the same procedure as Example 11-a) to obtain 0.54 g of the title compound as a pale yellow solid.

$^1$H-NMR(CDCl$_3$, ppm): δ 7.71(m, 1H), 7.49(m, 1H), 7.32–7.04(m, 6H), 6.30(s, 1H), 5.67(m, 1H), 4.86–4.72 (m, 2H), 4.59–4.46(m, 1H), 4.27–4.01(m, 3H), 3.83–3.58(m, 2H), 3.46–3.37(m, 2H), 3.09–2.66 (m, 4H), 2.27–1.69(m, 10H), 1.42(brs, 9H), 1.25(t, 3H)

ES-MS: 692(M+Na$^+$), 670(M+1)$^+$ b) Synthesis of phenylmethyl 2-amino-4-[(R)-2-[[(S)-2-[2-(6-cyano-1-ethylindol-2-yl)ethyl]pyrrolidinyl]carbonyl]pyrrolidinyl]-4-oxobutanoate:

0.53 g of the compound obtained in the above a) was treated according to the same procedure as Example 1—1) to obtain 0.40 g of the title compound as a pale yellow solid.

$^1$H-NMR(CDCl$_3$, ppm): δ 7.58(m, 2H), 7.40–7.21(m, 6H), 6.32(s, 1H), 5.08–4.96(m, 2H), 4.67–4.48(m, 1H), 4.28–4.08(m, 3H), 3.86–3.67(m, 3H), 3.59–3.38(m, 2H), 2.78(m, 4H), 2.30–1.76(m, 10H), 1.34(t, 3H)

ES-MS: 570(M+1)$^+$ c) Synthesis of phenylmethyl 4-[(R)-2-[[(S)-2-[2-(6-cyano-1-ethylindol-2-yl)ethyl]pyrrolidinyl]carbonyl]pyrrolidinyl]-(S)-2-[(methylsulfonyl)amino]-4-oxobutanoate:

395 mg of the compound obtained in the above b) and 0.08 ml of methanesulfonyl chloride were reacted according to the same procedure as Example 1-m) to obtain 300 mg of the title compound as a pale yellow solid.

$^1$H-NMR(CDCl$_3$, ppm): δ 7.51(m, 1H), 7.45(m, 1H), 7.39(m, 1H), 7.29 (m, 3H), 7.10(m, 2H), 6.31(s, 1H), 5.73(m, 1H), 4.87–4.69(m, 2H), 4.63–4.45(m, 1H), 4.29–4.06(m, 3H), 3.26–3.19(m, 1H), 2.96(s, 3H), 2.90–2.67(m, 3H), 2.30–1.79(m, 10H), 1.33(t, 3H)

ES-MS: 670(M+Na$^+$), 648(M+1)$^+$ d) Synthesis of 1-ethyl-2-[2-[(S)-1-[[1-[(R)-1-[3-carbamoyl-(S)-3-[(methanesulfonyl)amino]propanoyl]pyrrolidin-2-yl]carbonyl]pyrrolidin-2-yl]ethyl]indole-6-carboxamidine:

300 mg of the compound obtained in the above c) was treated according to the same procedure as Example 1-n) to obtain 25 mg of the title compound as a pale yellow solid.

$^1$H-NMR(MeOH-d$_4$, ppm): δ 7.76(m, 1H), 7.49(m, 1H), 7.28(m, 1H), 6.34(s, 1H), 4.53(m, 1H), 4.25–4.09(m, 4H), 3.75–3.38(m, 4H), 2.85–2.61(m, 4H), 2.55(s, 3H) 2.26–1.69(m, 10H), 1.28(t, 3H)

ES-MS: 574(M+1)$^+$

IR(KBr): 2993, 2385, 1681, 1632, 1472, 1389 cm$^{-1}$

EXAMPLE 104

Synthesis of 4-[(R)-2-[[(S)-2-[2-(6-amidino-1-ethylindol-2-yl)ethyl]pyrrolidinyl]carbonyl]pyrrolidinyl]-(S)-2-[(methanesulfonyl)amino]-4-oxobutanoic acid (Compound 163)

60 mg of 1-ethyl-2-[2-[(S)-1-[[1-[(R)-1-[3-carbamoyl-(S)-3-[(methanesulfonyl)amino]propanoyl]pyrrolidin-2-yl]carbonyl]pyrrolidin-2-yl]ethyl]indole-6-carboxamidine obtained in Example 103 was treated according to the same procedure as Example 44 to obtain 15 mg of the title compound as a pale yellow solid.

$^1$H-NMR(MeOH-d$_4$, ppm): δ 7.86(m, 1H), 7.52(m, 1H), 7.34(m, 1H), 6.36 (s, 1H), 4.53(m, 1H), 4.28–4.10(m, 4H), 3.77–3.39(m, 4H), 2.87–2.56(m, 7H), 2.24–1.68 (m, 10H), 1.32(t, 3H)

ES-MS: 575(M+1)$^+$

IR(KBr): 2998, 1628, 1468, 1332 cm$^{-1}$

EXAMPLE 105

Example of 1-ethyl-2-[2-[(S)-1-[[(R)-(1-(4-amino-butanoyl)pyrrolidin-2-yl]carbonyl]pyrrolidin-2-yl]ethyl]indole-6-carboxamidine (Compound 166)

a) Synthesis of 1-[4-[(R)-2-[[(S)-2-[2-(6-cyano-1-ethylindol-2-yl)ethyl]pyrrolidinyl]carbonyl]pyrrolidinyl]-4-oxobutyl](tert-butoxy)formamide:

400 mg of the compound II-a obtained in Example 57-b) and 270 mg of 4-[(tert-butoxy)carbonylamino]butanoic acid were reacted according to the same procedure as Example 11-a) to obtain 360 mg of the title compound as a yellow oil.

$^1$H NMR(CDCl$_3$, ppm): δ 7.55(m, 2H), 2.26(m, 1H), 6.37(s, 1H), 4.63(m, 1H), 4.28(m, 1H), 4.15(t, 2H, J=7.20 Hz), 3.82(m, 1), 3.66(m, 2H), 3.46(m, 3H), 2.80(m, 4H), 2.52(m, 2H), 2.17(m, 4H), 1.91(m, 2H), 1.42(m, 9H), 1.35(m, 3H)

b) Synthesis of 1-ethyl-2-[2-[(S)-1-[[(R)-1-(4-aminobutanoyl)pyrrolidin-2-yl]carbonyl]pyrrolidin-2-yl]ethyl]indole-6-carboxamidine:

350 mg of the compound obtained in the above a) was treated according to the same procedure as Example 1-n) to obtain 170 mg of the title compound as a pale yellow solid.

$^1$H NMR(CDCl$_3$, ppm): δ 7.92(m, 1H), 7.34(m, 2H), 6.19(s, 1H), 4.55 (m, 1H), 4.16(m, 3H), 3.78(m, 1H), 3.62(m, 2H), 3.41(m, 3H), 2.62 (m, 4H), 2.30(m, 2H), 2.07(m, 3H), 1.68(m, 4H), 1.24(m, 3H)

IR(KBr): 3400, 3000, 1630 cm$^{-1}$

ES-MS: 467(M+1)$^+$

EXAMPLE 106

Synthesis of 1-ethyl-2-[2-[2-[(S)-1-[[(R)-1-[(2-piperidinyl)carbonyl]pyrrolidin-2-yl]carbonyl]pyrrolidin-2-yl]ethyl]indole-6-carboxamidine (Compound 167)

a) Synthesis of tert-butyl-2-[[(R)-2-[[(S)-2-[2-(6-cyano-1-ethylindol-2-yl)ethyl]pyrrolidinyl]carbonyl]pyrrolidinyl]carbonyl]piperidine carboxylate:

400 mg of the compound II-a obtained in Example 57-b) and 300 mg of 1-(tert-butoxycarbonyl)piperidine-2-carboxylic acid were reacted according to the same procedure as Example 11-a) to obtain 350 mg of the title compound as a yellow oil.

$^1$H NMR(CDCl$_3$, ppm): δ 7.57(m, 2H), 7.26(m, 1H), 6.35(m, 1H), 4.66 (m, 1H), 4.24(m, 1H), 4.14(m, 2H), 3.87(m, 2H), 3.48(m, 2H), 2.80 (m, 2H), 2.15(m, 3H), 2.04–1.92(br, 7H), 1.46(m, 9H), 1.35(t, 3H)

b) Synthesis of 1-ethyl-2-[2-[(S)-1-[[(R)-1-[(2-piperidyl)carbonyl]pyrrolidin-2-yl]carbonyl]pyrrolidin-2-yl]ethyl]indole-6-carboxamidine:

330 mg of the compound obtained in the above a) was treated according to the same procedure as Example 1-n) to obtain 200 mg of the title compound as a yellowish white solid.

$^1$H NMR(CDCl$_3$, ppm): δ 7.62(m, 1H), 7.48(m, 1H), 7.21(m, 1H), 6.32 (m, 1H), 4.59(m, 1H), 4.19(m, 4H), 3.85(m, 2H), 3.71(m, 2H), 3.4 (m, 3H), 3.12(m, 2H), 2.76(t, 2H), 2.29–2.08(br, 3H), 1.81–1.65 (br, 5H), 1.39–1.29(br, 5H), 1.23(m, 3H)

IR(KBr): 3400, 2880, 1640 cm$^{-1}$

ES-MS: 493(M+1)$^+$

EXAMPLE 107

Synthesis of 1-ethyl-2-[2-[2-[(S)-1-[[(R)-1-(3-piperidinylcarbonyl)pyrrolidin-2-yl]carbonyl]pyrrolidin-2-yl]ethyl]indole-6-carboxamidine (Compound 168)

a) Synthesis of tert-butyl 3-[[(R)-2-[[(S)-2-[2-(6-cyano-1-ethylindol-2-yl)ethyl]pyrrolidinyl]carbonyl]pyrrolidinyl]carbonyl]piperidinecarboxylate:

300 mg of the compound II-a obtained in Example 57-b) and 226 mg of 1-(tert-butoxycarbonyl)piperidine-3-carboxylic acid were reacted according to the same procedure as Example 11-a) to obtain 380 mg of the title compound as a yellow oil.

$^1$H NMR(CDCl$_3$, ppm): δ 7.54(m, 2H), 7.24(m, 1H), 6.36(s, 1H), 4.60 (m, 1H), 4.26(m, 1H), 4.15(m, 3H), 3.84(m, 2H), 3.71(m, 1H), 3.60 (m, 1H), 3.47(m, 1H), 2.80(m, 3H), 2.17(m, 2H), 2.07–1.90(br, 4H), 1.45(m, 9H), 1.35(m, 3H)

ES-MS: 576(M+1)$^+$, 598(M+Na)

b) Synthesis of 1-ethyl-2-[2-[(S)-1-[[(R)-1-(3-piperidinylcarbonyl)pyrrolidin-2-yl]carbonyl]pyrrolidin-2-yl]ethyl]indole-6-carboxamidine:

350 mg of the compound obtained in the above a) was treated according to the same procedure as Example 1-n) to obtain 210 mg of the title compound as a yellowish white solid.

IR(KBr): 3400, 2880, 1640 cm$^{-1}$

ES-MS: 493(M+1)$^+$

EXAMPLE 108

Synthesis of 1-ethyl-2-[2-[(S)-1-[[(R)-1-[(4-piperidinyl)carbonyl]pyrrolidin-2-yl]carbonyl]pyrrolidin-2-yl]ethyl]indole-6-carboxamidine (Compound 169)

a) Synthesis of tert-butyl 4-[[(R)-2-[[(S)-2-[2-(6-cyano-1-ethylindol-2-yl)ethyl]pyrrolidinyl]carbonyl]pyrrolidinyl]carbonyl]piperidine carboxylate;

300 mg of the compound II-a obtained in Example 57-b) and 226 mg of 1-(tert-butoxycarbonyl)piperidine-4-carboxylic acid were reacted according to the same procedure as Example 11-a) to obtain 200 mg of the title compound as a yellow oil.

$^1$H NMR(CDCl$_3$, ppm): δ 7.56(m, 2H), 7.26(m, 1H), 6.38(s, 1H), 4.54 (m, 1H), 4.23(m, 1H), 4.12(m, 3H), 3.80(m, 2H), 3.72(m, 1H), 3.51 (m, 2H), 2.79(m, 4H), 2.55(m, 1H), 2.30–2.14(br, 3H), 2.01–1.92 (br, 6H), 1.75–1.66(br, 5H), 1.44(m, 9H), 1.32(m, 3H)

ES-MS: 576(M+1)$^+$, 598(M+Na)

b) Synthesis of 1-ethyl-2-[2-[(S)-1-[[(R)-1-[(4-piperidinyl)carbonyl]pyrrolidin-2-yl]carbonyl]pyrrolidin-2-yl]ethyl]indole-6-carboxamidine:

170 mg of the compound obtained in the above a) was treated according to the same procedure as Example 1-n) to obtain 100 mg of the title compound as a yellowish white solid.

$^1$H NMR(CDCl$_3$, ppm): δ 7.84(m, 1H), 7.46(m, 1H), 7.21(m, 1H), 6.25 (m, 1H), 4.58(m, 1H), 4.34(m, 2H), 4.16(m, 2H), 3.71(m, 1H), 3.56 (m, 2H), 3.12(m, 1H), 2.63(m, 1H), 2.57(m, 3H), 2.05(m, 2H), 1.99 (m, 3H), 1.62–1.55(br, 3H), 1.25(m, 3H)

IR(KBr): 3400, 3000, 1640 cm$^-$

ES-MS: 493(M+1)$^+$

EXAMPLE 109

Synthesis of 1-methyl-2-[2-[(S)-1-[(R)-1-acetyl-pyrrolidin-2-yl)carbonyl]pyrrolidin-2-yl]ethyl]indole-6-carboxamidine (Compound 170)

a) Synthesis of 1-methyl-2-[2-[(S)-1-[((R)-1-acetylpyrrolidin-2-yl)carbonyl]pyrrolidin-2-yl]ethyl]indole-6-carbonitrile:

90 mg of the compound II-b obtained in Example 58-a) was dissolved in dichloromethane and the resulting solution was cooled to −78° C. 182 μl of triethylamine was added thereto and after 20 minutes, 356 μl of acetyl chloride was added dropwise. After 20 minutes, water was added and the reaction solution was extracted twice with dichloromethane. The extracts were combined, dried over MgSO$_4$ and then concentrated. The residue was purified with silica gel column chromatography [eluent: dichloromethane/methanol (20:1)] to obtain 69 mg of the title compound as a white solid.

$^1$H NMR(CDCl$_3$, ppm): δ 7.68(s, 1H), 7.45(d, 1H), 7.14 (d, 1H), 6.32(s, 1H), 4.45(m, 1H), 4.09(m, 1H), 3.80(s, 3H), 3.44(m, 2H), 2.70(m, 2H), 1.97(s, 3H), 2.20–1.65 (m, 12H)

b) Synthesis of 1-methyl-2-[2-[(S)-1-[((R)-1-acetylpyrrolidin-2-yl)-carbonyl]pyrrolidin-2-yl]ethyl]indole-6-carboxamidine:

210 mg of the compound obtained in the above a) was treated according to the same procedure as Example 1-n) to obtain 117 mg of the title compound as a pale yellow solid.

$^1$H NMR(MeOH-d$_4$, ppm): δ 7.88(s, 1H), 7.59(d, 1H), 7.44(d, 1H), 6.46 (s, 1H), 4.65–4.57(m, 1H), 4.25–4.15 (m, 1H), 3.80(s, 3H), 3.62(m, 2H), 2.88(m, 2H), 2.11(s, 3H), 2.35–1.80(m, 12H)

EXAMPLE 110

Synthesis of 1-ethyl-2-[2-[(S)-1-[((R)-1-acetyl-pyrrolidin-2-yl)carbonyl]pyrrolidin-2-yl]ethyl] indole-6-carboxamidine (Compound 171)

a) Synthesis of 1-ethyl-2-[2-[(S)-1-[((R)-1-acetylpyrrolidin-2-yl)carbonyl]pyrrolidin-2-yl]ethyl]indole-6-carbonitrile:

45 mg of the compound II-a obtained in Example 57-b) was dissolved in dichloromethane and the resulting solution was cooled to −78° C. 34 μl of triethylamine was added thereto and after 20 minutes, 18 μl of acetyl chloride was added dropwise. After 20 minutes, water was added and the reaction solution was extracted three times with dichloromethane. The extracts were combined, dried over MgSO$_4$ and then concentrated. The residue was purified with silica gel column chromatography [eluent: dichloromethane/methanol(20:1)] to obtain 38 mg of the title compound as a white solid.

$^1$H NMR(CDCl$_3$, ppm): δ 7.60–7.48(m, 2H), 7.27 (s, 1H), 6.36 (s, 1H), 4.57 (t, 1H), 4.25 (bs, 1H), 4.20–4.08 (m, 1H), 3.55–3.36 (m, 2H), 2.80 (t, 2H), 2.09 (s, 3H), 2.40–1.70 (m, 12H), 1.34 (t, 3H)

b) Synthesis of 1-ethyl-2-[2-[(S)-1-[((R)-1-acetylpyrrolidin-2-yl)carbonyl]pyrrolidin-2-yl]ethyl]indole-6-carboxamidine:

800 mg of the compound obtained in the above a) was dissolved in 30 ml of ethanol solution saturated with HCl gas. The resulting solution was allowed to stand for 2 days at room temperature and then concentrated under reduced pressure. The remaining HCl was removed for 5 hours by means of a vaccum pump. The dried product was then dissolved in 30 ml of ethanol solution saturated with NH$_3$ gas. After 2 days, the resulting solution was concentrated under reduced pressure. The residue was purified with column chromatography [eluent: ethyl acetate/methanol (1:1)] on NH-DM1020 silica to obtain 467 mg of the title compound as a white solid.

$^1$H NMR(MeOH-d$_4$, ppm): δ 7.92(s, 1H), 7.65(d, 1H), 7.45(d, 1H), 6.49(s, 1H), 4.62(t, 1H), 4.27(m, 3H), 3.73–3.48(m, 2H), 2.89(t, 2H), 2.10(s, 3H), 2.30–1.80 (m, 12H), 1.40(t, 3H)

EXAMPLE 111

Synthesis of 1-ethyl-2-[2-[(S)-1-[[(R)-1-(2-propylpentanoyl)pyrrolidin-2-yl]carbonyl]pyrrolidin-2-yl]ethyl]indole-6-carboxamidine (Compound 173)

a) Synthesis of 1-ethyl-2-[2-[(S)-1-[[(R)-1-(2-propylpentanoyl)pyrrolidin-2-yl]carbonyl]pyrrolidin-2-yl] ethyl]indole-6-carbonitrile:

300 mg of the compound II-a obtained in Example 57-b) and 0.257 ml of 2-propylpentanoic acid were reacted according to the same procedure as Example 11-a) to obtain 380 mg of the title compound.

$^1$H NMR(CDCl$_3$, ppm): δ 7.65–7.47(m, 2H), 7.25(d, 1H), 6.35(s, 1H), 4.68 (m, 1H), 4.24(m, 2H), 4.14(q. 2H), 3.88(m, 1H), 3.73(m, 1H), 3.56 (m, 1H), 3.41(m, 1H), 2.77(m, 2H), 2.55(m, 1H), 2.37–1.50(m, 10H), 1.43–1.17(m, 11H), 0.87(t, 3H), 0.79(t, 3H)

b) Synthesis of 1-ethyl-2-[2-[(S)-1-[[(R)-1-(2-propylpentanoyl)pyrrolidin-2-yl]carbonyl]pyrrolidin-2-yl]ethyl]indole-6-carboxamidine:

380 mg of the compound obtained in the above a) was treated according to the same procedure as Example 1-n) to obtain 268 mg of the title compound.

$^1$H NMR(MeOH-d$_4$, ppm): δ 7.71(s, 1H), 7.60(d, 1H), 7.25(d, 1H), 6.33(s, 1H), 4.65(m, 1H), 4.21(m, 3H), 3.89(m, 1H), 3.74(m, 1H), 3.60(m, 1H), 3.46(m, 1H), 2.78(m, 2H), 2.54(m, 1H), 2.30–1.50(m, 12H), 1.42–0.92(m, 11H), 0.85(t, 3H), 0.77(t, 3H)

ES-MS: 508(M+1)$^+$

EXAMPLE 112

Synthesis of ethyl 3-[(R)-2-[[(S)-2-[2-(6-amidino-1-ethylindol-2-yl)ethyl]pyrrolidinyl]carbonyl]pyrrolidinyl]-3-oxopropanoate (Compound 174)

a) Synthesis of methyl 3-[(R)-2-[[(S)-2-[[(S)-2-[2-(6-cyano-1-ethylindol-2-yl)-ethyl]pyrrolidinyl]carbonyl]pyrrolidinyl]-3-oxopropanoate:

600 mg of the compound II-a obtained in Example 57-b) and 0.353 ml of ethylsuccinyl chloride were reacted according to the same procedure as Example 1-m) to obtain 414 mg of the title compound.

$^1$H NMR(CDCl$_3$, ppm): δ 7.52(t, 2H), 7.22(s, 1H), 6.32(s, 1H), 4.65 (m, 1H), 4.25(m, 1H), 4.16(q, 2H), 3.72(m, 5H), 3.62(m, 2H), 3.42 (m, 3H), 2.77(m, 2H), 2.30–1.80(m, 10H), 1.34(t, 3H)

b) Synthesis of ethyl 3-[(R)-2-[[(S)-2-[2-(6-amidino-1-ethylindol-2-yl)ethyl]pyrrolidinyl)carbonyl]pyrrolidinyl]-3-oxopropanoate:

300 mg of the compound obtained in the above a) was treated according to the same procedure as Example 1-n) to obtain 97 mg of the title compound as a pale yellow solid.

$^1$H NMR(MeOH-d$_4$, ppm): δ 7.87(s, 1H), 7.64(d, 1H, J=8.40 Hz), 7.44(d, 1H, J=6.67 Hz), 6.49(s, 1H), 4.30 (m, 3H), 4.18(q, 2H), 3.82(m, 1H), 3.75–3.50(m, 4H), 3.00–2.75(m, 2H), 2.45–1.75(m, 12H), 1.40(t, 3H), 1.20(t, 3H)

ES-MS: 496(M+1)$^+$

EXAMPLE 113

Synthesis of 1-ethyl-2-[2-[(S)-1-[[(R)-1-(2-carbamoylacetyl)pyrrolidin-2-yl]carbonyl]pyrrolidin-2-yl]ethyl]indole-6-carboxamidine (Compound 175)

300 mg of methyl 3-[(R)-2-[[(S)-2-[2-(6-cyano-1-ethylindol-2-yl)ethyl]pyrrolidinyl]carbonyl]pyrrolidinyl]-3-oxopropanoate obtained in Example 112-a) was treated according to the same procedure as Example 1-n) to obtain 64 mg of the title compound as a pale yellow solid.

$^1$H NMR(MeOH-d$_4$, ppm): δ 7.81(s, 1H), 7.48(d, 1H), 7.33(d, 1H), 6.36 (s, 1H), 4.16(m, 3H), 3.73(m, 1H), 3.56(m, 2H), 3.45(m, 2H), 2.75 (m, 2H), 2.29–1.50(m, 12H), 1.23(t, 3H)

EXAMPLE 114

Synthesis of ethyl 4-[(R)-2-[[(S)-2-[2-(6-amidino-1-ethylindol-2-yl)ethyl]pyrrolidinyl]carbonyl]pyrrolidinyl]-4-oxobutanoate (Compound 176)

a) Synthesis of ethyl 4-[(R)-2-[[(S)-2-[2-(6-cyano-1-ethylindol-2-yl)-ethyl]pyrrolidinyl]carbonyl]pyrrolidinyl]-4-oxobutanoate:

300 mg of the compound II-a obtained in Example 57-b) and 250 mg of ethyl 3-(chlorocarbonyl)propanoate were reacted according to the same procedure as Example 1-m) to obtain 380 mg of the title compound.

$^1$H NMR(CDCl$_3$, ppm): δ 7.82(s, 1H), 7.45(d, 1H, J=8.22 Hz), 7.13(d, 1H, J=6.83 Hz), 6.32(s, 1H), 4.50(m, 1H), 4.20–3.90(m, 5H), 3.70(m, 1H), 3.56(m, 1H), 3.43(m, 2H), 2.85–2.34(m, 6H), 2.22–1.65(m, 10H), 1.23(t, 3H), 1.13(t, 3H)

b) Synthesis of ethyl 4-[(R)-2-[[(S)-2-[2-(6-amidino-1-ethylindol-2-yl)ethyl]pyrrolidinyl]carbonyl]pyrrolidinyl]-4-ocobutanoate:

380 mg of the compound obtained in the above a) was treated according to the same procedure as Example 1-n) to obtain 117 mg of the title compound.

$^1$H NMR(MeOH-d$_4$, ppm): δ]7.82(s, 1H), 7.50(d, 1H), 7.40(d, 1H), 6.30 (s, 1H), 4.50(m, 1H), 4.30–3.80(m, 5H), 3.67(m, 1H), 3.60–3.30 (m, 3H), 2.90–2.35(m, 6H), 2.20–1.70(m, 10H), 1.30–1.05(m, 6H)

ES-MS: 510(M+1)

EXAMPLE 115

Synthesis of 4-[(R)-2)-2-[2-(6-amidino-1-ethylindol-2-yl)ethyl]pyrrolidinyl]carbonyl]pyrrolidinyl]-4-oxobutanoic acid (Compound 177)

153 mg of ethyl 4-[(R)-2-[[(S)-2-[2-(6-amidino-1-ethylindol-2-yl)ethyl]pyrrolidinyl]carbonyl]pyrrolidinyl]-4-oxobutanoate obtained in Example 114 was treated according to the same procedure as Example 44 to obtain 120 mg of the title compound as a white foamy solid.

$^1$H NMR(CDCl$_3$, ppm): δ 7.75(s, 1H), 7.40(ddd, 2H, J=8.28 Hz, 4.60 Hz, 1.61 Hz), 6.30(s, 1H), 4.50(m, 1H), 4.10(m, 2H), 3.80–3.30(m, 5H), 2.90–2.55(m, 2H), 2.55–1.60(m, 14H), 1.25(t, 3H, J=7.14 Hz)

ES-MS: 482(M+1)$^+$

IR(KBr): 3190, 2950, 1620 cm$^{-1}$

EXAMPLE 116

Synthesis of 1-ethyl-2-[2-[(S)-1-[[(R)-1-(3-sulfanylpropanoyl)pyrrolidin-2-yl]carbonyl]pyrrolidin-2-yl]ethyl]indole-6-carboxamidine (Compound 178)

a) Synthesis of 1-ethyl-2-[2-[(S)-1-[[(R)-1-(3-sulfanylpropanoyl)pyrrolidin-2-yl]carbonyl]pyrrolidin-2-yl]ethyl]indole-6-carbonitrile:

105 mg of the compound II-a obtained in Example 57-b) and 28 μl of 3-sulfanylpropanoic acid were reacted according to the same procedure as Example 11-n) to obtain 42 mg of the title compound as a white solid.

$^1$H NMR(CDCl$_3$, ppm): δ 7.61–7.24(m, 3H), 6.37(s, 1H), 4.64(m, 1H), 4.26 (brs, 1H), 4.14(q, 2H, J=6.83 Hz), 3.88–3.45(m, 4H), 2.80–2.61(m, 6H), 2.22–1.79(m, 10H), 2.70(t, 3H, J=7.25 Hz)

b) Synthesis of 1-ethyl-2-[2-[(S)-1-[[(R)-(1-(3-sulfanylpropanoyl)pyrrolidin-2-yl[carbonyl]pyrrolidin-2-yl]ethyl]indole-6-carboxamidine:

42 mg of the compound obtained in the above a) was treated according to the same procedure as Example 1-n) to obtain 14 mg of the title compound as a pale yellow solid.

$^1$H NMR(MeOH-d$_4$, ppm): δ 7.78(s, 1H), 7.49–7.29(m, 2H), 6.31(s, 1H), 4.51(m, 1H), 4.19–4.08(m, 3H), 3.71–3.34(m, 4H), 2.82–2.50(m, 6H), 2.10–1.71(m, 10H), 1.25(m, 3H)

IR(KBr): 3400, 3000, 1640, 1480 cm$^{-1}$

ES-MS: 470(M+1)$^+$

EXAMPLE 117

Synthesis of 1-ethyl-2-[2-[(S)-1-[[(R)-1-(3-hydroxybutanoyl)pyrrolidin-2-yl]carbonyl]pyrrolidin-2-yl]-ethyl]indole-6-carboxamidine (Compound 180)

a) Synthesis of 1-ethyl-2-[2-[(S)-1-[[(R)-1-(3-hydroxybutanpyl)pyrrolidin-2-yl[carbonyl[pyrrolidin-2-yl]ethyl]indole-6-carbonitrile:

0.5 g of the compound II-a obtained in Example 57-b) and 0.4 ml of 4-hydroxypentanoic acid were reacted according to the same procedure as Example 11-a) to obtain 0.6 g of the title compound as a pale yellow solid.

$^1$H NMR(CDCl$_3$, ppm): δ 7.61–7.51(m, 2H), 7.27(m, 1H), 6.38(s, 1H), 4.66–4.44(m, 1H), 4.37–4.14(m, 3H), 3.89–3.66(m, 2H), 3.59–3.40 (m, 2H), 2.83(m, 2H), 2.59–2.29(m, 3H), 2.24–1.72(m, 10H), 1.38 (t, 3H), 1.22(t, 3H)

ES-MS: 473(M+Na')$^+$, 451(M+1)$^+$ b) Synthesis of 1-ethyl-2-[2-[(S)-1-[[(R)-1-(3-hydroxybutanoyl)pyrrolidin-2-yl]carbonyl]pyrrolidin-2-yl]ethyl]indole-6-carboxamidine 0.6 g of the compound obtained in the above a) was treated according to the same procedure as Example 1-n) to obtain 0.6 g of the title compound as a pale yellow solid.

$^1$H NMR(MeOH-d$_4$, ppm): δ 7.78(m, 1H), 7.48(m, 1H), 7.29(m, 1H), 6.34 (s, 1H), 4.59–4.35(m, 1H), 4.29–4.07(m, 3H), 3.79–3.41(m, 4H), 2.80(m, 2H), 2.58–2.51(m, 3H), 2.11–1.78(m, 10H), 1.27(t, 3H), 1.10(t, 3H)

ES-MS: 468(M+1)$^+$

IR(KBr): 3167, 2973, 1614, 1508, 1451, 1322 cm$^{-1}$

EXAMPLE 118

Synthesis of 1-ethyl-2-[2-[(S)-1-[((R)-1-prop-2-enoyl-pyrrolidin-2-yl)carbonyl]pyrrolidin-2-yl]ethyl]indole-6-carboxamidine (Compound 182)

320 mg of 1-ethyl-2-[2-[(S)-1-[[(R)-1-(3-chloropropanoyl)pyrrolidin-2-yl]carbonyl]pyrrolidin-2-yl]ethyl]indole-6-carbonitrile obtained in Example 96-a) was treated according to the same procedure as Example 1-n) to obtain 84 mg of the title compound as a pale yellow solid.

$^1$H NMR(MeOH-d$_4$, ppm): δ 7.96(s, 1H), 7.64(d, 1H, J=8.29 Hz), 7.44(d, 1H, J=8.38 Hz), 6.70(q, 1H), 6.50(s, 1H), 6.29(d, 1H, J=16.85 Hz), 5.77(d, 1H, J=12.40 Hz), 4.32(m, 3H), 3.70(m, 3H), 3.68(m, 2H), 3.59(m, 2H), 2.90(m, 2H), 2.35–1.80(m, 12H), 1.39(t, 3H)

EXAMPLE 119

Synthesis of 1-methyl-2-[2-[(S)-1-[[(R)-1-(methanesulfonyl)pyrrolidin-2-yl]carbonyl]pyrrolidin-2-yl]ethyl]indole-6-carboxamidine (Compound 183)

a) Synthesis of 1-methyl-2-[2-[(S)-1-[[(R)-1-(methanesulfonyl)pyrrolidin-2-yl]carbonyl]pyrrolidin-2-yl]ethyl]indole-6-carbonitrile:

80 mg of the compound II-b obtained in Example 58-a) was dissolved in dichloromethane, and the resulting solution was cooled to −78° C. 64 μl of triethylamine was added thereto and, after 20 minutes, 40 μl of methensulfonyl chloride was added dropwise. After 20 minutes, water was added and the reaction solution was extracted two times with dichloromethane. The extracts were combined, dried over MgSO$_4$ and then concentrated. The residue was purified with silica gel column chromatography [eluent: dichloromethane/methanol(50:1)] to obtain 69 mg of the title compound as a yellowish white solid.

$^1$H NMR(CDCl$_3$, ppm): δ 7.56–7.50(m, 2H), 7.32(d, 1H), 6.38(s, 1H), 4.61(m, 1H), 3.79(bs, 1H), 3.70(s, 3H), 3.60–3.30(m, 2H), 2.98(s, 3H), 2.28(m, 2H), 2.30–1.70 (m, 12H)

b) Synthesis of 1-methyl-2-[2-[(S)-1-[[(R)-1-(methanesulfonyl)pyrrolidin-2-yl]carbonyl]pyrrolidin-2-yl]ethyl]indol-6-carboxamidine 56 mg of the compound obtained in the above a) was dissolved in 15 ml of ethanol solution saturated with HCl gas. The resulting solution was allowed to stand for one day at room temperature and then concentrated under reduced pressure. The remaining HCl was removed for 5 hours by means of a vacuum pump. The dried product was then dissolved in 15 ml of ethanol solution saturated with NH$_3$ gas. After 2 days, the resulting solution was concentrated under reduced pressure. The residue was purified with column chromatography [eluent: dichloromethane/methanol (3:1)] on NH-DM1020 silica to obtain 41 mg of the title compound as a yellowish white solid.

$^1$H NMR(CDCl$_3$, ppm): δ 8.03(s, 1H), 7.35(m, 2H), 6.19(s, 1H), 4.55(m, 1H), 4.14(bs, 1H), 3.64(s, 3H), 3.43(m, 2H), 2.92(s, 3H), 2.67(m, 2H), 2.30–1.70(m, 12H)

EXAMPLE 120

Synthesis of 1-ethyl-2-[2-[(S)-2-[[(R)-1-(methanesulfonyl)pyrrolidin-2-yl]carbonyl]pyrrolidin-2-yl]ethyl]indole-6-carboxamide (Compound 184)

a) Synthesis of 1-ethyl-2-[2-[(S)-1-[[(R)-1-(methanesulfonyl)pyrrolidin-2-yl]carbonyl]pyrrolidin-2-yl]ethyl]indole-6-carbonitrile 1.00 g of the compound II-a obtained in Example 57-b) was dissolved in dichloromethane, and the resulting solution was cooled to 0° C. 0.75 ml of triethylamine was added thereto and after 20 minutes, 0.42 ml of methanesulfonyl chloride was added dropwise. After 20 minutes, water was added and the reaction solution was extracted two times with dichloromethane. The extracts were combined, dried over MgSO$_4$ and then concentrated. The residue was purified with silica gel column chromatography [eluent: dichloromethane/methanol(50:1)] to obtain 524 mg of the title compound as a white solid.

$^1$H NMR(CDCl$_3$, ppm): δ 7.48(m, 2H), 7.29(d, 1H), 6.37(s, 1H), 4.57(t, 1H), 4.20(bs, 1H), 4.10(m, 2H), 3.49–3.32(m, 2H), 2.99(s, 3H), 2.86–2.70(m, 2H), 2.30–1.65(m, 12H), 1.33(t, 3H)

b) Synthesis of 1-ethyl-2-[2-[(S)-1-[[(R)-1-(methanesulfonyl)pyrrolidin-2-yl]carbonyl]pyrrolidin-2-yl]ethyl]indole-6-carboxamidine 430 mg of the compound obtained in the above a) was dissolved in 30 ml of ethanol solution saturated with HCl gas. The resulting solution was allowed to stand for two days at room temperature and then concentrated under reduced pressure. The remaining HCl was removed for 5 hours by means of a vaccum pump. The dried product was then dissolved in 30 ml of ethanol solution saturated with $NH_3$ gas. After 3 days, the resulting solution was concentrated under reduced pressure. The residue was purified with column chromatography [eluent: ethyl acetate/methanol (1:1)] on NH-DM1020 silica to obtain 184 mg of the title compound as an orange solid.

$^1$H NMR (CDCl$_3$, ppm): δ 8.90(bs, 1H), 8.54(bs, 1H), 7.35(s, 1H), 6.15(s, 1H), 4.55(s, 1H), 4.16(m, 1H), 3.70(q, 2H), 2.95(s, 3H), 2.70(m, 2H), 2.30–1.70(m, 12H), 1.18(t, 3H)

EXAMPLE 121

Synthesis of ethyl 2-[(S)-2-[[(S)-2-[2-(6-amidino-1-ethylindol-2-yl)ethyl]pyrrolidinyl]carbonyl]pyrrolidinyl]acetate (Compound 186)

a) Synthesis of tert-butyl (S)-2-[[(S)-2-[2-(6-cyano-1-ethylindol-2-yl)ethyl]pyrrolidinyl]carbonyl]pyrrolidine carboxylate 1.0 g of the compound I-a obtained in Example 1-l) and 0.94 g of 1-(tert-butoxycarbonyl)-L-proline were reacted according to the same procedure as Example 11-a) to obtain 736 mg of the title compound.

$^1$H NMR(CDCl$_3$, ppm): δ 7.61–7.51(m, 2H), 7.30(m, 1H), 6.38(d, 1H, J=9.95 Hz), 4.35(m, 1H), 4.20–4.05 (m, 2H), 3.85–3.35(m, 4H), 2.80(m, 2H), 2.30–1.70(m, 1H), 1.50–1.29(m, 11H)

IR(KBr): 3400, 3000, 2220, 1700, 1660 cm$^{-1}$ b) Synthesis of 1-ethyl-2-[2-[(S)-1-((S)-pyrrolidin-2-ylcarbonyl)pyrrolidine-2-yl]ethyl]indole-6-carbonitrile 736 mg of the compound obtained in the above a) was treated according to the same procedure as Example 1-l) to obtain 700 mg of the title compound.

$^1$H NMR(CDCl$_3$, ppm): δ 7.58(s, 1H), 7.54(d, 1H, J=8.28 Hz), 7.28(d, 1H, J=8.27 Hz), 6.36(s, 1H), 4.50–4.10(m, 10H), 3.70–3.24(m, 4H), 2.80(m, 2H), 2.50–1.71(m, 10H), 1.34(t, 3H)

c) Synthesis of ethyl 2-[(S)-2-[[(S)-2-[2-(6-cyano-1-ethylindol-2-yl)ethyl]pyrrolidinyl]carbonyl]pyrrolidinyl]acetate 700 mg of the compound obtained in the above b) was treated according to the same procedure as Example 1-m) to obtain 746 mg of the title compound.

$^1$H NMR(CDCl$_3$, ppm): δ 7.55(t, 1H), 7.24(d, 1H), 6.5(s, 1H), 4.31(m, 1H), 4.17(m, 4H), 3.85(m, 1H), 3.48(m, 3H), 3.22(m, 1H), 2.82(m, 2H), 2.35–1.60(m, 10H), 1.43–1.20(m, 6H)

d) Synthesis of ethyl 2-[(S)-2-[[(S)-2-[2-(6-amidino-1-ethylindol-2-yl)ethyl]pyrrolidinyl]carbonyl]pyrrolidinyl]acetate 746 mg of the compound obtained in the above c) was treated according to the same procedure as Example 1-n) to obtain 233 mg of the title compound.

$^1$H NMR(MeOH-d$_4$, ppm): δ 7.77(s, 1H), 7.51(d, 1H, J=8.29 Hz), 7.32(d, 1H, J=8.30 Hz), 6.35(s, 1H), 4.30–4.12(m, 3H), 3.72(m, 1H), 3.58–3.10(m, 5H), 2.77(m, 2H), 2.60(m, 1H), 2.22–1.61(m, 10H), 1.27(t, 3H), 1.12(t, 3H)

ES-MS: 458(M+1)$^+$

IR(KBr): 3200, 1630 cm$^{-1}$

EXAMPLE 122

Synthesis of 1-ethyl-2-[2-[(S)-1-[[(R)-1-(carbamolymethyl)-5-oxo-pyrrolidin-2-yl]carbonyl]pyrrolidin-2-yl]ethyl]indole-6-carboxamidine (Compound 187)

a) Synthesis of 1-ethyl-2-[2-[(S)-1-[(R)-5-oxopyrrolidin-2-yl)carbonyl]pyrrolidin-2-yl]ethyl]indole-6-carbonitrile 202 mg of the compound I-a obtained in Example 1-l) and 107 mg of 5-oxopyrrolidine-(R)-2-carboxylic acid were reacted according to the same procedure as Example 11-a) to obtain 136 mg of the title compound as a white solid.

$^1$H NMR(CDCl$_3$, ppm): δ 7.61–7.52(m, 2H), 7.25(m, 1H), 6.50(s, 1H), 6.40(s, 1H), 4.34–4.10(m, 4H), 3.58–3.46(m, 2H), 2.78(t, 2H, J=7.89 Hz), 2.44–1.66 (m, 10H), 1.34(t, 3H, J=7.20 Hz)

b) Synthesis of ethyl 2-[(R)-2-[[(S)-2-[2-(6-cyano-1-ethylindol-2-yl)ethyl]pyrrolidinyl]carbonyl]-2-oxopyrrolidinyl]ethanoate 160 mg of the compound obtained in the above a) and 0.052 ml of ethyl bromoacetate were dissolved in 3 ml of anhydrous tetrahydrofuran, and 19 mg of NaH was added thereto. The reaction mixture was heated under refluxing for 5 hours with stirring. After 0.5 ml of water was added dropwise, the reaction solution was evaporated under reduced pressure. The residue was diluted with 150 ml of dichloromethane, washed with 30 ml of water, dried over sodium sulfate and then filtered. The filtrate was then evaporated under reduced pressure. The residue was purified with silica gel column chromatography [eluent: dichloromethane/methanol(40:1)]. The fractions containing the desired product were combined and then evaporated to obtain 141 mg of the title compound as a viscous oil.

$^1$H NMR(CDCl$_3$, ppm): δ 7.62–7.55(m, 2H), 7.32(m, 1H), 6.41(s, 1H), 4.69(m, 2H), 4.29–4.11(m, 6H), 3.67–3.41(m, 2H), 2.79(t, 2H, J=7.98 Hz), 2.56–1.65 (m, 10H), 1.37(t, 3H, J=7.21 Hz), 1.24(t, 3H, J=7.09 Hz)

c) Synthesis of 1-ethyl-2-[2-[(S)-1-[[(R)-1-(carbamoylmethyl)-5-oxo-pyrrolidin-2-yl]carbonyl]pyrrolidin-2-yl]ethyl]indole-6-carboxamidine 141 mg of the compound obtained in the above b) was treated according to the same procedure as Example 1-n) to obtain 25 mg of the title compound as a pale yellow solid.

$^1$H NMR(MeOH-d$_4$, ppm): δ 7.80(s, 1H), 7.58–7.31(m, 2H), 6.40(s, 1H), 4.59(m, 1H), 4.21–4.14(m, 4H), 3.64–3.32(m, 3H), 2.82–2.73(m, 2H), 2.37–1.79(m, 10H), 1.30(t, 3H, J=7.15 Hz)

ES-MS: 453(M+1)$^+$

EXAMPLE 123

Synthesis of 2-[(R)-5-[[(S)-2-[2-(6-amidino-1-ethylindol-2-yl)ethyl]pyrrolidinyl]carbonyl]-2-oxopyrrolidinyl]acetic acid (Compound 188)

12 mg of 1-ethyl-2-[2-[(S)-1-[[(R)-1-(carbamoylmethyl)-5-oxo-pyrrolidin-2-yl]carbonyl]pyrrolidin-2-yl]ethyl]indole-6-carboxamidine obtained in Example 122-c) was treated according to the same procedure as Example 44 to obtain 6 mg of the title compound as a pale yellow solid.

¹H NMR(MeOH-d₄, ppm): δ 7.79(s, 1H), 7.54–7.30(m, 2H), 6.38(s, 1H), 4.34(d, 1H, J=17.12 Hz), 4.22–4.05 (m, 3H), 3.63–3.34(m, 3H), 3.13(d, 1H, J=17.17 Hz), 2.81–2.70(m, 2H), 2.37–1.71(m, 10H), 1.29(t, 3H, J=7.15 Hz)
ES-MS: 454(M+1)⁺

EXAMPLE 124

Synthesis of 1-ethyl-2-[2-[(S)-1-[(2-piperidyl) carbonyl]pyrrolidin-2-yl]ethyl]indole-6-carboxamidine (Compound 189)

a) Synthesis of tert-butyl-2-[[(S)-[2-(6-cyano-1-ethylindol-2-yl)ethyl]-pyrrolidinyl]carbonyl]piperilidine carboxylate 1.7 g of 1-ethyl-2-[[(S)-pyrrolidin-2-yl)ethyl]indole-6-carbonitrile was reacted with 1.75 g of 1-(tert-butoxycarbonyl)-pipecolinic acid according to the same procedure as Example 11-a) to obtain 1.17 g of the title compound as a pale yellow foam.

¹H NMR(CDCl₃, ppm): δ 7.63–7.53(m, 2H), 7.29–7.26 (m, 1H), 6.37(s, 1H), 4.77(br, 1H), 4.31(br, 1H), 4.19–4.14(m, 2H), 3.93–3.89(m, 1H), 3.74–3.70(m, 1H), 3.52–3.48(m, 2H), 2.80–2.75(m, 2H), 2.19–2.14 (m, 1H), 2.01–1.62(m, 11H), 1.49–1.42(m, 9H), 1.35(t, 3H, J=7.20 Hz)

b) Synthesis of 1-ethyl-2-[2-[(S)-1-[(2-piperidyl) carbonyl]pyrrolidin-2-yl]ethyl]indole-6-carboxamidine 40 mg of the compound obtained in the above a) was treated according to the same procedure as Example 1-n) to obtain 19 mg of the title compound as a white solid.

¹H NMR(MeOH-d₄, ppm): δ 7.77(s, 1H), 7.52–7.30(m, 2H), 6.33(s, 1H), 4.20–4.01(m, 3H), 3.56(m, 1H), 3.47–3.31(m, 2H), 3.02–2.50(m, 4H), 2.23–1.04(m, 12H), 1.26(m, 3H)
IR(KBr): 3400, 2980, 1640, 1550, 1480 cm⁻¹
ES-MS: 396(M+1)⁺

EXAMPLE 125

Synthesis of ethyl 2-[2-[[(S)-[2-(6-amidino-1-ethylindol-2-yl)ethyl]pyrrolidin-2-yl]carbonyl] piperidinyl]ethanoate (Compound 190)

a) Synthesis of ethyl 2-[2-[[(S)-[2-(6-cyano-1-ethylindol-2-yl)ethyl]-pyrrolidin-2-yl]carbonyl]piperidinyl]ethanoate 120 mg of tert-butyl-2-[[(S)-[2-(6-cyano-1-ethylindol-2-yl)ethyl]pyrrolidinyl]carbonyl]piperidine carboxylate obtained in Example 124-a) was treated according to the same procedure as Example 1-l) to obtain 86 mg of the white solid product, which was then reacted with ethyl 2-bromoacetate according to the same procedure as Example 1-m) to obtain 85 mg of the title compound as a pale yellow solid.

¹H NMR(CDCl₃, ppm): δ 7.58(s, 1H), 7.56–7.27(m, 2H), 6.44(d, 1H, J=7.62 Hz), 3.71(brs, 2H), 3.60–3.49(m, 2H), 3.40–3.28(m, 1H), 3.03–2.56(m, 4H), 2.36–1.65 (m, 12H), 1.36(t, 3H, J=8.58 Hz), 1.27–1.17(m, 3H)

b) Synthesis of ethyl 2-[2-[[(S)-2-[2-(6-amidino-1-ethylindol-2-yl)ethyl]pyrrolidinyl]carbonyl]piperidinyl] ethanoate 78 mg of the compound obtained in the above a) was treated according to the same procedure as Example 1-n) to obtain 32 mg of the title compound as a pale yellow solid.

¹H NMR(MeOH-d₄, ppm): δ 7.79(s, 1H), 7.56–7.31(m, 2H), 6.36(s, 1H), 4.27–4.11(m, 3H), 4.02–3.83(m, 2H), 3.69–3.21(m, 5), 3.94–2.50(m, 4H), 2.22–1.46(m, 12H), 1.29(m, 3H), 1.14–1.05(m, 3H)
IR(KBr): 3400, 2990, 1755, 1690, 1640, 1550, 1485 cm⁻¹
ES-MS: 482(M+1)⁺

EXAMPLE 126

Synthesis of ethyl 2-[2-[[(S)-2-[2-(6-amidino-1-ethylindol-2-yl)ethyl]piperidinyl]carbonyl] piperidinyl]acetate (Compound 191)

a) Synthesis of tert-butyl 2-[[(S)-2-[2-(6-cyano-1-ethylindol-2-yl)ethyl]piperidinyl]carbonyl]piperidine carboxylate 600 mg of 1-ethyl-2-[2-((S)-piperidinyl)ethyl]indole-6-carbonitrile and 500 mg of 1-[(tert-butoxy)carbonyl] piperidine-2-carboxylic acid were reacted according to the same procedure as Example 11-a) to obtain 300 mg of the title compound as a yellow oil.

¹H NMR(CDCl₃, ppm): δ 7.57(m, 2H), 7.30(m, 1H), 6.35(s, 1H), 4.95(br, 1H), 4.12(m, 2H), 3.90(br, 1H), 3.72(m, 1H), 2.71(m, 2H), 2.21(m, 1H), 1.84(m, 2H), 1.45(m, 9H), 1.33(m, 3H)

b) Synthesis of 1-ethyl-2-[2-[1-[((S)-2-piperidinyl) carbonyl]-2-piperidyl]ethyl]indole-6-carbonitrile 280 mg of the compound obtained in the above a) was treated according to the same procedure as Example 1-l) to obtain 210 mg of the title compound as a pale yellow solid.

c) Synthesis of ethyl 2-[2-[[(S)-2-[2-(6-cyano-1-ethylindol-2-yl)ethyl]piperidyl]carbonyl]piperidinyl]acetate 200 mg of the compound obtained in the above b) and 0.085 ml of ethyl 2-bromoacetate were reacted according to the same procedure as Example 1-m) to obtain 120 mg of the title compound as a pale yellow oil.

¹H NMR(CDCl₃, ppm): δ 7.56(m, 2H), 7.29(m, 1H), 6.38(s, 1H), 5.03(br, 1H), 4.11(m, 4H), 3.40(2H), 3.02 (m, 2H), 2.75(m, 1H), 2.60(m, 2H), 2.20(m, 1H), 1.73(m, 3H), 1.32(m, 5H), 1.26(m, 3H), 1.17(m, 3H)
ES-MS: 479(M+1)⁺, 501(M+Na)

d) Synthesis of ethyl 2-[2-[[(S)-2-[2-(6-amidino-1-ethylindol-2-yl)ethyl]piperidinyl]carbonyl]piperidinyl] acetate 110 mg of the compound obtained in the above c) was treated according to the same procedure as Example 1-n) to obtain 40 mg of the title compound as a pale yellow solid.

¹H NMR(CDCl₃, ppm): δ 7.75(m, 1H), 7.56(m, 1H), 7.32(m, 1H), 6.34(s, 1H), 5.01(br, 1H), 4.12(m, 4H), 3.46(1H), 3.39(m, 2H), 3.02(m, 2H), 2.75(m, 1H), 2.59(M, 2H), 2.18(m, 1H), 1.76(m, 3H), 1.67(br, 6H), 1.32(m, 5H), 1.17(m, 3H)
IR(KBr):3400, 2900, 1610, 1460 cm⁻¹
ES-MS: 497(M+2), 519(M+Na)

EXAMPLE 127

Synthesis of methyl-2-[2-[[(S)-2-[2-(6-amidino-1-ethylindol-2-yl)ethyl]pyrrolidinyl]carbonyl] piperidinyl]acetate (Compound 192)

a) Synthesis of methyl-2-[2-[[(S)-2-[2-(6-cyano-1-ethylindol-2-yl)ethyl]pyrrolidinyl]carbonyl]piperidinyl] acetate 1 g of tert-butyl-2-[[(S)-2-[2-(6-cyano-1-ethylindol-2-yl) ethyl]pyrrolidinyl]carbonyl]piperidine carboxylate obtained in Example 124-a) was treated according to the same procedure as Example 1-l) to obtain 1-ethyl-2-[2-[(S)-1-[(2-piperidinyl)carbonyl]pyrrolidin-2-yl]ethyl]indole-6-carbonitrile, which was then reacted with methyl 2-bromoacetate according to the same procedure as Example 1-m) to obtain 631 mg of the title compound as a pale yellow oil.

ES-MS: 450(M+1)+

$^1$H NMR(CDCl$_3$, ppm): δ 7.58–7.53(m, 2H), 7.30–7.27 (m, 1H), 6.46–6.43(m, 1H), 4.35(br, 1H), 4.17–4.14(m, 2H), 3.67–3.64(m, 4H), 3.54–3.48(m, 2H), 3.40–3.32 (m, 1H), 2.98(br, 1H), 2.79(br, 2H), 2.60–2.56(m, 1H), 2.24–2.21(m, 1H), 2.00–1.98(m, 4H), 1.74–1.64(m, 8H), 1.35(br, 3H)

b) Synthesis of methyl-2-[2-[[(S)-2-[2-(6-amidino-1-ethylindol-2-yl)ethyl]pyrrolidinyl]carbonyl]piperidinyl] acetate 630 mg of the compound obtained in the above a) was treated according to the same procedure as Example 1-n) to obtain 200 mg of the title compound as a pale yellow foam.

ES-MS: 468(M+1)+

$^1$H NMR(MeOH-d$_4$, ppm): δ 7.79(s, 1H), 7.57–7.51(m, 1H), 7.37–7.31(m, 1H), 6.37(s, 1H), 4.21–4.18(m, 3H), 3.62–3.58(m, 1H), 3.58–3.54(m, 3H), 3.49–3.45(m, 2H), 3.29–3.23(m, 2H), 2.89–2.85(m, 1H), 2.76–2.72 (m, 2H), 2.51–2.44(m, 1H), 2.18–2.05(m, 1H), 1.94–1.86(m, 3H), 1.74–1.69(m, 4H), 1.55–1.50(m, 4H), 1.26–1.19(m, 3H)

EXAMPLE 128

Synthesis of 2-[2-[[(S)-2-[2-(6-amidino-1-ethylindol-2-yl)ethyl]pyrrolidinyl]carbonyl] piperidinyl]acetic acid (Compound 193)

30 mg of methyl-2-[2-[[(S)-2-[2-(6-amidino-1-ethylindol-2-yl)ethyl]pyrrolidinyl]carbonyl]piperidinyl] acetate obtained in Example 127-b) was treated according to the same procedure as Example 44 to obtain 17 mg of the title compound as a pale yellow solid.

ES-MS: 454(M+1)+

$^1$H NMR(MeOH-d$_4$, ppm): δ 7.80–7.78(m, 1H), 7.55–7.50(m, 1H), 7.35–7.31(m, 1H), 6.37(s, 1H), 4.22–4.18(m, 3H), 3.75–3.69(m, 1H), 3.61–3.50(m, 2H), 2.99–2.91(m, 3H), 2.78–2.75(m, 2H), 2.47–2.42 (m, 1H), 2.12–1.55(m, 12H), 1.25–1.19(m, 3H)

IR(KBr): 3420, 2980, 1580 cm$^{-1}$

EXAMPLE 129

Synthesis of 1-ethyl-2-[2-[(S)-1-[(3-piperidinyl) carbonyl]pyrrolidin-2-yl]ethyl]indole-6-carboxamidine (Compound 194)

a) Synthesis of tert-butyl 3-[[(S)-2-[2-(6-cyano-1-ethylindol-2-yl)ethyl]pyrrolidinyl]carbonyl]piperidine carboxylate 130 mg of the compound I-a obtained in Example 1-l) and 1-[(tert-butoxy)carbonyl]piperidine-3-carboxylic acid were reacted according to the same procedure as Example 11-a) to obtain 76 mg of the title compound as a white solid.

$^1$H NMR(CDCl$_3$, ppm): δ 7.60–7.29(m, 3H), 6.40(d, 1H, J=3.62 Hz), 4.28–4.02(m, 5H), 3.71–3.42(m, 2H), 2.77(m, 4H), 2.54–1.59(m, 11H), 1.46(s, 9H), 1.38(t, 3H, J=7.10 Hz)

b) Synthesis of 1-ethyl-2-[2-[(S)-1-[(3-piperidinyl) carbonyl]pyrrolidin-2-yl]ethyl]indole-6-carboxamidine 71 mg of the compound obtained in the above a) was treated according to the same procedure as Example 1-n) to obtain 35 mg of the title compound as a pale yellow solid.

$^1$H-NMR(MeOH-d$_4$, ppm): δ 7.80(s, 1H), 7.54–7.31(m, 2H), 6.36(s, 1H), 4.22–4.02(m, 3H), 3.52(m, 2H), 2.92–2.28(m 6H), 2.18–1.41(m, 11H)

IR(KBr): 3380, 2990, 1630, 1540, 1480 cm$^{-1}$

ES-MS: 396(M+1)+

EXAMPLE 130

Synthesis of 1-ethyl-2-[2-[(S)-1-[(4-piperidinyl) carbonyl]pyrrolidin-2-yl]ethyl]indole-6-carboxamidine (Compound 195)

a) Synthesis of tert-butyl 4-[[(S)-2-[2-(6-cyano-1-ethylindol-2-yl)ethyl]pyrrolidinyl]carbonyl]piperidine carboxylate 148 mg of the compound I-a obtained in Example 1-l) and 1-[(tert-butoxy)carbonyl]piperidine-4-carboxylic acid were reacted according to the same procedure as Example 11-a) to obtain 63 mg of the title compound as a white solid.

$^1$H NMR(CDCl$_3$, ppm): δ 7.58–7.24(m, 3H), 6.39(s, 1H), 4.30–3.95(m, 5H), 3.54(m, 2H), 2.89–2.68(m, 4H), 2.52–1.58(m, 11H), 1.46(s, 9H), 1.36(t, 3H, J=7.25 Hz)

b) Synthesis of 1-ethyl-2-[2-[(S)-1-[(4-piperidinyl) carbonyl]pyrrolidin-2-yl]ethyl]indole-6-carboxamidine 59 mg of the compound obtained in the above a) was treated according to the same procedure as Example 1-n) to obtain 26 mg of the title compound as a pale yellow solid.

$^1$H NMR(MeOH-d$_4$, ppm): δ 7.81–7.32(m, 3H), 6.37(s, 1H), 4.24–4.06(m, 4H), 3.53(m, 2H), 3.00–2.53(m, 7H), 2.18–1.50(m, 9H)

IR(KBr): 3300, 2980, 1620, 1530, 1470 cm$^{-1}$

ES-MS: 396(M+1)+

EXAMPLE 131

Synthesis of ethyl 1-[2-[(S)-2-[2-(6-amidino-1-ethylindol-2-yl)ethyl]pyrrolidinyl]-2-oxoethyl] pyrrolidine-2-carboxylate (Compound 196)

a) Synthesis of ethyl 1-[2-[(S)-2-[2-(6-cyano-1-ethylindol-2-yl)ethyl]pyrrolindyl]-2-oxoethyl]pyrrolidine-2-carboxylate 109 mg of 1-ethyl-2-[2-[(S)-1-(2-chloroacetyl)pyrrolidin-2-yl]ethyl]indole-6-carbonitrile was treated according to the same procedure as Example 45-b) to obtain 133 mg of the title compound as a viscous brown oil.

$^1$H NMR(CDCl$_3$, ppm): δ 7.61–7.54(m, 2H), 7.32(m, 1H), 6.41(s, 1H), 4.20–4.13(m, 5H), 3.61(dd, J=14.52 Hz, 6.38 Hz), 3.50(m, 2H), 3.33(t, 1H, J=15.46 Hz), 3.12(brs, 1H), 2.83–2.74(m, 2H), 2.38–1.70(m, 11H), 1.36(t, 3H, J=7.17 Hz), 1.24(t, 3H, J=6.71 Hz)

b) Synthesis of ethyl 1-[2-[(S)-2-[2-(6-amidino-1-ethylindol-2-yl)ethyl]pyrrolidinyl]-2-oxoethyl]pyrrolidine-2-carboxylate 130 mg of the compound obtained in the above a) was treated according to the same procedure as Example 1-n) to obtain 35 mg of the title compound as a pale yellow solid.

$^1$H NMR(MeOH-d$_4$, ppm): δ 7.78(s, 1H), 7.52–7.30(m, 2H), 6.36(s, 1H), 4.21–3.97(m, 5H), 3.56–3.27(m, 5H), 3.01(m, 1H), 2.83–2.74(m, 2H), 2.56–1.72(m, 11H), 1.29(t, 3H, J=7.12 Hz), 1.08(t, 3H), J=7.04 Hz)

IR(KBr): 3350, 2980, 1730, 1620, 1520, 1460, 1160 cm$^{-1}$

ES-MS: 468(M+1)+

EXAMPLE 132

Synthesis of 1-[2-[(S)-2-[2-(6-amidino-1-ethylindol-2-yl)ethyl]pyrrolidinyl]-2-oxoethyl]pyrrolidine-2-carboxylic acid (Compound 197)

22 mg ethyl 1-[2-[(S)-2-[2-(6-amidino-1-ethylindol-2-yl) ethyl]pyrrolidinyl]-2-oxoethyl]pyrrolidine-2-carboxylate was treated according to the same procedure as Example 44 to obtain 15 mg of the title compound as a pale yellow solid.

$^1$H NMR(MeOH-d$_4$, ppm): δ 7.88–7.32(m, 3H), 6.42–6.33(m, 1H), 4.25–4.13(m, 3H), 3.50–3.08(m, 5H), 3.00–2.86(m, 1H), 2.76(m, 2H), 2.47–1.51(m, 11H), 1.28(t, 3H, J=7.20 Hz)
IR(KBr): 3350, 2960, 1700, 1650, 1450 cm$^{-1}$
ES-MS: 440(M+1)$^+$

EXAMPLE 133

Synthesis of ethyl 1-[2-[(S)-2-[2-(6-amidino-1-ethylindol-2-yl)ethyl]pyrrolidinyl]-2-oxoethyl]piperidine-2-carboxylate (Compound 198)

a) Synthesis of ethyl 1-[2-[(S)-2-[2-(6-cyano-1-ethylindol-2-yl)ethyl]pyrrolidinyl]-2-oxoethyl]piperidine-2-carboxylate 112 mg of 1-ethyl-2-[2-[(S)-1-(2-chloroacetyl)pyrrolidin-2-yl]ethyl]indol-6-carbonitrile was treated according to the same procedure as Example 45-b) to obtain 140 mg of the title compound as a viscous brown oil.

$^1$H NMR(CDCl$_3$, ppm): δ 7.61–7.54(m, 2H), 7.30(m, 1H), 6.41(d, 1H, J=3.07 Hz), 4.28–4.13(m, 5H), 3.73–3.30(m, 4H), 3.91(t, 1H), 3.03–2.95(m, 1H), 2.79 (t, 2H, J=7.98 Hz), 2.64–1.60(m, 13H), 1.36(t, 3H, J=7.22 Hz), 1.29–1.23(m, 3H)

b) Synthesis of ethyl 1-[2-[(S)-2-[2-(6-amidino-1-ethylindol-2-yl)ethyl]pyrrolidinyl]-2-oxoethyl]piperidine-2-carboxylate 136 mg of the compound obtained in the above a) was treated according to the same procedure as Example 1-n) to obtain 43 mg of the title compound as a pale yellow solid.

$^1$H NMR(MeOH-d$_4$, ppm): δ 7.77(s, 1H), 7.53–7.30(m, 2H), 6.35(s, 1H), 4.21–4.02(m, 5H), 3.59–3.03(m, 5H), 2.96–2.88(m, 1H), 2.79–2.69(m, 2H), 2.45–1.37(m, 13H), 1.29(t, 3H, J=7.13 Hz), 1.18–1.13(m, 3H)
IR(KBr): 3300, 2960, 1730, 1520, 1460, 1180 cm$^{-1}$
ES-MS: 481.62(M+1)$^+$

EXAMPLE 134

Synthesis of 1-[2-[(S)-2-[2-(6-amidino-1-ethylindol-2-yl)ethyl]pyrrolidinyl]-2-oxoethyl]piperidine-2-carboxylic acid (Compound 199)

27 mg of ethyl 1-[2-[(S)-2-[2-(6-amidino-1-ethylindol-2-yl)ethyl]pyrrolidinyl]-2-oxoethyl]piperidine-2-carboxylate was treated according to the same procedure as Example 44 to obtain 14 mg of the title compound as a pale yellow solid.

$^1$H NMR(MeOH-d$_4$, ppm): δ 7.71(s, 1H), 7.55–7.27(m, 2H), 6.29(s, 1H), 4.20–4.06(m, 3H), 3.61–3.35(m, 3H), 3.41(d, 1H, J=14.55 Hz), 2.82 (d, 1H, J=14.65 Hz), 2.93–2.64(m, 3H), 2.28–1.50(m, 13H), 1.27–1.19(m, 3H)
ES-MS: 454(M+1)$^+$

EXAMPLE 135

Synthesis of ethyl 2-[2-[2-[(S)-1-[((R)-1-acetylpyrrolidin-2-yl)carbonyl]pyrrolidin-2-yl]ethyl]-6-amidinoindolyl]acetate (Compound 222)

a) Synthesis of 2-(hydroxymethyl)indole-6-carbonitrile 10 g of ethyl 6-cyanoindole-2-carboxylate was treated according to the same procedure as Example 1-e) to obtain 6.8 g of the title compound as a yellow solid.

$^1$H NMR(MeOH-d$_4$, ppm): δ 7.63(s, 1H), 7.52(d, 1H), 7.15(m, 1H), 6.38(s, 1H), 4.67(s, 2H)

b) Synthesis of tert-butyl (S)-2-[2-(6-cyanoindol-2-yl)vinyl]pyrrolidine carboxylate 1 g of 2-(hydroxymethyl)indole-6-carbonitrile was treated according to the same procedure as Examples 1-f) and 1-m) to obtain 800 mg of the title compound as a yellow oil.

$^1$H NMR(CDCl$_3$, ppm): δ 7.47(m, 2H), 7.24(m, 1H), 6.33(s, 1H), 4.40(m, 1H), 3.36(m, 2H), 2.15–1.70(m, 6H), 1.47(m, 9H)

c) Synthesis of tert-butyl (S)-2-[2-(6-cyanoindol-2-yl)ethyl]pyrrolidine carboxylate 800 mg of the compound obtained in the above b) was treated according to the same procedure as Example 1-k) to obtain 620 mg of the title compound as a yellow oil.

$^1$H NMR(CDCl$_3$, ppm): δ 7.66(s, 1H), 7.50(t, 1H), 7.20 (m, 1H), 6.21(s, 1H), 3.92(m, 1H), 3.32(m, 2H), 2.80 (m, 2H), 2.1–1.7(m, 6H), 1.6–1.35(m, 9H)

d) Synthesis of ethyl 2-[6-cyano-2-[2-[(S)-1-[(tert-butoxy)carbonyl]pyrrolidin-2-yl]ethyl]indolyl]acetate 620 mg of the compound obtained in the above c) and 0.3 ml of ethyl 2-bromoacetate were reacted with NaH in the presence of N,N-dimethylformamide to obtain 850 mg of the title compound as a brown oil.

$^1$H NMR(CDCl$_3$, ppm): δ 7.60(s, 1H), 7.51(s, 1H), 7.36 (d, 1H), 6.46(s, 1H), 4.84(s, 2H), 4.32–4.20(m, 2H), 3.98(m, 1H), 3.43–3.27(m, 2H), 2.80–2.65(m, 2H), 1.95–1.67(m, 6H), 1.60–1.42(m, 9H), 1.37–1.23(m, 3H)

e) Synthesis of ethyl 2-[6-cyano-2-[2-[(S)-1-[[(R)-1-[(tert-butoxy)carbonyl]pyrrolidin-2-yl]carbonyl]pyrrolidin-2-yl]ethyl]indolyl]acetate 800 mg of the compound obtained in the above d) was treated according to the same procedure as Examples 1-l) and 11-a) to obtain 340 mg of the title compound as a pale yellow solid.

$^1$H NMR(MeOH-d$_4$, ppm): δ 7.63(s, 1H), 7.50(d, 1H), 7.20(d, 1H), 6.42(m, 1H), 4.68(s, 2H), 4.30–4.20(m, 1H), 4.10(m, 2H), 3.67–3.57(m, 1H), 351(m, 2H), 3.32(m, 2H), 2.10–1.60(m, 2H), 1.36–1.25(m, 9H), 1.10(m, 3H)

f) Synthesis of ethyl 2-[2-[2-[(S)-1-[((R)-1-acetylpyrrolidin-2-yl)carbonyl]pyrrolidin-2-yl]ethyl]-6-cyanoindolyl]acetate 300 mg of the compound obtained in the above e) was treated according to the same procedure as Examples 1-l) and 1-m) to obtain 180 mg of the title compound as a yellow solid.

$^1$H NMR(CDCl$_3$, ppm): δ 7.60(m, 1H), 7.50(s, 1H), 7.34(m, 1H), 6.47(s, 1H), 4.86(m, 2H), 4.35–4.17(m, 3H), 3.89(m, 1H), 3.70(m, 2H), 3.54(m, 2H), 2.30–1.90 (m, 9H), 1.35(m, 6H)

g) Synthesis of ethyl 2-[2-[2-[(S)-1-[((R)-1-acetylpyrrolidin-2-yl)carbonyl]pyrrolidin-2-yl]ethyl]-6-amidinoindolyl]acetate 150 mg of the compound obtained in the above f) was treated according to the same procedure as Example 1-n) to obtain 80 mg of the title compound as a pale yellow solid.

$^1$H NMR(CDCl$_3$, ppm): δ 7.50(m, 2H), 6.32(s, 1H), 4.97(s, 2H), 4.65(m, 1H), 4.15(m, 3H), 3.86(m, 1H), 3.68(m, 2H), 3.39(m, 2H), 2.70(m, 2H), 2.19–1.82(m, 12H), 1.22(m, 3H)
ES-MS: 482(M+1)$^+$

EXAMPLE 136

Synthesis of 2-[2-[(S)-1-[((R)-1-acetylpyrrolidin-2-yl)carbonyl]pyrrolidin-2-yl]ethyl]-1-(carbamoylmethyl)indole-6-carboxamidine (Compound 224)

30 mg of ethyl 2-[2-[2-[(S)-1-[((R)-1-acetylpyrrolidin-2-yl)carbonyl]pyrrolidin-2-yl]ethyl]-6-cyanoindolyl]acetate obtained in Example 135-g) was treated according to the same procedure as Example 1-n) to obtain 30 mg of the title compound as a yellowish white solid.

$^1$H NMR(MeOH-d$_4$, ppm): δ 7.74(s, 1H), 7.59(m, 1H), 7.36(m, 1H), 6.39(s, 1H), 4.87(s, 2H), 4.59(m, 1H), 4.29(m, 1H), 3.73(m, 3H), 2.75(m, 2H), 2.21(m, 2H), 2.09(s, 3H), 2.00–1.89(m, 9H)

ES-MS: 453(M+1)$^+$

EXAMPLE 137

Synthesis of 2-[2-[2-[(S)-1-[((R)-1-acetylpyrrolidin-2-yl)carbonyl]pyrrolidin-2-yl]ethyl]-6-amidinoindolyl]acetic acid (Compound 225)

40 mg of ethyl 2-[2-[2-[(S)-1-[((R)-1-acetylpyrrolidin-2-yl)carbonyl]pyrrolidin-2-yl]ethyl]-6-amidinoindolyl]acetate obtained in Example 135 was treated according to the same procedure as Example 44 to obtain 15 mg of the title compound as a white solid.

$^1$H NMR(MeOH-d$_4$+CDCl$_3$, ppm): δ 7.45(m, 2H), 7.28 (m, 1H), 6.37(s, 1H), 4.64(s, 2H), 4.53(s, 1H), 4.19(br, 1H), 3.79(m, 1H), 3.64(m, 3H), 2.75(m, 2H), 2.17(m, 3H), 2.03(s, 3H), 2.01–1.78(m, 7H), 1.28(m, 2H)

ES-MS: 451(M+1)$^+$

EXAMPLE 138

Synthesis of ethyl 2-[(R)-2-[[(S)-2-[2-(5-amidino-1-methylindol-2-yl)ethyl]pyrrolidinyl]carbonyl] pyrrolidinyl]acetate (Compound 242)

a) Synthesis of ethyl 5-bromoindole-2-carboxylate

In a 500 ml flask, 14 g of 4-bromophenylhydrazine hydrochloride was dissolved in 170 ml of ethanol, and 1.2 ml of sulfuric acid and 8.5 ml of ethyl pyruvate were added. The reaction mixture was stirred for about 2 hours at room temperature and evaporated under reduced pressure to dryness. To the residue was added 23 ml of polyphosphoric acid, and the resulting solution was then stirred for 2 hours at 100° C.–110° C. After water was added, the reaction solution was neutralized with saturated aqueous NaHCO$_3$ solution and then extracted to times with ethyl acetate. The extracts were combined, dried over MgSO$_4$ and then evaporated. The residue was purified with silica gel column chromatography [eluent: n-hexane/ethyl acetate(9:1)] to obtain 10 g of the title compound as a brown solid.

$^1$H NMR(CDCl$_3$, ppm): δ 9.03(br, 1H), 7.82(s, 1H), 7.41(m, 1H), 7.31(m, 1H), 7.14(s, 1H), 4.40(q, 2H, J=7.1 Hz), 1.41(t, 3H, J=7.1 Hz)

b) Synthesis of ethyl 5-bromo-1-methylindole-2-carboxylate 4.5 g of the compound obtained in the above a) and 2.1 ml of iodomethane were reacted according to the same procedure as Example 1-d) to obtain 5.9 g of the title compound as a yellow oil.

c) Synthesis of ethyl 5-cyano-1-methylindole-2-carboxylate

In a 500 ml flask, 8.7 g of the compound obtained in the above b) was dissolved in 430 ml of 1-methylpyrrolidin-2-one, and 4.1 g of CuCN was added thereto. The reaction mixture was stirred for 14 hours at 190° C.–200° C., cooled to room temperature and then filtered. To the filtrate was added water, and the reaction solution as extracted two times with chloroform. The extracts were combined, dried over MgSO$_4$ and then evaporated. The reside was purified with silica gel column chromatography [eluent: n-hexane/ethyl acetate(3:1)] to obtain 6.5 g of the title compound as a brown solid.

d) Synthesis of 1-methyl-2-(hydroxymethyl)indole-5-carbonitrile 6 g of the compound obtained in the above c) was treated according to the same procedure as Example 1-e) to obtain 2.4 g of the title compound as a yellowish white solid.

$^1$H NMR(CDCl$_3$, ppm): δ 7.90(s, 1H), 7.42(m, 1H), 7.33(m, 1H), 6.53(s, 1H), 4.83(s, 2H), 3.84(s, 3H)

IR(KBr): 3250, 2200, 1600, 1480 cm$^{-1}$ e) Synthesis of (5-cyano-1-methyl-2-indolyl) methyltriphenylphosphonium bromide 2.4 g of the compound obtained in the above d) was treated according to the same procedure as Example 1-f) to obtain 5.3 g of the title compound as a pale pink solid.

$^1$H NMR(MeOH-d$_4$, ppm): δ 7.82(m, 3H), 7.62(m, 15H), 6.26(m, 1H), 5.19(d, 2H), 3.08(s, 3H)

f) Synthesis of tert-butyl (S)-2-[2-(5-cyano-1-methylindol-2-yl)vinyl]pyrrolidine carboxylate 5 g of the compound obtained in the above e) was treated according to the same procedure as Example 1-j) to obtain 1.6 g of the title compound as a yellow oil.

g) Synthesis of tert-butyl (S)-2-[2-(5-cyano-1-methylindol-2-yl)ethyl]pyrrolidine carboxylate 1.4 g of the compound obtained in the above f) was treated according to the same procedure as Example 1-k) to obtain 1.3 g of the title compound as a yellow oil.

h) Synthesis of 1-methyl-2-((S)-2-pyrrolidin-2-ylethyl)indole-5-carbonitrile 1.2 g of the compound obtained in the above g) was treated according to the same procedure as Example 1-l) to obtain 710 mg of the title compound as a yellow oil.

$^1$H NMR(CDCl$_3$, ppm): δ 7.82(s, 1H), 7.35(m, 1H), 7.26(m, 1H), 6.32(s, 1H), 3.66(s, 3H), 3.19(m, 1H), 3.06(m, 2H), 2.97(m, 1H), 2.81(m, 2H), 1.94(m, 5)

i) Synthesis of tert-butyl (R)-2-[[(S)-2-[2-(5-cyano-1-methylindol-2-yl)ethyl]pyrrolidinyl]carbonyl]pyrrolidine carboxylate 700 mg of the compound obtained in the above h) was treated according to the same procedure as Example 11-a) to obtain 1 g of the title compound as a yellow oil.

$^1$H NMR(CDCl$_3$, ppm): δ 7.85(m, 1H), 7.36(m, 1H), 7.27(m, 1H), 6.34(s, 1H), 4.11(m, 1H), 3.80(m, 1H), 3.68(s, 3H), 3.61(m, 2H), 3.43(m, 3H), 2.82(m, 2H), 2.16–1.87(m, 9H), 1.42(s, 9H)

j) Synthesis of 1-methyl-2[2-[(S)-1-((R)-pyrrolidin-2ylcarbonyl)pyrrolidin-2-yl]ethyl]indole-5-carbonitrile:

1 g of the compound obtained in the above i) was treated according to the same procedure as Example 1—1) to obtain 730 mg of the title compound as a yellow oil k) Synthesis of methyl 2-[(R)-2-[[(S)-2[2-(5-cyano-1-ethylindol-2-yl)-ethyl]pyrrolidinyl]carbonyl]pyrrolidinyl] acetate:

720 mg of the compound obtained in the above j) and 350 ml of ethyl 2-bromoacetate were reacted according to the same procedure as Example 1-m) to obtain 680 mg of the title compound as a pale yellow oil.

$^1$H NMR(CDCl$_3$, ppm): δ 7.87(s, 1H), 7.44(m, 1H), 7.29(m, 1H), 6.40(s, 1H), 4.23(m, 1H), 4.12(m, 2H), 3.87(m, 1H), 3.72(s, 3H), 3.53(m, 2H), 3.22(m, 1H), 2.82(m, 3H), 2.01-1.89(m, 9H), 1.22(t, 3H, J=7.1Hz)

l) Syntheses of ethyl 2-[(R)-2[[(S)-2[2-(5amidino-1-methylindol-2-yl)ethyl]pyrrolidinyl]carbonyl]pyrrolidinyl] acetate:

670 mg of the compound obtained in the above k) was treated according to the same procedure as Example 1-n) to obtain 200 g of the title compound as a yellowish white solid.

231

¹H NMR(CDCl₃, ppm):δ 7.98(s, 1H), 7.49(m, 1H), 6.56 (s, 1H), 4.70-4.39(br, 2H), 4.28(m, 1H), 4.12(q, 2H), 3.81(m, 1H), 3.66(s, 3H), 3.60(m, 2H), 3.29(m, 1H), 2.77(m, 3H), 2.35(m, 1H), 2.17(m, 1H), 2.00-1.78(m, 9H), 1.24(t, 3H)
IR(KBr): 3300, 2900, 1720, 1620 cm⁻¹
ES-MS: 454(M+1)⁺, 476(M+Na)

EXAMPLE 139

Synthesis of ethyl 2-[(R)-2-[[(S)-2-[(S)-2-(5-amidino-1-ethylindol-2-yl)ethyl]pyrrolidinyl]carbonyl]pyrrolidinyl]-acetate (Compound 243)

a) Synthesis of ethyl 5-bromo-1-ethylindole-2-carboxylate:

4.5 g of ethyl 5-bromoindole-2-carboxylate and 2.7 ml of iodoethane were reacted according to the same procedure as Example 1-d) to obtain 5.2 g of the title compound as a yellow oil.

b) Synthesis of ethyl 5-cyano-1-ethylindole-2-carboxylate:

In a 500 ml flask, 7.7 g of the compound obtained in the above a) was dissolved in 360 ml of 1-methylpyrrolidin-2-one, and 3.5 g of CuCN was added thereto. The reaction mixture was stirred for 14 hours at 190° C.–200° C., cooled to room temperature and then filtered. To the filtrate was added water, and the reaction solution was extracted two times with chloroform. The extracts were combined, dried over MgSO₄ and then evaporated. The residue was purified with silica gel column chromatography [eluent: n-hexane/ethyl acetate(3:1)] to obtain 5.4 g of the title compound as a brown solid.

c) Synthesis of 1-ethyl-2-(hydroxymethyl)indole-5-carbonitrile:

5 g of the compound obtained in the above b) was treated according to the same procedure as Example 1-e) to obtain 2.9 g of the title compound as a yellowish white solid.

¹H NMR(CDCl₃, ppm): 67 7.91(s, 1H), 7.44(m, 1H), 7.38(m, 1H), 6.52(s, 1H), 4.83(s, 2H), 4.32(q, 2H, J=7.2Hz), 1.42(t, 3H, J=7.2Hz)
IR(KBr): 3450, 2200, 1600, 1480 cm⁻¹ d) Synthesis of (5-cyano-1-ethyl-2-indolyl)methyltriphenylphosphonium bromide:

2.8 g of the compound obtained in the above c) was treated according to the same procedure as Example 1-f) to obtain 6 g of the title compound as a pale pink solid.

¹H NMR(MeOH-d₄, ppm): δ 7.92(m, 3H), 7.74(m, 15H), 6.29(m, 1H), 3.78 (q, 2H, J=7.1Hz), 3.33(m, 2H), 1.12(t, 3H, J=7.1Hz)

e) Synthesis of tert-butyl (S)-2-[2-(5-cyano-1-ethylindol-2-yl)vinyl]-pyrrolidine carboxylate:

5 g of the compound obtained in the above d) was treated according to the same procedure as Example 1-j) to obtain 1.7 g of the title compound as a yellow oil.

f) Synthesis of tert-butyl (S)-2-[2-(5-cyano-1-ethylindol-2-yl)ethyl]-pyrrolidine carboxylate:

1.6 g of the compound obtained in the above e) was treated according to the same procedure as Example 1-k) to obtain 1.5 g of the title compound as a yellow oil.

¹H NMR(CDCl₃, ppm): δ 7.85(s, 1H), 7.38(m, 1H), 7.26(m, 1H), 6.35(s, 1H), 4.14(q, 2H, J=7.2Hz), 3.95 (br, 1H), 3.37(m, 2H), 2.75(m, 2H), 1.92-1.76(m, 6H), 1.47(s, 9H), 1.35(t, 3H, J=7.2Hz)

232 g) Synthesis of 1-ethyl-2-((S)-2-pyrrolidin-2-ylethyl)indole-5-carbonitrile:

1.4 g of the compound obtained in the above f) was treated according to the same procedure as Example 1-l) to obtain 940 mg of the title compound as a yellow oil.

h) Synthesis of tert-butyl (R)-2-[[(S)-2-[2-(5-cyano-1-ethylindol-2-yl)-ethyl]pyrrolidinyl]carbonyl]pyrrolidine carboxylate:

930 mg of the compound obtained in the above g) was treated according to the same procedure as Example 11-a) to obtain 960 mg of the title compound as a yellow oil.

¹H NMR(CDCl₃, ppm): δ 7.85(m, 1H), 7.35(m, 1H), 7.28(m, 1H), 6.36(s, 1H), 4.15(m, 3H), 3.80(m, 1H), 3.62(m, 2H), 3.43(m, 3H), 2.79(m, 2H), 2.11-1.85(m, 9H), 1.42(s, 9H)

i) Synthesis of 1-ethyl-2-[2-[(S)-1-((R)-pyrrolidin-2-ylcarbonyl)pyrrolidin-2-yl]ethyl]indole-5-carbonitrile:

960 mg of the compound obtained in the above h) was treated according to the same procedure as Example 1-l) to obtain 650 mg of the title compound as a yellow oil.

j) Synthesis of ethyl 2-[(R)-2-[[(S)-2-[2-(5-cyano-1-ethylindol-2-yl)-ethyl]pyrrolidinyl]carbonyl]pyrrolidinyl]acetate:

640 mg of the compound obtained in the above i) and 0.3 ml of ethyl 2-bromoacetate were reacted according to the same procedure as Example 1-m) to obtain 650 mg of the title compound as a pale yellow oil.

¹H NMR(CDCl₃, ppm): δ 7.80(s, 1H), 7.38(m, 1H), 7.28(m, 1H), 6.40(s, 1H), 4.27(m, 1H), 4.13(m, 4H), 3.87(m, 1H), 3.56(m, 2H), 3.22(m, 1H), 2.78(m, 3H), 2.02-1.86(m, 9H), 1.35(t, 3H, J=7.1Hz), 1.22(t, 3H, J=7.1Hz)

k) Synthesis of ethyl 2-[(R)-2[[(S)-2-[2-(5-amidino-1-ethylindol-2-yl)-ethyl]pyrrolidinyl]carbonyl]pyrrolidinyl]acetate:

630 mg of the compound obtained in the above j) was treated according to the same procedure as Example 1-n) to obtain 150 mg of the title compound as a yellowish white solid.

¹H NMR(CDCl₃, ppm): δ 8.15(s, 1H), 7.55(m, 1H), 7.30(m, 1H), 6.71(s, 1H), 6.10-5.80(br, 2H), 4.38(m, 1H), 4.11(m, 4H), 3.73(m, 1H), 3.44(m, 2H), 3.38(m, 1H), 2.72(m, 3H), 2.45(m, 1H), 2.20(m, 1H), 1.99-170 (m, 9H), 1.26(m, 6H)
IR(KBr): 3200, 3000, 1740, 1620 cm⁻¹
ES-MS: 4.68(M+1)⁺

EXAMPLE 140

Synthesis of 6-[2-[(S)-1-(2-phenylacetyl)pyrrolidine-2-yl]ethyl]naphthalene-2-carboxamidine (Compound 244)

1 g of 7-cyanonaphthalene-3-methyltriphenylphosphonium bromide and 390 mg of (S)-1-(t-butoxycarbonyl)-2-pyrrolidinal were dissolved in a mixed solvent of 15 ml of tetrahydrofuran and 15 ml of ethanol, and 360 μl of DBU (1,8-diazabicyclo[5.4.0]undec-7-ene) was added at room temperature. The reaction solution was stirred overnight at room temperature and distilled under reduced pressure to remove the solvent. The residue was purified with silica gel column chromatography [eluent: n-hexane/ethyl acetate (3:1)]. The fractions containing the desired product were combined and distilled under reduced pressure to obtain the product, tert-butyl (S)-2[2-(6-cyano-2-naphthyl)vinyl]pyrrolidine carboxylate. 410 mg of this product thus obtained was dissolved in 15 ml of ethanol and then hydrogenated in the presence of 50 mg of Pd/C(10% w/w) for 2 hours under normal pressure with stirring. The reaction solution was filtered under reduced pressure to remove Pd/C, and the filtrate was distilled under reduced pressure and dried under reduced pressure. The residue was dissolved in 10 ml of dichloromethane, and 3 ml of trifluoroacetic acid was added. The mixture thereby obtained was stirred overnight at room temperature, and excess of dichloromethane was added thereto. The organic layer was separated, washed with aqueous sodium bicarbonate solution, dried over anhydrous magnesium sulfate and then filtered under reduced pressure. The filtrate was distilled under reduced pressure to obtain 320 mg of the oily product, 6-((S)-2-pyrrolidin-2-ylethyl)naphthalene-2-carbonitrile. 85 mg of the resulting oily product was then treated according to the same procedure as Example 1-m) to obtain 50 mg of the compound 6-[2O[(S)- 1-(2-phenylacetyl)pyrrolidin-2-yl]ethyl]naphthalene-2-carbonitrile, which was then treated according to the same procedure as Example 1-n) to obtain 30 mg of the title compound as a yellow solid.

$^1$H NMR(MeOH-d$_4$, ppm): δ 8.20(d, 1H), 7.83(m, 2H), 7.37 (d, 1H), 7.21-7.12(m, 5H), 6.98(d, 1H), 6.76(d, 1H), 4.05(m, 1H), 3.59(m, 2H), 3.37(m, 4H), 2.70(t, 2H), 2.15(m, 1H), 1.93-1.79(m, 7H), 1.70(m, 1H)

EXAMPLE 141

Synthesis of methyl 2-[(R)-2-[[(S)-2-[2-(6-amidino-2-naphthyl)ethyl]pyrrolidinyl]carbonyl]pyrrolidinyl]acetate (Compound 245)

a) Synthesis of methyl 2-[(R)-2-[[(S)-2-[2-(6-cyano-2-naphthyl)ethyl]-pyrrolidinyl]carbonyl]pyrrolidinyl]acetate:

250 mg of 6-((S)-2-pyrrolidin-2-ylethyl)naphthalene-2-carbonitrile was treated according to the same procedure as Example 11-a) to obtain 256 mg of tert-butyl (R)-2-[[(S)-2-[2-(6-cyano-2-naphthyl)ethyl]pyrrolidinyl]carbonyl] pyrrolidine carboxylate. 150 mg of the compound thereby obtained was reacted according to the same procedure as Example 1-l) to obtain 134 mg of 6-[2-[(S)-1-((R)-pyrrolidin-2-ylcarbonyl)pyrrolidin-2-yl]-ethyl]naphthalene-2-carbonitrile. Thereafter, 130 mg of the compound thus obtained was treated according to the same procedure as Example 1-m) to obtain 129 mg of the title compound as a yellow solid.

$^1$H NMR(CDCl$_3$, ppm): δ 8.17(s, 1H), 7.92-7.79(m, 2H), 7.73(s, 1H), 7.50 (m, 2H), 4.19(bs, 1H)

b) Synthesis of methyl 2-[(R)-2-[[(S)-2-[2-(6-amidino-2-naphthyl)-ethyl]pyrrolidinyl]carbonyl]pyrrolidinyl]acetate:

124 mg of the compound obtained in the above a) was treated according to the same procedure as Example 1-n) to obtain 48 mg of the title compound as a pale yellow solid.

$^1$H NMR(MeOH-d$_4$, ppm): δ 8.35(s, 1H), 7.95(m, 2H), 7.89(m, 2H), 7.54(d, 1H, J=11.73Hz), 4.20-4.00(m, 3H), 3.79(m, 1H), 3.62(m, 2H), 3.46 (d, 2H, J=19.11Hz), 3.20(m, 1H), 3.00(m, 1H), 2.98-2.70(m, 3H), 2.33-1.70(m, 11H)
ES-MS: 451(M+1)$^{30}$

EXAMPLE 142

Synthesis of 7-[2-[(S)-1-2-phenylacetyl)pyrrolidin-2-yl]ethyl]naphthalene-2-carboxamidine (Compound 246)

a) Synthesis of tert-butyl (S)-2-(2-(7-cyano-2-naphthyl)vinyl)pyrrolidine carboxylate:

5.6 g of 7-cyanonaphthalene-2-methyltriphenylphosphonium bromide was reacted according to the same procedure as Example 1-j) to obtain 2.9 g of the title compound.

$^1$H NMR(CDCl$_3$, ppm): δ 8.24-7.54(m, 6H), 6.55(bs, 1H), 6.30(bs, 1H), 4.51(bd, 1H), 3.49(s, 2H), 2.17-1.82(m, 4H), 1.83-1.26(m, 9H)

b) Synthesis of 7-((S)-2pyrrolidin-2ylethyl)naphthalene-2-carbonitrile:

2.9 g of the compound obtained in the above a) was treated according to the same procedure as Example 1-k) to obtain 2.7 g of the product, which was then treated according to the same procedure as Example 1-l) to obtain 1.6 g of the title compound as a yellow oil.

$^1$H NMR(CDCl$_3$, ppm): δ 7.79(s, 1H), 7.76(d, 1H, J=8.46Hz), 7.68(d, 1H, J=8.42Hz), 7.54-7.48(t, 2H), 7.37(d, 1H, J=8.43Hz), 3.49(t, 1H), 3.26(m, 2H), 2.91-2.82(m, 2H), 2.30-1.68(m, 6H)
ES-MS: 251(M+1)$^+$ c) Synthesis of 7-[2-[(S)-1-(2-phenylacetyl)pyrrolidin-2-yl]ethyl]naphthalene-2-carbonitrile:

445 mg of the compound obtained in the above b) and 0.47 ml of phenyl acetylchloride were reacted according to the same procedure as Example 1-m) to obtain 298 mg of the title compound.

$^1$H NMR(CDCl$_3$, ppm): δ 8.14(s, 1H), 7.86-7.78(q, 2H), 7.67(s, 1H), 7.55-7.51(m, 2H), 7.32-6.92(m, 5H), 4.21 (m, 1H), 3.64(s, 1H), 3.46(m, 2H), 2.80(t, 2H, J=8.16Hz), 2.33(m, 1H), 2.04-1.59(m, 5H)

d) Synthesis of 7-[2-[2-[(S)-1-2-phenylacetyl)pyrrolidin-2-yl]naphthalene-2-carboxamidine:

270 mg of the compound obtained in the above c) was treated according to the same procedure as Example 1-n) to obtain 128 mg of the title compound as a pale yellow solid.

$^1$H NMR(MeOH-d$_1$, ppm): δ 8.08(s, 1H), 7.77-7.61(m, 4H), 7.34-7.32(d, 1H, J=8.33Hz), 7.20-7.13(m, 3H), 6.94(m, 1H), 6.73(d, 1H), 4.08 (bs, 1H), 3.56(s, 2H), 3.45-3.30(m, 2H), 2.67(t, 2H), 2.20-1.50(m, 6H)
ES-MS: 386(M+1)$^+$

EXAMPLE 143

Synthesis of ethyl 2-[(R)-2-[[(S)-2-[2-(7-amidino-2-naphthyl)ethyl]pyrrolidinyl]carbonyl]pyrrolidinyl]acetate (Compound 247)

a) Synthesis of 7-[2-[(S)-1-((R)-pyrrolidin-2-ylcarbonyl)pyrrolidin-2-yl]ethyl]naphthalene-2-carbonitrile:

450 mg of 7-((S)-2-pyrrolidin-2-ylethyl)naphthalene-2-carbonitrile obtained in Example 142-b) was treated according to the same procedure as Example 11-a) to obtain 643 mg of tert-butyl (R)-2-[[(S)-2-[2-(7-cyano-2-naphthyl)ethyl]pyrrolidinyl]carbonyl]pyrrolidine carboxylate, which was then treated according to the same procedure as Example 1-l) to obtain 472 mg of the title compound as a brown oil.

$^1$H NMR(CDCl$_3$, ppm): δ 8.17(s, 1H), 7.90(d, 1H, J=8.83Hz), 7.79(d, 1H, J=8.49Hz), 7.73(s, 1H), 7.49(d, 2H), 4.35(t, 1H), 4.02(m, 1H), 3.52(m, 1H), 3.32(m, 2H), 2.76(m, 2H), 2.36(m, 1H), 2.23(m, 1H), 2.10-1.80 (m, 8H), 1.74-1.60(m, 1H) p ES-MS: 348(M+1)$^+$ b) Synthesis of ethyl 2-[(R)-2-[[(S)-2-[2-(7-cyano-2-naphthyl)ethyl]-pyrrolidinyl]carbonyl]pyrrolidinyl]acetate:

572 mg of the compound obtained in the above a) was treated according to the same procedure as Example 1-m) to obtain 700 mg of the title compound as a yellow solid.

$^1$H NMR(CDCl$_3$, ppm): δ 8.18(s, 1H), 7.90-7.70(m, 3H), 7.50(m, 2H), 4.01(m, 2H), 3.89(m, 1H), 3.67(m, 1H), 3.54-3.12(m, 5H), 3.05(m, 1H), 2.92(m, 1H), 2.73(m, 2H), 2.20-1.50(m, 10H), 1.06(t, 3H)
ES-MS: 434(M+1)$^+$, 456(M+Na)

c) Synthesis of ethyl 2-[(R)-2-[[(S)-2-[2-(7-amidino-2-naphthyl)ethyl]-pyrrolidinyl]carbonyl]pyrrolidinyl]acetate:

650 mg of the compound obtained in the above b) was treated according to the same procedure as Example 1-n) to obtain 148 mg of the title compound as a pale yellow solid.

$^1$H NMR(MeOH)-d$_4$, ppm): δ 8.08(s, 1H), 7.78-7.76(m, 4H), 7.34(m, 1H), 4.00(m, 2H), 3.90(m, 1H), 3.65(m, 1H), 3.57-3.15(m, 4H), 3.07(m, 1H), 2.88(m, 1H), 2.65(m, 2H), 2.17-1.50(m, 10H), 1.07(t, 3H)

ES-MS: 451(M+1)$^+$, 474(M+Na)

IR(KBr): 3200, 1220 cm$^{-1}$

EXAMPLE 144

Synthesis of 2-[2-[(S)-1-(2-phenylacetyl)pyrrolidin-2-yl]ethyl]benzo]b]furan-5-carboxamidine (Compound 248)

a) Synthesis of ethyl 2-(4-bromo-2-formylphenoxy)acetate:

In a 1 l flask, 30 g of 5-bromosalicyl aldehyde was stirred in 500 ml of acetate solvent at room temperature, and then 26.8 g of K$_2$CO$_3$ was slowly added thereto. After the mixture thereby obtained was stirred for 30 minutes, 21.5 ml of ethyl bromoacetate was slowly added dropwise thereto and the reaction mixture was refluxed for 2 hours with stirring. After the reaction was completed, the reaction solution was evaporated. To the residue was added dichloromethane and the resulting precipitate was filtered and washed two times with water. The organic layers were combined, dried over MgSO$_4$ and then evaporated. The residue was purified with silica gel column chromatography [eluent: ethyl acetate/n-hexane (1:3)]. The fractions containing the desired product were combined and then evaporated to obtain 43 g of the title compound as a yellow liquid.

$^1$H NMR(CDCl$_3$, ppm): δ 10.45(s, 1H), 7.95(d, 1H, J=2.59Hz), 7.60(dd, 1H, J=8.79Hz, 2.61Hz), 6.75(d, 1H, J=8.62Hz), 4.75(s, 2H), 4.20(q, 2H, J=7.14Hz), 1.25(t, 3H, J=7.15Hz)

ES-MS: 288(M+1)$^+$ b) Synthesis of ethyl 5-bromobenzo[d]furan-2-carboxylate:

In a 1 l flask, 2.96 g of Na was slowly added to 250 ml of ethanol solvent, and this mixture was stirred for 30 minutes. 42 g of the compound obtained in the above a) was slowly added dropwise thereto at room temperature. The reaction solution was stirred for 2 hours and then evaporated under reduced pressure. The residue was extracted two times with ethyl acetate. The combined organic layer was dried over MgSO$_4$ and then evaporated to obtain 11.7 g of the title compound as a yellow solid.

$^1$H NMR(CDCl$_3$, ppm): δ 7.80(s, 1H), 7.45(m, 2H), 4.40(q, 2H, J=7.13Hz), 1.40(t, 3H, J=7.13Hz)

ES-MS: 270(M+1)$^+$ c) Synthesis of ethyl 5-cyanobenzo[d]furan-2-carboxylate:

In a 250 ml flask, 24.7 g of the compound obtained in the above b) was dissolved in 100 ml of N-methylpyrrolidinone, and 16.53 g of CuCN and 1.48 g of CuSO$_4$ catalyst were added thereto. The reaction mixture was refluxed for one hour at 200–200° C. with stirring. The reaction solution was then stirred for 30 minutes at room temperature. After excessive amount of water was added, the reaction solution was stirred and then filtered. The residue was washed three times with ethyl acetate. The organic layers were combined, dried over MgSO$_4$ and then evaporated under reduced pressure. The residue was purified with silica gel column chromatography [eluent: ethyl acetate/n-hexane(1:5)]. The fractions containing the desired product were combined and then evaporated to obtain 6.39 g of the title compound as a white solid.

$^1$H NMR(CDCl$_3$, ppm): δ 8.0(s, 1H), 7.60(s, 2H), 6.75(s, 1H), 4.80(s, 1H), 4.65(s, 1H)

ES-MS: 174(M+1)$^+$ e) Synthesis of benzo[b]furan-5-carbonitrile-2-methyltriphenylphosphonium bromide:

5.34 g of the compound obtained in the above d) was treated according to the same procedure as Example 1-f) to obtain 14.8 g of the title compound as a white solid.

$^1$H NMR(CDCl$_3$, ppm): δ 7.95-7.60(m, 16H), 7.45(m, 1H), 7.25(m, 2H), 6.05(d, 2H)

f) Synthesis of tert-butyl (S)-2-[2-(5-cyanobenzo[d]furan-2-yl)vinyl]-pyrrolidine carboxylate:

11.8 g of the compound obtained in the above e) was treated according to the same procedure as Example 1-j) to obtain 3.99 g of the title compound as a fluorescent yellow liquid.

$^1$H NMR(CDCl$_3$, ppm): δ 7.80(s, 1H), 7.45(m, 2H), 6.55(s, 1H), 6.50-6.10 (m, 2H), 4.45(m, 1H), 3.45(br, 2H), 2.0-1.70(m, 4H), 1.40(br, 9H)

ES-MS: 339(M+1)$^+$ g) Synthesis of tert-butyl (S)-2-[2-(5-cyanobenzo[d]furan-2-yl)ethyl]-pyrrolidine carboxylate:

2.09 g of the compound obtained in the above f) was treated according to the same procedure as Example 1-k) to obtain 1.75 g of the title compound as a colorless liquid.

$^1$H NMR(CDCl$_3$, ppm): δ 7.80(s, 1H), 7.45(m, 2H), 6.50(s, 1H), 3.90(m, 1H), 3.40(m, 2H), 2.80(m, 2H), 2.30-1.60(m, 6H), 1.40(br, 9H)

h) Synthesis of 2-((S)-2-pyrrolidin-2-ylethyl)benzo[b]furan-5-carbonitrile:

1.55 g of the compound obtained in the above g) was treated according to the same procedure as Example 1-l) to obtain a stoichiometric amount of the title compound as a colorless foamy solid.

$^1$H NMR(CDCl$_3$, ppm): δ 9.30(br, 1H), 7.75(s, 1H), 7.40(m, 2H), 3.50(m, 1H), 3.25(m, 2H), 2.90(m, 2H), 2.35-1.80(m, 4H), 1.70(m, 1H)

ES-MS: 241(M+1)$^+$ i) Synthesis of 1-((S)-2-(2-(5-ethynylbenzo[d]furan-2-yl)ethyl)pyrrolidinyl)-2-phenylethan-1-one:

220 mg of 2-((S)-2-pyrrolidin-2-ylethyl)benzo[b]furan-5-carbonitrile obtained in the above h) and 180 mg of phenylacetyl chloride were reacted according to the same procedure as Example 1-m) to obtain 200 mg of the title compound as a colorless liquid.

$^1$H NMR(CDCl$_3$, ppm): δ 7.80(s, 2H), 7.45(m, 2H), 7.25(m, 5H), 6.55(s, 1H), 4.25(m, 1H), 3.65(m, 2H), 3.45(m, 2H), 2.80(m, 2H), 2.30(m, 1H), 2.10-1.80(m, 3H), 1.70(m, 2H)

ES-MS: 358(M+1)$^+$ j) Synthesis of 2-[2-[(S)-1-(2-phenylacetyl)pyrrolidin-2-yl]ethyl]benzo-[b]furan-5-carboxamidine:

190 mg of the compound obtained in the above i) was treated according to the same procedure as Example 1-n) to obtain 180 mg of the title compound as a colorless foamy solid.

$^1$H NMR(CDCl$_3$, ppm): δ 7.70( s, 1H), 7.55-7.10(m, 7H), 6.50(s, 1H), 4.25 (m, 1H), 3.65(s, 2H), 3.45(m, 1H), 2.80(t, 2H, J=7.80Hz), 2.30(m, 1H), 2.10-1.80(m, 3H), 1.70(m, 2H)

ES-MS: 376(M+1)$^+$

IR(KBr): 3300, 2950, 2800, 1650 cm$^{-1}$

EXAMPLE 145

Synthesis of 2-[2-[(S)-1-(2-phenylacetyl)pyrrolidin-2-yl]vinyl]benzo[b]furan-5-carboxamidine (Compound 249)

a) Synthesis of 2-(2-pyrrolidin-(S)-ylvinyl)benzo[b]furan-5-carbonitrile:

490 mg of tert-butyl (S)-2-[2-(5-cyanobenzo[b]furan-2-yl)vinyl]-pyrrolidine carboxylate obtained in Example 144-f) was treated according to the same procedure as Example 1-l) to obtain a stoichiometric amount of the title compound as a colorless solid.

$^1$H NMR(CDCl$_3$, ppm): δ 7.75(m, 1H), 7.45(m, 2H), 6.65-6.30(m, 3H), 4.10(m, 1H), 3.35-3.15(m, 2H), 2.40-1.75(m, 4H)

ES-MS: 239(M+1)$^+$ b) Synthesis of 2-[2-[(S)-1-(2-phenylacetyl)pyrrolidin-2-yl]vinyl]benzo-[b]furan-5-carbonitrile:

450 mg of the compound obtained in the above a) and 0.3 ml of phenylacetyl chloride were reacted according to the same procedure as Example 1-m) to obtain 344 mg of the title compound as a colorless foamy solid.

$^1$H NMR(CDCl$_3$, ppm): δ 7.75(m, 1H), 7.45(m, 2H), 7.40-7.15(m, 5H), 6.65-6.20(m, 3H), 4.75(m, 1H), 3.80-3.40(m, 4H), 2.25-1.75(m, 4H)

ES-MS: 357(M+1)$^+$ c) Synthesis of 2-[2-[(S)-1-(2-phenylacetyl)pyrrolidin-2-yl]vinyl]benzo-[b]furan-5-carboxamidine:

223 mg of the compound obtained in the above b) was treated according to the same procedure as Example 1-n) to obtain 190 mg of the title compound as a colorless foamy solid.

$^1$H NMR(CDCl$_3$, ppm): δ 7.75(m, 2H), 7.60-7.0(m, 7H), 6.70-6.20(m, 3H), 5.20-4.80(br, 3H), 3.75-3.40(m, 4H), 2.25-1.75(m, 4H)

ES-MS: 374(M+1)$^+$

IR(KBr): 3200, 2950, 2850, 1650 cm$^{-1}$

EXAMPLE 146

Synthesis of ethyl 2-[(R)-2-[[(S)-2-[2-(5-amidinobenzo[d]furan-2-yl)ethyl]pyrrolidinyl]carbonyl]pyrrolidinyl]acetate (Compound 250)

a) Synthesis of tert-butyl (R)-2-[[(S)-2-[2-(5-cyanobenzo[d]furan-2-yl)-ethyl]pyrrolidinyl]carbonyl]pyrrolidine carboxylate:

447 mg of 2-((S)-2-pyrrolidin-2-ylethyl)benzo[b]furan-5-carbonitrile obtained in Example 144-h was treated according to the same procedure as Example 11-a) to obtain 370 mg of the title compound as a colorless foamy solid.

$^1$H NMR(CDCl$_3$, ppm): δ 7.80(m, 1H), 7.40(m, 2H), 6.55(d, 1H), 4.40(m, 1H), 4.20(m, 1H), 3.85-3.30(m, 4H), 2.85(m, 2H), 2.45-1.60(m, 10H), 1.40(br, 9H)

ES-MS: 438(M+1)$^+$ b) Synthesis of 2-[2-[(S)-1-((R)-pyrrolidin-2-ylcarbonyl)pyrrolidin-2-yl]-ethyl]benzo[b]furan-5-carbonitrile:

240 of the compound obtained in the above a) was treated according to the same procedure as Example 1-l) to obtain 200 mg of the title compound as a pale yellow foamy solid.

$^1$H NMR(CDCl$_3$, ppm): δ 7.75(s, 1H), 7.40(m, 2H), 6.55(s, 1H), 4.55(m, 1H), 4.15(m, 1H), 3.60(m, 1H), 3.40(m, 3H), 2.75(m, 2H), 2.45(m, 1H), 2.25(m, 1H), 2.15-1.70(m, 8H)

c) Synthesis of ethyl 2-[(R)-2-[[(S)-2-[2-(5-cyanobenzo[d]furan-2-yl)-ethyl]pyrrolidinyl]carbonyl]pyrrolidinyl]acetate:

230 mg of the compound obtained in the above b) was treated according to the same procedure as Example 1-m) to obtain 248 mg of the title compound as a pale yellow liquid.

$^1$H NMR(CDCl$_3$, ppm): δ 7.80(s, 1H), 7.45(m, 2H), 6.65(s, 1H), 4.30-4.0 (m, 3H), 3.85(m, 1H), 3.65-3.35 (m, 4H), 3.20(m, 1H), 2.80(m, 3H), 2.30(m, 1H), 2.15(m, 1H), 2.10-1.60(m, 8H), 1.25(t, 3H), J=7.14Hz)

ES-MS: 424(M+1)$^+$ d) Synthesis of ethyl 2-[(R)-2-[[(S)-2-[2-(5-amidinobenzo[d]furan-2-yl)-ethyl]pyrrolidinyl]carbonyl]pyrrolidinyl]acetate:

200 mg of the compound obtained in the above c) was treated according to the same procedure as Example 1-n) to obtain 100 mg of the title compound as a pale yellowish white foamy solid.

$^1$H NMR(CDCl$_3$, ppm): δ 7.90(s, 1H), 7.50(m, 2H), 6.65(s, 1H), 4.45(m, 1H), 4.20-3.95(m, 4H), 3.65(m, 1H), 3.50(m, 1H), 3.35(m, 1H), 3.15(m, 1H), 2.80(m, 1H), 2.45(m, 1H), 2.25(m, 1H), 2.10-1.70(m, 9H), 1.15(t, 3H, J=7.1Hz)

ES-MS: 441(M+1)$^+$

IR(KBr): 3200, 2950, 1750, 1670 cm$^{-1}$

EXAMPLE 147

Synthesis of ethyl 2-[(R)-2-[[(S)-2-[2-(6-amidino-benzo[d]furan-2-yl)ethyl]pyrrolidinyl]carbonyl]pyrrolidinyl]acetate (Compound 251) and 2-[2-[(S)-1-[[(R)-1-(carbamoylmethyl)pyrrolidin-2-yl]carbonyl]pyrrolidin-2-yl]ethyl]benzo[b]furan-6-carboxamidine a) Synthesis of 3-bromo-1-(2-bromoprop-2-enyloxy)benene:

In a 1 l flask, 25 g of 5-bromophenol was stirred in 250 ml of dimethylformamide at room temperature, and 39.9 g of K$_2$CO$_3$ was slowly added thereto. After the mixture thereby obtained was stirred for 30 minutes, 22.4 ml of 2,3-dibromopropene was slowly added dropwise thereto and the reaction was completed, excessive amount of water was added to the reaction solution, which was then extracted three times with ether. The combined organic layer was dried over MgSO$_4$ and then evaporated. The residue was purified with silica gel column chromatography [eluent:hexane]. The fractions containing the desired product were combined and then evaporated to obtain 37.1 g of the title compound as a yellow liquid.

$^1$H NMR(CDCl$_3$, ppm): δ 7.10(m, 3H), 6.82(m, 1H), 5.96(s, 1H), 5.68s, 1H), 4.60(s, 2H)

b) Synthesis of 5-bromo-2-(2-bromoprop-2-enyl)phenol:

In a 500 ml flask, 240 ml of 1N-BBr$_3$ was slowly added over one hour to 37 g of the compound obtained in the above a) in 250 ml of CS$_2$ solvent, and this mixture was then stirred for 6 hours. The reaction was quenched with 5N HCl at 0° C. The reaction solution was evaporated under reduced pressure and extracted two times with ether. The combined organic layer was dried over MgSO$_4$ and then evaporated to obtain 24.0 g of the title compound as a yellow oil $^1$H NMR(CDCl$_3$, ppm): δ 7.10-6.90(m, 3H), 5.55(d, 1H, J=1.40Hz), 5.50(d, 1H, J=1.60Hz), 5.05(s, 1H), 3.70(s, 2H)

c) Synthesis of 6-bromo-2-methylbenzo[b]furan:

In a 250 ml flask, 24.0 g of the compound obtained in the above b) was dissolved in 50 ml of ethanol at room temperature, and 200 ml of 2 M NaOEt was slowly added dropwise thereto. The reaction solution was refluxed for 5 hours with stirring and then evaporated under reduced pressure. The residue was extracted three times with ethyl acetate. The combined organic layer was dried over MgSO$_4$ and then evaporated under reduced pressure. The residue was purified with silica gel column chromatography [eluent: ethyl acetate/n-hexane(1:30)]. The fractions containing the desired product were combined and then evaporated to obtain 11.3 g of the titel compound as a pale yellow liquid.

$^1$H NMR(CDCl$_3$, ppm): δ 7.75(s, 1H), 7.30(s, 2H), 6.30(s, 1H), 2.40(s, 3H)

d) Synthesis of 2-methylbenzo[b]furan-6-carbonitrile:

11.3 g of the compound obtained in the above c) was treated according to the same procedure as Example 144-c) to obtain 381 mg of the title compound as a pale yellow solid.

$^1$H NMR(CDCl$_3$, ppm): δ 7.69(s, 1H), 7.50(ddd, 2H, J=24.96Hz, 8.02Hz, 1.04Hz), 6.45(s, 1H), 2.50(s, 2H)

e) Synthesis of 2-(bromomethyl)benzo[b]furan-6-carbonitrile:

380 mg of the compound obtained in the above d) was dissolved in 100 ml of carbon tetrachloride, and 472 mg of NBS (N-bromosuccinimide) was added thereto. The reaction solution was refluxed for 6 hours with stirring and then evaporated under reduced pressure. The residue was then extracted three times with ethyl acetate. The combined oragnic layer was dried over MgSO$_4$ and evaporated under reduced pressure. The residue was purified with silica gel column chromatography [eluent:ethyl acetate/ n-hexane (1:7)]. The fractions containing the desired product were combined and then evaporated to obtain 520 mg of the title compound as a pale yellow solid.

$^1$H NMR(CDCl$_3$, ppm): δ 7.75(s, 1H), 7.55(m, 2H), 6.80(s, 1H), 4.60(s, 2H)

f) Synthesis of benzo[b]furan-6-carbonitrile-2-methyl-triphenylphosphonium bromide:

520 mg of the compound obtained in the above e) was treated according to the same procedure as Example 1-f) to obtain 770 mg of the title compound as a pale yellow solid.

$^1$H NMR(CDCl$_3$, ppm): δ 7.90-7.35(m, 19H), 6.10(d, 2H)

g) Synthesis of tert-butyl (S)-2-[2-(5-cyanobenzo[d]furan-2-yl)vinyl]-pyrrolidine carboxylate:

770 mg of the compound obtained in the above f) was treated according to the same procedure as Example 1-j) to obtain 308 mg of the title compound as a fluorescent yellow liquid.

$^1$H NMR(CDCl$_3$, ppm): δ 7.70(m, 1H), 7.50(m, 2H), 6.70-6.20(m, 3H), 4.50 (m, 1H), 3.45(br, 2H), 2.25-1.70(m, 4H), 1.40(br, 9H)

h) Synthesis of 2-((2S)-2-pyrrolidin-2-ylethyl)benzo[b]furan-6-carbonitrile:

308 mg of the compound obtained in the above g) was treated according to the same procedure as Example 1-k) to obtain 270 mg of the yellow liquid product, which was then treated according to the same procedure as Example 1-l) to obtain 229 mg of the title compound as a yellow liquid.

$^1$H NMR(CDCl$_3$, ppm): δ 7.61(s, 1H), 7.45(dd, 2H, J=23.51Hz, 8.02Hz), 6.50(s, 1H), 3.50(m, 1H), 3.30(m, 2H), 2.92(m, 2H), 2.49-1.88(m, 5H), 1.71(m, 1H)

ES-MS: 241(M+1)$^+$ i) Synthesis of tert-butyl (R)-2-[[(S)-2-[2-(6-cyanobenzo[d]furan-2-yl)-ethyl]pyrrolidinyl]carbonyl]pyrrolidine carboxylate:

228 mg of 2-((S)-2-pyrrolidin-2-ylethyl)benzo[b]furan-6-carbonitrile obtained in the above h) was treated according to the same procedure as Example 11-a) to obtain 167 mg of the title compound as a yellowish white foamy solid.

$^1$H NMR(CDCl$_3$, ppm): δ 7.80(m, 1H), 7.40(m, 2H), 6.55(d, 1H), 4.40(m, 1H), 4.20(m, 1H), 3.85-3.30(m, 4H), 2.85(m, 2H), 2.45-1.60(m, 10H), 1.40(br, 9H)

j) Synthesis of ethyl 2-[(R)-2-[[(S)-2-[2-(6-cyanobenzo[d]furan-2yl)-ethyl]pyrrolidinyl]carbonyl]pyrrolidine]acetate:

228 mg of 2-((S)-2-pyrrolidin-2-ylethyl)benzo[b]furan-6-carbonitrile obtained in the above h) was treated according to the same procedure as Example 11-a) to obtain 167 mg of the title compound as a yellowish white foamy solid.

$^1$H NMR(CDCl$_3$, ppm): δ 7.80(m, 1H), 7.40(m, 2H), 6.55(d, 1H), 4.40(m, 1H), 4.20(m, 1H), 3.85-3.30(m, 4H), 2.85(m, 2H), 2.45-1.60(m, 10H), 1.40(br, 9H)

j) Synthesis of ethyl 2-[(R)-2-[[(S)-2-[2-(6-cyanobenzo[d]furan-2-yl)-ethyl]pyrrolidinyl]carbonyl]pyrrolidinyl]acetate:

167 mg of the compound obtained in the above i) was treated according to the same procedure as Example 1-l) to obtain 100 mg of the white foamy product, which was then reacted with ethyl 2-bromoacetate according to the same procedure as Example 1-m) to obtain 60 mg of the title compound as a white foamy solid.

$^1$H NMR(CDCl$_3$, ppm): δ 7.75(s, 1H), 7.55(m, 2H), 6.80(s, 1H), 4.30-4.0 (m, 3H), 3.85(m, 1H), 3.50(m, 2H), 3.20(m, 1H), 2.80(m, 3H), 2.40-1.60(m, 12H), 1.25(t, 3H, J=7.14Hz)

k) Synthesis of ethyl 2-[(R)-2-[[(S)-2-[2-(6-amidinobenzo[d]furan-2-yl)-ethyl]pyrrolidinyl]carbonyl]pyrrolidinyl]acetate:

60 mg of the compound obtained in the above j) was treated according to the same procedure as Example 1-n) to obtain 4.2 mg of the title compound as a white foamy solid.

$^1$H NMR(CDCl$_3$, ppm): δ 7.65(s, 1H), 7.45(m, 2H), 6.60(s, 1H), 5.05(br, 3H), 4.30-4.0(m, 3H), 3.85(m, 1H), 3.50(m, 4H), 3.20(m, 1H), 2.80 (m, 3H), 2.40-1.60(m, 10H), 1.47(t, 3H, J=7.14Hz)

ES-MS: 442(M+2)$^+$ l) Synthesis of 2-[2-[(S)-1-[[(R)-1-(carbamoylmethyl)pyrrolidin-2-yl]-carbonyl]pyrrolidin-2-yl]ethyl]benzo[b]furan-6-carboxamidine:

60 mg of ethyl 2-[(R)-2-[[(S)-2-[2-(6-cyanobenzo[d]furan-2-yl)-ethyl]pyrrolidinyl]carbonyl]pyrrolidinyl]acetate obtained in the above j) was treated according to the same procedure as Example 1-n) to obtain 3.2 mg of the title compound as a yellow foamy solid.

$^1$H NMR(CD$_3$OD, ppm): δ 7.75(s, 1H), 7.50(m, 2H), 6.55(s, 1H), 4.05(m, 1H), 3.60-3.25(m, 3H), 3.10(m, 1H), 3.0-2.60(m, 3H), 2.40(m, 1H), 2.15(m, 1H), 2.15-1.55(m, 10H)

ES-MS: 413(M+2)$^+$

EXAMPLE 148

Synthesis of ethyl 2-[(R)-2-[[(S)-2-[2-(6-amidino-3-methylbenzo[d]furan-2-yl)ethyl]pyrrolidinyl]carbonyl]pyrrolidinyl)-acetate (Compound 252)

a) Synthesis of 1-(4-bromo-2-hydroxyphenyl)ethan-1-one:

In a 1 l flask, 25 g of 5-bromoanisole was stirred in 250 ml of CS$_2$ solvent at 0° C., and 12.4 ml of acetyl chloride was added and 53.5 g of AlCl$_3$ was slowly added portionwise thereto. After the addition was completed, the reaction solution was refluxed for one hour with stirring. The reaction was quenched with 2N HCl. Excessive amount of water was added and the reaction solution was extracted three times with ethyl acetate. The combined organic layer was dried over MgSO$_4$ and then evaporated. The residue was purified with silica gel column chromatography [eluent: ethyl acetate/n-hexane(1:10)]. The fractions containing the desired product were combined and then evaporated to obtain 7.68 g of the title compound as a white solid.

$^1$H NMR(CDCl$_3$, ppm): δ 12.3(s, 1H), 7.57(d, 1H, J=8.56 Hz), 7.17(d, 1H, J=1.92 Hz), 7.04(dd, 1H, J=8.49 Hz, 1.98 Hz)

ES-MS: 237(M+1)$^+$ b) Synthesis of ethyl 2-(5-bromo-2-acetylphenoxy) acetate:

7.68 g of the compound obtained in the above a) was treated in acetone solvent according to the same procedure as Example 42 to obtain 3.58 g of the title compound as a white solid.

$^1$H NMR(CDCl$_3$, ppm): δ 7.65(d, 1H, J=8.34 Hz), 7.20 (dd, 1H, J=8.32 Hz, 1.76 Hz), 6.95(d, 1H, J=1.64 Hz), 4.70(s, 2H), 4.25(q, 2H, J=7.15 Hz), 2.65(s, 3H), 1.35(t, 3H, J=7.11 Hz)

c) Synthesis of ethyl 6-bromo-3-methylbenzo[d]furan-2-carboxylate:

3.58 g of the compound obtained in the above b) was treated according to the same procedure as Example 144-b) to obtain 1.26 g of the title compound as a white solid.

$^1$H NMR(CDCl$_3$, ppm): δ 7.70(s, 1H), 7.40(m, 2H), 4.40(q, 2H, J=7.13 Hz), 2.50(s, 3H), 1.40(t, 3H, J=7.13 Hz)

ES-MS: 283(M+1)$^+$ d) Synthesis of ethyl 6-cyano-3-methylbenzo[d]furan-2-carboxylate:

7.52 g of the compound obtained in the above c) was treated according to the same procedure as Example 144-c) to obtain 790 mg of the title compound as a white solid.

$^1$H NMR(CDCl$_3$, ppm): δ 7.85(s, 1H), 7.70(d, 1H, J=8.24 Hz), 7.55(dd, 1H, J=8.15 Hz, 1.26 Hz), 4.45(q, 2H, J=7.14 Hz), 2.60(s, 3H), 1.45(t, 3H, J=7.12 Hz

ES-MS: 230(M+1)$^+$ e) Synthesis of 2-(hydroxymethyl)-3-methylbenzo[b]furan-6-carbonitrile:

789 mg of the compound obtained in the above d) was treated according to the same procedure as Example 1-e) to obtain 459 mg of the title compound as a yellow solid.

$^1$H NMR(CDCl$_3$, ppm): δ 7.75(s, 1H), 7.55(d, 1H, J=7.96 Hz), 7.40(d, 1H, J=8.03 Hz), 4.60(s, 2H), 2.15(s, 3H)

f) Synthesis of benzo[b]furan-6-carbonitrile-2-methyl-triphenylphosphonium bromide:

459 mg of the compound obtained in the above e) was treated according to the same procedure as Example 1-f) to obtain 855 mg of the title compound as a yellow solid. $^1$H NMR(CDCl$_3$, ppm): δ 7.95–7.35(m, 18H), 5.85(d, 2H), 2.25(s, 3H)

g) Synthesis of tert-butyl (S)-2-[2-(6-cyano-3-methylbenzo[d]furan-2-yl)vinyl]pyrrolidine carboxylate:

850 mg of the compound obtained in the above f) was treated according to the same procedure as Example 1-j) to obtain 344 mg of the title compound as a fluorescent yellow liquid.

$^1$H NMR(CDCl$_3$, ppm): δ 7.65(s, 1H), 7.45(m, 2H), 6.40(br, 2H), 4.50(m, 1H), 3.45(br, 2H), 2.25(s, 3H), 2.05–1.70(m, 4H), 1.40(br, 9H)

h) Synthesis of 3-methyl-2-((S)-2-pyrrolidin-2-ylethyl) benzo[b]furan-6-carbonitrile:

344 mg of the compound obtained in the above g) was treated according to the same procedure as Example 1-k) to obtain 340 mg of the colorless liquid product, which was then treated according to the same procedure as Example 1-l to obtain 187 mg of the title compound as a colorless liquid.

$^1$H NMR(CDCl$_3$, ppm): δ 7.55(s, 1H), 7.40(s, 2H), 3.50 (m, 1H), 3.25(m, 2H), 2.85(m, 2H), 2.35–1.85(m, 8H), 1.65(m, 1H)

i) Synthesis of 3-methyl-2-[2-[(S)-1-((R)-pyrrolidin-2-ylcarbonyl)pyrrolidin-2-yl]ethyl]benzo[b]furan-6-carbonitrile:

185 mg of the compound obtained in the above h) was treated according to the same procedure as Example 11-a) to obtain 161 mg of the colorless foamy solid product, which was then treated according to the same procedure as Example 1-l) to obtain 100 mg of the title compound as a colorless foamy solid.

j) Synthesis of ethyl 2-[(R)-2-[[(S)-2-[2-(6-cyano-3-methylbenzo[d]-furan-2-yl)ethyl]pyrrolidinyl]carbonyl]pyrrolidinyl]acetate:

100 mg of the compound obtained in the above i) was treated according to the same procedure as Example 1-m) to obtain 61 mg of the title compound as a colorless foamy solid.

$^1$H NMR(CDCl$_3$, ppm): δ 7.65(s, 1H), 7.45(s, 2H), 4.20–4.0(m, 3H), 3.90(m, 1H), 3.50(m, 2H), 3.15(m, 1H), 2.80(m, 3H), 2.15(s, 3H), 2.10–1.60(m, 12H), 1.20(t, 3H, J=7.19 Hz)

k) Synthesis of ethyl 2-[(R)-2-[[(S)-2-[2-(6-amidino-3-methylbenzo[d]furan-2-yl)ethyl]pyrrolidinyl]carbonyl]pyrrolidinyl]acetate:

60 mg of the compound obtained in the above j) was treated according to the same procedure as Example 1-n) to obtain 2.9 mg of the title compound as a colorless foamy solid.

$^1$H NMR(CDCl$_3$, ppm): δ 7.65(m, 1H), 7.45(m, 2H), 4.80(br, 3H), 4.20–4.0(m, 3H), 3.85(m, 1H), 3.50(m, 4H), 3.15(m, 1H), 2.80(m, 3H), 2.15(s, 3H), 2.10–1.60 (m, 10H), 1.20(t, 3H, J=7.19 Hz)

ES-MS: 456(M+2)$^+$

EXAMPLE 149

Synthesis of 2-[2-[(S)-1-(2-phenylacetyl)pyrrolidin-2-yl] ethyl]benzo[b]thiophene-5-carboxamidine (Compound 253)

a) Synthesis of 5-bromo-2-((dimethylamino) thioxomethoxy)benzaldehyde:

In a 500 ml flask, 35.6 g of 5-bromosalicyl aldehyde was dissolved in 150 ml of acetone, and 29.38 g of anhydrous potassium carbonate was added. Thereafter, 21.9 g of N,N-dimethylthiocarbamoyl chloride was slowly added, and the reaction solution thereby obtained was then stirred for 2 hours, poured into ice-water and then stirred. The resulting precipitate was filtered and washed three times with water. The filtered solid product was dried and then recrystallized from ethyl acetate/n-hexane(1:3) solvent system to obtain 42.3 g of the title compound as a white solid.

$^1$H NMR(CDCl$_3$, ppm): δ 10.03(s, 1H), 8.01(m, 1H), 7.72(m, 1H), 7.02(m, 1H), 3.47(s, 3H), 3.42(s, 3H)

ES-MS: 311(M+Na$^+$), 289(M+1)$^+$ b) Synthesis of N,N-dimethyl(4-bromo-2-formylphenylthio)formamide:

In a 100 ml flask, 42.3 g of 5-bromo-2-((dimethylamino) thioxomethoxy)benzaldehyde was introduced, melted for 10 minutes in oil bath at 210–220° C. and then dissolved in 30 ml of toluene. After 100 ml of methanol was added, the resulting precipitate was filtered, washed several times with n-hexane and then dried to obtain 12.3 g of the title compound as a white solid.

¹H-NMR(CDCl₃, ppm): δ 10.25(s, 1H), 8.13(m, 1H), 7.70(m, 1H), 7.31(m, 1H), 3.15(s, 3H), 3.03(s, 3H)

Mass: 311(M+Na⁺), 289(M+1)⁺ c) Synthesis of 1-(5-bromobenzo[b]thiophen-2-yl)ethan-1-one:

In a 100 ml flask, 12.3 g of N,N-dimethyl(4-bromo-2-formylphenylthio)formamide was dissolved in 35 ml of methyl orthoformate, and 0.6 g of p-toluenesulfonate was added. The reaction solution was stirred for 50 minutes of refluxing temperature and then cooled, and saturated NaHCO₃ solution was added. The organic layer was then extracted three times with benzene. After the extract was evaporated to remove the solvent, the residue was dissolved in 60 ml of methanol, and 20 ml of 2N-NaOH was added thereto. The reaction solution was refluxed under nitrogen atmosphere for one hour, cooled, adjusted to pH 1 with concentrated hydrochloric acid, and then extracted with benzene. After the solvent was removed from the extract, the residue was dissolved in 13 ml of acetone. To the resulting solution was slowly added 3.5 g of chloroacetone at room temperature. 1.3 g of anhydrous potassium carbonate and 90 ml of acetone were slowly added thereto. The reaction solution was stirred for 30 minutes at room temperature, refluxed again for 30 minutes, cooled and then filtered to remove the unsoluble material. The filtrate was evaporated and then purified with silica gel column chromatography [eluent: ethyl acetate/n-hexane(1:3)]. The fractions containing the desired product were combined and then evaporated to obtain 1.66 g of the title compound as a white solid.

¹H NMR(CDCl₃, ppm): δ 8.03(m, 1H), 7.85(s, 1H), 7.75(m, 1H), 7.54(m, 1H), 2.66(s, 3H)

d) Synthesis of 5-bromobenzo[b]thiophene-2-carboxylic acid:

1.25 ml of bromine was slowly added to 10 ml of 5N aqueous NaOH solution with stirring and the resulting solution was cooled to −5° C.–0° C. At the same temperature, a solution of 1.66 g of 1-(5-bromobenzo[b]thiophen-2-yl)ethan-1-one in 15 ml of 1,4-dioxane was slowly added thereto. The reaction solution was stirred for 30 minutes at room temperature and then for 30 minutes at 50° C., cooled, poured into ice-water and then adjusted to pH 2 with concentrated hydrochloric acid. The resulting precipitate was filtered, washed several times with water, dried and then purified with silica gel column chromatography [eluent: ethyl acetate/n-hexane(1:2)]. The fractions containing the desired product were combined and then evaporated to obtain 1.42 g of the title compound as a white solid.

¹H NMR(CDCl₃, ppm): δ 8.03(m, 1H), 7.92(s, 1H), 7.76(m, 1H), 7.50(m, 1H)

e) Synthesis of ethyl 5-bromobenzo[b]thiophene-2-carboxylate:

In a 100 ml flask, 1.42 g of 5-bromobenzo[b]thiophene-2-carboxylic acid and 25 ml of methanol were introduced and then stirred. The resulting suspension was cooled in ice bath and 0.6 ml of thionyl chloride was slowly added thereto. The reaction solution was refluxed for one hour and then cooled. After 1.1 ml of thionyl chloride was added, the reaction solution was refluxed for further 2 hours, cooled and then adjusted to pH 9 with saturated NaHCO₃ solution. The resulting precipitate was filtered, dried and then purified with silica gel column chromatography [eluent: ethyl acetate/n-hexane(1:3)]. The fractions containing the desired product were combined and then evaporated to obtain 1.3 g of the title compound as a white solid.

¹H NMR(CDCl₃, ppm): δ 8.01(m, 1H), 7.96(s, 1H), 7.73(m, 1H), 7.54(m, 1H), 4.41(q, 2H, J=7.0 Hz), 1.42(t, 3H, J=7.0 Hz)

f) Synthesis of ethyl 5-cyanobenzo[b]thiophene-2-carboxylate:

In a 50 ml flask, 1.3 g of 5-bromobenzo[b]thiophene-2-carboxylate and 1.02 g of CuCN were introduced and 20 ml of N-methyl-2-pyrrolidone was then added thereto. The mixture was stirred and the resulting suspension was refluxed under nitrogen atmosphere for 2 hours at 200° C. The reaction solution was cooled, poured into ice-water, vigorously stirred and then filtered to remove the unsoluble material. The filtrate was then extracted with ethyl acetate. The extract was evaporated to removed the solvent, and the residue was then purified with silica gel column chromatography [eluent: ethyl acetate/n-hexane(1:3)]. The fractions containing the desired product were combined and evaporated to obtain 330 mg of the title compound as a white solid.

¹H NMR(CDCl₃, ppm): δ 8.21(m, 1H), 8.09(s, 1H), 7.97(m, 1H), 7.70(m, 1H), 4.45(q, 2H, J=7.0 Hz), 1.43(t, 3H, J=7.0 Hz)

g) Synthesis of 2-(hydroxymethyl)benzo[b]thiophene-5-carbonitrile:

220 mg of the compound obtained in the above f) was treated according to the same procedure as Example 1-e) to obtain 120 mg of the title compound as a white solid.

¹H NMR(CDCl₃, ppm): δ 8.03(m, 1H), 7.90(m, 1H), 7.51(m, 1H), 7.26(s, 1H), 4.97(s, 2H)

h) Synthesis of (5-cyanobenzo[b]thiophen-2-yl)methyltriphenylphosphonium bromide:

120 mg of the compound obtained in the above g) was treated according to the same procedure as Example 1-f) to obtain 215 mg of the title compound as a yellowish white solid.

¹H NMR(CDCl₃, ppm): δ 8.09–7.27(m, 19H), 6.70(s, 2H)

i) Synthesis of tert-butyl (S)-2-[2-(5-cyanobenzo[b]thiophen-2-yl)vinyl]pyrrolidine carboxylate:

211 mg of (5-cyanobenzo[b]thiophen-2-yl)methyltriphenylphosphonium bromide obtained in the above h) was reacted according to the same procedure as Example 1-j) to obtain 150 mg of the title compound as a white solid.

¹H NMR(CDCl₃, ppm): δ 8.01(m, 1H), 7.81(m, 1H), 7.48(m, 1H), 7.14(s, 1H), 6.69–6.49(m, 1H), 6.13–6.05 (m, 1H), 4.57–4.32(m, 1H), 3.42(m, 2H), 2.38–1.73(m, 4H), 1.48(brs, 9H)

ES-MS: 377(M+Na⁺), 355(M+1)⁺ j) Synthesis of tert-butyl (S)-[2-(5-cyanobenzo[b]thiophen-2-yl)ethyl]pyrrolidine carboxylate:

155 mg of the compound obtained in the above i) was treated according to the same procedure as Example 1-k) to obtain 130 mg of the title compound as a white solid.

¹H NMR(CDCl₃, ppm): δ 7.93(m, 1H), 7.82(m, 1H), 7.41(m, 1H), 7.08(s, 1H), 3.90(brs, 1H), 3.52–3.27(m, 2H), 2.89(m, 2H), 2.35–1.65(m, 6H), 1.41(brs, 9H)

ES-MS: 379(M+Na⁺), 357(M+1)⁺ k) Synthesis of 2-((S)-2-pyrrolidin-2-ylethyl)benzo[b]thiophene-5-carbonitrile:

128 mg of the compound obtained in the above j) was treated according to the same procedure as Example 1-l) to obtain 72 mg of the title compound as a white solid.

l) Synthesis of 2-[2-[(S)-1-(2-phenylacetyl)pyrrolidin-2-yl]ethyl]benzo[b]thiophene-5-carbonitrile:

72 mg of the compound obtained in the above k) and phenylacetyl chloride were reacted according to the same procedure as Example 1-m) to obtain 55 mg of the title compound as a white solid.

¹H NMR(CDCl₃, ppm): δ 7.94(m, 1H), 7.80(m, 1H), 7.43(m, 1H), 7.36–7.23(m, 5H), 7.11(s, 1H), 4.22(m, 1H), 3.66(m, 2H), 3.48(m, 2H), 2.93(m, 2H), 2.39–1.75 (m, 6H)

ES-MS: 397(M+Na$^+$), 375(M+1)$^+$ m) Synthesis of 2-[2-[(S)-1-(2-phenylacetyl)pyrrolidin-2-yl]ethyl]-benzo[b]thiophene-5-carboxamidine:

55 mg of the compound obtained in the above l) was treated according to the same procedure as Example 1-n) to obtain 45 mg of the title compound as a white solid.

$^1$H NMR(CDCl$_3$, ppm): δ 7.91(m, 1H), 7.75(m, 1H), 7.46(m, 1H), 7.32–7.13(m, 5H), 7.07(s, 1H), 4.23(m, 1H), 3.66–3.58(m, 2H), 3.48(m, 2H), 2.89(m, 2H), 2.38–1.75(m, 6H)

ES-MS: 392(M+1)$^+$

IR(KBr): 3079, 2954, 1613 cm$^{-1}$

EXAMPLE 150

Synthesis of 3-methoxy-2-[2-[(S)-1-(2-phenylacetyl)pyrrolidin-2-yl]ethyl]benzo[b]thiophene-6-carboxamidine (Compound 255)

a) Synthesis of prop-2-enyl 3-nitro-4-(prop-2-enoxycarbonyl)benzoate:

In a 500 ml flask, 25 g of 2-nitrobenzene-1,4-dicarboxylic acid and 21.88 g of NaHCO$_3$ were dissolved in 150 ml of N,N-dimethylformamide. To the resulting solution was slowly added 25.6 ml of allyl bromide. The reaction solution was stirred for 3 hours at 50° C., cooled, adjusted to pH 6 with 2N-HCl and then extracted three times with ethyl acetate. The combined extract was dried and then purified with silica gel column chromatography [eluent: ethyl acetate/n-hexane(1:3)]. The fractions containing the desired product were combined and then evaporated to obtain 34 g of the title compound as a pale yellow liquid.

$^1$H NMR(CDCl$_3$, ppm): δ 8.61(m, 1H), 8.33(m, 1H), 7.82(m, 1H), 6.14–5.94(m, 2H), 5.49–5.32(m, 4H), 4.92–4.86(m, 4H)

ES-MS: 314(M+Na$^+$)

b) Synthesis of methyl 3-hydroxy-6-(prop-2-enyloxycarbonyl)benzo[b]thiophene-2-carboxylate:

In a 500 ml flask, 34 g of the compound obtained in the above a) and 15.66 ml of methyl thioglycolate were dissolved in 150 ml of N,N-dimethylformamide. The resulting solution was cooled in ice-bath and lithium hydroxide was added portionwise thereto. The reaction solution was stirred for 30 minutes under ice-bath and then for 2 hours at room temperature, poured into ice-water, treated with concentrated hydrochloric acid and then extracted three times with ethyl acetate. The combined extract was dried and purified with silica gel column chromatography [eluent: ethyl acetate/n-hexane(1:7)]. The fractions containing the desired product were combined and then evaporated to obtain 13.1 g of the title compound as a white solid.

$^1$H NMR(CDCl$_3$, ppm): δ 10.08(s, 1H), 8.52(s, 1H), 8.09–7.98(m, 2H), 6.12–6.01(m, 1H), 5.49–5.33(m, 2H), 4.89(m, 2H), 3.97(s, 3H)

ES-MS: 315(M+Na$^+$), 293(M+1)$^+$ c) Synthesis of 3-hydroxy-2-(methoxycarbonyl)benzo[b]thiophene-6-carboxylic acid;

In a 500 ml flask, 22.8 g of the compound obtained in the above b) and 32.8 g of dimedone were dissolved in 150 ml of tetrahydrofuran, and 4.5 g of tetrakis(triphenylphosphine)palladium [Pd(PPh$_3$)$_4$] was added thereto. The reaction solution was stirred for 3 hours at room temperature. The resulting precipitate was filtered, washed several times with ethyl acetate and then dried in air to obtain 18.2 g of the title compound as a white solid.

$^1$H NMR(DMSO-d$_6$, ppm): δ 8.56(s, 1H), 8.01–7.91(m, 2H), 3.87(s, 3H)

d) Synthesis of methyl 6-carbamoyl-3-hydroxybenzo[b]thiophene-2-caboxylate:

In a 100 ml flask, 18.2 g of the compound obtained in the above c) was dissolved in 40 ml of thionyl chloride. The resulting solution was refluxed for 30 minutes, cooled and then distilled under reduced pressure to remove thionyl chloride. The remaining thionyl chloride was removed for 5 hours by means of a vacuum pump. To the dried product was slowly added 40 ml of NH$_4$OH at 0° C. The reaction solution was stirred for 4 hours at room temperature, and the resulting precipitate was filtered, washed several times with ethyl acetate and then dried to obtain 17.5 g of the title compound as a white solid.

$^1$H NMR(DMSO-d$_6$, ppm): δ 8.17(s, 1H), 7.98(brs, 1H), 7.79–7.69(m, 2H), 7.30(brs, 1H), 3.69(s, 3H)

e) Synthesis of methyl 6-cyano-3-hydroxybenzo[b]thiophene-2-caboxylate

In a 500 ml flask, 17.5 g of the compound obtained in the above d) was dissolved in 50 ml of tetrahydrofuran, and a solution of 54.8 g of triphenylphosphine in 100 ml of carbon tetrachloride was slowly added. The reaction solution was stirred for 30 minutes at room temperature and then for one day at 60° C., cooled and filtered to remove the unsoluble material. The filtrate was purified with silica gel column chromatography [eluent: ethyl acetate/n-hexane(1:3)]. The fractions containing the desired product were combined and evaporated to obtain 457 mg of the title compound as a pale pink solid.

$^1$H NMR(CDCl$_3$, ppm): δ 10.14(s, 1H), 8.06–7.99(m, 2H), 7.62(m, 1H), 3.99(s, 3H)

ES-MS: 489(2M+Na$^+$), 256(M+Na$^+$)

f) Synthesis of methyl 6-cyano-3-methoxybenzo[b]thiophene-2-carboxylate:

In a 50 ml flask, 227 mg of the compound obtained in the above e) was dissolved in 10 ml of N,N-dimethylformamide, and 47 mg of NaH was added thereto at 0° C. To this mixture was slowly added 0.15 ml of methyliodide. The reaction solution was stirred for 4 hours at 60° C. and ice-water was then added. This solution was extracted three times with dichloromethane. The extract was dried and purified with silica gel column chromatography [eluent: ethyl acetate/n-hexane(1:3)]. The fractions containing the desired product were combined and evaporated to obtain 153 mg of the title compound as a white solid.

$^1$H NMR(CDCl$_3$, ppm): δ 8.08(m, 1H), 7.95(m, 1H), 7.59(m, 1H), 4.22(s, 3H), 3.97(s, 3H)

ES-MS: 270(M+Na$^+$)

g) Synthesis of 2-(hydroxymethyl)-3-methoxybenzo[b]thiophene-6-carbonitrile:

260 mg of the compound obtained in the above f) was treated according to the same procedure as Example 1-e) to obtain 176 mg of the title compound as a white solid.

$^1$H NMR(CDCl$_3$, ppm): δ 8.06(m, 1H), 7.79(m, 1H), 7.58(m, 1H), 4.97(s, 2H), 4.01(s, 3H)

ES-MS: 461(2M+Na$^+$), 242(M+Na$^+$)

h) Synthesis of (6-cyano-3-methoxybenzo[b]thiophen-2-yl)methyltriphenylphosphonium bromide:

176 mg of the compound obtained in the above g) was treated according to the same procedure as Example 1-f) to obtain 340 mg of the title compound as a white solid.

$^1$H NMR(CDCl$_3$, ppm): δ 7.91–7.52(m, 18H), 5.89(m, 2H), 3.89(s, 3H)

i) Synthesis of tert-butyl (S)-[2-(6-cyano-3-methoxybenzo[b]thiophen-2-yl)vinyl]pyrrolidine carboxylate:

335 mg of (6-cyano-3-methoxybenzo[b]thiophen-2-yl)methyltriphenylphosphonium bromide obtained in the above h) was treated according to the same procedure as Example 1-j) to obtain 230 mg of the title compound as a white solid.

$^1$H NMR(CDCl$_3$, ppm): δ 8.00(m, 1H), 7.76(m, 1H), 7.57(m, 1H), 6.78(m, 1H), 6.10–5.77(m, 1H), 4.96(m, 1H), 3.95(s, 3H), 3.48(m, 2H), 2.38–1.74(m, 4H), 1.42(m, 9H)

j) Synthesis of tert-butyl (S)-[2-(6-cyano-3-methoxybenzo[b]thiophen-2-yl)ethyl]pyrrolidine carboxylate:

230 mg of the compound obtained in the above i) was treated according to the same procedure as Example 1-k) to obtain 233 mg of the title compound as a white solid.

$^1$H NMR(CDCl$_3$, ppm): δ 8.01(m, 1H), 7.72(m, 1H), 7.51(m, 1H), 3.92(s, 3H), 3.57–3.28(m, 3H), 2.86(m, 2H), 2.28–1.66(m, 6H), 1.43(m, 9H)

ES-MS: 409(M+Na$^+$)

k) Synthesis of 3-methoxy-2-[((S)-2-pyrrolidin-2-yl)ethyl]benzo[b]thiophene-6-carbonitrile:

230 mg of the compound obtained in the above j) was treated according to the same procedure as Example 1-l) to obtain 39 mg of the title compound as a colorless oil.

$^1$H NMR(CDCl$_3$, ppm): δ 7.97(m, 1H), 7.71(m, 1H), 7.55(m, 1H), 3.90(s, 3H), 3.58(m, 1H), 3.47–3.29(m, 2H), 3.08(m, 2H), 2.50–1.80(m, 6H)

ES-MS: 287(M+1)$^+$ l) Synthesis of 3-methoxy-2-[2-[(S)-1-(2-phenylacetyl)pyrrolidin-2-yl]ethyl]benzo[b]thiophene-6-carbonitrile:

39 mg of the compound obtained in the above k) and phenylacetyl cloride were reacted according to the same procedure as Example 1-m) to obtain 18 mg of the title compound as a colorless oil.

$^1$H NMR(CDCl$_3$, ppm): δ 7.98(m, 1H), 7.68(m, 1H), 7.48(m, 1H), 7.23(m, 5H), 4.24(m, 1H), 3.89(s, 3H), 3.65(m, 2H), 3.47(m, 2H), 2.88(m, 2H), 2.32–1.65(m, 6H)

ES-MS: 427(M+Na$^+$), 405(M+1)$^+$ m) Synthesis of 3-methoxy-2-[2-[(S)-1-(2-phenylacetyl)pyrrolidin-2-yl]ethyl]benzo[b]thiophene-6-carboxamidine:

18 mg of the compound obtained in the above l) was treated according to the same procedure as Example 1-n) to obtain 10 mg of the title compound as a pale yellow solid.

$^1$H NMR(CDCl$_3$): δ 7.97(m, 1H), 7.68–7.52(m, 2H), 7.26–6.98(m, 5H), 4.16(m, 1H), 3.87(s, 3H), 3.65(m, 2H), 3.44(m, 2H), 2.87(m, 2H), 2.26–1.58(m, 6H)

ES-MS: 422(M+1)$^+$

IR(KBr): 2992, 1612, 1460 cm$^{-1}$

EXAMPLE 151

Synthesis of N-methyl [3-[[(S)-2-[2-[6-[imino(methylamino)methyl]-1-methylindol-2-yl]ethyl]pyrrolidinyl]methyl]benzo[b]thiophen-2-yl]formamide (Compound 258)

68 mg of 1-methyl-2-[2-[(S)-1-[[2-(N-methylcarbamoyl)benzo[b]thiophene-3-yl]methyl]pyrrolidin-2-yl]indole-6-carboxamidine obtained in Example 10 was dissolved in 10 ml of 40% methylamine methanol solution and then stirred overnight at room temperature. The reaction solution was distilled under reduced pressure to remove the reaction solvent and the residue was purified with column chromatography [eluent: dichloromethane/methanol(10:1)] on NH-DM1020 silica. The fractions containing the desired product were combined and distilled under reduced pressure to obtain 52 mg of the title compound as a pale yellow solid.

$^1$H NMR(MeOH-d$_4$, ppm): δ 7.91(d, 1H), 7.84(d, 1H, J=6.54 Hz), 7.67(s, 1H), 7.52(d, 1H), 7.39–7.31(m, 3H), 6.15(s, 1H), 4.12(d, 1H), 3.83(d, 1H), 3.62(s, 3H), 3.05(s, 3H), 2.99(s, 1H), 2.85(m, 1H), 2.77–2.70(m, 2H), 2.41(m, 1H), 2.19(m, 1H), 2.05(m, 1H), 1.79–1.58 (m, 4H)

EXAMPLE 152

Synthesis of 1-[(S)-2-[2-(6-[(hydroxyimino)aminomethyl]-1-ethylindol-2-yl]ethyl]pyrrolidinyl]-2-phenylethan-1-one (Compound 260)

190 mg of 1-ethyl-2-[2-[(S)-1-(2-phenylacetyl)pyrrolidin-2-yl]ethyl]indole-6-carbonitrile obtained in Example 14-a) was dissolved in methanol. 103 mg of hydroxylamine hydrochloride and 210 mg of sodium carbonate were added and the reaction solution was refluxed overnight with stirring. After water was added, the reaction solution was extracted two times with dichloromethane. The extract was dried over MgSO$_4$ and distilled under reduced pressure. The residue was purified with silica gel column chromatography [eluent: dichloromethane/methanol (20:1)] to obtain 11 mg of the title compound.

$^1$H NMR(MeOH-d$_4$): δ 7.52(s, 1H), 7.34(d, 1H, J=8.38 Hz), 7.27–6.80(m, 6H), 6.18(s, 1H), 4.08(m, 3H), 3.60 (d, 2H, J=5.36 Hz), 3.44(m, 2H), 2.66(t, 2H, J=8.00 Hz), 2.13(m, 1H), 1.92–1.60(m, 6H), 1.21(t, 3H, J=7.15 Hz)

ES-MS: 419(M+1)$^+$, 441(M+Na)

EXAMPLE 153

Synthesis of ethyl 2-[(R)-2-[[(S)-2-[2-[6-[(hydroxyimino)aminomethyl]-1-ethylindol-2-yl]ethyl]pyrrolidinyl]carbonyl]pyrrolidinyl]acetate (Compound 261)

480 mg of ethyl 2-[(R)-2-[[(S)-2-[2-(6-cyano-1-ethylindol-2-yl)ethyl]pyrrolidinyl]carbonyl]pyrrolidinyl]acetate obtained in Example 60-a) was dissolved in methanol. 304 mg of hydroxylamine hydrochloride and 695 mg of sodium carbonate were added and the reaction solution was refluxed overnight with stirring. After water was added, the reaction solution was extracted two times with dichloromethane. The extract was dried over MgSO$_4$ and distilled under reduced pressure. The residue was purified with silica gel column chromatography [eluent: dichloromethane/methanol(20:1)] to obtain 27 mg of the title compound.

$^1$H NMR(MeOH-d$_4$, ppm): δ 7.53(s, 1H), 7.35(m, 1H, J=8.25 Hz), 7.21(d, 1H, J=4.43 Hz), 6.21(s, 1H), 4.11 (m, 3H), 3.99(m, 2H), 3.68(t, 1H), 3.49(m, 2H), 3.34(d, 2H, J=18.9 Hz), 3.12(m, 1H), 2.68(m, 2H), 2.25–1.60 (m, 11H), 1.25(t, 3H), 1.10(t, 3H)

ES-MS: 482(M+1)$^+$

EXAMPLE 154

Synthesis of ethyl 2-[(R)-2-[[(S)-2-[2-[1-ethyl-6-[(acetylamino)iminomethyl]indol-2-yl]ethyl]pyrrolidinyl]carbonyl]pyrrolidinyl]acetate (Compound 265)

52 mg of ethyl 2-[(R)-2-[[(S)-2-[2-(6-amidino-1-ethylindol-2-yl)ethyl]pyrrolidinyl]carbonyl]pyrrolidinyl] acetate obtained in Example 60 was dissolved in dry dichloromethane. To the resulting solution was added 31 μl of triethylamine, and the mixture was cooled to −78° C. After 16 μl of acetyl chloride was added, the reaction solution was stirred for 3 hours and warmed to room temperature. Water was added and the mixture was extracted with dichloromethane. The extract was dried over MgSO$_4$ and evaporated under reduced pressure to remove the solvent. The residue was purified with silica gel column chromatography [eluent: ethyl acetate/methanol(50:1)] to obtain 7 mg of the title compound as a pale yellow solid.

$^1$H NMR(MeOH-d$_4$, ppm): δ 7.72(s, 1H), 7.44(d, 1H, J=8.00 Hz), 7.29(d, 1H, J=8.27 Hz), 6.28(s, 1H), 4.17

(m, 3H), 4.02(m, 2H), 3.70(m, 1H), 3.49(m, 4H), 3.33(d, 2H, J=20.26 Hz), 3.09(m, 1H), 2.75(m, 2H), 2.64(m, 1H), 2.30–1.60(m, 8H), 1.25(t, 3H), 1.19(s, 3H), 1.07(t, 3H)

EXAMPLE 155
Synthesis of N-[[1-ethyl-2-[2-[(S)-1-(2-phenylacetyl)pyrrolidin-2-yl]ethyl]indol-6-yl]iminomethyl]ethoxyformamide (Compound 266)

170 mg of 1-ethyl-2-[2-[(S)-1-(2-phenylacetyl)pyrrolidin-2-yl]ethyl]indole-6-carboxamidine obtained in Example 14 was dissolved in dichloromethane. 90 μl of triethylamine and 70 mg of ethyl chloroformate were added at 0° C. The reaction solution was stirred for one hour at room temperature and distilled under reduced pressure to remove the reaction solvent. The residue was purified with column chromatography [eluent: ethyl acetate] on NH-DM1020 silica. The fractions containing the desired product were combined and distilled under reduced pressure to obtain 110 mg of the title compound as a white solid.

$^1$H NMR(MeOH-d$_4$, ppm): δ 8.34(s, 1H), 7.49(d, 1H), 7.42(m, 1H), 7.38–7.22(m, 5H), 6.36(s, 1H), 4.34–4.22 (m, 6H), 3.66(s, 2H), 3.50(m, 3H), 2.77(m, 2H), 2.33 (m, 1H), 1.98(m, 5H), 1.74(m, 3H), 1.37(m, 6H)

EXAMPLE 156
Synthesis of ethyl 2-[(R)-2-[[(S)-2-[2-[1-ethyl-6-[(ethoxycarbonylamino)iminomethyl]indol-2-yl]ethyl]pyrrolidinyl]carbonyl]pyrrolidinyl]acetate (Compound 267)

200 mg of ethyl 2-[(R)-2-[[(S)-2-[2-(6-amidino-1-ethylindol-2-yl]ethyl]pyrrolindinyl]carbonyl]pyrrolidinyl]acetate obtained in Example 60 was dissolved in dichloromethane and then cooled to 0° C. 119 μl of triethylamine was added and after 30 minutes, 49 μl of ethyl chlorocarbonate was added. After one hour, water was added to the reaction solution, which was then extracted two times with dichloromethane. The combined extract was dried over MgSO$_4$ and then concentrated. The residue was subjected to column chromatography [eluent: ethyl acetate] on NH-DM1020 silica to obtain 124 mg of the title compound.

$^1$H NMR(MeOH-d$_4$, ppm): δ 8.03(s, 1H), 7.20(s, 1H), 6.40(s, 1H), 4.35–4.05(m, 7H), 3.81(q, 1H), 3.74–3.34 (m, 4H), 3.25(m, 1H), 2.85(m, 2H), 2.77(m, 1H), 2.40–1.70(m, 10H), 1.35(m, 6H), 1.22(m, 3H)

EXAMPLE 157
Synthesis of ethyl 2-[(R)-2-[[(S)-2-[2-[1-ethyl-6-[imino[(methylethoxy)carbonylamino]methyl]indol-2-yl]ethyl]pyrrolidinyl]carbonyl]pyrrolidinyl]acetate (Compound 270)

200 mg of ethyl 2-[(R)-2-[[(S)-2-[2-(6-amidino-1-ethylindol-2-yl)ethyl]pyrrolidinyl]carbonyl]pyrrolidinyl]acetate obtained in Example 60 was reacted with 67 μl of isobutylchloroformate according to the same procedure as Example 154 to obtain 195 mg of the title compound.

$^1$H NMR(MeOH-d$_4$, ppm): δ 7.91(s, 1H), 7.42(m, 2H), 6.32(s, 1H), 4.18(m, 3H), 3.75(d, 2H, J=6.66 Hz), 3.67(t, 1H), 3.50(m, 3H), 3.30(d, 2H), 3.08(m, 1H), 2.74(m, 2H), 2.62(q, 1H), 2.30–1.60(m, 12H), 1.28(t, 3H), 1.08(t, 3H), 0.92(d, 6H)

EXAMPLE 158
Synthesis of ethyl 2-[(R)-2-[[(S)-2-[2-[6-[[(trichloromethoxy)carbonylamino]iminomethyl]-1-ethylindol-2-yl]ethyl]pyrrolidinyl]carbonyl]pyrrolidinyl]acetate (Compound 272)

100 mg of ethyl 2-[(R)-2-[[(S)-2-[2-(6-amidino-1-ethylindol-2-yl)ethyl]pyrrolidinyl]carbonyl]pyrrolidinyl]acetate obtained in Example 60 was reacted with 35 μl of trichloroethylchloroformate treated according to the same procedure as Example 154 to obtain 92 mg of the title compound.

$^1$H NMR(MeOH-d$_4$, ppm): δ 7.97(s, 1H), 7.46(m, 2H), 6.29(s, 1H), 4.81(s, 2H), 4.18(m, 3H), 3.67(t, 1H), 3.57–3.05(m, 7H), 2.76(m, 2H), 2.64(q, 1H), 2.30–1.60 (m, 10H), 1.27(t, 3H), 1.07(t, 3H)

EXAMPLE 159
Synthesis of ethyl 2-[(R)-2-[[(S)-2-[2-[1-ethyl-6-[imino(phenylcarbonylamino)methyl]indol-2-yl]ethyl]pyrrolidinyl]carbonyl]pyrrolidinyl]acetate (Compound 273)

60 mg of ethyl 2-[(R)-2-[[(S)-2-[2-(6-amidino-1-ethylindol-2-yl)ethyl]pyrrolidinyl]carbonyl]pyrrolidinyl]acetate obtained in Example 60 was reacted with 24 μl of benzylchloroformate according to the same procedure as Example 154 to obtain 64 mg of the title compound.

$^1$H NMR(MeOH-d$_4$, ppm): δ 8.10–6.60(m, 8H), 6.30(s, 1H), 4.16(m, 3H), 4.00(m, 2H), 3.65(m, 1H), 3.49(m, 2H), 3.34(d, 2H, J=19.08 Hz), 3.11(m, 1H), 2.75(m, 2H), 2.66(q, 1H), 2.40–1.60(m, 10H), 1.26(t, 3H), 1.11(t, 3H)

ES-MS: 588(M+1)$^+$

Test 1
Inhibitory activity for thrombin and trypsin

20 μl of each compound of the present invention was dissolved in 50% methanol in various concentrations and then added to each well of a microplate, to each of which 160 μl of the reaction medium containing 125 mM NaCl, 50 mM Tris-HCl (pH 8.0) and 2 mM synthetic substrate (N-benzoyl-Phe-Val-Arg-p-nitroanilide, Sigma B-7632) were added. 20 μl of human thrombin solution (5 units/ml, Sigma T-6759, manufactured by Sigma Co.) containing 0.1% bovine serum albumin was added to each well to initiate the enzymatic reaction. After 20 minutes, the hydrolysis of substrate was determined by measuring the absorbance at 405 nm. The concentration of the test compound showing half the change of the absorbance in the well that did not contain the test compound was represented as IC$_{50}$ value. The selectivity index was calculated by dividing the IC$_{50}$ value for trypsin by the IC$_{50}$ value for thrombin. The thrombin inhibitory activity and the trypsin inhibitory activity for the compound of the present invention are shown in the following Table 2.

TABLE 2

| | Inhibitory activity for thrombin and trypsin | | |
|---|---|---|---|
| Compound No. | Inhibitory activity (IC$_{50}$) | | Selectivity (trypsin/thrombin) |
| | Thrombin(nM) | Trypsin(nM) | |
| 8 | 9.47 | 460.0 | 48.6 |
| 9 | 33.9 | | |
| 15 | 20.1 | 608.0 | 30.2 |
| 24 | 8.45 | 706.0 | 83.6 |
| 30 | 9.01 | 420.0 | 46.6 |
| 37 | 5.40 | | |
| 38 | 7.59 | 184.0 | 24.2 |
| 39 | 6.91 | | |
| 40 | 7.95 | | |
| 43 | 9.96 | 401.0 | 40.3 |
| 44 | 9.23 | 313.0 | 33.9 |
| 46 | 28.9 | | |
| 57 | 7.73 | | |
| 58 | 3.00 | 52.2 | 17.4 |
| 62 | 11.7 | 582.0 | 49.7 |

TABLE 2-continued

Inhibitory activity for thrombin and trypsin

| Compound No. | Inhibitory activity (IC$_{50}$) | | Selectivity (trypsin/thrombin) |
|---|---|---|---|
| | Thrombin(nM) | Trypsin(nM) | |
| 64 | 15.2 | 349.0 | 22.9 |
| 65 | 22.1 | | |
| 72 | 9.4 | 128.0 | 13.6 |
| 73 | 33.2 | 268.0 | |
| 83 | 30.9 | | |
| 84 | 51.6 | 4490.0 | 87.0 |
| 86 | 27.0 | 674.0 | 25.0 |
| 88 | 15.9 | 128.0 | 8.1 |
| 98 | 20.3 | | |
| 109 | 31.9 | | |
| 110 | 37.7 | 1460.0 | 38.6 |
| 112 | 29.2 | | |
| 114 | 17.4 | 500.0 | 28.8 |
| 115 | 31.8 | | |
| 116 | 31.7 | 869.0 | 27.4 |
| 117 | 16.7 | 811.0 | 48.6 |
| 118 | 12.3 | 178.0 | 14.5 |
| 123 | 32.9 | | |
| 125 | 22.3 | 775.0 | 34.7 |
| 126 | 40.5 | | |
| 127 | 21.7 | | |
| 128 | 26.2 | | |
| 129 | 13.1 | 139.0 | 10.6 |
| 130 | 36.5 | | |
| 131 | 9.29 | 137.0 | 14.7 |
| 142 | 33.1 | | |
| 143 | 5.46 | 410.0 | 75.2 |
| 144 | 25.3 | | |
| 145 | 26.1 | 524.0 | 20.1 |
| 146 | 22.1 | 464.0 | 21.0 |
| 147 | 25.5 | | |
| 148 | 23.0 | 443.0 | 19.2 |
| 149 | 10.4 | | |
| 155 | 11.6 | 287.0 | 24.7 |
| 156 | 28.6 | | |
| 157 | 26.9 | | |
| 158 | 5.50 | | |
| 159 | 19.3 | 399.0 | 20.7 |
| 160 | 15.3 | 382.0 | 25.0 |
| 161 | 5.21 | 255.0 | 48.9 |
| 162 | 7.3 | 329.0 | 45.0 |
| 163 | 19.4 | 497.0 | 25.6 |
| 166 | 33.1 | 617.0 | 18.6 |
| 167 | 18.3 | 322.0 | 17.6 |
| 168 | 31.6 | | |
| 169 | 30.2 | | |
| 170 | 33.5 | 1070.0 | 31.9 |
| 171 | 10.6 | 373.0 | 35.1 |
| 173 | 34.6 | | |
| 174 | 16.2 | 416.0 | 25.7 |
| 175 | 9.92 | | |
| 176 | 21.7 | 450.0 | 20.7 |
| 177 | 18.8 | 500.0 | 26.6 |
| 180 | 11.0 | 351.0 | 31.8 |
| 182 | 10.1 | 304.0 | 30.0 |
| 184 | 9.51 | 551.0 | 57.9 |
| 187 | 25.6 | | |
| 192 | 33.8 | | |
| 194 | 31.7 | | |
| 196 | 37.2 | 536.0 | 14.4 |
| 222 | 11.4 | | |
| 224 | 24.1 | | |
| 244 | 53.6 | | |

Test 2

Measurement of the thrombin time (TT) in rat plasma

SD male rats weighing 220±20 g which had fasted overnight were used as experimental animals. Blood taken from the hearts of the experimental animals just before administration of the test compound and at 30, 60, 120 and 240 minutes after oral administration of the test compound was mixed with 0.108M sodium citrate in the ratio of 9:1. The mixtures thereby obtained were centrifuged at 15,000 rpm for 5 minutes at 4° C. to separate the plasma, which was stored at −20° C. until the TT was measured by means of the method described below.

200 $\mu$l of Owren's buffer was added to 50 $\mu$l of the plasma and 100 $\mu$l of the diluted plasma thereby obtained was injected into the vial of a coagulometer and then incubated for 2 minutes at 37° C. To each vial was added 100 $\mu$l of thrombin at a concentration of 20 U/ml, which had prewarmed at 37° C., to measure the time (TT) until clotting occurred. The ratio of the TT in rat plasma after administration of the test compound to the TT in rat plasma before administration of the test compound was calculated. The TT ratios for the compounds of the present invention are shown in the following Table 3.

TABLE 3

Plasma TT ratio after administration to rat

| Compound No | Dosage | | |
|---|---|---|---|
| | 30 mg/kg | 50 mg/kg | 100 mg/kg |
| 86 | 1.49 | 4.51 | 5.19 |
| 88 | 2.62 | 7.83 | |
| 118 | | 8.80 | |
| 126 | | 5.40 | |
| 127 | | 8.00 | |
| 149 | | 9.24 | |
| 155 | | 3.93 | 7.36 |
| 159 | | 6.23 | |
| 160 | | 2.30 | |
| 161 | | 7.62 | |
| 171 | | | 4.23 |
| 267 | | 4.48 | |
| 270 | 1.46 | 4.30 | |
| 272 | 1.76 | 2.84 | |

Test 3

Pharmacokinetic test

Test method:

S.D. male rats weighing 200±20 g which had fasted overnight were subjected to cannulation at their femoral veins and arteries. Compound 88 prepared in Example 62 was dissolved in physiological saline and then administered to the rats both by intravenous injection and oral administration. Blood was taken at prescribed intervals of time and then immediately mixed with methanol. The mixture was centrifuged (15,000 rpm, 5 min., 4° C.) to obtain quantitative amount of the supernatant which was then subjected to HPLC in Diode Array Detector at 254 nm to analyse the concentration of the test compound in the blood.

Test Results

The blood concentrations of compound 88 according to the present invention analysed after intravenous injection and oral administration are shown in the following Tables 4 and 5, and the pharmacokinetic parameter is described in the following Table 6. As can be seen from the experimental results shown in these tables, where compound 88 of the present invention was administered via intravenous injection, it was rapidly distributed in the body and slowly disappeared. In rats, compound 88 of the present invention exhibited a good result, i.e. an elimination half-time of 64 minutes and a bioavailability of 32.6%.

TABLE 4

Blood concentration of the compound 88 of example 62 following intravenous injection of 10 mg/kg in rats

| Time | Blood concentration (μg/ml) | | | | | | |
|---|---|---|---|---|---|---|---|
| (h) | Rat-1 | Rat-2 | Rat-3 | Rat-4 | Rat-5 | Mean | SE |
| 0.000 | 0.000 | 0.000 | 0.000 | 0.000 | 0.000 | 0.000 | 0.000 |
| 0.033 | 11.186 | 25.999 | 23.841 | 28.971 | 18.505 | 21.700 | 1.975 |
| 0.083 | 8.793 | 11.984 | 10.776 | 14.222 | 11.623 | 11.480 | 0.658 |
| 0.250 | 2.707 | 4.629 | 3.531 | 5.982 | 3.895 | 4.149 | 0.484 |
| 0.500 | 0.816 | 1.963 | 1.685 | 2.939 | 1.516 | 1.784 | 0.284 |
| 1.000 | 0.784 | 0.773 | 0.577 | 1.204 | 0.535 | 0.775 | 0.137 |
| 2.000 | 0.204 | 0.098 | 0.000 | 0.424 | 0.162 | 0.178 | 0.081 |
| 4.000 | 0.000 | 0.000 | 0.000 | 0.121 | 0.055 | 0.035 | 0.026 |
| 6.000 | 0.000 | 0.000 | 0.000 | 0.090 | 0.051 | 0.028 | 0.020 |
| 24.000 | 0.000 | 0.000 | 0.000 | 0.000 | 0.000 | 0.000 | 0.000 |

TABLE 5

Blood concentration of the compound 88 of example 62 following oral administration of 100 mg/kg in rats

| Time | Blood concentration (μg/ml) | | | | | | |
|---|---|---|---|---|---|---|---|
| (h) | Rat-1 | Rat-2 | Rat-3 | Rat-4 | Rat-5 | Mean | SE |
| 0.000 | 0.000 | 0.000 | 0.000 | 0.000 | 0.000 | 0.000 | 0.000 |
| 0.033 | 11.186 | 25.999 | 23.841 | 28.971 | 18.505 | 21.700 | 1.975 |
| 0.083 | 8.793 | 11.984 | 10.776 | 14.222 | 11.623 | 11.480 | 0.658 |
| 0.250 | 2.707 | 4.629 | 3.531 | 5.982 | 3.895 | 4.149 | 0.484 |
| 0.500 | 0.816 | 1.963 | 1.685 | 2.939 | 1.516 | 1.784 | 0.284 |
| 1.000 | 0.784 | 0.773 | 0.577 | 1.204 | 0.535 | 0.775 | 0.137 |
| 2.000 | 0.204 | 0.098 | 0.000 | 0.424 | 0.162 | 0.178 | 0.081 |
| 4.000 | 0.000 | 0.000 | 0.000 | 0.121 | 0.055 | 0.035 | 0.026 |
| 6.000 | 0.000 | 0.000 | 0.000 | 0.090 | 0.051 | 0.028 | 0.020 |
| 24.000 | 0.000 | 0.000 | 0.000 | 0.000 | 0.000 | 0.000 | 0.000 |

TABLE 6

Pharmacokinetic parameters of the compound 88 of Example 62 in rats

| Parameter | Mean ± error |
|---|---|
| Elimination Half-life (hr) | 1.07 ± 0.27 |
| Bioavailability (%) | 32.62 ± 7.69 |

What is claimed is:

1. A compound represented by formula (I):

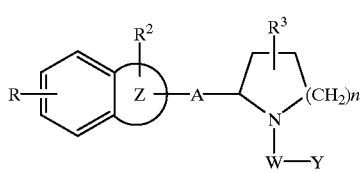

(I)

and pharmaceutically acceptable salts thereof, in which

R represents a group of formula

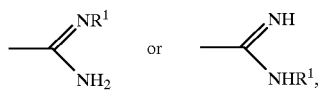

wherein $R^1$ represents hydrogen, hydroxy, alkyl, alkoxy, alkylcarbonyl, alkycarbonyloxy, aralkoxycarbonyl, or a radical of formula (a),

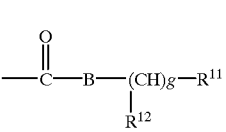

(a)

wherein

B represents oxygen or sulfur;

$R^{11}$ and $R^{12}$ independently of one another represent hydrogen, haloalkyl, alkylcarbonyloxy, dialkylamino, or substituted or unsubstituted 3- to 7-membered saturated or unsaturated heterocyclic or carbocyclic ring; and g denotes an integer of 0 to 3;

$R^2$ represents hydrogen, hydroxy, halogen, carboxy, aminocarbonyl, alkyl, alkoxy, hydroxyalkyl, aminoalkyl, alkylcarbonyl, alkylsulfonyl, carboxyalkyl, aminocarbonylalkyl, alkoxycarbonylalkyl, or substituted or unsubstituted arylsulfonyl;

$R^3$ represents hydrogen, halogen, alkyl, hydroxyalkyl, carboxyalkyl, alkoxycarbonylalkyl, alkoxycarbonyl, carboxy, amino, aminoalkyl, aminocarbonyl, aminocarbonylakyl, or a radical of formula (b),

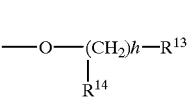

(b)

wherein $R^{13}$ and $R^{14}$ independently of one another represent hydrogen, alkyl, or substituted or unsubstituted 3- to 7-membered saturated or unsaturated heterocyclic or carbocyclic ring; and h denotes an integer of 0 to 3;

the group of formula

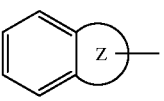

represents a radical selected from the group consisting of indolyl, benzofuranyl, benzothienyl, benzoimidazolyl, benzoxazolyl, benzothiazolyl, naphthyl, tetrahydronaphthyl, indanyl, dihydrobenzofuranyl and dihydrobenzothienyl;

A represents a saturated or unsaturated alkylene group having 2 to 4 carbon atoms, which may have 1 or 2 substituents selected from the group consisting of carboxy, alkyl, hydroxyalkyl, carboxyalkyl, alkylcarbonyl, alkoxycarbonyl and alkoxycarbonylalkyl;

W represents a group of formula (c), (d) or (e),

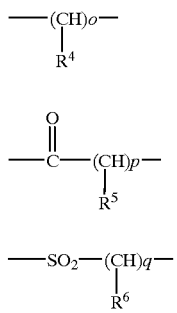

(c)

(d)

(e)

wherein o, p and q independently of one another denote an integer of 0 to 3, $R^4$, $R^5$ and $R^6$ independently of one another represent hydrogen, hydroxy, carboxy, alkoxycarbonyl, substituted or unsubstituted arylsulfonyl, or substituted or unsubstituted 3- to 7-membered saturated or unsaturated heterocyclic or carbocyclic ring, or represents a group of formula (f), (g) or (h),

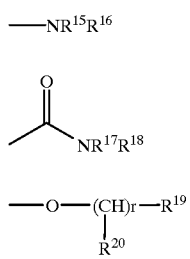

(f)

(g)

(h)

wherein $R^{15}$, $R^{16}$, $R^{17}$ and $R^{18}$ independently of one another represent hydrogen, alkyl, alkylsulfonyl, carboxyalkyl, alkylcarbonyl, aminocarbonylalkyl, alkoxycarbonylalkyl, substituted or unsubstituted arylsulfonyl, substituted or unsubstituted aralkyl, or substituted or unsubstituted 3- to 7-membered saturated or unsaturated heterocyclic or carbocyclic ring;

$R^{19}$ and $R^{20}$ independently of one another represent hydrogen, carboxy, aminocarbonyl or alkoxycarbonyl, or represents 3- to 7-membered saturated or unsaturated heterocyclic or carbocyclic ring which may be fused with one or more 3- to 7-membered saturated or unsaturated heterocyclic or carbocyclic rings; and r denotes an integer of 0 to 3;

Y represents hydrogen or a 3- to 7-membered saturated or unsaturated heterocyclic or carbocyclic ring which may be fused with one or more 3- to 7-membered saturated or unsaturated heterocyclic or carbocyclic rings and which may be substituted on any atom of the ring with a substituent selected from the group consisting of oxygen, halogen, nitro, alkyl, haloalkyl, hydroxyalkyl, alkylsulfonyl, substituted or unsubstituted arylsulfonyl, substituted or unsubstituted 3- to 7-membered saturated or unsaturated heterocyclic or carbocyclic ring, and a group of formula (i), (j) and (k),

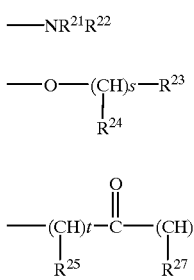

(i)

(j)

(k)

$R^{21}$ and $R^{22}$ independently or one another represent hydrogen, alkyl, alkylsulfonyl, carboxyalkyl, alkylcarbonyl, alkoxycarbonylalkyl, or substituted or unsubstituted arylsulfonyl;

$R^{23}$ and $R^{24}$ independently of one another represent hydrogen, carboxy, aminocarbonyl, alkoxycarbonyl, or 3- to 7-membered saturated or unsaturated heterocyclic or carbocyclic ring which may be fused with one or more 3- to 7-membered saturated or unsaturated heterocyclic or carbocyclic rings;

$R^{25}$, $R^{26}$ and $R^{27}$ independently of one another represent hydrogen, hydroxy, thio, amino, carboxy, aminocarbonyl, alkoxy, alkoxycarbonyl, alkylsulfonylamino, alkenyl, alkoxycarbonylamino, cycloalkylamino, alkylamino, alkoxycarbonylalkylamino, substituted or unsubstituted arylsulfonylamino, or substituted or unsubstituted 3- to 7-membered saturated or unsaturated heterocyclic or carbocyclic ring;

s denotes an integer of 0 to 3;

t denotes an integer of 0 to 6; and u denotes an integer of 0 to 8; and n denotes an integer of 0 to 2, provided that when each of g, h, o, p, q, r, s, t and u denotes number of 3 or more, the corresponding alkylene chain may be straight or branched.

2. The compound as defined in claim 1, wherein

R represents a group of formula

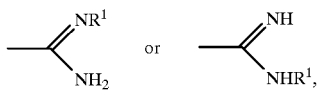

$R^1$ represents hydrogen, hydroxy, $C_1$–$C_4$ alkyl, $C_1$–$C_4$ alkoxy, $C_{2-C4}$ alkylcarbonyl, $C_2$–$C_4$ alkylcarbonyloxy, or a radical of formula (a),

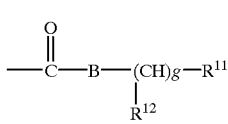

(a)

wherein

B represents oxygen or sulfur, $R^{11}$ and $R^{12}$ independently of one another represents hydrogen, $C_1$–$C_4$ haloalkyl, $C_2$–$C_4$ alkylcarbonyloxy, $C_2$–$C_6$ dialkylamino, or substituted or unsubstituted 6-membered carbocyclic ring, and g denotes an integer of 0 to 3;

$R^2$ represents hydrogen, halogen, carboxy, $C_1$–$C_4$ alkyl, $C_1$–$C_4$ alkoxy, $C_1$–$C_4$ hydroxyalkyl, $C_1$–$C_4$ aminoalkyl, $C_2$–$C_4$ alkylcarbonyl, $C_1$–$C_4$ alkylsulfonyl, $C_2$–$C_4$ carbonylalkyl, $C_2$–$C_4$ aminocarbonylakyl or $C_3$–$C_7$ alkoxycarbonylalkyl;

$R^3$ represents hydrogen, halogen, $C_1$–$C_4$ alkyl, $C_1$–$C_4$ hydroxyalkyl, $C_2$–$C_4$ carboxyalkyl, $C_3$–$C_7$ alkoxycarbonylalkyl, or a radical of formula (b),

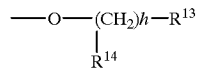 (b)

wherein $R^{13}$ and $R^{14}$ independently of one another represent hydrogen or phenyl, and h denotes an integer of 0 to 1;

the group of formula

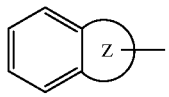

represents a radical selected from the group consisting of indolyl, benzofuranyl, benzothienyl, benzoimidazolyl and naphthyl;

A represents saturated or unsaturated alkylene group having 2 to 4 carbon atoms, which may have 1 or 2 substituents selected from the group consisting of carboxy, $C_1$–$C_4$ hydroxyalkyl and $C_2$–$C_4$ alkoxycarbonyl;

W represents a group of formula (c), (d) or (e),

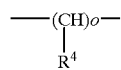 (c)

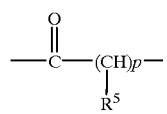 (d)

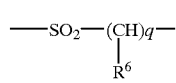 (e)

wherein o, p and q independently of one another denote an integer of 0 to 3, $R^4$, $R^5$ and $R^6$ independently of one another represent hydrogen, hydroxy, carboxy, $C_2$–$C_4$ alkoxycarbonyl, phenylsulfonyl, or substituted or unsubstituted 3- to 5-membered saturated heterocyclic or carbocyclic ring, or represents a group of formula (f), (g) or (h),

 (f)

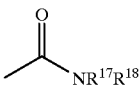 (g)

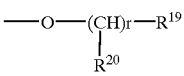 (h)

wherein $R^{15}$, $R^{16}$, $R^{17}$ and $R^{18}$ independently of one another represent hydrogen, $C_1$–$C_4$ alkyl, $C_1$–$C_4$ alkylsulfonyl, $C_2$–$C_4$ carboxyalkyl, $C_2$–$C_4$ alkylcarbonyl, $C_2$–$C_4$ aminocarbonylalkyl, $C_3$–$C_7$ alkoxycarbonylalkyl, or substituted or unsubstituted 3- to 5-membered saturated or unsaturated heterocyclic or carbocyclic ring, $R^{19}$ and $R^{20}$ independently of one another represent hydrogen, carboxy, aminocarbonyl or $C_2$–$C_4$ alkoxycarbonyl, or represents 5- to 6-membered saturated or unsaturated heterocyclic or carbocyclic ring which may be fused with other one or more 5- to 6-membered saturated or unsaturated heterocyclic or carbocyclic ring, and r denotes an integer of 0 to 3;

Y represents hydrogen, or represents 5- to 6-membered saturated or unsaturated heterocyclic or carbocyclic ring which may be fused with other one or more 5- to 6-membered saturated or unsaturated heterocyclic or carbocyclic ring and which can be substituted on any atom of the ring with substituent selected from the group consisting of oxygen, halogen, nitro, $C_1$–$C_4$ alkyl, $C_1$–$C_4$ haloalkyl, $C_1$–$C_4$ hydroxyalkyl, $C_1$–$C_4$ alkylsulfonyl, phenylsulfonyl, substituted or unsubstituted 3- to 5-membered saturated or unsaturated heterocyclic or carbocyclic ring, and a group of formula (i), (j) and (k),

 (i)

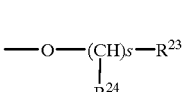 (j)

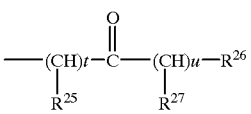 (k)

wherein $R^{21}$ and $R^{22}$ independently of one another represent hydrogen, $C_1$–$C_4$ alkyl, $C_1$–$C_4$ alkylsulfonyl, $C_2$–$C_5$ carboxyalkyl, $C_2$–$C_5$ alkylcarbonyl, $C_3$–$C_7$ alkoxycarbonylalkyl or phenylsulfonyl, $R^{23}$ and $R^{24}$ independently of one another represent hydrogen, carboxy, aminocarbonyl, $C_2$–$C_4$ alkoxycarbonyl, or 3- to 5-membered saturated or unsaturated heterocyclic or carbocyclic ring which may be fused with other one or more 3- to 5-membered saturated or unsaturated heterocyclic or carbocyclic ring, $R^{25}$, $R^{26}$ and $R^{27}$ independently of one another represent hydrogen, hydroxy, thio, amino, carboxy, aminocarbonyl, $C_1$–$C_4$ alkoxy, $C_2$–$C_4$ alkoxycarbonyl, $C_1$–$C_4$ alkylamino, $C_1$–$C_4$ alkylsulfonylamino, $C_2$–$C_5$ alkenyl, $C_2$–$C_4$ alkoxycarbonylamino, $C_3$–$C_6$ alkoxycarbonylalkylamino, $C_3$–$C_6$ cycloalkylamino, phenylsulfonylamino, or substituted or unsubstituted 3- to 5-membered saturated or unsaturated heterocyclic or carbocyclic ring, s denotes an integer of 0 to 3, t denotes an integer of 0 to 6, and u denotes an integer of 0 to 8, and n denotes an integer of 0 to 2, provided that when each of g, h, o, p, q, r, s, t and u denotes number of 3 or more, the corresponding alkylene chain may be straight or branched.

3. The compound as defined in claim 1, which is selected from the group consisting of:

3-[[(S)-2-[2-(6-amidino-1-ethylindol-2-yl)ethyl]pyrrolidin-2-yl]methyl]-benzo[b]thiophene-2-carboxamide, 3-[[(S)-2-[2-(6-amidino-1-methylindol-2-yl)ethyl]pyrrolidin-2-yl]methyl]-benzo[b]thiophene-2-carboxamide, 1-ethyl-2-[2-[(S)-1-[2-(3-chlorophenyl)acetyl]pyrrolidin-2-yl]ethyl]indole-6-carboxyamidine, 2-[2-[(S)-2-[2-(6-amidino-1-ethylindol-2-yl)ethyl]pyrrolidinyl]-2-oxoethy-yl]benzoic acid, 1-ethyl-2-[2-[(S)-1-(2-cyclopenyl-2-phenylacetyl)pyrrolidin-2-yl]ethyl]-indole- 6-carboxamidine, 1-ethyl-2-[2-[(S)-1-((R)-2-methylsulfonylamino-2-phenylacetyl)pyrrolidin-2-yl]ethyl]indole-6-carboxyamidine, ethyl 2-[[(R)-2-[2-[(S)-2-[2-(6-amidino-1-ethylindol-2-yl)ethyl]pyrrolidinyl]-2-oxo-1-phenyl]ethyl]amino]acetate, 1-ethyl-2-[2-[(S)-1-[(R)-2-carbamoylmethylamino)-2-phenylacetyl]pyrrolidin-2-yl]ethyl]indole-6-carboxamide, 2-[[(R)-2-[2-[(S)-2-[2-(6-amidino-1-ethylindol-2-yl)ethyl]pyrrolidinyl]-2-oxo-1-phenylethyl]amino]acetic acid, 1-ethyl-2-[2-[(S)-1-(2-cyclopenylacetyl)pyrrolidin-2-yl]ethyl]indole-6-carboxamidine, ethyl 3-[(S)-2-[2-(6-amidino-1-ethylindol-2-yl)ethyl]pyrrolidinyl]-2-cyclopentyl-3-oxopropanoate, 1-ethyl-2-[2-[(S)-1-(2-cyclohexylacetyl)pyrrolidin-2-yl]ethyl]indole-6-carboxamidine, 1-ethyl-2-[2-[(S)-1-(2-cyclopropylaminoacetyl)pyrrolidin-2-yl]ethyl]indole-6-carboxamidine, 1-ethyl-2-[2-[(S)-1-[2-[cyclopropyl(methylsulfonyl)amino]acetyl]pyrrolidin-2-yl]ethyl]indole-6-carboxamidine, ethyl 2-[[2-[(S)-2-[2-(6-amidino-1-ethylindol-2-yl)ethyl]pyrrolidinyl]-2oxoethyl]cyclopropylamino]acetate, ethyl 2-[[2-[(S)-2-[2-(6-amidino-1-ethylindol-2-yl)ethyl]pyrrolidinyl]-1-methyl-2-oxoethyl]cyclopropylamino]acetate, 2-[[2-[(S)-2-[2-(6-amidino-1-ethylindol-2yl)ethyl]pyrrolidinyl]-1-methyl-2-oxoethyl]cyclopropylamino]acetic acid, ethyl 4-[(S)-2-[2-(6-amidino-1-ethylindol-2-yl)ethyl]pyrrolidinyl]-2-cyclopropylamino-4-oxobutanoate, 4-[(S)-2-[2-(6-amidino-1-ethylindol-2-yl)ethyl]pyrrolidinyl]-3-cyclopropylamino-4-oxobutanoic acid, 1-ethyl-2-[2-[(S)-1-((R)-pyrrolidin-2-ylcarbonyl)pyrrolidin-2-yl]ethyl]-indole-6-carboxamidine, ethyl 2-[(R)-2-[[(S)-2-[2-(6-amidino-1-methylindol-2-yl)ethyl]pyrrolidinyl]carbonyl]pyrrolidinyl]acetate, ethyl 2-[(R)-2-[[(S)-2-[2-(6-amidino-1-ethylindol-2-yl)ethyl]pyrrolidinyl]-carbonyl]pyrrolidinyl]acetate, 2-[(R)-2-[[(S)-2-[2-(6-amidino-1-ethylindol-2yl)ethyl]pyrrolidinyl]carbonyl]pyrrolidinyl]acetic acid, 2-[(R)-2-[[(S)-2-[2-(6-amidino-1-ethylindol-2yl)ethyl]-(S)-4-methylpyrrolidinyl]carbonyl]pyrrolidinyl]acetic acid, ethyl-2-[(R)-2-[[(S)-2-[2-(6-amidino-1-ethylindol-2yl)ethyl]pyrrolidinyl]carbonyl]pyrrolidinyl]propionate, ethyl-2-[(R)-2-[[(S)-2-[2-(6-amidino-1-ethylindol-2yl)ethyl]pyrrolidinyl]carbonyl]pyrrolidinyl]butanoate, ethyl-2-[(R)-2-[[(S)-2-[2-(6-amidino-1-ethylindol-2yl)ethyl]pyrrolidinyl]carbonyl]pyrrolidinyl]2-phenylacetate, 1-ethyl-2-[2-[(S)-1-[[(R)-1-(carbamoylmethyl)pyrrolidin-2-yl]carbonyl]pyrrolidin-2-yl)ethyl]indole-6-carboxamidine, 1-ethyl-2-[2-[(S)-1-[[(R)-1-](N-cyclopropylacarbamoyl)methyl]pyrrolidin-2-yl]carbonyl]pyrrolidin-2-yl)ethyl]indole-6-carboxamidine, ethyl (S)-2-[2-[(R)-2-[[(S)-2-[2-(6-amidino-1-ethylindol-2-yl)ethyl]pyrrolidinyl]carbonyl]pyrrolidinyl]acetylamino]propanoate, 1-ethyl-2-[2-[(S)-1-[[(R)-1-(1-carbamoyl-3-hydroxypropyl)pyrrolidin-2-yl]carbonyl]pyrrolidin-2-yl]ethyl]indole-6-carboxamidine, 2-[(R)-2-[[(S)-2-[2-(6-amidino-1-ethylindol-2yl)ethyl]pyrrolidinyl]carbonyl]pyrrolidinyl]-4-hydroxyburanoic acid, 1-[(R)-2-[[(S)-2-[2-(6-amidino-1-ethylindol-2yl)ethyl]pyrrolidinyl]carbonyl]pyrrolidinyl]ethane-1,2-dicarboxylic acid, 1-ethyl-2-[2-[(S)-1-[[1-(2-oxo-3-oxolanyl)pyrrolidin-2-yl]carbonyl]pyrrolidin-2-yl)ethyl]indole-6-carboxamidine, ethyl 4-[(R)-2-[[(S)-2-[2-(6-amidino-1-ethylindol-2yl)ethyl]pyrrolidinyl]-carbonyl]pyrrolidinyl]butanoate, 4-[(R)-2-[[(S)-2-[2-(6-amidino-1-ethylindol-2yl)ethyl]pyrrolidinyl]carbonyl]pyrrolidinyl]butanoic acid, ethyl 5-[(R)-2-[[(S)-2-[2-(6-amidino-1-ethylindol-2yl)ethyl]pyrrolidinyl]-carbonyl]pyrrolidinyl]pentanoate, 5-[(R)-2-[[(S)-2-[2-(6-amidino-1-ethylindol-2yl)ethyl]pyrrolidinyl]carbonyl]pyrrolidinyl]pentanoic acid, ethyl 6-[(R)-2-[[(S)-2-[2-(6-amidino-1-ethylindol-2yl)ethyl]pyrrolidinyl]-carbonyl]pyrrolidinyl]hexanoate, 6-[(R)-2-[[(S)-2-[2-(6-amidino-1-ethylindol-2yl)ethyl]pyrrolidinyl]carbonyl]pyrrolidinyl]hexanoic acid, 1-ethyl-2-[2-[(S)-1-[[(R)-1-[2-(methylamino)acetyl]pyrrolidin-2-yl]carbonyl]pyrrolidin-2-yl]ethyl]indol-6-carboxamidine, 1-ethyl-2-[2-[(S)-1-[[(R)-1-((S)-2-aminopropanoyl)pyrrolidin-2-yl]carbonyl]pyrrolidin-2-yl]ethyl]indol-6-carboxamidine, 1-ethyl-2-[2-[(S)-1-[[(R)-1-[2-methylamino)acetyl]pyrrolidin-2-yl]carbonyl]pyrrolidin-2-yl]ethyl]indol-6-carboxamidine, 1-ethyl-2-[2-[(S)-1-[[(R)-1-((S)-2-amino-3-methylbutanoyl)pyrrolidin-2-yl]carbonyl]pyrrolidin-2-yl]ethyl]indole-6-carboxamidine, 1-ethyl-2-[2-[(S)-1-[[(R)-1-[(S)-2-(methanesulfonyl-amino)propanoyl]pyrrolidin-2-yl]carbonyl]pyrrolidin-2-yl]ethyl]indole-6-carboxamidine, ethyl 4-[(R)-2-[[(S)-2-[2-(6-amidino-1-ethylindol-2-yl)ethyl]pyrrolidinyl]-carbonyl]pyrrolidinyl]-(S)-3-amino-4-oxobutanoate, 1-ethyl-2-[2-[(S)-1-[[(R)-1-(S)-2-amino-3-carbamoylpropanoyl)pyrrolidin-2-yl]carbonyl]pyrrolidin-2-yl]ethyl]indole-6-carboxamidine, 4-[(R)-2-[[(S)-2-[2-(6-amidino-1-ethylindol-2-yl)ethyl]pyrrolidinyl]carbonyl]pyrrolidinyl]-(S)-3-amino-4-oxobutanoic acid, 1-ethyl-2-[2-[((S)-1-[[(R)-1-(3-aminopropanoyl)pyrrolidin-2-yl]carbonyl]-pyrrolidin-2-yl]ethyl]indole-6-carboxamidine, 1-ethyl-2-[2-[(S)-1-[[(R)-1-(3-amino-2-methyl-propanoyl)pyrrolidin-2-yl]-carbonyl]pyrrolidin-2-yl]ethyl]indole-6-carboxamidine, 1-ethyl-2-[2-[((S)-1-[[(R)-1-(3-aminobutanoyl)pyrrolidin-2-yl]carbonyl]-pyrrolidin-2-yl]ethyl]indole-6-carboxamidine, 1-ethyl-2-[2-[(S)-1-[[(R)-1-[3-[(methylsulfonyl)amino]propanoyl]pyrrolidin-2-yl]carbonyl]-pyrrolidin-2-yl]ethyl]indole-6-carboxamidine, ethyl 4-[(R)-2-[[(S)-2-[2-(6-amidino-1-ethylindol-2-yl)ethyl]pyrrolidinyl]-carbonyl]pyrrolidinyl]-(S)-2-amino-4-oxobutanoate, 1-ethyl-2-[2-[(S)-1-[[(R)-1-((S)-3-amino-3-carbamoylpropanoyl)pyrrolidin-2-yl]-carbonyl]pyrrolidin-2-yl]ethyl]indole-6-carboxamidine, 4-[(R)-2-[[(S)-2-[2-(6-amidino-1-ethylindol-2-yl)ethyl]pyrrolidinyl]carbonyl]pyrrolidinyl]-(S)-2-amino-4-oxobutanoic acid, 1-ethyl-2-[2-[(S)-1-[[1-[(R)-1-[3-carbamoyl-(S)-3-[(methanesulfonyl)amino]propanoyl]pyrrolidin-2-yl]carbonyl]pyrrolidin-2-yl]ethyl]indole-6-carboxamidine, 4-[(R)-2-[[(S)-2-[2-(6-amidino-1-ethylindol-2-yl)ethyl]pyrrolidinyl]carbonyl]pyrrolidinyl]-(S)-2-](methanesulfonyl)amino]-4-oxobutanoic acid, 1-ethyl-2-[2-[(S)-1-[[(R)-1-(4-aminobutanoyl)pyrrolidin-2-yl]carbonyl]pyrrolidin-2-yl]ethyl]indole-6-carboxamidine, 1-ethyl-2-[2-[(S)-1-[[(R)-1-[(2-piperidinyl)carbonyl]pyrrolidin-2-yl]carbonyl]pyrrolidin-2-yl]ethyl]indole-6-carboxamidine, 1-ethyl-2-[2-[(S)-1-[[(R)-1-(3-piperidinylcarbonyl)pyrrolidin-2-yl]carbonyl]pyrrolidin-2-yl]ethyl]indole-6-carboxamidine, 1-ethyl-2-[2-[(S)-1-[[(R)-1-[(4-piperidinyl)carbonyl]pyrrolidin-2-yl]carbonyl]pyrrolidin-2-yl]ethyl]indole-6-carboxamidine, 1-methyl-2-[2-[(S)-1-[[(R)-1-acetylpyrrolidin-2-yl)carbonyl]pyrrolidin-2-yl]ethyl]indole-6-carboxamidine, 1-ethyl-2-[2-[(S)-1-[((R)-1-acetylpyrrolidin-2-yl)carbonyl]pyrrolidin-2yl]ethyl]indol-6-carboxamidine, 1-ethyl-2-[2-[(S)-1-[[(R)-1-(2-propylpentanoyl)pyrrolidin-2-yl]carbonyl]pyrrolidin-2-yl]ethyl]indole-6-carboxamidine, ethyl 3-[(R)-2-[[(S)-2-[2-(6-amidino-1-ethylindol-2-yl)ethyl]pyrrolidinyl]-carbonyl]pyrrolidin-3-oxopropanoate, 1-ethyl-2-[2-[(S)-1-[[(R)-1-(2-carbamoylacetyl)pyrrolidin-2-yl]carbonyl]pyrrolidin-2-yl]ethyl]indole-6-carboxamidine, ethyl 4-[(R)-2-[[(S)-2-[2-(6-amidino-1-ethylindol-2-yl)ethyl]pyrrolidinyl]-carbonyl]pyrrolidinyl]-4-oxobutanoate, 4-[(R)-2-[[(S)-2-[2-(6-amidino-1-ethylindol-2-yl)ethyl]pyrrolidinyl]-carbonyl]pyrrolidin-4-oxo-butanoic acid, 1-ethyl-2-[2-[(S)-1-[[(R)-1-(3-hydroxybutanoyl)pyrrolidin-2-yl]carbonyl]-pyrrolidin-2-yl]ethyl]indole-6-carboxamidine, 1-ethyl-2-[2-[(S)-1-[((R)-1-prop-2-enoylpyrrolidin-2-yl)carbonyl]pyrrolidin-2-yl]ethyl]indole-6-carboxamidine, 1-ethyl-2-[2-[(S)-1-[[(R)-1-(methanesulfonyl)pyrrolidin-2-yl]carbonyl]-pyrrolidin-2-yl]ethyl]indole-6-carboxamidine, 1-ethyl-2-[2-[(S)-1-[[(R)-1-(carbamoylmethyl)-5-oxopyrrolidin-2-yl]carbonyl]pyrrolidin-2-yl]ethyl]indole-6-carboxamidine, methyl-2-[2-[[(S)-2-[2-(6-amidino-1-ethylindol-2-yl)ethyl]pyrrolidinyl]-carbonyl]piperidinyl]acetate, 1-ethyl-2-[2-[(S)-1-[(3-piperidinyl)carbonyl]pyrrolidin-2-yl]ethyl]indole-6-carboxamidine, ethyl 1-[2-[(S)-2-[2-(6-amidino-1-ethylindol-2-yl)ethyl]pyrrolidinyl]-2-oxoethyl]pyrrolidine-2-carboxylate, ethyl 2-[2-[2-[(S)-1-[((R)-1-acetylpyrrolidin-2-ylcarbonyl]pyrrolidin-2-yl]ethyl]-6-amidinoindolyl]acetate, 2-[2-[(S)-1-[((R)-1-acetylpyrrolidin-2-yl)carbonyl]pyrrolidin-2-yl]ethyl]-1-(carbamoylmethyl)indole-6-carboxamidine, and 6-[2-[(S)-1-(2-phenylacetyl)pyrrolidin-2-yl]ethyl]naphthalene-2-carboxamidine.

4. A thrombin inhibitor composition containing as an active component the compound of formula (I) as defined in claim 1 or the pharmaceutically acceptable salt thereof together with a pharmaceutically acceptable carrier.

5. The thrombin inhibitor composition as defined in claim 4, which is formulated into the oral preparation.

6. A process for preparing the compound of formula (I) as defined in claim 1 and its salts characterized in that:

(a) an amino-protecting group of a compound of formula (V):

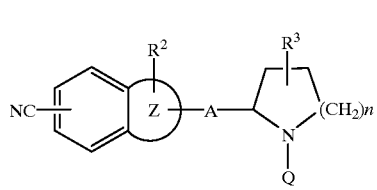

(V)

wherein

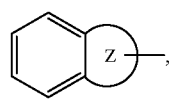

$R^2$, $R^3$, A and n are defined as in claim 1 and Q represents an amino-protecting group, is removed to obtain a compound of formula (IV):

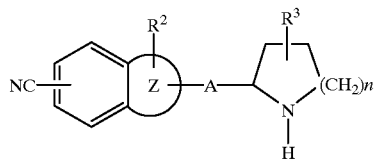

wherein

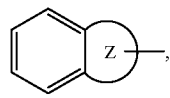

$R^2$, $R^3$, A and n are defined as in claim 1;

(b) the nitrile compound of formula (IV) thereby obtained is reacted with a compound of formula (VI):

 (VI)

wherein Y and W are defined as in claim 1 and D represents hydroxy or halogen, to obtain a compound of formula (III):

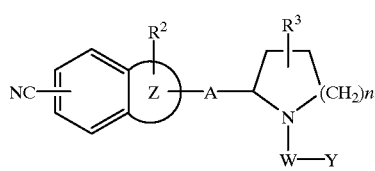

wherein

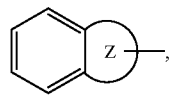

$R^2$, $R^3$, A, Y, W and n are defined as in claim 1;

(c) the compound of formula (III) is reacted with an alcohol compound of formula (VII):

 (VII)

wherein $R^1$ is defined as in claim 1, in the presence of a hydrogen halide to obtain a compound of formula (II):

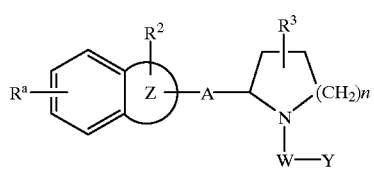

wherein

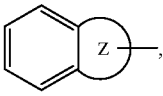

$R^2$, $R^3$, A, Y, W and n are defined as in claim 1 and $R^a$ is a group of formula

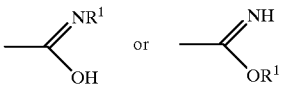

wherein $R^1$ is defined as in claim 1; and (d) the compound of formula (II) is reacted with ammonia.

7. A compound of formula (II):

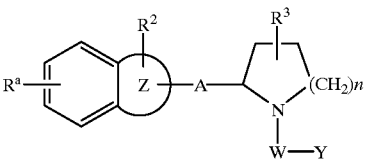

and its salt, wherein

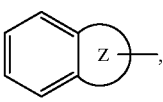

$R^2$, $R^3$, A, Y, W and n are defined as in claim 1 and $R^a$ is a group of formula

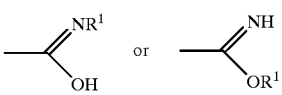

wherein $R^1$ is defined in claim 1.

8. A compound of formula (III):

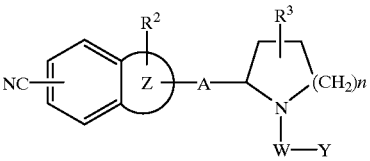

and its salt, wherein

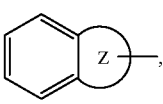

$R^2$, $R^3$, A, Y, W and n are defined as in claim 1.

9. A compound of formula (IV):

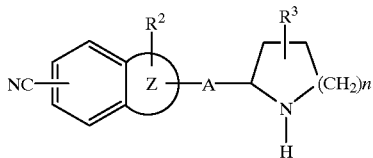

(IV)

and its salt, wherein

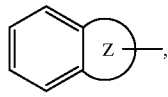

$R^2$, $R^3$, A and n are defined as in claim 1.

10. A compound of formula (V):

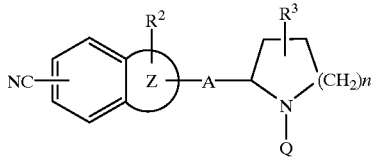

(V)

and its salt, wherein

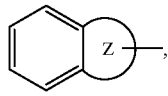

$R^2$, $R^3$, A and n are defined as in claim 1 and Q represents an amino-protecting group.

11. A process for preparing the compound of formula (V) as defined in claim 10 and its salt, which comprises reacting compound of formula (4):

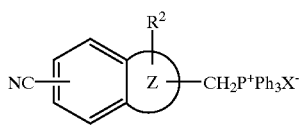

(4)

wherein

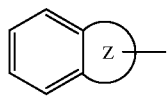

and $R^2$ are defined as in claim 1, with a compound of formula (5):

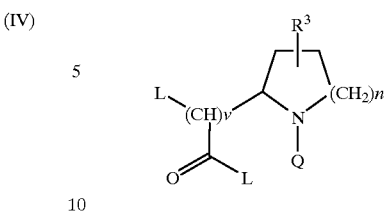

(5)

wherein $R^3$ and n are defined as in claim 1, two L groups may be same or different and represent hydrogen, alkyl, alkoxycarbonyl or alkoxycarbonylalkyl, Q represents an amino-protecting group, X represents halogen, and v denotes an integer of 0 to 2.

12. A process for preparing the compound of formula (V) as defined in claim 10 and its salt, which comprises reacting a compound of formula (7):

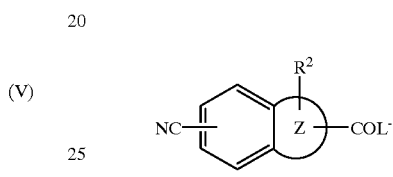

(7)

wherein

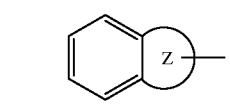

and $R^2$ are defined as in claim 1 and L represents hydrogen, alkyl, alkoxycarbonyl or alkoxycarbonylalkyl, with a compound of formula (8):

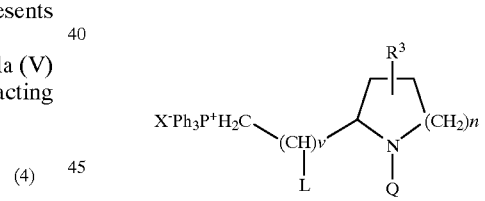

(8)

wherein $R^3$ and n are defined as in claim 1, Q represents an amino-protecting group, X represents halogen, L represents hydrogen, alkyl, alkoxycarbonyl or alkoxycarbonylalkyl and v denotes an integer or 0 to 2.

13. The method of treating thrombosis comprising administering to a person in need thereof a thrombin inhibiting effective amount of a composition comprising the compound according to claim 1.

14. A method for preventing thrombosis, comprising administering to a person in need thereof a thrombin inhibiting effective amount of a composition comprising the compound according to claim 1.

* * * * *